(12) United States Patent
Cavarec et al.

(10) Patent No.: US 7,442,519 B2
(45) Date of Patent: Oct. 28, 2008

(54) KCNQ2-15 POTASSIUM CHANNEL

(75) Inventors: Laurent Cavarec, Paris (FR); Ilya Chumakov, Vaux-le-Penil (FR); Benoit Destenaves, Brunoy (FR); Catherine Gonthier, Corbeil-Essonnes (FR); Isabelle Elias, Sonchamp (FR)

(73) Assignee: Serono Genetics Institute, S.A., Evry (FR)

( * ) Notice: Subject to any disclaimer, the term of this patent is extended or adjusted under 35 U.S.C. 154(b) by 47 days.

(21) Appl. No.: 10/519,335

(22) PCT Filed: Jun. 20, 2003

(86) PCT No.: PCT/EP03/50246

§ 371 (c)(1), (2), (4) Date: Jul. 25, 2005

(87) PCT Pub. No.: WO04/000875

PCT Pub. Date: Dec. 31, 2003

(65) Prior Publication Data

US 2006/0099210 A1    May 11, 2006

Related U.S. Application Data

(60) Provisional application No. 60/391,359, filed on Jun. 25, 2002.

(51) Int. Cl.
  C12P 21/06 (2006.01)
  C12N 15/00 (2006.01)
  C12N 5/00 (2006.01)
  C07K 1/00 (2006.01)
  C07H 21/02 (2006.01)

(52) U.S. Cl. .................. 435/69.1; 435/320.1; 435/325; 530/350; 536/23.1

(58) Field of Classification Search ........................ None
See application file for complete search history.

(56) References Cited

U.S. PATENT DOCUMENTS 6,372,767 B1   4/2002   McNaughton-Smith et al.
6,472,165 B1   10/2002  Rundfeldt et al.

FOREIGN PATENT DOCUMENTS

WO   WO 99/31232       6/1999
WO   WO 01/09612 A2    2/2001
WO   WO 01/91026 A2    11/2001
WO   WO 02/12279 A2    2/2002
WO   WO 03/019186 A2   3/2003

OTHER PUBLICATIONS

Altschul, S. F. et al. "Basic Local Alignment Search Tool" *J. Mol. Biol.*, 1990, pp. 403-410, vol. 215.

Altschul, S. F. et al. "Gapped Blast and PSI-Blast: A New Generation of Protein Database Search Programs" *Nucleic Acids Research*, 1997, pp. 3389-3402, vol. 25, No. 17.

Andrieux, A. et al. "The Suppression of Brain Cold-Stable Microtubules in Mice Induces Synaptic Defects Associated with Neuroleptic-Sensitive Behavioral Disorders" *Genes and Development*, 2002, pp. 2350-2364, vol. 16.

Biervert, C. et al. "A Potassium Channel Mutation in Neonatal Human Epilepsy" *Science*, Jan. 16, 1998, pp. 403-406, vol. 279.

Biervert, C. et al. "Structural and Mutational Analysis of *KCNQ2*, the Major Gene Locus for Benign Familial Neonatal Convulsions" *Hum. Genet.*, 1999, pp. 234-240, vol. 104.

Borresen, A-L. et al. "Detection of Base Mutations in Genomic DNA using Denaturing Gradient Gel Electrophoresis (DGGE) followed by Transfer and Hybridization with Gene-Specific Probes" *Mutation Research*, 1988, pp. 77-83, vol. 202.

Dempster, A. P. et al. "Maximum Likelihood from Incomplete Data via the EM Algorithm" *JRSSB*, 1977, pp. 1-38, vol. 39.

Detera-Wadleigh, S. D. et al. "A High-Density Genome Scan Detects Evidence for a Bipolar-Disorder Susceptibility Locus on 13q32 and other Potential Loci on 1q32 and 18p11.2" *Proc. Natl. Acad. Sci. USA*, May 1999, pp. 5604-5609, vol. 96.

Devereux, J. et al. "A Comprehensive Set of Sequence Analysis Programs for the VAX" *Nucleic Acids Research*, 1984, pp. 387-395, vol. 12, No. 1.

Elbashir, S. M. et al. "RNA Interference is Mediated by 21 and 22-Nucleotide RNAs" *Genes and Development*, 2001, pp. 188-200, vol. 15.

Ellington, A. D. et al. "In vitro Selection of RNA Molecules that Bind Specific Ligands" *Nature*, Aug. 30, 1990, pp. 818-822, vol. 346.

Excoffier, L. et al. "Maximum-Likelihood Estimation of Molecular Haplotype Frequencies in a Diploid Population" *Mol. Biol. Evol.*, 1995, pp. 921-927, vol. 12, No. 5.

Gamper, N. et al. "Subunit-Specific Modulation of KCNQ Potassium Channels by Src Tyrosine Kinase" *Journal of Neuroscience*, Jan. 1, 2003, pp. 84-95, vol. 23, No. 1.

Grantham, R. "Amino Acid Difference Formula to Help Explain Protein Evolution" *Science*, Sep. 6, 1974, pp. 862-864, vol. 185.

Grompe, M. et al. "Scanning Detection of Mutations in Human Ornithine Transcarbamoylase by Chemical Mismatch Cleavage" *Proc. Natl. Acad. Sci. USA*, Aug. 1989, pp. 5888-5892, vol. 86.

Hu, P. et al. "Molecular Cloning and Mapping of the Brain-Abundant B1γ Subunit of Protein Phosphatase 2A, *PPP2R2C*, to Human Chromosome 4p16" *Genomics*, 2000, pp. 83-86, vol. 67.

Kaelin, W. G. et al. "Identification of Cellular Proteins That Can Interact Specifically with the T/E1A-Binding Region of the Retinoblastoma Gene Product" *Cell*, Feb. 8, 1991, pp. 521-532, vol. 64.

(Continued)

*Primary Examiner*—Olga N Chernyshev
(74) *Attorney, Agent, or Firm*—Saliwanchik, Lloyd & Saliwanchik

(57) ABSTRACT

The invention encompasses polypeptides and polynucleotides of three novel bipolar disorder-associated potassium channel polypeptides, KCNQ2-15bx, KCNQ2-15by and KCNQ2-15bz. The invention further relates to the use of potassium channels comprising KCNQ2 subunits for screening for modulators thereof, the use of these modulators for treating mental disorders such as bipolar disorder, schizophrenia and depression, and drugs comprising these modulators. The invention also discloses biallelic markers located in the KCNQ2 gene and their use for diagnosing mental disorders.

8 Claims, 4 Drawing Sheets

OTHER PUBLICATIONS

Kaelin, W. G. et al. "Expression Cloning of a cDNA Encoding a Retinoblastoma-Binding Protein with E2F-Like Properties" *Cell*, Jul. 24, 1992, pp. 351-364, vol. 70.

Kim, S. et al. "Multiplex Genotyping of the Human β2-Adrenergic Receptor Gene using Solid-Phase Capturable Dideoxynucleotides and Mass Spectrometry" *Analytical Biochemistry*, 2003, pp. 251-258, vol. 316.

Lessa, E. P. et al. "Screening Techniques for Detecting Allelic Variation in DNA Sequences" *Molecular Ecology*, 1993, pp. 119-129, vol. 2.

Main, M. J. et al. "Modulation of KCNQ2/3 Potassium Channels by the Novel Anticonvulsant Retigabine" *Molecular Pharmacology*, 2000, pp. 253-262, vol. 58.

Newton, C. R. et al. "Analysis of any Point Mutation in DNA. The Amplification Refractory Mutation System (ARMS)" *Nucleic Acids Research*, Nov. 7, 1989, pp. 2503-2516, vol. 17, No. 7.

Orita, M. et al. "Detection of Polymorphisms of Human DNA by Gel Electrophoresis as Single-Strand Conformation Polymorphisms" *Proc. Natl. Acad. Sci. USA*, Apr. 1989, pp. 2766-2770, vol. 86.

Pan, Z. et al. "Alternative Splicing of KCNQ2 Potassium Channel Transcripts Contributes to the Functional Diversity of M-Currents" *Journal of Physiology*, 2001, pp. 347-358, vol. 531.2.

Pearson, W. R. "Rapid and Sensitive Sequence Comparison with FASTP and FASTA" *Methods in Enzymology*, 1990, pp. 63-98, vol. 183.

Pearson, W. R. et al. "Improved Tools for Biological Sequence Comparison" *Proc. Natl. Acad. Sci. USA*, Apr. 1988, pp. 2444-2448, vol. 85.

Ruano, G. et al. "Haplotype of Multiple Polymorphisms Resolved by Enzymatic Amplification of Single DNA Molecules" *Proc. Natl. Acad. Sci. USA*, Aug. 1990, pp. 6296-6300, vol. 87.

Sarkar, G. et al. "Haplotyping by Double PCR Amplification of Specific Alleles" *BioTechniques*, 1991, pp. 436-440, vol. 10, No. 4.

Schwake, M. et al. "Surface Expression and Single Channel Properties of KCNQ2/KCNQ3, M-Type K+ Channels Involved in Epilepsy" *Journal of Biological Chemistry*, May 5, 2000, pp. 13343-13348, vol. 275, No. 18.

Singh, N. A. et al. "sA Novel Potassium Channel Gene, *KCNQ2*, is Mutated in an Inherited Epilepsy of Newborns" *Nature Genetics*, Jan. 1998, pp. 25-29, vol. 18.

Smith, T. F. et al. "Comparison of Biosequences" *Advances in Applied Mathematics*, 1981, pp. 482-489, vol. 2.

Towbin, H. et al. "Electrophoretic Transfer of Proteins from Polyacrylamide Gels to Nitrocellulose Sheets: Procedure and some applications" *Proc. Natl. Acad. Sci. USA*, Sep. 1979, pp. 4350-4354, vol. 76, No. 9.

Wang, H-S. et al. "KCNQ2 and KCNQ3 Potassium Channel Subunits: Molecular Correlates of the M-Channel" *Science*, Dec. 4, 1998, pp. 1890-1893, vol. 282.

Wen, S-Y. et al. "Rapid Detection of the Known SNPs of CYP2C9 using Oligonucleotide Microarray" *World J. Gastroenterol.*, 2003, pp. 1342-1346, vol. 9, No. 6.

Wu, D. Y. et al. "Allele-Specific Enzymatic Amplification of β-Globin Genomic DNA for Diagnosis of Sickle Cell Anemia" *Proc. Natl. Acad. Sci. USA*, Apr. 1989, pp. 2757-2760, vol. 86.

Jentsch, T. J. et al. "Pathophysiology of KCNQ Channels: Neonatal Epilepsy and Progressive Deafness" *Epilepsia*, 2000, pp. 1068-1069, vol. 41, No. 8.

Tinel, N. et al. "The KCNQ Potassium Channel: Splice Variants, Functional and Developmental Expression. Brain Localization and Comparison with KCNQ3" *FEBS Letters*, Nov. 6, 1998, pp. 171-176, vol. 438, No. 3.

Smith, J. S. et al. "Differential Expression of KCNQ2 Splice Variants: Implications to M Current Function during Neuronal Development" *Journal of Neuroscience*, Feb. 15, 2001, pp. 1096-1103, vol. 21, No. 4.

SwissProt Accession No. O43526, Jul. 10, 2007.
EMBL Accession No. NM_172107, Jun. 27, 2007.
EMBL Accession No. NM_172106, Jun. 26, 2007.
EMBL Accession No. NM_004518, Jun. 26, 2007.
EMBL Accession No. NM_172108, Jun. 26, 2007.
EMBL Accession No. NM_172109, Jun. 26, 2007.
Genbank Accession No. AF086924, Dec. 12, 2000.
Genbank Accession No. AF033348, Jan. 21, 1998.
RefseqN Accession No. NT_006051, Aug. 29, 2006.

|  | Ex 13-17 | Ex-13-15b | Ex 13-15 |
|---|---|---|---|
| Ex 13-17 | ++ | - / + | - / + |
| Ex 13-15b | - | ++ | ++ |
| Ex 13-15 | - | ++ | + |

SEQUENCE LISTING

<160> NUMBER OF SEQ ID NOS: 47

<210> SEQ ID NO 1
<211> LENGTH: 1932
<212> TYPE: DNA
<213> ORGANISM: Homo sapiens
<220> FEATURE:
<221> NAME/KEY: CDS
<222> LOCATION: (1)..(1932)

<400> SEQUENCE: 1

```
atg gtg cag aag tcg cgc aac ggc ggc gta tac ccc ggc ccg agc ggg      48
Met Val Gln Lys Ser Arg Asn Gly Gly Val Tyr Pro Gly Pro Ser Gly
1               5                   10                  15 gag aag aag ctg aag gtg ggc ttc gtg ggg ctg gac ccc ggc gcg ccc      96
Glu Lys Lys Leu Lys Val Gly Phe Val Gly Leu Asp Pro Gly Ala Pro
            20                  25                  30 gac tcc acc cgg gac ggg gcg ctg ctg atc gcc ggc tcc gag gcc ccc     144
Asp Ser Thr Arg Asp Gly Ala Leu Leu Ile Ala Gly Ser Glu Ala Pro
        35                  40                  45 aag cgc ggc agc atc ctc agc aaa cct cgc gcg ggc ggc gcg ggc gcc     192
Lys Arg Gly Ser Ile Leu Ser Lys Pro Arg Ala Gly Gly Ala Gly Ala
    50                  55                  60 ggg aag ccc ccc aag cgc aac gcc ttc tac cgc aag ctg cag aat ttc     240
Gly Lys Pro Pro Lys Arg Asn Ala Phe Tyr Arg Lys Leu Gln Asn Phe
65                  70                  75                  80 ctc tac aac gtg ctg gag cgg ccg cgc ggc tgg gcg ttc atc tac cac     288
Leu Tyr Asn Val Leu Glu Arg Pro Arg Gly Trp Ala Phe Ile Tyr His
                85                  90                  95 gcc tac gtg ttc ctc ctg gtt ttc tcc tgc ctc gtg ctg tct gtg ttt     336
Ala Tyr Val Phe Leu Leu Val Phe Ser Cys Leu Val Leu Ser Val Phe
            100                 105                 110 tcc acc atc aag gag tat gag aag agc tcg gag ggg gcc ctc tac atc     384
Ser Thr Ile Lys Glu Tyr Glu Lys Ser Ser Glu Gly Ala Leu Tyr Ile
        115                 120                 125 ctg gaa atc gtg act atc gtg gtg ttt ggc gtg gag tac ttc gtg cgg     432
Leu Glu Ile Val Thr Ile Val Val Phe Gly Val Glu Tyr Phe Val Arg
    130                 135                 140 atc tgg gcc gca ggc tgc tgc tgc cgg tac cgt ggc tgg agg ggg cgg     480
Ile Trp Ala Ala Gly Cys Cys Cys Arg Tyr Arg Gly Trp Arg Gly Arg
145                 150                 155                 160 ctc aag ttt gcc cgg aaa ccg ttc tgt gtg att gac atc atg gtg ctc     528
Leu Lys Phe Ala Arg Lys Pro Phe Cys Val Ile Asp Ile Met Val Leu
                165                 170                 175 atc gcc tcc att gcg gtg ctg gcc gcc ggc tcc cag ggc aac gtc ttt     576
Ile Ala Ser Ile Ala Val Leu Ala Ala Gly Ser Gln Gly Asn Val Phe
            180                 185                 190 gcc aca tct gcg ctc cgg agc ctg cgc ttc ctg cag att ctg cgg atg     624
Ala Thr Ser Ala Leu Arg Ser Leu Arg Phe Leu Gln Ile Leu Arg Met
        195                 200                 205 atc cgc atg gac cgg cgg gga ggc acc tgg aag ctg ctg ggc tct gtg     672
Ile Arg Met Asp Arg Arg Gly Gly Thr Trp Lys Leu Leu Gly Ser Val
    210                 215                 220 gtc tat gcc cac agc aag gag ctg gtc act gcc tgg tac atc ggc ttc     720
Val Tyr Ala His Ser Lys Glu Leu Val Thr Ala Trp Tyr Ile Gly Phe
225                 230                 235                 240 ctt tgt ctc atc ctg gcc tcg ttc ctg gtg tac ttg gca gag aag ggg     768
Leu Cys Leu Ile Leu Ala Ser Phe Leu Val Tyr Leu Ala Glu Lys Gly
                245                 250                 255
```

```
gag aac gac cac ttt gac acc tac gcg gat gca ctc tgg tgg ggc ctg      816
Glu Asn Asp His Phe Asp Thr Tyr Ala Asp Ala Leu Trp Trp Gly Leu
        260                 265                 270 atc acg ctg acc acc att ggc tac ggg gac aag tac ccc cag acc tgg      864
Ile Thr Leu Thr Thr Ile Gly Tyr Gly Asp Lys Tyr Pro Gln Thr Trp
            275                 280                 285 aac ggc agg ctc ctt gcg gca acc ttc acc ctc atc ggt gtc tcc ttc      912
Asn Gly Arg Leu Leu Ala Ala Thr Phe Thr Leu Ile Gly Val Ser Phe
        290                 295                 300 ttc gcg ctg cct gca ggc atc ttg ggg tct ggg ttt gcc ctg aag gtt      960
Phe Ala Leu Pro Ala Gly Ile Leu Gly Ser Gly Phe Ala Leu Lys Val
305                 310                 315                 320 cag gag cag cac agg cag aag cac ttt gag aag agg cgg aac ccg gca     1008
Gln Glu Gln His Arg Gln Lys His Phe Glu Lys Arg Arg Asn Pro Ala
                325                 330                 335 gca ggc ctg atc cag tcg gcc tgg aga ttc tac gcc acc aac ctc tcg     1056
Ala Gly Leu Ile Gln Ser Ala Trp Arg Phe Tyr Ala Thr Asn Leu Ser
            340                 345                 350 cgc aca gac ctg cac tcc acg tgg cag tac tac gag cga acg gtc acc     1104
Arg Thr Asp Leu His Ser Thr Trp Gln Tyr Tyr Glu Arg Thr Val Thr
        355                 360                 365 gtg ccc atg tac agt tcg caa act caa acc tac ggg gcc tcc aga ctt     1152
Val Pro Met Tyr Ser Ser Gln Thr Gln Thr Tyr Gly Ala Ser Arg Leu
370                 375                 380 atc ccc ccg ctg aac cag ctg gag ctg ctg agg aac ctc aag agt aaa     1200
Ile Pro Pro Leu Asn Gln Leu Glu Leu Leu Arg Asn Leu Lys Ser Lys
385                 390                 395                 400 tct gga ctc gct ttc agg aag gac ccc ccg ccg gag ccg tct cca agt     1248
Ser Gly Leu Ala Phe Arg Lys Asp Pro Pro Pro Glu Pro Ser Pro Ser
                405                 410                 415 aaa ggc agc ccg tgc aga ggg ccc ctg tgt gga tgc tgc ccc gga cgc     1296
Lys Gly Ser Pro Cys Arg Gly Pro Leu Cys Gly Cys Cys Pro Gly Arg
            420                 425                 430 tct agc cag aag gtc agt ttg aaa gat cgt gtc ttc tcc agc ccc cga     1344
Ser Ser Gln Lys Val Ser Leu Lys Asp Arg Val Phe Ser Ser Pro Arg
        435                 440                 445 ggc gtg gct gcc aag ggg aag ggg tcc ccg cag gcc cag act gtg agg     1392
Gly Val Ala Ala Lys Gly Lys Gly Ser Pro Gln Ala Gln Thr Val Arg
450                 455                 460 cgg tca ccc agc gcc gac cag agc ctc gag gac agc ccc agc aag gtg     1440
Arg Ser Pro Ser Ala Asp Gln Ser Leu Glu Asp Ser Pro Ser Lys Val
465                 470                 475                 480 ccc aag agc tgg agc ttc ggg gac cgc agc cgg gca cgc cag gct ttc     1488
Pro Lys Ser Trp Ser Phe Gly Asp Arg Ser Arg Ala Arg Gln Ala Phe
                485                 490                 495 cgc atc aag ggt gcc gcg tca cgg cag aac tca gaa gaa gca agc ctc     1536
Arg Ile Lys Gly Ala Ala Ser Arg Gln Asn Ser Glu Glu Ala Ser Leu
            500                 505                 510 ccc gga gag gac att gtg gat gac aag agc tgc ccc tgc gag ttt gtg     1584
Pro Gly Glu Asp Ile Val Asp Asp Lys Ser Cys Pro Cys Glu Phe Val
        515                 520                 525 acc gag gac ctg acc ccg ggc ctc aaa gtc agc atc aga gcc gtg tgt     1632
Thr Glu Asp Leu Thr Pro Gly Leu Lys Val Ser Ile Arg Ala Val Cys
530                 535                 540 gtc atg cgg ttc ctg gtg tcc aag cgg aag ttc aag gag agc ctg cgg     1680
Val Met Arg Phe Leu Val Ser Lys Arg Lys Phe Lys Glu Ser Leu Arg
545                 550                 555                 560 ccc tac gac gtg atg gac gtc atc gag cag tac tca gcc ggc cac ctg     1728
Pro Tyr Asp Val Met Asp Val Ile Glu Gln Tyr Ser Ala Gly His Leu
                565                 570                 575
```

```
gac atg ctg tcc cga att aag agc ctg cag tcc agg caa gag ccc cgc    1776
Asp Met Leu Ser Arg Ile Lys Ser Leu Gln Ser Arg Gln Glu Pro Arg
        580                 585                 590 ctg cct gtc cag cag ggg aca aga acg ggg tgg gct tct ggg aca aag    1824
Leu Pro Val Gln Gln Gly Thr Arg Thr Gly Trp Ala Ser Gly Thr Lys
    595                 600                 605 ccc act gtg gcc cat ggt ggg agt gca ggg ggt gtg tgg gcg ggg cct    1872
Pro Thr Val Ala His Gly Gly Ser Ala Gly Gly Val Trp Ala Gly Pro
610                 615                 620 cct ccc cac cca cgt cgg cct ctg tca gct tct gtt gtg tct tca caa    1920
Pro Pro His Pro Arg Arg Pro Leu Ser Ala Ser Val Val Ser Ser Gln
625                 630                 635                 640 agt ctg ttt taa                                                    1932
Ser Leu Phe
```

<210> SEQ ID NO 2
<211> LENGTH: 643
<212> TYPE: PRT
<213> ORGANISM: Homo sapiens

<400> SEQUENCE: 2

```
Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
            20                  25                  30

Asp Ser Thr Arg Asp Gly Ala Leu Leu Ile Ala Gly Ser Glu Ala Pro
        35                  40                  45

Lys Arg Gly Ser Ile Leu Ser Lys Pro Arg Ala Gly Ala Gly Ala
    50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Val Phe Gly Val Glu Tyr Phe Val Arg
    130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270
```

```
Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
    290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
                340                 345                 350

Arg Thr Asp Leu His Ser Thr Trp Gln Tyr Tyr Glu Arg Thr Val Thr
                355                 360                 365

Val Pro Met Tyr Ser Ser Gln Thr Gln Thr Tyr Gly Ala Ser Arg Leu
370                 375                 380

Ile Pro Pro Leu Asn Gln Leu Glu Leu Leu Arg Asn Leu Lys Ser Lys
385                 390                 395                 400

Ser Gly Leu Ala Phe Arg Lys Asp Pro Pro Glu Pro Ser Pro Ser
                405                 410                 415

Lys Gly Ser Pro Cys Arg Gly Pro Leu Cys Gly Cys Cys Pro Gly Arg
                420                 425                 430

Ser Ser Gln Lys Val Ser Leu Lys Asp Arg Val Phe Ser Ser Pro Arg
                435                 440                 445

Gly Val Ala Ala Lys Gly Lys Gly Ser Pro Gln Ala Gln Thr Val Arg
                450                 455                 460

Arg Ser Pro Ser Ala Asp Gln Ser Leu Glu Asp Ser Pro Ser Lys Val
465                 470                 475                 480

Pro Lys Ser Trp Ser Phe Gly Asp Arg Ser Arg Ala Arg Gln Ala Phe
                485                 490                 495

Arg Ile Lys Gly Ala Ala Ser Arg Gln Asn Ser Glu Glu Ala Ser Leu
                500                 505                 510

Pro Gly Glu Asp Ile Val Asp Asp Lys Ser Cys Pro Cys Glu Phe Val
                515                 520                 525

Thr Glu Asp Leu Thr Pro Gly Leu Lys Val Ser Ile Arg Ala Val Cys
                530                 535                 540

Val Met Arg Phe Leu Val Ser Lys Arg Lys Phe Lys Glu Ser Leu Arg
545                 550                 555                 560

Pro Tyr Asp Val Met Asp Val Ile Glu Gln Tyr Ser Ala Gly His Leu
                565                 570                 575

Asp Met Leu Ser Arg Ile Lys Ser Leu Gln Ser Arg Gln Glu Pro Arg
                580                 585                 590

Leu Pro Val Gln Gln Gly Thr Arg Thr Gly Trp Ala Ser Gly Thr Lys
                595                 600                 605

Pro Thr Val Ala His Gly Gly Ser Ala Gly Gly Val Trp Ala Gly Pro
                610                 615                 620

Pro Pro His Pro Arg Arg Pro Leu Ser Ala Ser Val Val Ser Ser Gln
625                 630                 635                 640

Ser Leu Phe
```

<210> SEQ ID NO 3
<211> LENGTH: 1878
<212> TYPE: DNA
<213> ORGANISM: Homo sapiens
<220> FEATURE:
<221> NAME/KEY: CDS
<222> LOCATION: (1)..(1878)

<400> SEQUENCE: 3

```
atg gtg cag aag tcg cgc aac ggc ggc gta tac ccc ggc ccg agc ggg        48
Met Val Gln Lys Ser Arg Asn Gly Gly Val Tyr Pro Gly Pro Ser Gly
 1               5                  10                  15 gag aag aag ctg aag gtg ggc ttc gtg ggg ctg gac ccc ggc gcg ccc        96
Glu Lys Lys Leu Lys Val Gly Phe Val Gly Leu Asp Pro Gly Ala Pro
            20                  25                  30 gac tcc acc cgg gac ggg gcg ctg ctg atc gcc ggc tcc gag gcc ccc       144
Asp Ser Thr Arg Asp Gly Ala Leu Leu Ile Ala Gly Ser Glu Ala Pro
        35                  40                  45 aag cgc ggc agc atc ctc agc aaa cct cgc gcg ggc ggc gcg ggc gcc       192
Lys Arg Gly Ser Ile Leu Ser Lys Pro Arg Ala Gly Gly Ala Gly Ala
    50                  55                  60 ggg aag ccc ccc aag cgc aac gcc ttc tac cgc aag ctg cag aat ttc       240
Gly Lys Pro Pro Lys Arg Asn Ala Phe Tyr Arg Lys Leu Gln Asn Phe
65                  70                  75                  80 ctc tac aac gtg ctg gag cgg ccg cgc ggc tgg gcg ttc atc tac cac       288
Leu Tyr Asn Val Leu Glu Arg Pro Arg Gly Trp Ala Phe Ile Tyr His
                85                  90                  95 gcc tac gtg ttc ctc ctg gtt ttc tcc tgc ctc gtg ctg tct gtg ttt       336
Ala Tyr Val Phe Leu Leu Val Phe Ser Cys Leu Val Leu Ser Val Phe
           100                 105                 110 tcc acc atc aag gag tat gag aag agc tcg gag ggg gcc ctc tac atc       384
Ser Thr Ile Lys Glu Tyr Glu Lys Ser Ser Glu Gly Ala Leu Tyr Ile
       115                 120                 125 ctg gaa atc gtg act atc gtg gtg ttt ggc gtg gag tac ttc gtg cgg       432
Leu Glu Ile Val Thr Ile Val Val Phe Gly Val Glu Tyr Phe Val Arg
   130                 135                 140 atc tgg gcc gca ggc tgc tgc tgc cgg tac cgt ggc tgg agg ggg cgg       480
Ile Trp Ala Ala Gly Cys Cys Cys Arg Tyr Arg Gly Trp Arg Gly Arg
145                 150                 155                 160 ctc aag ttt gcc cgg aaa ccg ttc tgt gtg att gac atc atg gtg ctc       528
Leu Lys Phe Ala Arg Lys Pro Phe Cys Val Ile Asp Ile Met Val Leu
                165                 170                 175 atc gcc tcc att gcg gtg ctg gcc gcc ggc tcc cag ggc aac gtc ttt       576
Ile Ala Ser Ile Ala Val Leu Ala Ala Gly Ser Gln Gly Asn Val Phe
            180                 185                 190 gcc aca tct gcg ctc cgg agc ctg cgc ttc ctg cag att ctg cgg atg       624
Ala Thr Ser Ala Leu Arg Ser Leu Arg Phe Leu Gln Ile Leu Arg Met
        195                 200                 205 atc cgc atg gac cgg cgg gga ggc acc tgg aag ctg ctg ggc tct gtg       672
Ile Arg Met Asp Arg Arg Gly Gly Thr Trp Lys Leu Leu Gly Ser Val
    210                 215                 220 gtc tat gcc cac agc aag gag ctg gtc act gcc tgg tac atc ggc ttc       720
Val Tyr Ala His Ser Lys Glu Leu Val Thr Ala Trp Tyr Ile Gly Phe
225                 230                 235                 240 ctt tgt ctc atc ctg gcc tcg ttc ctg gtg tac ttg gca gag aag ggg       768
Leu Cys Leu Ile Leu Ala Ser Phe Leu Val Tyr Leu Ala Glu Lys Gly
                245                 250                 255 gag aac gac cac ttt gac acc tac gcg gat gca ctc tgg tgg ggc ctg       816
Glu Asn Asp His Phe Asp Thr Tyr Ala Asp Ala Leu Trp Trp Gly Leu
            260                 265                 270 atc acg ctg acc acc att ggc tac ggg gac aag tac ccc cag acc tgg       864
Ile Thr Leu Thr Thr Ile Gly Tyr Gly Asp Lys Tyr Pro Gln Thr Trp
        275                 280                 285 aac ggc agg ctc ctt gcg gca acc ttc acc ctc atc ggt gtc tcc ttc       912
Asn Gly Arg Leu Leu Ala Ala Thr Phe Thr Leu Ile Gly Val Ser Phe
    290                 295                 300
```

|  |  |
|---|---|
| ttc gcg ctg cct gca ggc atc ttg ggg tct ggg ttt gcc ctg aag gtt<br>Phe Ala Leu Pro Ala Gly Ile Leu Gly Ser Gly Phe Ala Leu Lys Val<br>305                     310                    315                320 | 960 |
| cag gag cag cac agg cag aag cac ttt gag aag agg cgg aac ccg gca<br>Gln Glu Gln His Arg Gln Lys His Phe Glu Lys Arg Arg Asn Pro Ala<br>                    325                    330                    335 | 1008 |
| gca ggc ctg atc cag tcg gcc tgg aga ttc tac gcc acc aac ctc tcg<br>Ala Gly Leu Ile Gln Ser Ala Trp Arg Phe Tyr Ala Thr Asn Leu Ser<br>             340                    345                    350 | 1056 |
| cgc aca gac ctg cac tcc acg tgg cag tac tac gag cga acg gtc acc<br>Arg Thr Asp Leu His Ser Thr Trp Gln Tyr Tyr Glu Arg Thr Val Thr<br>355                     360                    365 | 1104 |
| gtg ccc atg tac agt tcg caa act caa acc tac ggg gcc tcc aga ctt<br>Val Pro Met Tyr Ser Ser Gln Thr Gln Thr Tyr Gly Ala Ser Arg Leu<br>370                     375                    380 | 1152 |
| atc ccc ccg ctg aac cag ctg gag ctg ctg agg aac ctc aag agt aaa<br>Ile Pro Pro Leu Asn Gln Leu Glu Leu Leu Arg Asn Leu Lys Ser Lys<br>385                     390                    395                    400 | 1200 |
| tct gga ctc gct ttc agg aag gac ccc ccg ccg gag ccg tct cca agc<br>Ser Gly Leu Ala Phe Arg Lys Asp Pro Pro Pro Glu Pro Ser Pro Ser<br>                    405                    410                    415 | 1248 |
| cag aag gtc agt ttg aaa gat cgt gtc ttc tcc agc ccc cga ggc gtg<br>Gln Lys Val Ser Leu Lys Asp Arg Val Phe Ser Ser Pro Arg Gly Val<br>             420                    425                    430 | 1296 |
| gct gcc aag ggg aag ggg tcc ccg cag gcc cag act gtg agg cgg tca<br>Ala Ala Lys Gly Lys Gly Ser Pro Gln Ala Gln Thr Val Arg Arg Ser<br>                    435                    440                    445 | 1344 |
| ccc agc gcc gac cag agc ctc gag gac agc ccc agc aag gtg ccc aag<br>Pro Ser Ala Asp Gln Ser Leu Glu Asp Ser Pro Ser Lys Val Pro Lys<br>450                     455                    460 | 1392 |
| agc tgg agc ttc ggg gac cgc agc cgg gca cgc cag gct ttc cgc atc<br>Ser Trp Ser Phe Gly Asp Arg Ser Arg Ala Arg Gln Ala Phe Arg Ile<br>465                     470                    475                    480 | 1440 |
| aag ggt gcc gcg tca cgg cag aac tca gaa gaa gca agc ctc ccc gga<br>Lys Gly Ala Ala Ser Arg Gln Asn Ser Glu Glu Ala Ser Leu Pro Gly<br>                    485                    490                    495 | 1488 |
| gag gac att gtg gat gac aag agc tgc ccc tgc gag ttt gtg acc gag<br>Glu Asp Ile Val Asp Asp Lys Ser Cys Pro Cys Glu Phe Val Thr Glu<br>             500                    505                    510 | 1536 |
| gac ctg acc ccg ggc ctc aaa gtc agc atc aga gcc gtg tgt gtc atg<br>Asp Leu Thr Pro Gly Leu Lys Val Ser Ile Arg Ala Val Cys Val Met<br>515                     520                    525 | 1584 |
| cgg ttc ctg gtg tcc aag cgg aag ttc aag gag agc ctg cgg ccc tac<br>Arg Phe Leu Val Ser Lys Arg Lys Phe Lys Glu Ser Leu Arg Pro Tyr<br>530                     535                    540 | 1632 |
| gac gtg atg gac gtc atc gag cag tac tca gcc ggc cac ctg gac atg<br>Asp Val Met Asp Val Ile Glu Gln Tyr Ser Ala Gly His Leu Asp Met<br>545                     550                    555                    560 | 1680 |
| ctg tcc cga att aag agc ctg cag tcc agg caa gag ccc cgc ctg cct<br>Leu Ser Arg Ile Lys Ser Leu Gln Ser Arg Gln Glu Pro Arg Leu Pro<br>                    565                    570                    575 | 1728 |
| gtc cag cag ggg aca aga acg ggg tgg gct tct ggg aca aag ccc act<br>Val Gln Gln Gly Thr Arg Thr Gly Trp Ala Ser Gly Thr Lys Pro Thr<br>             580                    585                    590 | 1776 |
| gtg gcc cat ggt ggg agt gca ggg ggt gtg tgg gcg ggg cct cct ccc<br>Val Ala His Gly Gly Ser Ala Gly Gly Val Trp Ala Gly Pro Pro Pro<br>595                     600                    605 | 1824 |

```
cac cca cgt cgg cct ctg tca gct tct gtt gtg tct tca caa agt ctg    1872
His Pro Arg Arg Pro Leu Ser Ala Ser Val Val Ser Ser Gln Ser Leu
    610             615                 620 ttt taa                                                            1878
Phe
625

<210> SEQ ID NO 4
<211> LENGTH: 625
<212> TYPE: PRT
<213> ORGANISM: Homo sapiens

<400> SEQUENCE: 4

Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
            20                  25                  30

Asp Ser Thr Arg Asp Gly Ala Leu Leu Ile Ala Gly Ser Glu Ala Pro
        35                  40                  45

Lys Arg Gly Ser Ile Leu Ser Lys Pro Arg Ala Gly Ala Gly Ala
    50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Val Phe Gly Val Glu Tyr Phe Val Arg
    130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
    290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335
```

Ala Gly Leu Ile Gln Ser Ala Trp Arg Phe Tyr Ala Thr Asn Leu Ser
        340                 345                 350

Arg Thr Asp Leu His Ser Thr Trp Gln Tyr Tyr Glu Arg Thr Val Thr
            355                 360                 365

Val Pro Met Tyr Ser Ser Gln Thr Gln Thr Tyr Gly Ala Ser Arg Leu
        370                 375                 380

Ile Pro Pro Leu Asn Gln Leu Glu Leu Leu Arg Asn Leu Lys Ser Lys
385                 390                 395                 400

Ser Gly Leu Ala Phe Arg Lys Asp Pro Pro Glu Pro Ser Pro Ser
            405                 410                 415

Gln Lys Val Ser Leu Lys Asp Arg Val Phe Ser Pro Arg Gly Val
            420                 425                 430

Ala Ala Lys Gly Lys Gly Ser Pro Gln Ala Gln Thr Val Arg Arg Ser
            435                 440                 445

Pro Ser Ala Asp Gln Ser Leu Glu Asp Ser Pro Ser Lys Val Pro Lys
        450                 455                 460

Ser Trp Ser Phe Gly Asp Arg Ser Arg Ala Arg Gln Ala Phe Arg Ile
465                 470                 475                 480

Lys Gly Ala Ala Ser Arg Gln Asn Ser Glu Glu Ala Ser Leu Pro Gly
                485                 490                 495

Glu Asp Ile Val Asp Asp Lys Ser Cys Pro Cys Glu Phe Val Thr Glu
        500                 505                 510

Asp Leu Thr Pro Gly Leu Lys Val Ser Ile Arg Ala Val Cys Val Met
            515                 520                 525

Arg Phe Leu Val Ser Lys Arg Lys Phe Lys Glu Ser Leu Arg Pro Tyr
        530                 535                 540

Asp Val Met Asp Val Ile Glu Gln Tyr Ser Ala Gly His Leu Asp Met
545                 550                 555                 560

Leu Ser Arg Ile Lys Ser Leu Gln Ser Arg Gln Glu Pro Arg Leu Pro
                565                 570                 575

Val Gln Gln Gly Thr Arg Thr Gly Trp Ala Ser Gly Thr Lys Pro Thr
        580                 585                 590

Val Ala His Gly Gly Ser Ala Gly Gly Val Trp Ala Gly Pro Pro Pro
            595                 600                 605

His Pro Arg Arg Pro Leu Ser Ala Ser Val Val Ser Ser Gln Ser Leu
        610                 615                 620

Phe
625

<210> SEQ ID NO 5
<211> LENGTH: 1848
<212> TYPE: DNA
<213> ORGANISM: Homo sapiens
<220> FEATURE:
<221> NAME/KEY: CDS
<222> LOCATION: (1)..(1848)

<400> SEQUENCE: 5 atg gtg cag aag tcg cgc aac ggc ggc gta tac ccc ggc ccg agc ggg    48
Met Val Gln Lys Ser Arg Asn Gly Gly Val Tyr Pro Gly Pro Ser Gly
1               5                   10                  15 gag aag aag ctg aag gtg ggc ttc gtg ggg ctg gac ccc ggc gcg ccc    96
Glu Lys Lys Leu Lys Val Gly Phe Val Gly Leu Asp Pro Gly Ala Pro
            20                  25                  30 gac tcc acc cgg gac ggg gcg ctg ctc atc gcc ggc tcc gag gcc ccc    144
Asp Ser Thr Arg Asp Gly Ala Leu Leu Ile Ala Gly Ser Glu Ala Pro
        35                  40                  45

```
aag cgc ggc agc atc ctc agc aaa cct cgc gcg ggc gcg ggc gcc      192
Lys Arg Gly Ser Ile Leu Ser Lys Pro Arg Ala Gly Ala Gly Ala
 50              55                  60 ggg aag ccc ccc aag cgc aac gcc ttc tac cgc aag ctg cag aat ttc  240
Gly Lys Pro Pro Lys Arg Asn Ala Phe Tyr Arg Lys Leu Gln Asn Phe
 65              70                  75                  80 ctc tac aac gtg ctg gag cgg ccg cgc ggc tgg gcg ttc atc tac cac  288
Leu Tyr Asn Val Leu Glu Arg Pro Arg Gly Trp Ala Phe Ile Tyr His
                 85                  90                  95 gcc tac gtg ttc ctc ctg gtt ttc tcc tgc ctc gtg ctg tct gtg ttt  336
Ala Tyr Val Phe Leu Leu Val Phe Ser Cys Leu Val Leu Ser Val Phe
            100                 105                 110 tcc acc atc aag gag tat gag aag agc tcg gag ggg gcc ctc tac atc  384
Ser Thr Ile Lys Glu Tyr Glu Lys Ser Ser Glu Gly Ala Leu Tyr Ile
        115                 120                 125 ctg gaa atc gtg act atc gtg gtg ttt ggc gtg gag tac ttc gtg cgg  432
Leu Glu Ile Val Thr Ile Val Val Phe Gly Val Glu Tyr Phe Val Arg
130                 135                 140 atc tgg gcc gca ggc tgc tgc tgc cgg tac cgt ggc tgg agg ggg cgg  480
Ile Trp Ala Ala Gly Cys Cys Cys Arg Tyr Arg Gly Trp Arg Gly Arg
145                 150                 155                 160 ctc aag ttt gcc cgg aaa ccg ttc tgt gtg att gac atc atg gtg ctc  528
Leu Lys Phe Ala Arg Lys Pro Phe Cys Val Ile Asp Ile Met Val Leu
            165                 170                 175 atc gcc tcc att gcg gtg ctg gcc gcc ggc tcc cag ggc aac gtc ttt  576
Ile Ala Ser Ile Ala Val Leu Ala Ala Gly Ser Gln Gly Asn Val Phe
        180                 185                 190 gcc aca tct gcg ctc cgg agc ctg cgc ttc ctg cag att ctg cgg atg  624
Ala Thr Ser Ala Leu Arg Ser Leu Arg Phe Leu Gln Ile Leu Arg Met
    195                 200                 205 atc cgc atg gac cgg cgg gga ggc acc tgg aag ctg ctg ggc tct gtg  672
Ile Arg Met Asp Arg Arg Gly Gly Thr Trp Lys Leu Leu Gly Ser Val
210                 215                 220 gtc tat gcc cac agc aag gag ctg gtc act gcc tgg tac atc ggc ttc  720
Val Tyr Ala His Ser Lys Glu Leu Val Thr Ala Trp Tyr Ile Gly Phe
225                 230                 235                 240 ctt tgt ctc atc ctg gcc tcg ttc ctg gtg tac ttg gca gag aag ggg  768
Leu Cys Leu Ile Leu Ala Ser Phe Leu Val Tyr Leu Ala Glu Lys Gly
            245                 250                 255 gag aac gac cac ttt gac acc tac gcg gat gca ctc tgg tgg ggc ctg  816
Glu Asn Asp His Phe Asp Thr Tyr Ala Asp Ala Leu Trp Trp Gly Leu
        260                 265                 270 atc acg ctg acc acc att ggc tac ggg gac aag tac ccc cag acc tgg  864
Ile Thr Leu Thr Thr Ile Gly Tyr Gly Asp Lys Tyr Pro Gln Thr Trp
    275                 280                 285 aac ggc agg ctc ctt gcg gca acc ttc acc ctc atc ggt gtc tcc ttc  912
Asn Gly Arg Leu Leu Ala Ala Thr Phe Thr Leu Ile Gly Val Ser Phe
290                 295                 300 ttc gcg ctg cct gca ggc atc ttg ggg tct ggg ttt gcc ctg aag gtt  960
Phe Ala Leu Pro Ala Gly Ile Leu Gly Ser Gly Phe Ala Leu Lys Val
305                 310                 315                 320 cag gag cag cac agg cag aag cac ttt gag aag agg cgg aac ccg gca  1008
Gln Glu Gln His Arg Gln Lys His Phe Glu Lys Arg Arg Asn Pro Ala
            325                 330                 335 gca ggc ctg atc cag tcg gcc tgg aga ttc tac gcc acc aac ctc tcg  1056
Ala Gly Leu Ile Gln Ser Ala Trp Arg Phe Tyr Ala Thr Asn Leu Ser
        340                 345                 350 cgc aca gac ctg cac tcc acg tgg cag tac tac gag cga acg gtc acc  1104
Arg Thr Asp Leu His Ser Thr Trp Gln Tyr Tyr Glu Arg Thr Val Thr
    355                 360                 365
```

| | | |
|---|---|---|
| gtg ccc atg tac aga ctt atc ccc ccg ctg aac cag ctg gag ctg ctg<br>Val Pro Met Tyr Arg Leu Ile Pro Pro Leu Asn Gln Leu Glu Leu Leu<br>370                                    375                              380 | | 1152 |
| agg aac ctc aag agt aaa tct gga ctc gct ttc agg aag gac ccc ccg<br>Arg Asn Leu Lys Ser Lys Ser Gly Leu Ala Phe Arg Lys Asp Pro Pro<br>385                                390                          395                      400 | | 1200 |
| ccg gag ccg tct cca agc cag aag gtc agt ttg aaa gat cgt gtc ttc<br>Pro Glu Pro Ser Pro Ser Gln Lys Val Ser Leu Lys Asp Arg Val Phe<br>                          405                                410                          415 | | 1248 |
| tcc agc ccc cga ggc gtg gct gcc aag ggg aag ggg tcc ccg cag gcc<br>Ser Ser Pro Arg Gly Val Ala Ala Lys Gly Lys Gly Ser Pro Gln Ala<br>                    420                                425                          430 | | 1296 |
| cag act gtg agg cgg tca ccc agc gcc gac cag agc ctc gag gac agc<br>Gln Thr Val Arg Arg Ser Pro Ser Ala Asp Gln Ser Leu Glu Asp Ser<br>                435                                440                          445 | | 1344 |
| ccc agc aag gtg ccc aag agc tgg agc ttc ggg gac cgc agc cgg gca<br>Pro Ser Lys Val Pro Lys Ser Trp Ser Phe Gly Asp Arg Ser Arg Ala<br>450                                    455                          460 | | 1392 |
| cgc cag gct ttc cgc atc aag ggt gcc gcg tca cgg cag aac tca gaa<br>Arg Gln Ala Phe Arg Ile Lys Gly Ala Ala Ser Arg Gln Asn Ser Glu<br>465                                  470                          475                      480 | | 1440 |
| gaa gca agc ctc ccc gga gag gac att gtg gat gac aag agc tgc ccc<br>Glu Ala Ser Leu Pro Gly Glu Asp Ile Val Asp Asp Lys Ser Cys Pro<br>                    485                                490                          495 | | 1488 |
| tgc gag ttt gtg acc gag gac ctg acc ccg ggc ctc aaa gtc agc atc<br>Cys Glu Phe Val Thr Glu Asp Leu Thr Pro Gly Leu Lys Val Ser Ile<br>                          500                                505                          510 | | 1536 |
| aga gcc gtg tgt gtc atg cgg ttc ctg gtg tcc aag cgg aag ttc aag<br>Arg Ala Val Cys Val Met Arg Phe Leu Val Ser Lys Arg Lys Phe Lys<br>                515                                520                          525 | | 1584 |
| gag agc ctg cgg ccc tac gac gtg atg gac gtc atc gag cag tac tca<br>Glu Ser Leu Arg Pro Tyr Asp Val Met Asp Val Ile Glu Gln Tyr Ser<br>530                                  535                          540 | | 1632 |
| gcc ggc cac ctg gac atg ctg tcc cga att aag agc ctg cag tcc agg<br>Ala Gly His Leu Asp Met Leu Ser Arg Ile Lys Ser Leu Gln Ser Arg<br>545                                  550                          555                      560 | | 1680 |
| caa gag ccc cgc ctg cct gtc cag cag ggg aca aga acg ggg tgg gct<br>Gln Glu Pro Arg Leu Pro Val Gln Gln Gly Thr Arg Thr Gly Trp Ala<br>                    565                                570                          575 | | 1728 |
| tct ggg aca aag ccc act gtg gcc cat ggt ggg agt gca ggg ggt gtg<br>Ser Gly Thr Lys Pro Thr Val Ala His Gly Gly Ser Ala Gly Gly Val<br>                          580                                585                          590 | | 1776 |
| tgg gcg ggg cct cct ccc cac cca cgt cgg cct ctg tca gct tct gtt<br>Trp Ala Gly Pro Pro Pro His Pro Arg Arg Pro Leu Ser Ala Ser Val<br>                595                                600                          605 | | 1824 |
| gtg tct tca caa agt ctg ttt taa<br>Val Ser Ser Gln Ser Leu Phe<br>          610                    615 | | 1848 |

<210> SEQ ID NO 6
<211> LENGTH: 615
<212> TYPE: PRT
<213> ORGANISM: Homo sapiens

<400> SEQUENCE: 6

Met Val Gln Lys Ser Arg Asn Gly Gly Val Tyr Pro Gly Pro Ser Gly
1                  5                        10                      15

Glu Lys Lys Leu Lys Val Gly Phe Val Gly Leu Asp Pro Gly Ala Pro
                  20                        25                      30

-continued

```
Asp Ser Thr Arg Asp Gly Ala Leu Leu Ile Ala Gly Ser Glu Ala Pro
         35                  40                  45

Lys Arg Gly Ser Ile Leu Ser Lys Pro Arg Ala Gly Ala Gly Ala
 50                  55                  60

Gly Lys Pro Pro Lys Arg Asn Ala Phe Tyr Arg Lys Leu Gln Asn Phe
 65                  70                  75                  80

Leu Tyr Asn Val Leu Glu Arg Pro Arg Gly Trp Ala Phe Ile Tyr His
                 85                  90                  95

Ala Tyr Val Phe Leu Leu Val Phe Ser Cys Leu Val Leu Ser Val Phe
                100                 105                 110

Ser Thr Ile Lys Glu Tyr Glu Lys Ser Ser Glu Gly Ala Leu Tyr Ile
            115                 120                 125

Leu Glu Ile Val Thr Ile Val Val Phe Gly Val Glu Tyr Phe Val Arg
        130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
    290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
            340                 345                 350

Arg Thr Asp Leu His Ser Thr Trp Gln Tyr Tyr Glu Arg Thr Val Thr
        355                 360                 365

Val Pro Met Tyr Arg Leu Ile Pro Pro Leu Asn Gln Leu Glu Leu Leu
    370                 375                 380

Arg Asn Leu Lys Ser Lys Ser Gly Leu Ala Phe Arg Lys Asp Pro Pro
385                 390                 395                 400

Pro Glu Pro Ser Pro Ser Gln Lys Val Ser Leu Lys Asp Arg Val Phe
                405                 410                 415

Ser Ser Pro Arg Gly Val Ala Ala Lys Gly Lys Gly Ser Pro Gln Ala
            420                 425                 430

Gln Thr Val Arg Arg Ser Pro Ser Ala Asp Gln Ser Leu Glu Asp Ser
        435                 440                 445
```

```
Pro Ser Lys Val Pro Lys Ser Trp Ser Phe Gly Asp Arg Ser Arg Ala
    450                 455                 460

Arg Gln Ala Phe Arg Ile Lys Gly Ala Ala Ser Arg Gln Asn Ser Glu
465                 470                 475                 480

Glu Ala Ser Leu Pro Gly Glu Asp Ile Val Asp Asp Lys Ser Cys Pro
                485                 490                 495

Cys Glu Phe Val Thr Glu Asp Leu Thr Pro Gly Leu Lys Val Ser Ile
            500                 505                 510

Arg Ala Val Cys Val Met Arg Phe Leu Val Ser Lys Arg Lys Phe Lys
        515                 520                 525

Glu Ser Leu Arg Pro Tyr Asp Val Met Asp Val Ile Glu Gln Tyr Ser
    530                 535                 540

Ala Gly His Leu Asp Met Leu Ser Arg Ile Lys Ser Leu Gln Ser Arg
545                 550                 555                 560

Gln Glu Pro Arg Leu Pro Val Gln Gln Gly Thr Arg Thr Gly Trp Ala
                565                 570                 575

Ser Gly Thr Lys Pro Thr Val Ala His Gly Ser Ala Gly Gly Val
            580                 585                 590

Trp Ala Gly Pro Pro His Pro Arg Arg Pro Leu Ser Ala Ser Val
        595                 600                 605

Val Ser Ser Gln Ser Leu Phe
    610                 615

<210> SEQ ID NO 7
<211> LENGTH: 872
<212> TYPE: PRT
<213> ORGANISM: Homo sapiens

<400> SEQUENCE: 7

Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
                20                  25                  30

Asp Ser Thr Arg Asp Gly Ala Leu Leu Ile Ala Gly Ser Glu Ala Pro
            35                  40                  45

Lys Arg Gly Ser Ile Leu Ser Lys Pro Arg Ala Gly Ala Gly Ala
50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Val Phe Gly Val Glu Tyr Phe Val Arg
    130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205
```

-continued

```
Ile Arg Met Asp Arg Arg Gly Gly Thr Trp Lys Leu Leu Gly Ser Val
210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
            245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
            275                 280                 285

Asn Gly Arg Leu Leu Ala Ala Thr Phe Thr Leu Ile Gly Val Ser Phe
290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
                340                 345                 350

Arg Thr Asp Leu His Ser Thr Trp Gln Tyr Tyr Glu Arg Thr Val Thr
                355                 360                 365

Val Pro Met Tyr Ser Ser Gln Thr Gln Thr Tyr Gly Ala Ser Arg Leu
370                 375                 380

Ile Pro Pro Leu Asn Gln Leu Glu Leu Leu Arg Asn Leu Lys Ser Lys
385                 390                 395                 400

Ser Gly Leu Ala Phe Arg Lys Asp Pro Pro Glu Pro Ser Pro Ser
                405                 410                 415

Lys Gly Ser Pro Cys Arg Gly Pro Leu Cys Gly Cys Cys Pro Gly Arg
                420                 425                 430

Ser Ser Gln Lys Val Ser Leu Lys Asp Arg Val Phe Ser Ser Pro Arg
                435                 440                 445

Gly Val Ala Ala Lys Gly Lys Gly Ser Pro Gln Ala Gln Thr Val Arg
            450                 455                 460

Arg Ser Pro Ser Ala Asp Gln Ser Leu Glu Asp Ser Pro Ser Lys Val
465                 470                 475                 480

Pro Lys Ser Trp Ser Phe Gly Asp Arg Ser Arg Ala Arg Gln Ala Phe
                485                 490                 495

Arg Ile Lys Gly Ala Ala Ser Arg Gln Asn Ser Glu Glu Ala Ser Leu
                500                 505                 510

Pro Gly Glu Asp Ile Val Asp Asp Lys Ser Cys Pro Cys Glu Phe Val
            515                 520                 525

Thr Glu Asp Leu Thr Pro Gly Leu Lys Val Ser Ile Arg Ala Val Cys
530                 535                 540

Val Met Arg Phe Leu Val Ser Lys Arg Lys Phe Lys Glu Ser Leu Arg
545                 550                 555                 560

Pro Tyr Asp Val Met Asp Val Ile Glu Gln Tyr Ser Ala Gly His Leu
                565                 570                 575

Asp Met Leu Ser Arg Ile Lys Ser Leu Gln Ser Arg Val Asp Gln Ile
            580                 585                 590

Val Gly Arg Gly Pro Ala Ile Thr Asp Lys Asp Arg Thr Lys Gly Pro
            595                 600                 605

Ala Glu Ala Glu Leu Pro Glu Asp Pro Ser Met Met Gly Arg Leu Gly
610                 615                 620
```

```
Lys Val Glu Lys Gln Val Leu Ser Met Glu Lys Lys Leu Asp Phe Leu
625                 630                 635                 640

Val Asn Ile Tyr Met Gln Arg Met Gly Ile Pro Pro Thr Glu Thr Glu
            645                 650                 655

Ala Tyr Phe Gly Ala Lys Glu Pro Glu Pro Ala Pro Pro Tyr His Ser
        660                 665                 670

Pro Glu Asp Ser Arg Glu His Val Asp Arg His Gly Cys Ile Val Lys
    675                 680                 685

Ile Val Arg Ser Ser Ser Thr Gly Gln Lys Asn Phe Ser Ala Pro
690                 695                 700

Pro Ala Ala Pro Pro Val Gln Cys Pro Pro Ser Thr Ser Trp Gln Pro
705                 710                 715                 720

Gln Ser His Pro Arg Gln Gly His Gly Thr Ser Pro Val Gly Asp His
                725                 730                 735

Gly Ser Leu Val Arg Ile Pro Pro Pro Ala His Glu Arg Ser Leu
        740                 745                 750

Ser Ala Tyr Gly Gly Asn Arg Ala Ser Met Glu Phe Leu Arg Gln
        755                 760                 765

Glu Asp Thr Pro Gly Cys Arg Pro Pro Glu Gly Asn Leu Arg Asp Ser
770                 775                 780

Asp Thr Ser Ile Ser Ile Pro Ser Val Asp His Glu Glu Leu Glu Arg
785                 790                 795                 800

Ser Phe Ser Gly Phe Ser Ile Ser Gln Ser Lys Glu Asn Leu Asp Ala
                805                 810                 815

Leu Asn Ser Cys Tyr Ala Ala Val Ala Pro Cys Ala Lys Val Arg Pro
                820                 825                 830

Tyr Ile Ala Glu Gly Glu Ser Asp Thr Asp Ser Asp Leu Cys Thr Pro
            835                 840                 845

Cys Gly Pro Pro Pro Arg Ser Ala Thr Gly Glu Gly Pro Phe Gly Asp
        850                 855                 860

Val Gly Trp Ala Gly Pro Arg Lys
865                 870

<210> SEQ ID NO 8
<211> LENGTH: 27
<212> TYPE: DNA
<213> ORGANISM: Artificial
<220> FEATURE:
<223> OTHER INFORMATION: oligonucleotide

<400> SEQUENCE: 8
acctctgcgg attgcatcgg tgtgtgg                                        27

<210> SEQ ID NO 9
<211> LENGTH: 25
<212> TYPE: DNA
<213> ORGANISM: Artificial
<220> FEATURE:
<223> OTHER INFORMATION: oligonucleotide

<400> SEQUENCE: 9
ggatgacttg catgaggctg ggtgg                                          25

<210> SEQ ID NO 10
<211> LENGTH: 35
<212> TYPE: DNA
<213> ORGANISM: Artificial
<220> FEATURE:
<223> OTHER INFORMATION: oligonucleotide
```

```
<400> SEQUENCE: 10
agcgaattct caatgggcga ggacacggac acgcg                         35

<210> SEQ ID NO 11
<211> LENGTH: 34
<212> TYPE: DNA
<213> ORGANISM: Artificial
<220> FEATURE:
<223> OTHER INFORMATION: oligonucleotide

<400> SEQUENCE: 11
tccggatcct cctgtgtcca cacactgcca cctc                          34

<210> SEQ ID NO 12
<211> LENGTH: 35
<212> TYPE: DNA
<213> ORGANISM: Artificial
<220> FEATURE:
<223> OTHER INFORMATION: oligonucleotide

<400> SEQUENCE: 12
aatattaaaa cagactttgt gaagacacaa cagaa                         35

<210> SEQ ID NO 13
<211> LENGTH: 33
<212> TYPE: DNA
<213> ORGANISM: Artificial
<220> FEATURE:
<223> OTHER INFORMATION: oligonucleotide

<400> SEQUENCE: 13
atcagaattc acatggtgca gaagtcgcgc aac                           33

<210> SEQ ID NO 14
<211> LENGTH: 42
<212> TYPE: DNA
<213> ORGANISM: Artificial
<220> FEATURE:
<223> OTHER INFORMATION: oligonucleotide

<400> SEQUENCE: 14
tgacagatct taaaacagac tttgtgaaga cacaacagaa gc                 42

<210> SEQ ID NO 15
<211> LENGTH: 17
<212> TYPE: DNA
<213> ORGANISM: Artificial
<220> FEATURE:
<223> OTHER INFORMATION: oligonucleotide

<400> SEQUENCE: 15
gtgtggatgc tgccccg                                             17

<210> SEQ ID NO 16
<211> LENGTH: 18
<212> TYPE: DNA
<213> ORGANISM: Artificial
<220> FEATURE:
<223> OTHER INFORMATION: oligonucleotide

<400> SEQUENCE: 16
tcccgcctca aaacctcg                                            18
```

```
<210> SEQ ID NO 17
<211> LENGTH: 35
<212> TYPE: DNA
<213> ORGANISM: Artificial
<220> FEATURE:
<223> OTHER INFORMATION: oligonucleotide

<400> SEQUENCE: 17
actagaattc agccagaagg tcagtttgaa agatc                              35

<210> SEQ ID NO 18
<211> LENGTH: 27
<212> TYPE: DNA
<213> ORGANISM: Artificial
<220> FEATURE:
<223> OTHER INFORMATION: oligonucleotide

<400> SEQUENCE: 18
atcaggatcc gcgccgcctc acttcct                                       27

<210> SEQ ID NO 19
<211> LENGTH: 35
<212> TYPE: DNA
<213> ORGANISM: Artificial
<220> FEATURE:
<223> OTHER INFORMATION: oligonucleotide

<400> SEQUENCE: 19
actagaattc agccagaagg tcagtttgaa agatc                              35

<210> SEQ ID NO 20
<211> LENGTH: 36
<212> TYPE: DNA
<213> ORGANISM: Artificial
<220> FEATURE:
<223> OTHER INFORMATION: oligonucleotide

<400> SEQUENCE: 20
actaggatcc ctactggact gcaggctctt aattcg                             36

<210> SEQ ID NO 21
<211> LENGTH: 31
<212> TYPE: DNA
<213> ORGANISM: Artificial
<220> FEATURE:
<223> OTHER INFORMATION: oligonucleotide

<400> SEQUENCE: 21
aactagaatt cgtggaccag atcgtggggc g                                  31

<210> SEQ ID NO 22
<211> LENGTH: 27
<212> TYPE: DNA
<213> ORGANISM: Artificial
<220> FEATURE:
<223> OTHER INFORMATION: oligonucleotide

<400> SEQUENCE: 22
atcaggatcc gcgccgcctc acttcct                                       27

<210> SEQ ID NO 23
<211> LENGTH: 28
<212> TYPE: DNA
<213> ORGANISM: Artificial
<220> FEATURE:
<223> OTHER INFORMATION: oligonucleotide
```

<400> SEQUENCE: 23
aatcagaatt ccaagagccc cgcctgcc                                    28

<210> SEQ ID NO 24
<211> LENGTH: 22
<212> TYPE: DNA
<213> ORGANISM: Artificial
<220> FEATURE:
<223> OTHER INFORMATION: oligonucleotide

<400> SEQUENCE: 24
gcacgatgca cagttgaagt ga                                          22

<210> SEQ ID NO 25
<211> LENGTH: 29
<212> TYPE: DNA
<213> ORGANISM: Artificial
<220> FEATURE:
<223> OTHER INFORMATION: oligonucleotide

<400> SEQUENCE: 25
tactgaattc ttcctggtgt ccaagcgga                                   29

<210> SEQ ID NO 26
<211> LENGTH: 37
<212> TYPE: DNA
<213> ORGANISM: Artificial
<220> FEATURE:
<223> OTHER INFORMATION: oligonucleotide

<400> SEQUENCE: 26
acatggatcc tcacctggac tgcaggctct taattcg                          37

<210> SEQ ID NO 27
<211> LENGTH: 37
<212> TYPE: DNA
<213> ORGANISM: Artificial
<220> FEATURE:
<223> OTHER INFORMATION: oligonucleotide

<400> SEQUENCE: 27
acatgaattc cagaaggtca gtttgaaaga tcgtgtc                          37

<210> SEQ ID NO 28
<211> LENGTH: 31
<212> TYPE: DNA
<213> ORGANISM: Artificial
<220> FEATURE:
<223> OTHER INFORMATION: oligonucleotide

<400> SEQUENCE: 28
tgatggatcc tcaccgcatg acacacacgg c                                31

<210> SEQ ID NO 29
<211> LENGTH: 30
<212> TYPE: DNA
<213> ORGANISM: Artificial
<220> FEATURE:
<223> OTHER INFORMATION: oligonucleotide

<400> SEQUENCE: 29
cacggatcca gcagccagaa ggtcagtttg                                  30

```
<210> SEQ ID NO 30
<211> LENGTH: 31
<212> TYPE: DNA
<213> ORGANISM: Artificial
<220> FEATURE:
<223> OTHER INFORMATION: oligonucleotide

<400> SEQUENCE: 30
cacgaattct ggacggacca aactgcgtat a                              31

<210> SEQ ID NO 31
<211> LENGTH: 32
<212> TYPE: DNA
<213> ORGANISM: Artificial
<220> FEATURE:
<223> OTHER INFORMATION: oligonucleotide

<400> SEQUENCE: 31
agcggatcca tgggcgagga cacggacacg cg                             32

<210> SEQ ID NO 32
<211> LENGTH: 34
<212> TYPE: DNA
<213> ORGANISM: Artificial
<220> FEATURE:
<223> OTHER INFORMATION: oligonucleotide

<400> SEQUENCE: 32
tccgaattct cctgtgtcca cacactgcca cctc                           34

<210> SEQ ID NO 33
<211> LENGTH: 25
<212> TYPE: DNA
<213> ORGANISM: Artificial
<220> FEATURE:
<223> OTHER INFORMATION: oligonucleotide

<400> SEQUENCE: 33
gagcctcgag gacagcccca gcaag                                     25

<210> SEQ ID NO 34
<211> LENGTH: 35
<212> TYPE: DNA
<213> ORGANISM: Artificial
<220> FEATURE:
<223> OTHER INFORMATION: oligonucleotide

<400> SEQUENCE: 34
aagaattctg taaaaggtca ctgccaggag ccccc                          35

<210> SEQ ID NO 35
<211> LENGTH: 31
<212> TYPE: DNA
<213> ORGANISM: Artificial
<220> FEATURE:
<223> OTHER INFORMATION: oligonucleotide

<400> SEQUENCE: 35
cggaattccc atggtgcaga agtcgcgcaa c                              31

<210> SEQ ID NO 36
<211> LENGTH: 32
<212> TYPE: DNA
<213> ORGANISM: Artificial
<220> FEATURE:
<223> OTHER INFORMATION: oligonucleotide
```

<400> SEQUENCE: 36
ccagatcttg taaaaggtca ctgccaggag cc                                              32

<210> SEQ ID NO 37
<211> LENGTH: 151830
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n = a or c or g or t
<220> FEATURE:
<221> NAME/KEY: misc_feature
<222> LOCATION: (60402)..(60402)
<223> OTHER INFORMATION: n = a or c or g or t
<220> FEATURE:
<221> NAME/KEY: misc_feature
<222> LOCATION: (61110)..(61110)
<223> OTHER INFORMATION: n = a or c or g or t
<220> FEATURE:
<221> NAME/KEY: misc_feature
<222> LOCATION: (98207)..(98207)
<223> OTHER INFORMATION: n = a or c or g or t
<220> FEATURE:
<221> NAME/KEY: misc_feature
<222> LOCATION: (98208)..(98208)
<223> OTHER INFORMATION: n = a or c or g or t
<220> FEATURE:
<221> NAME/KEY: misc_feature
<222> LOCATION: (98209)..(98209)
<223> OTHER INFORMATION: n = a or c or g or t
<220> FEATURE:
<221> NAME/KEY: misc_feature
<222> LOCATION: (98210)..(98210)
<223> OTHER INFORMATION: n = a or c or g or t
<220> FEATURE:
<221> NAME/KEY: misc_feature
<222> LOCATION: (98211)..(98211)
<223> OTHER INFORMATION: n = a or c or g or t
<220> FEATURE:
<221> NAME/KEY: misc_feature
<222> LOCATION: (99743)..(99743)
<223> OTHER INFORMATION: n = a or c or g or t
<220> FEATURE:
<221> NAME/KEY: misc_feature
<222> LOCATION: (108055)..(108055)
<223> OTHER INFORMATION: n = a or c or g or t
<220> FEATURE:
<221> NAME/KEY: misc_feature
<222> LOCATION: (109094)..(109094)
<223> OTHER INFORMATION: n = a or c or g or t
<220> FEATURE:
<221> NAME/KEY: misc_feature
<222> LOCATION: (109125)..(109125)
<223> OTHER INFORMATION: n = a or c or g or t
<220> FEATURE:
<221> NAME/KEY: misc_feature
<222> LOCATION: (118900)..(118900)
<223> OTHER INFORMATION: n = a or c or g or t
<220> FEATURE:
<221> NAME/KEY: misc_feature
<222> LOCATION: (119024)..(119052)
<223> OTHER INFORMATION: n = a or c or g or t
<220> FEATURE:
<221> NAME/KEY: misc_feature
<222> LOCATION: (119053)..(119112)
<223> OTHER INFORMATION: n = a or c or g or t
<220> FEATURE:
<221> NAME/KEY: misc_feature
<222> LOCATION: (119115)..(119121)
<223> OTHER INFORMATION: n = a or c or g or t
<220> FEATURE:
<221> NAME/KEY: misc_feature
<222> LOCATION: (119123)..(119123)
<223> OTHER INFORMATION: n = a or c or g or t

```
<220> FEATURE:
<221> NAME/KEY: misc_feature
<222> LOCATION: (141674)..(141674)
<223> OTHER INFORMATION: n = a or c or g or t
<220> FEATURE:
<221> NAME/KEY: misc_feature
<222> LOCATION: (142063)..(142063)
<223> OTHER INFORMATION: n = a or c or g or t
<220> FEATURE:
<221> NAME/KEY: misc_feature
<222> LOCATION: (142137)..(142137)
<223> OTHER INFORMATION: n = a or c or g or t
<220> FEATURE:
<221> NAME/KEY: misc_feature
<222> LOCATION: (142967)..(142967)
<223> OTHER INFORMATION: n = a or c or g or t
<220> FEATURE:
<221> NAME/KEY: misc_feature
<222> LOCATION: (143077)..(143077)
<223> OTHER INFORMATION: n = a or c or g or t
<220> FEATURE:
<221> NAME/KEY: misc_feature
<222> LOCATION: (143506)..(143506)
<223> OTHER INFORMATION: n = a or c or g or t
<220> FEATURE:
<221> NAME/KEY: misc_feature
<222> LOCATION: (143587)..(143587)
<223> OTHER INFORMATION: n = a or c or g or t
<220> FEATURE:
<221> NAME/KEY: misc_feature
<222> LOCATION: (143629)..(143629)
<223> OTHER INFORMATION: n = a or c or g or t
<220> FEATURE:
<221> NAME/KEY: misc_feature
<222> LOCATION: (149079)..(149079)
<223> OTHER INFORMATION: n = a or c or g or t
<220> FEATURE:
<221> NAME/KEY: misc_feature
<222> LOCATION: (5363)..(5363)
<223> OTHER INFORMATION: n = a or c or g or t
<220> FEATURE:
<221> NAME/KEY: misc_feature
<222> LOCATION: (8080)..(8080)
<223> OTHER INFORMATION: n = a or c or g or t
<220> FEATURE:
<221> NAME/KEY: misc_feature
<222> LOCATION: (10296)..(10296)
<223> OTHER INFORMATION: n = a or c or g or t
<220> FEATURE:
<221> NAME/KEY: misc_feature
<222> LOCATION: (14528)..(14528)
<223> OTHER INFORMATION: n = a or c or g or t
<220> FEATURE:
<221> NAME/KEY: misc_feature
<222> LOCATION: (15336)..(15336)
<223> OTHER INFORMATION: n = a or c or g or t
<220> FEATURE:
<221> NAME/KEY: misc_feature
<222> LOCATION: (15457)..(15457)
<223> OTHER INFORMATION: n = a or c or g or t
<220> FEATURE:
<221> NAME/KEY: misc_feature
<222> LOCATION: (16288)..(16288)
<223> OTHER INFORMATION: n = a or c or g or t
<220> FEATURE:
<221> NAME/KEY: misc_feature
<222> LOCATION: (16306)..(16307)
<223> OTHER INFORMATION: n = a or c or g or t
<220> FEATURE:
<221> NAME/KEY: misc_feature
<222> LOCATION: (16316)..(16316)
<223> OTHER INFORMATION: n = a or c or g or t
<220> FEATURE:
<221> NAME/KEY: misc_feature
<222> LOCATION: (16397)..(16397)
<223> OTHER INFORMATION: n = a or c or g or t
```

```
<220> FEATURE:
<221> NAME/KEY: misc_feature
<222> LOCATION: (56012)..(56012)
<223> OTHER INFORMATION: n = a or c or g or t
<220> FEATURE:
<221> NAME/KEY: misc_feature
<222> LOCATION: (57662)..(57662)
<223> OTHER INFORMATION: n = a or c or g or t
<220> FEATURE:
<221> NAME/KEY: 5'UTR
<222> LOCATION: (1)..(54)
<223> OTHER INFORMATION: exon 1
<220> FEATURE:
<221> NAME/KEY: exon
<222> LOCATION: (55)..(124)
<223> OTHER INFORMATION: exon 1
<220> FEATURE:
<221> NAME/KEY: exon
<222> LOCATION: (91147)..(91244)
<223> OTHER INFORMATION: exon 2
<220> FEATURE:
<221> NAME/KEY: exon
<222> LOCATION: (93669)..(93834)
<223> OTHER INFORMATION: exon 3
<220> FEATURE:
<221> NAME/KEY: exon
<222> LOCATION: (96310)..(96422)
<223> OTHER INFORMATION: exon 4
<220> FEATURE:
<221> NAME/KEY: exon
<222> LOCATION: (99546)..(99723)
<223> OTHER INFORMATION: exon 5
<220> FEATURE:
<221> NAME/KEY: exon
<222> LOCATION: (125441)..(125605)
<223> OTHER INFORMATION: exon 6
<220> FEATURE:
<221> NAME/KEY: exon
<222> LOCATION: (141176)..(141345)
<223> OTHER INFORMATION: exon 7
<220> FEATURE:
<221> NAME/KEY: exon
<222> LOCATION: (145556)..(145647)
<223> OTHER INFORMATION: exon 8
<220> FEATURE:
<221> NAME/KEY: exon
<222> LOCATION: (151316)..(151608)
<223> OTHER INFORMATION: exon 9
<220> FEATURE:
<221> NAME/KEY: 3'UTR
<222> LOCATION: (151609)..(151829)
<223> OTHER INFORMATION: exon 9
<220> FEATURE:
<221> NAME/KEY: allele
<222> LOCATION: (84026)..(84026)
<223> OTHER INFORMATION: complement of biallelic marker 99-24169/139
<220> FEATURE:
<221> NAME/KEY: allele
<222> LOCATION: (109663)..(109663)
<223> OTHER INFORMATION: complement of biallelic marker 24-257/320
<220> FEATURE:
<221> NAME/KEY: allele
<222> LOCATION: (117460)..(117460)
<223> OTHER INFORMATION: complement of biallelic marker 99-24175/218
<220> FEATURE:
<221> NAME/KEY: allele
<222> LOCATION: (99505)..(99505)
<223> OTHER INFORMATION: biallelic marker 24-247/216

<400> SEQUENCE: 37
attgcatcgn tgtgtggcgg cggggcatgc ccagagcacc gggcacggcc ttca atg      57
                                                             Met
                                                             1 ggc gag gac acg gac acg cgg aaa att aac cac agc ttc ctg cgg gac     105
Gly Glu Asp Thr Asp Thr Arg Lys Ile Asn His Ser Phe Leu Arg Asp
        5                  10                  15
```

-continued

| | |
|---|---|
| cac agc tat gtg act gaa g gtaacgtacg tgttgtctga gacccctccg<br>His Ser Tyr Val Thr Glu<br>           20 | 154 |
| gccggccgcg gcgtggggat gccgtcgcac cgaatgccct ccgaaggttt ggaccgcgcg | 214 |
| atgtgtgtcg tgtccccccg ccccacccca ccccacccca tcccacccca ccccacccca | 274 |
| tcccatccca ccctgcccgg ggcccaggag ggagggagcc cgagggtacc ggcctccgct | 334 |
| gcccagcgcc ggcacagggc agcgcctcc tccgcgccgc cctccgggag gcagctttcc | 394 |
| tctcccaagc caggtggcat cctgattcgg ccctgaccat aatttttaa aaggccacgg | 454 |
| ctgtggctaa tctggtgaag aaatctcggg gaaatttaat ggtttaaatc ctggatttgc | 514 |
| catttcagcc ctgcccaaag cccgcagaat tttctaggct gccctctccc tggagaagaa | 574 |
| gagggacccg ggggaaaaa aacataatcc attgccagat cctcctggga ggcccgcctg | 634 |
| cccgggcccc tccctgtcct ccagaggcag ggtccctgag tgggagggag aaggcggctg | 694 |
| gtttggggct ggccttttta ttcctggtga gttatattga gacaggagca gctgggctaa | 754 |
| ctgtcgggat tttccaaaaa agtgggacat gccatcccaa acaggccctg tttaaaatcc | 814 |
| cctaagttgg ccctacaagc caaccccca ccccaccct accccgagg ctggtgggtc | 874 |
| agcgcccctc tcttacaggc ctggaacttc cggggggcccc ctggtctgcc tcgctagggg | 934 |
| aacagtggga acagcttccg tgcgcaggca gggcccgcgg agtgacccccg atggaggatg | 994 |
| gggaccggga ggtctgggct cggggccgcc tgtgctggag ccctgcccga gtgcggggac | 1054 |
| tgtcagccgc taacccacgg gctggcgccc ggccgcaga agtgtgcgcg gattccccgg | 1114 |
| gtgggtgccc cagtgggagg ggccctgggc acgggtcccg cggggcaggt gcgcgtgggt | 1174 |
| gcctgtgtca gggagaccga gtgggccagg cggcggagac cgggctcctg cggctgggtc | 1234 |
| cgcctcctcg aagcctggct ctgccggaaa tgaggccgag cggagccgga gccccgcgga | 1294 |
| ggcccgggga gcgcagcgcg agcgcgggcg cgggcgggct cggggcgccc tggcccggga | 1354 |
| ggcagaggct gggcgtggga cctgggcgga gggaggctgc ggggccgcg cccgctcccg | 1414 |
| gcgggagaac cgctgagtca cgcacgcttc gccgccgggt gtgtgcgaga gaggggcagg | 1474 |
| gctgccgggg cctccgggcc ggtggggctc tgacccggcc gcggctttgg gaggcccggg | 1534 |
| gagctgagag cggtccttg tcgcctgctt cggcgaggct gagtcgggat cagcgtgggt | 1594 |
| ccgggatgtg gtttctgctc gcagcctgca gcgacagagg gttggaggaa gccgccgggt | 1654 |
| tgctggcccg tgcctcggtg gcctggctcg ggccgagagc ggatcttggc aggttgcccc | 1714 |
| gctgctccca ggctcgctgt ggtctggctt cctggagcaa gcctctgttt gctcatctct | 1774 |
| acgttgggga tgacggtggg atggggcgca gggctcgttg tgggaccagg cgtaaaaagc | 1834 |
| gccatggtgg acattttcaa acattaattc cctctgcacc ctgcccgtcc cctttctctt | 1894 |
| cataaattca ccagccctca gcagggcaca ggaacgggga cggcacagtt ctggaggtca | 1954 |
| gagcagtgct atccaatcct tcatccagac acgagatatt taccgagcac ctgctgcatg | 2014 |
| ccgggcactg ttttatccct ggggactgga caaagactcc ctgcccttgt gcggcctgaa | 2074 |
| ttctatcagg gagctatatg accttgaggt ctgtcttctc accagggctc agtctcccca | 2134 |
| tctgtaaaat gggagtgaat cctgcctaca gggtctggag gtttctgtga ggagcaggtg | 2194 |
| caacggtgtt gaaggagccg ttcagagcta tgcattgcta acgtgcagcc aaaggatgct | 2254 |
| gagcacctgc tgtgtgctgg gacctcatac gaaggctcac ctacgcctta tccccacctt | 2314 |
| gagatgaaca aaccaaggcc tggccttgtg cctggtccag accgagtgcc agtgtgtgca | 2374 |
| gggcataggg ctcaggtgct gcggatgcag agagcaggat cggaacaaga aacaataata | 2434 |

```
atcattataa taggtagaat tctggcctcc ctaatgaaaa acacactttc acactgttgc    2494
atcctgacta tatttcatgc tcagagcaca gggaaggtca cagatttgaa tgtcagaatg    2554
tcagacttga atcatgttaa agtcctgcct ctgactcctg actgctgtgc agccttggac    2614
aagttactac accttcctga gcttcacttt ccctttgtaa agggagaaat aataacgacc    2674
tttcatacag ggttgctggg atgatcagtg attttgctaa tatcaaaagt gcccagcaca    2734
gtgcttgggt tgttggaggc attgaacaca cggcattgtt attatttata tgccttgtaa    2794
ctggaagagc ctgtgggcaa acagtggatg ctaaaattca gtttgtggaa gaaccaggtg    2854
cacaaactcc tgttctacct gtggttgagt ctacactccc ccaccacacc ccagctgctc    2914
tgatctacct cctgttcctt gagcaggcca ttttctttct tgcttcaggg catttgcaat    2974
ggctgttccc tggaataccc acctcctgcc tttctcacca ctgactcttt ctcatccttt    3034 gggcccatg tccaatgtca tctttgcccg tgggagccct gcttgggttc ctgagtctct    3094
tgtaaaatct caaacatctt aggaagagtt taggttttgt tagtcattca catcttggtg    3154
tgaattcgtc agagcaggtt ggattttttt tttttttttt tttttttttg gtggcagggc    3214
tgggtggctt actcttggct gggctcaact gcattgaggg ttatggtgat gattaggtgt    3274
acctgcaggc cacctggggg cacagagaac tttgcatgaa tggggtcagg gtgtggggag    3334
agcagtgtag ctgatagggc actgggccct ggaccctgga ccctgagggg tgctaggaag    3394
tctccatcta gttagacatt tctcaagagc tggatatggt tccaggaagg actcttcctg    3454
gctctgttct ttctcttttt gcggcaggcc tcagtactta gctttagagt gagttgaata    3514
agcacttcca gactagactg aacttacaaa acccatccat ccttcctttg cttagcacca    3574
tttgccaagc acatcctgcc ctgggcagca gtgatgacca agacacagga gctcagccaa    3634
ggggaggtag ttcaggctga ccaggtagat cctggcagtg actgggtctt tctggggagc    3694
aacagtcact ctcatgtgcc tgacaggtaa ggcacttccg gagcacactt ttcagctgag    3754
gccagaggca cagcttcccc ttgtttgagc atctcagcca tcacacactg ttggacactc    3814 atgcttttg catctgcata aaggatgtac ccatgttttc ctaactccca tccctggatg    3874
tcctgtgtga tttcagagta gtctgtttat tcccacagag ttgtcctgat tttatagttg    3934
aggaagtgaa gggtgcttgg gaattgctaa ggtcatcatg gggtcctgag gctgtctgaa    3994
cgcagcaggc aggcaggttt tcctgcatgg aattgtctgc aggttttgaa ctggttgtgc    4054
cctggatacc atctactttc tgcccaggaa accacactga agaggggatg ctgcttgtgg    4114
gagactcagc attcagtgaa atctgcaccc ttatggtgga cgttgcagct gatctccaca    4174
acagttagtc tctcttcttc caaggagaac acatatggtt cctagtaaga gatctcaggc    4234
catagctgga tgtgatcagt gcaaggatga tctcattccc cttgcagtga ctggttccag    4294
aatggatgtg ggagtcagtt ctggaggttg agtggaaagt agggagaacc acaggtagtt    4354
ggtccctctc ttgtgatggg aacagggaaa ccttgtggtg gctggcagcc atctgacacc    4414
atgaggggag caagtcttag gccaccaccg ttgatggcag gcagagagt gagtgagatc    4474 caggacatag aggcctgatg tccaggccgc ctctgaactt ccagttacat gagctgttac    4534
ttttcctttt cgttgtgcac tttcaagtct ccgttacttg cagcccatag caccccaact    4594
cgtacagccc tgactgctta tcaagaaaac caggaggctg atctgtaacc cacagctaag    4654
actcgagata cataaaaccc agagggattt tgtttgctt tctgttttga gaaccctctt    4714
tcatttcact caagtcaagg ttgccaattt ctggttttcc ctcctcagtc ctattgagga    4774
ggtatttttg gtcagataag agagcctgag atctggcatc gggagatctg ggttcctggt    4834
```

```
ggggtctgac cctgggtctg taatattggg caggtcacac ggtctctctg agcctcagtt   4894
tattcttaat agatcagtaa gtgatgatgt ctattcttta ggggccagag ttagactagc   4954
ccttagaact gtcatcagac tggctagcct aacttccacc ccaacctatg gggaaactga   5014
ggctaagagg ggggacatta gtggtggcac agagggagat tagggagagt cagcctttga   5074
cttttgaaaa tcaagatgtg gactgttcag attctgtgtt cctttcgctt ctgtttggaa   5134
acgccactta cataagcttc ccttgggctt cacagcgagt gtgggctcca tttcagtgct   5194
ggggtgccct ccatcaaatc acatcacttt ctgagcctca gtttccctgc actgcctggt   5254
gccctgggtt gtcatgaggc tgtaaggagc caagggcatg tggactctga agttctacac   5314
gtgtaaaagg cgactgctgt caatttcccc aaattgtagt gtaggccanc tcccacgccc   5374
ctgctgtaag caatgtgctc ctttcttttt aatcaacccg aacttaaagc ttggcgcagt   5434
cacagagcac ggttttttgtc attttctttc tggaagatga aaatcaaatt ctaataaaat   5494
ttttccactc catctcctga ctgttgtcat ttgctacact ttttagtgtt tatccttaaa   5554
gcttgcagag ctaagggatg tttggtaaga agtgtttagg ccttgagact ggaagagccg   5614
ctgtatgaag cgctaggctc catggagagt gtgatgggga gtaagagaag gagagtgaac   5674
tcctgtgagt ccaccaagca gagggacata ctctcagcaa ctggggtatt tccttccagt   5734
cttttttaa tgcccatgtc tgttttaat gaaaactgta atctgtctgt atcaacaatt   5794
ttgaaggcta cttttctagt ttggcatgag attataggaa ttttccaggg ctttgctcca   5854
gggctggctt catggatatg caacctgtgt ggtcatctag gtccccacac tcagaaggac   5914
ctgtgcttgg gttcatgttc tgctgttact atcttgaaat tttaagaat ttcactttgg    5974
atcctgtgtt ttgtaagcga aatctgatgg gacgggggag cctgggaatg agcagagggg   6034
tacgtgcggc aggcgagtct gtggttacac acattggctc ccacagcacg ctaccctgtg   6094
ttcacttgag cgtctgagcc ccacgcacag tggacagctc atgcaccttc tcagtgcgtc   6154
tgtagtttca caggcagggg ccatgctttc aactgatgct ccaaggcatt gatgttctca   6214
tgcagtgact tctaagaaac atgaatgacg caggaaccct atggtgtcct ttcttaacgt   6274
gtgttacgtg cccatatttg ccaatcgctg acactgaaaa tgattacaca aagggaagg   6334
gaaaaagagg gcacctatag ttccttttcc tcctagtcct tccttgttta ttattgaacc   6394
aagggtagag ggtgttggaa gaatgtacac atatccagaa atgaaataag aacagttaag   6454
ttagtttcct ctgctctggt aagaacaaaa tccatatgcg aaatataact tgtgcatttt   6514
ggtgagtcta cattccagtt acgtgctctt atgtttgcat ttaaaattgg aggtgcacac   6574
tagaatggtg agtgataaaa tgcacgctga gagtttaagc ttttttttttt ttaaatttga   6634
attgacatta aatagcaaat aacaccatga caaaatatgg aaggcatgaa aaggctttgt   6694
atcttagcac ctttaatgat gcttttcctt tgcttttttga ataagaggct ctgcattttc   6754
atttttccct gtgccccacg aattataggg ttggccctgc tttgctggaa ctctgggtag   6814
ggtgaactcc ttggccctgc cttctacctc cttggctttc gtgattggtg gaaatggtga   6874
gagcctgcca tccattgggc agctcttccc tatgggagg ggttacaata ttaaatgtcc     6934
gtgctcctct ctcacccatt gggtccatgg gcctctgact tccaggttgc tctacagggg   6994
agaggccaac agttatctta ttttacaagc tagaagttag acctacctct ccccgcagga   7054
ccaaggggtg gggaggtgaa gtaggggtcc atagctcttt ttttttcctac aggtttacca   7114
ttaataaagc agattttttt attcctgtct tgcggccagt cttttctgtg taatcccaag   7174
tcccagcaag gaagaggggt gactggttac cttggccccg cccccaagtc acacagtaca   7234
```

```
cgtattgaca accatcattt cattggctgc atactattcc tgtgatacat gtgtcatcat    7294
tcagtagttc aattaatcat ttccttatgg ctggatattt agttccctcc cttccctccc    7354
tccctcccct cctcccttcc ttccttctct ctctctctgt ctctccccca cacactttct    7414
tattttcata actaacactg caggaatgaa caccatttgt gtgtgtgaag accccctact    7474
cccatcgttc cccctaaccc ttggaatgat gctcttcaga aggaattcca cacgtgctat    7534
ttcatataaa gatcactagc attttaatg ttgttgacac acattggcag attattctcc    7594
agaaagtttt tctctttaac cacatgctga tcaacattag gtagtctaat ttgtttgacc    7654
tttgcaaata tcaaagatga aaaatatttg ttgtaattca cgtctgcata ccaatgaggt    7714
tgaacatttt ttccttttgt tcagcgggta ttggctgatc cctgttatgt gccagggtga    7774
cattagattc tagacataca aagttgaaga gcaaggctgt gtctgccttg aaatgtggac    7834
tctcctctcc cagtgtcttg ggtgccactg cgggacctag ctacttctca ggagagagtc    7894
tgaagctgct ggaggagtct gtacatccct cagcaccctg gggagtcctg ttagttacac    7954
agggccttgc aaagacaggc atctcaccat taagcccttg agcagaatga tccaagtgga    8014
ctttaggatg aaataattac aaaacaaaca caatagccat tattatgatt caccatttat    8074
tggctntgta ctataatact atatgctgga catgaggctg cgtgcatctc attggtgatg    8134
ccccagacct gatgttgtgt atattatttc cccattttac agaggagaaa actgaggctg    8194
aggtgcttgt tcaatgtcac atggtttgta agggacagag ctgagttttg aatgcagcct    8254
gccaaaccca cgctcctgac tgctacatta attggctggg acccacaggg cagggttagg    8314
tggcctgttc agttctgatt atgcaccaca cttaggaggt tttgggattt gaactagact    8374
acctggcttg gtgctcttgc tatctgtgtt gcgatgaaag gcaatcgaga ggggtcagca    8434
ggaggagaga cccccttcac ggcacaggta gatggcagtg gcagaggcca caagtggaca    8494
cgtggtccag ggactgaagg gcaggtggca tttccaggtt gggggggtgat gatgtgctgg    8554 gacatggtat tctagcgcat tctgggcagg aggaacggtg tgtgcaaagt ggcataacac    8614
ttgtcccctg acagtgtccg gctcctctgc ttgagaccag gaggcagtta gttagttgcc    8674
agccggcccg ggagcaggac acacctgggg gcccctgtgc tgcccaggac aggcactgcc    8734
ctccttgcac agtgggggcc attgtcctcc agaacccagg gctgaatgtc ccattgaggc    8794
agaacaaagg ctgctcagag gttcccagct ggggtgtggg ctgccccaag cagggatggg    8854
atctccaact gcaggccaag ggcctcctcc aggctggcct ggcctcctgc agccccaccc    8914
ccacccctcc tcaggaccag gactgttgct gctggaggct ggacctgggc ttgggctccc    8974
aggcctgtgc tctgggtctg gcacagctgc cgtgcccttg gcagcttctt catccctgg    9034 gcaatttccc catctatgaa gcagagagag agcgagctcc caaccagcaa ggctttcagg    9094
cagaattgaa tgaaatagtg cacactctgt aggttaatct caataaaagg gagctctttc    9154
atgatcatga ttagcttctg aatgttttt tacaatttca aaaagtttt gatgcaaact     9214 ttcaaatttg tgccacttct gggccaaagt gtttaagaag ggagtgcacc ttccccctc     9274 cctctgtccc agagaaggga gagatgccgc tccctggagc ccctcatcac tctgtggaag    9334
ggactgctgg ccaactgtta caagaggaga aacttctttg catttgtgag aaaatagtct    9394
attgaactgc ttccaatcta tcaagatctt gctgtacttc cttcatttac tctcccctgc    9454
ttttggctga agaatttta ggcaaatcca agactcctgt cgtttccccg ttccatctgc    9514
aggcatctct gagtgttgag ggcatttctt gtagcccagt gctgttatcc cacctcacaa    9574
aacatatcct gattctttgt tacctaaatt ctggtccatt ttatgaacgt ccccagttgt    9634
```

```
ctgagaaatg tctcttatgg ttgggtggtt tggcccagga tccaaagtcc tgcacctgcg    9694
tttggctgtt ctgtctcttg tcttttctga cctagactca gcctccatcc ccttttcagg    9754
ctaccaactt gttgaagaca tttgttatta ttttattta ttttttttaa gacggagttt    9814
cactctgtcg cccaggctgg agtgcaatgg cgtgatcttg gctcactgaa accccgcct    9874 cccgggttca agtgattctc ctgcctcagc atcctgagca gctgggacta catacaggtg    9934
cccaccacca cgcccgacta ttttttgtat ttttagtaga cggggtttt caccatgttg    9994 gtcaggctgg tcttgaactc ctgacctcag ataatctgcc ttcattatta ttttagagat   10054
tacagtgtca ctcccactgt ccctaatttg tgcctggatt ccatttgccc tgtgggtctg   10114
gaaggctgag aggtggttgc tgggacctgg gcatcggcct tggggctgcc cctctctcct   10174
ccaggacccc tttctgcaga gtggtgccct cgccactccc tggctgagtg atcttgggca   10234
agttgtccag ccaggccgtg cctgggtgac acatctgag ctgggggtga gcgtggctgc    10294
ancatcctct ctgggatgtg gtgggtgttg aatgagatgg tgcatgccac gtgctccgtg   10354
ggcctggtgc ctgtgggtcc ctgtcttacc cccatgatgg ggatgtggca ggaactgggg   10414
tagccaccgc ctgcccacac agtgctcact ttctgtaggg gagacacccc tcagctggtc   10474
actacataca gcaggaccag cactttctga gggaagaggg atgttctctt gggaagtctg   10534
gatgctgaag acagtttgtt actctgatta ataccagtta caaagaaatc cccacattcc   10594
aggggttgat gtcatagaag tttatccctt tgtaacagtt cattgtggat gatcccagtt   10654
ggcccaggag tctcttccac agagtgatgc ggggctccag accttctca tctgtcagct    10714 cccatgtcct ctccattctc cggggaagag ggtatgggga aggtgcactc cctccttaaa   10774
cactttggcc cagacatggc acttgtgact tccctcacat tccattggcc agagctagtc   10834
acatggcccc acctaatgca agggggctcta ggaaatgtag tccctggctg ggcagcccag   10894
tggctactct gcagtgggaa gaacctgcat cttggtggat gtcttgccat ctttgccaca   10954
tgaccccaca aaacaaacct ttacattctc agtccaaaaa accctactaa gaatcctgtg   11014
ctggagacac cctcactcaa cccctgaccc tcccctctcc ctgcttcagt gtccacacgt   11074
gcacggtgct gtgagatgca gagtccagag tcatgcggtg gctaggaggt cagggacgcc   11134
ttcctgggag aggcgatgtc tgagctgagt ctgcaaagcc aaataggtgg tgcccaggtg   11194
gatcaggtag gagagggatt ccgggcttcg gctgcagcag gggtaaaggc tggtgtcttg   11254
ggagagggca tcctgtgtag agaggggtct gtgggccact gagatttaga ggatgtgtgt   11314
ggggtggggt ggagtgggag aggagctgga gcgggatggg aagtgggagg caggactgtt   11374
tgtgaaaggc ttcaaatgcc gagataagga gtttggattg tatcctattg acattgtgga   11434
accagatgga gatgggcat ttccctttgt ttgaaagtat tttgatttct attggctgtc    11494
ttactacaaa aaacatatgt agtcatagca aaagttcag aaatttaga aagagaaaag     11554 gaggaaaaga aaatcctacc actgaaaata ttttggtata tgtgttttg cctatgggta    11614 tacatactat ctaggtatat atatattcct acatttttt attcactgaa agatggtttt    11674
tgagcatcta ctgtgtgcgt atcctatttt gtaatcttta aaattttctc ttaatgatat   11734
gggagctttc tagcttagaa aataacacag cccatttttct tagcttgctg ggacttctat  11794
aacacagtgc cacataccgg gcagttgaaa caacagagac ttaccgcctc acagtgctag   11854
agcttgggag tccaagatca aggtgttggc agggttgatt ccttctgagg cccctctcct   11914
tggcttatag atgaacatct ccctactgtg tcttcacatg gtctttcctg tgtgtgtctg   11974
tgtccttaga gggacaccag gcatattgag ttagggctca tccatatgac tgcattttac   12034
```

```
cttcgtcacc ttgttaaagg tccttttgt caaacacagt cacatttga ggttctaggg    12094 gttaggactt caacaaagga atcttgggga gggggcacat ttcagcccaa agcacccgtc    12154
atcattggta atatcagtca catgcttctt ctatgtattt taaagagttc catgctggtg    12214
ggtatcagaa gttatggttg gtttaggatc atgagcagtg ttgtgagggc atctttgcac    12274 cttttgcgt gcatatttgg ttatttccct agggtgtgga atggctgctt ctgagagttt    12334
ggtctttctg aagtatcttc atctaatgtc aacttttcct gatgaccaaa cttggtacta    12394
acaactccct ttccccagag cattgctagt ggcgactaga tccaacatat ttaatatttg    12454
ccaatattat ggtaaaaatt gctgttttt tttgtgtgtg tgacagaggc ttgctctgtt    12514
gctcaggctg gagtgcagtg tcgtgatctt ggctcactgc aacctctgcc tcccaggctc    12574
aagcaattct tgtctctcag tctcccaaga agctggcatt ataggctgtg ttctttttaaa    12634 gcatttttca gtgagattga acttccttta ttatattat tgaccatggc atatattcaa    12694
ttgtaagttt ttttgtgcac cgttcttggc ctgtttctct actgtaattg tcatctctct    12754
tgcaaacact gacccttggt ttgttgtttc tggtagcatt gatttatgt ggttagatgt    12814 catgactctt gtcctgctga gcatggatct cccattccac aatcatgaga agaaccaaca    12874
atatggagga ggtgacaccg tgtagctttg gaggctaagt aaaaaatagg tcatgtgctt    12934
ctgccttgga gccagccacc atattgtgag gaagcccaag cagtttgtgg agaggcacat    12994
gcagagagga accaaggtcc tggttgagct gcctgcctaa tatccagcac caccttgcca    13054
gcaggtgagt gagccatctt acaggtagag cctccagccc tcaggcaagc catccatatg    13114
gaacagagat gagccattcc caccaagatc tacccaaact gcagattcat gaaccaaata    13174
aatggtttct gcttgaagcc attaagttt gaagtgcttt gttacacagc agtgggtaac    13234
tggaagagtc atggattcct gacattgaat tcctggtcct cctccttctc aggctacttg    13294
tctagatgtt ctgttctctc catgattctg tggatccctc agagccttcc ggtaacttcc    13354
ttctttgctt gtgttagcct gggtcaatct ctgttgctta taactgacag acatgggaaa    13414
ccagccccag caatgagagg tgacccagct cagatcatga gacaggacag gaatccaggc    13474
ctttctgaaa catagcccag ggtcccatcc cacaacgtgt cagtagacac catgcctgct    13534
gggtcatgcc tgcttccgct gcaccctgca cccagctcag cacctgctat cttccaaagg    13594
ccattgctga ttgcttgtac acacctgtta gttcatgcac agacagcaaa gcacgtagtt    13654
gtgctgcctc cttgccttcc tgctatgatc tgaatgttta agtaccccct ccaaattcac    13714
aggttgaaat ccagaccccc aatgtgaggg tatttaaaag gtggggactt tgggagtgat    13774
gaggttgtga gggtggagcc ctcatgggtg ggattagtgc ccttataaaa gaccttagag    13834
agctcccttg cccttctgtc acgtgaggac gcagcgagaa ggcactgttt gtgagtcagg    13894
aagttggacc tcagtggaca ccaaatctgc tgtgccttga tcttggactt ccagcctcca    13954
gaattgtgag gaataaatgc ttgttgttta taagccaccc ggtctatgat attttgttat    14014
agcagcctga acagactaag ccactcccag tgatgagcct gcatgatgtt ttacacaaac    14074
agatcactga aagaaggaat tggccagcaa agatgatgct cagcagagat gtgaaagatg    14134
ttaatgctgg aagtgaaatt taaattggag gtaaatggag tcatagaaga aatccatgat    14194
cttgggaagc tgaagctacc cttcaagaag ctccttatatg cagccagagg agttgagtga    14254
aggtgaacac actgatgtaa accaggaaag gagttgtgcc ccaaagcatg gagatgtccc    14314
agaggaagcg aggctgggaa aaacgttaaa ggaactcttg aagatatttc acagtgttga    14374
aagtgcaaag gataaaatct tggaagctgg tctggagaaa gataattctg caaagcatag    14434
```

```
aaagggtgct tttttggtat cgtaaggtat acaataacag tagcgagcac tgtgcaaact  14494
ctctccatat gtcttttaca aagaaataaa gcanttgaca tctcaatgtt tctaatgctt  14554
taaattacat tgtaccaaat aaatattagt tgtactattt taaaaaaact ttcccggttg  14614
ggcattgtgg ctcacacctg taatccaagc actttgggag gctgaggtgg gaggatcgct  14674
tgagcccagg agttcgagac cagcctgggc aatatagtga gaccctgtct cttcaaaaaa  14734
taaaaaaaaa ttagccaagg atggtggcat gtacctgcag tcccagctac tcaggaggct  14794
gaggctggag gatcacttga acccaggagg ttgaggctgc agtgagctat gattgcacca  14854
ctgtactcca gcctgggtga cagagccaga ccctgtctca aaagaaaaa aaaattccct  14914
gtgcattccc tatggacatt tgtaactgtc cataaaagac ttttttaatgt cttgacaaaa  14974
aattttaaag gccacagaag aattgtaatt tcctcattga ttattaggat ggctttaaat  15034
ggttttagct ttcatgctct attttttttt tttttttttt gagatggagt ctcgctctgt  15094
cgcccaggtc ggggtacagt ggtgtcatgt cagctcactg caacttctgt ctcctggttc  15154
aagcaattct cctgcctcag cctcctgagt agctgggatt acaggtgcct gccacggcat  15214
ctggctaatt tttgtatttt tagtagagac ggaatttcaa ccatgttggt caagctgatc  15274
ttgaactcct gacctcaggt gatctgcccg ccttagcctc ccaaagtgct ggaattatag  15334
gngcaagcca ccgcacctgg ctcatgctca tttttatgga tccacaccac ccgtacagca  15394
aggactgcct gcactcattc caagtggtca gagtggtcac cgcatgggcc ctccacgtgg  15454
ccnggccaca gtgatgtttc aaaccctggc tgggggattg cattcaatat ccccttatta  15514
aaggcggcag ctcaagaata ttaaatcatg ggaattcctc actgtggaag tgggaaggca  15574
gcccgtggtt caccgtgagg ggcacccaga gctcccctc cactgcgttc agtgtgcagc  15634
cctccagcca gcctgtctgc ttcgggagca atccatcatg gaatgaactg accgaaggag  15694
cgaggggctg aatgatgtgg ttcctacgcc gactttcaat gtgaaggtg ataaaaacag  15754
ccctgaatat tttatggccc caaggagagg taaggctctt tattgaagct gtgaaaatat  15814
aatccatcat gataatgtgt cccatatcgt cagactctgc gagctaagtt gtgtgtatgt  15874
taaggtgctc tttttgagaa gatcttaatt ttatttctct atttattttc attacagaaa  15934
cgtttgaacg tgtagacagt agaataaagg gggggggga aataacatcc ttcatttcac  15994
tactccagaa acactgctca catttttgttg catttccttc taactacccc ctgcagattg  16054
tactatgttt tgtgtctttt aaaatattaa atgcactgtc aacatttttcc cagatcatcc  16114
tgcactctga gttaacaatt tttattggct gcataatact tcacgatgta ggtattatta  16174
ttcattcaat aactatttat ggattcattg atccgattag tgttgattgt ctataacagg  16234
tgtgtgggtg gggtaggggg attcaggaag aaggaatagg gcgcagctcc cccncccag  16294
gatttctgga annagggaga cntaacagat ggctgtgatc cggtgtgagg ggcagggatg  16354
cagtgggccc ggttgcagcc tgggagcagg tggtcagaga tgnaaggctg tgggcagcag  16414
tggttggtgg tccacagcag taggcagcag ggggagggg cgacattcat ggcaggaggg  16474
acattatggg cacagcacgg cgtggtgtgt tcagggttgg tggagcgttc acttacagtc  16534
ttgcagatcc tggcaggtgt ggtggtgatc tgtccaggca ggggagggag agggaactga  16594
gagtcatcaa aagtctctgg gagtttggaa aggagagtag ggggctcaga gggagtgtga  16654
gcacttccag cagaggtgag aaagcccca gtcagttgcc cagggtgggc agtggaaggg  16714
aagtggaggg gaacgttgtg gggtggagag ggttttcagg caggctggga gctgcccagt  16774
gtgctggagg aaggctgggt ctccttgaat ggtgtttggt caatgcaaga ccacaggagt  16834
```

```
gtgactagaa ggctgggggt gcagatggtg gcaggtggag gatggagaga gctgctccca    16894
ctgctgaaca acgactgccc caactttatg ggatgagcat tcttatgaat gcccattgtc    16954
ctgtattcca gattattctt gtgtctgtcc aggtagggat gcaatttctt gatgtaaggc    17014
tataggtgtt tttaagggct tgcataaaga tttgaatatg atgttgtcta gtagagtaaa    17074
aatcaaattg ggcaaaacat ttttgtttgg gtgattttg gaagagtaag tccacgaatg     17134
caacgcagct ctggagtcat ctgtagatta cagcaagccc atcagtctct atgtctcttg    17194
cttacaacaa aggattgatt tcagctccag cactaggtga cttgtgctgt gttcattatc    17254
tcttgatagg tgtctgacag gagatggggc ttgggctgtg ccagggagga gccgtgtggt    17314
gcaccaccta tctccgcagg cataactatt ttgtcttcat ggcaaaataa tagcgatgat    17374
ggtgatgagg agggaagcta ccatttcttg actgctcctg tgtaatgaca tgttggtgat    17434
cacattaggg ctttatgtcc actctgggag gtggtgagaa tgacatcgcg tttgcacatc    17494
aggacgctga gcctcagaga ggttgagtcc caggacgaag gccacacagt gagtgccaca    17554
ggtaccatta ccacctaaca aatgactctg gagctcagtg atgtgatgag aaccattta    17614
ttctgtctcc tggattctgt gagtcaggaa tttgggcaga gcttggctgg gcaaaccttc    17674
tgctctaaat ggccacccat gagtcttcca agctggtggg tggactgatc tggagggact    17734
gagatggtct cactcacaca ttttctgcgg ggtggggaga gttggaaggc ggggctcccc    17794
tccccagcgt gcagtctcag ggcagttgga ctcctttgat ggcagctggc tttcccgaat    17854
caagtatccc cagataccca ggtggaagct gcttggccct tcctgacccc tgggacatct    17914
cagtgtcaat tgtgtcatct tcatttagtt caagcaagtc acaggccggc ccaggttgaa    17974
gggcagttgg actcaacctt tgcatgtggg aagggccagg ttacatggta gaaaagcaga    18034
tgggatagga gaccgtgctc tggccctccc tgggaaacac ggtgtgccac agacgccctg    18094
ggcagagcca agaccccac tgggctctgt ctgaccttgg agccactgcc ccgctcctga     18154
gcaacaccct cttgtccccc tgaacagtca caggaagaac gggtccctct ctccatgcca    18214
ttttcctgtt aaaaaatgca aaacatccc atacttttgc tcatttaaac acagaggaaa     18274
ggaggtgagt gaaagctttc tttaggggta gattagatgt gaggcagacc ggtggccctg    18334
ggtgtgcacc gggtggaaat tattcttaca aacagggccg ggtgggggtg cagcctgcca    18394
ccgcccctct ggccgtctgc ctccacagga ggcttgcagg tgcccacatc agccaacgtg    18454
gccctcggtg gggctgtgct tgccttcttg ccagggccac tgcagtaggg aggagtgcag    18514
agcagaaaca ggtgagctgg gctgaatttt ctgcttggct aattcagtgt ggcttgactc    18574
caagaaggac acaccgacct ccccatcatc ttgtttgttc agccttgcag aagcagtttt    18634
atgagaaacc attacagccc cggtggtctg ggcccagacc cggtgcacac cacgtgcccg    18694
cactggtgcg ggggaccat tctcggtgaa tatgatggat gcacaggaag ccgccctgcc     18754
attcagtgag agctcaccat gtgtctgccc ctggggtggg gtggggtggg cagtttccag    18814
cctttgccca tgggatagag ctgctggaag tctccccgag ctgaggaggc agagctgggg    18874
tggctggggc tggggttgc catggatact tcctgcaagt cctgacgccg ctccttcctc     18934
tttggggatc tgtctcccat actgtccctg ctgcctttac atcttcaggg tggagaggga    18994
ctctggccat cctgggccca accatcctgt gtcactgctg gtgtttgtga cctgcggtgg    19054
gccctccctc aactccgtat ctccagctct aagccagaga caagaatatc ctctgtgggg    19114
gggtcccttc aagggtggat ggagatgagg cgttaggtgt atccgatgct caggaacggc    19174
cccgcacctg ctcatctttta tgatgagcag tgggactgcg ggcagaggga gccacacgca    19234
```

```
tccatcctgg ctctcagcat cccagggaaa gatgttctgc tctatcctga tcagcctcgc   19294
cctttaacca accacaggct gcctgcagtg tggccgtggg gagctggagt caggcatggt   19354
ggcagcccct ctagacagta ggcagtaggt aagcctgctg atcacggagc cgagattctc   19414
tgtgggacag agctggtccc cagcatccct gtggcctttg ggccaagaac tcagtcggct   19474
actttgcttc caggcttggg aacactcagg gtaggctggg agtcccctgg tctcaccctg   19534 tgagcccac ataagcctgt ggatagcacc agctcagcag gtgaccccct catcaaaacc    19594
ccaaactggg atgcttctct ggctacatag gcatggccac atggggacag tgggaggaca   19654
tgtgataatt tggggcagcg gctgaaagcc taggggttag ggctactgtg tccttctaag   19714
gtggtgcagg gcgcacagcc ctctgggcct cagtttcctc ttctgtgaaa tggggactct   19774
atcttggggc cgcaaatgcc agtgtcttct ctggaagaaa gggcgactgc tgagggaagc   19834
agcacacagg tgtgagggtc caggcccag acgggatccc acaaagacct aggacagtga   19894
gccaagagtg gagagagggg acgagggtgg actggggtgg gccccaggag ctggaaagtg   19954
aggaaaatcc agctgtgtcc tgagggttag actccactgc cagtgttcac aggatctgga   20014
gctgatgggg acctgcggtg tcaccctgaa gggacagatg gcccccaggc tagcaggagg   20074
tggcagtgtc cgtttggcag caacatttga caagcagaag gcagttggtc cctcctgctt   20134
cctgtccagg ctcttgggc tgggacccca ctcccagccc tgtcctcccc aacctcccca    20194
cacttacaca ggccactctg gggcagagga ggggtgctgt gatttgtggg tttgggagaa   20254
gttggaagca taatgggtca ggcctgcagc tcggtccaca ctgcctgtgc caggtggagc   20314
aggtgagggc atccctggct ctggggtggt gtcactgttc acactttgtc ctatagccag   20374
gcccttcttg ggggtgaggg ttccgtggag ccctccatct gcctggctct gccgatccaa   20434
ctcttttctc tctcttgggg gtttcaaact tagacaggaa taggggtgtc atttattggg   20494
ccccagacaa cctgaccagg tccctcagag cactgaggcc gggaggagga gggtggaagg   20554
agatgggaag agtttccttt gtcctctctc cctggccatc cccaaacctc cacacaaacc   20614
tggggtggct gagcattcat tatgctttgt ctttgtaaat aggcagctat aaaaacctat   20674
cagcttgcag caccttctcc ataacacagg ctggatggat ttataaccca ggtcccctcc   20734
ccgagagaag ctggcaaagc agaccccagc ccgcgctggc tgccatcacc ctccctgccc   20794
ctgccccacc tcatgcaaga aacagaaggg aaagcacatt gagttgtaat atgttttcga   20854
tggaatttgt cacaataaga aactggattt tgttggggct catgggatgt ttaggaaaga   20914
gccagagagt ggtgcaagct gtgggccctg ccgagaagcc tggctacag agggcaggg    20974 gctggagtgt tggcagggtc gcacagtggc tcatctggac agtccacagc ggatccagcc   21034
cacactgtgt caggcacttt gctggactg ggggatgtgg ctgtgggtac gattgacaag    21094
gtctgtgtcc tgaggagccc gcagagcaga tgagatggac atgtggtcag tgatggtacc   21154
gtgtcgggtg gaagagacaa taggctgagc tgcccagagc atcgcctgac cagcttgggt   21214
ggtggcacgt ccaggagggc ttcctggaag aagtgaattt attcaacaca tgttcactag   21274
agccagtgat gcttaggcac tgagagtgtt gccagggata caggagagaa tgggagagtc   21334
cctgagtcat tccagactgt ggggctgaag tgtccgccga tggaggtgtg gaagggcac    21394 agcggcttcc cacgtgagca aggagctatg caatgtggca ggtggcaggg ccaggcgag    21454 gtgcctccac ctgtctccag accccacccc ctacccaggt atggaattgt tgtctccagt   21514
tggcagagaa ggaaactgaa atgggggttt cacctctcag gaatgggtag gccaggattt   21574
taacccaggc ctgcagacac caaatctatc cctcgctcag gcctgcactg acctccgtgc   21634
```

-continued

```
acctctgggg ctccaggcag ctgcctgggt gggtgctgtg tctgggtct ctcctggcgt    21694 tccttaggcc cctcccctat caccgtcctt cattattcac ttggatgcct tgatggtcgg    21754
ggctggaacc ccccgagctg acccaccatg cggctcatct tccttctcct tccagtgctt    21814
ggtgatcttg agagtgaggc tgaaccgttg cttgatttt ctgtgaccca gatgaagagc    21874
tgggtaacca tttgctcaat aaagtgagag accccatgtt ctggttaaag tggaggcact    21934
gaggaccagc gaggggaagg cagtacttgt atttgtcagc ctggaggaga cgccagatac    21994
cagccagagc accccagcct gtatctcgac caccacctgc agttggtgct gaaccccca    22054 ctccacccca tagatgagac aattgaagcc cagagaggcc aggcttcttg ccgagggctg    22114
cacagccggc agggatgctg gaattgggat ttggccccag ccttgtctga ctccaaagcc    22174
aatgctattt ccaccatacc cagtgtctcc cagagctaat tttgcggctg gaactgcaac    22234
ccgcaaagct atctaggaca ggcaactcga tgaaagagaa ttaggaggga atcctagaaa    22294 aatgggctc ggcagctccc ggggaagcct ggagaggagg tggcgccgaa gcctctgcca    22354
gcagattggg gtggggctgt tttcagtcct ctctggcgag gtgttttgaa gcctcctctg    22414
ggaaccgtgt gcctctgtcc aggactggct gtctctctgg aaatcatacc ctggcagcat    22474
ttggctttgg gtgaaaggag aagagaagat tctggccatt cagagcaggc ccttgtgcgg    22534 gatgaaccc attttccaga actcttggga cagggaccag ggtggcaggc aggggcccgt    22594
ggactgcctg ggggacctgg tgcttgggga cttagagatt tgttttcctg ctgaatatat    22654
tgctttctcg tgcctgcttt gtgcaaccac gtgaggatgt gggggtgagg atggccgaca    22714
ggacacggga gtccctcccg acaggggcca ggcggcggcg ggggtccgca tgtctcacgt    22774
cagcatggct ctgtgttttc actcctctcc agcacatatt tagtggaaat gaactcatt    22834 tattattaaa aattaaagtc atgcattcat agggtaaaca agattgagag catgtggagg    22894
tgcactgtga aagtgcagtt ctctcggaat gggcacttag agacgcgcct gttctctgca    22954
gctgccgcag gggtctcatc ttgttgggac agaacacggt tgattcatgc aattggctgt    23014
tgatcaacat caggttgtgt ctagttttgt ttttttcccg tttcgcacgg tgctgcgaat    23074
tcacagctgt gccagtgtat ctgaaggtaa atcccacgag tgggccttgg agagtcagag    23134 gatgggcct tctacgtgga cttggtgtgg ttgggtgtgt gatgcctgca tggggctatg    23194 tgttttagc ccttccttct gacaggttct ggaggcctcc tctgtgcctg ccagccatgc    23254
agccgctgag ccgagcatca cccaaggctt gcctgaacct ggcctgggtc ccaaaggaac    23314
actgctctgg ggcatggagg ttggctggtt gagaactaaa gccacatcag caggggcact    23374 gccccccacct gctggggtca gccccgccc ggagttcagc aggacctccg tgagccttcg    23434
tgcaggtggc tcattgcagc acgtcccctt ggggtggtgg ccattggctt gtggttcctt    23494
tgctcactgc ggggaggagg acagccaggc acaggtgaaa ggggcttgcg ggtgacgatt    23554
ctagtccttg gccggggaa tgtccctggg cttctgagcc ctcacctccc tgggtagtca    23614
ggagggttac gagggtgggg cctggccctg gggactccag ggtgtggcag cggtgggagt    23674
gaggaaacag ccctgagacg gagggagaga agggcgatcc agatggcggt ggcctcctca    23734
cccctcggcc agtgatgcat ggtagtggtt ttgacgggct gacctcgagg gtctgcctgg    23794
gagccgcttg gaactctctg gaggtggggc cggcctggt ggggcagga aggtcccaga    23854 gcagcttgtt aagtgggctg aggacaagtg tcaggagacc tgggtctgga tcccgctcca    23914 ataccctct ccgtgtgacc tccaagggat ccacctgcct tggcctctca aagtgctggg    23974
attacaggtg tgagccactg tgcccagcct gtgcccagtg tacccatcag taaagcaggg    24034
```

```
atcaaacagt tcttaaatcc tgcagcggtg gtgagagcca cctgaggaaa cgatgcaaag    24094
ggctttgacg gagtctggca cagagaacgc acccaataaa tgactgccgt gacgatcttt    24154
cttctcgccc tcaggtggtc tctggaagct cctctgtgcg gggttttctc atttgccagc    24214
tgtgcatccc ccggtcgtag tgcggctccc acggggtgt accaggagcc tctgctcctc     24274
ctatgcttcc tgaaaaaggg cccagagaat atttccatca ggataactg agtgaatccc      24334
agaaacttcc tatcacattt agggtgatta ggcagatgca tacgattctc actgtgggaa    24394
aggagctggc gacctcgatg ggttgtggtt cccgcaggga tgtgcttgcg ctgctgttac    24454
tccagccgta gctgaggcac gggagaaaac ggagacccca agaagttcag aggcttgtgc    24514
aggtcacgct gttcctacga ggtagaccct gactttgacc ccaggctgtg tccctgccaa    24574
gcttggagcc tctttctcaa aagggcgacg aaggatgtt gttacagatg tggttgccag      24634
tttcctcctt ttcattaaat caccagggaa atggtctctt gcaacccccc taaagcaggg    24694
ggaaggagga ggacaaaggt caggtcacca tctttgctgg catgtgagtg gggtgggggt    24754
gggggtgggg agctaggaga cctggcgctg ggcccttgaa atatccacat ttccacaaca    24814
ttctgggtgt cagtgagccc ctgccttcct ccctcacatt tatccggagc tcttcctccg    24874
caggaagaa caacagcccg agatggggtt atttcaaggg gatttccatg gaaacgggag      24934
ggtgggaggt tcctcccagc acttgtataa tgggagttgg ctgaggtggc agcgtgtccc    24994
cacggaaggg tgcgagggac cttctctgca ccgcaggcct cctcagagtg ggaggcaccg    25054
acccgagagt ggctggctcc cctttcatgc tcccaccctc tctacccagc tcaagacccc    25114
ggggctcctt ggtgtgagtg agagccaggc cagctcccca gggaccccca aggcctggtc    25174
cttcccatgg tctcttttct ctagcaggtc tttgtcttgg gctgctgcca gccacagctt    25234
cctggcagga cctcctggca ggacctctgt gctttgagcc gctgttgctc tgccaagacc    25294
ttgccccgca ccgtggtctg aatcagccca gcacccttc gcctctgttg cagtgctcac      25354
atttatccct cactcctcca tccagcatgt tttgtttttt ttttttttac aagcagacac    25414
tttgctttat aaaagaattc tgctgtgagc tgccgtatcc tctctgagcc tcccttttgt    25474
catctgctga atggtaacag cagcgcctgc catgcctgct tggtgaggat tccatcaagc    25534
agggagacag tgggccgttg gcggggagtc tgagcaggtg taccagtatt tccagtcagc    25594
tgatggctga tggacatgtt cttggaggca gggaactcgg aggcctgcag acgtgcccca    25654
ggatgacaag attcatcagt tcctacaagc cctgcctggg cctcatgctt ttcagtgtgt    25714
cctgggcttt cccgtgtgaa atcttacctg atttttatgc caccttgaga agagtgatat    25774
tcatctccgt tgtacagatg aggaaactga ggctcaggga ggcaacgtga tctttgcaag    25834
gatccgtctg ttccccccgt ggcctggctg ccctcctgg cagtgcaggt ggagttaaaa      25894
ccatacagga gttaaaatga gcctcgatgg gggtgggaag ctacgactgg aaaacgtccg    25954
atgctctccc aagtcaaatt gtgcttggtg tctgtgggtg tgtcggtgtg ggggagggaa    26014
gctcagccct tttgaaaagt ggggggtggt ttgacgacgc tgcaggggca gctccgagtt    26074
ctagagtctc agaacgtggt tctaggcggt tcatgtggat caagtgctgt tctgagcact    26134
ttaatatcca gcgtgaccat aaggataagt gccactgtta ctggcttttt cacagatgag    26194
gaaactgagg cacagaggga ttaggtaaag tgactggagt cactcagcca ggatgtgaat    26254
cacagcccac acccatgtgc accaggaagc cttggctttc aggtccttg gagggtgtgc      26314
cgggcagtcg cctaagctgg gaaaccttgg gcttgtctcc aggccatgtg gccatgtgag    26374
ataggagtcc tcctgtgtta tgttctgcga cactgtgggc agagggctga ggaccccagc    26434
```

-continued

```
cctcccttag aacatcatgt tggtgtgaga catttagagc caggcctccc tgcttagaaa    26494
gcacctcttg ggtcgcttgc attagtgaag ttatacattt gaaactccat ttatttattt    26554
atttatttag agacagggtc tctccttgtc acccagacta gagtaccgtg gtgccatcat    26614
agctcactgc agcctcaaac tcctagactc aagtgatccc cctgccgggg cctcccagag    26674
tgctggcatt acaggcatgg gccacagcac ctggctgaaa ctcccttttc atgaaaagaa    26734
acagcttcaa ctttgcaatc tcatctgtct gtctatgagg ctgtgccttt gtgtgagatg    26794
agagcagtca ctgtcacttg ctctttgaat atttgattaa caggtaaaca gcctgaaatc    26854
catttgacat cttatccttt tgcaaacttg gctaaattct cttaaattgg ttccagttgg    26914
attaattaaa tgcatggttg cttatacatg tgtgtggaaa tgattctggc aggtcatgtc    26974
ttagctagat agtgaacata agcgtctaga atattctcag ctgttgcaga gactgccagg    27034
aatgaccttg aaaaagtttg ggagagggtt tttttttttg tttttatttt gcttttgttg    27094
agacagggtc tcactctgtc acctaggctg gagtgcagtg atgtgatctc agctcactgt    27154
aacctctgcc tcccaggctc aagcggtcct cctgcctcag cctcccgagt agctgggact    27214
acaggcaggc accaacatac ccggctaatt tttgtatttt ttttttgtag agttggggtc    27274
tcaccatgtt gcccagactg atctggaacc cctaggctga agggatccac ctgccttggc    27334
ctctcaaagt gctgggatta taggcgtgag ccactgtgcc caggctggag aggttttggg    27394
atgcactggg ccatggatgt gaaggtgaac acatggaaac gatccctgcc acctgcttgt    27454
gtgtccagtg gacatgtctc tgatctatcc agattgttac actgtcaaag tgaaaactgc    27514
tgagagtaga gccatctgcc tggccaggca tcgcttggaa gcgtgaagac actttgcctt    27574
tttgtctcat gattctctct ccatgtgcag cttcgttggc ttaaaagaaa ttaagaaact    27634
gggccccccgc ttaggacctg ctgaagtgca gagttactgt ctttgaagtg gtggggtagg    27694
gaaaaatagg aaataagggg tctgatcatt ttgagaaacc tcaggagat ttacacctgg    27754
gctgtgcgag gaccccggag agtggcagag tgtatttgga atttccagta gtcctcattc    27814
ctcccttaat atccagggga tctgggggcct cagtcttctt atctgttaaa tgggacaagt    27874
aacgactagg ctttggggtt gtcaggaaga ctgaataaga aaatgggtat gaaaacagtg    27934
gtcacggtgc ctggccctcc atccctgtct ccaccaggcc tacctgtctg gcccaggcct    27994
ccctgatctc cgcgggagca gacctcctgt aatggtgtca aaggacccctt gttctattta    28054
tccatctgat ttccattttc ggggccactg cctctagcca tgttaggcac atggtgagtg    28114
tctgtcccat caatccttgt cgattctgtg gtcctgggtg ggccatagcg tttctaacct    28174
gtccactctc tcctaatcag gcatttggac ctgtttgggt tcccaaactc tgtcacgggc    28234
agagggctgc aggaggctac tcacgggcca gggttgtttg gacctggttg ggtttccaag    28294
ctctctcgca gtcaggggggc tgcaagaggc tacacatggg ccagggttgg gctgctgggc    28354
tgctgggctg ctgctgtgtt ggagctgcct agcacttgct tcgttgctgc acctgagagg    28414
ctgtgtgggc tgagacagcc agaaaagatg caccgggagc catctgtttg cagcccttgg    28474
accagatgct ctgcaaggac tccggggggg cggtggggtg gggagggaat acatttgctg    28534
agcacccagc atctttcaga gcctcagcac agccctacaa gctgggcatt gccatcatgt    28594
ttatacggac caggaacacg aggctcagag tgactgagtc actggtgaca gtcacccagc    28654
caggaagtgg cataggtggg gcttgaaccc agggcttcct gagtcccagg ctagtgttct    28714
ttgcctcagg ctgctgaggt tccagctgaa tgttgcggca gagtgacttc tgagaagtac    28774
cacggaaggg ggtgactcac gccggggtgg tctggcttct ctgcccagtg cctgaggaca    28834
```

```
cccaggtccc tctgcggcct tggggcttta cccagcgtct gcatggcatc ccgcagcacc   28894
ctgcctctgg agcgcaccct gtgtgtatcc taaagtgcgc tttgcctaga aaacctttct   28954
aatgaaactg gtggaagatg gagaagccaa attcagtttt cagagatgac actaatccta   29014
ttaaggttga tggggccaga gcatgtgtgg aattagtcct gccaggcggc ggccgggcac   29074
ctgcctggaa ggctggaggg gatcctaaca agagtggtgc cgaggagaga gagggaaggg   29134
gcctcatctc tcccagaggt ttaaaaaaac tgaggccact gtagagcttg gttctcccag   29194
gttcctgggg tggaaaacag ggcttcccac agcagacgga aatgggaggt gggcagtagt   29254
caccgagcag ggaggctgtg aagtagtcat ttaggtcggg aaagtcacgc aagatctcca   29314
agcttcagtc tccttagctg tgatgggggg aatgggtgcc ccccttgggc gacttgtggg   29374
acccagaact catcacgcag agcgtcccac tgctgtgcag ccactagctg ctcggtgctg   29434
gggctgtggt atgagcatgg actctggagt cagaattcct gccttcaaag ccccactcct   29494
caccttgcta gctgtgtggc ctggggtgag ttgcgtaacc tctccatgcc tcagttcctt   29554
catctatgaa atggggagac tgaaactgta ccccacaccc tagggtgtt ggaacttaag    29614
tgagttaatt catataaaac acggagtgag tgcctggtac gcaggaagtg ctcagttcct   29674
cttggtgcct gtgattattc ccataatcat cactggtgtc accttgtcgc ctctcccagc   29734
ccttggggcc atgctatttg tggtaggaaa tggggcctga aaccatcaaa ctaaactgga   29794
ctgaatgatc agtccaccga ccaccacagt cacggcttgg tggccccacg gactgaagca   29854
cgtggccaag ggcagttttc ccttctctgt gtgggttcca ctgggtccaa gtacattgtt   29914
cctaagccca ggcctctggc cactcaccca cctcctgctg agagcgggca gagctgatgc   29974
ccctctctgg gcagaatcag cccacggctg ggagggagg ccaggcctgc tgctgggggt    30034
gcagatagtg gggagctgca ggccagccac tggaaacctg gcctgtgtgc tgagacagca   30094
cattggacac agtctggtgg ccttcccata gatcaggcca cagagtcctc atcctgggtc   30154
cacccaaggc actggccatt tccagatcaa agagcaggtg gattccaggg tgagacggtc   30214
ctctctgctg gctgccttcc cccacccacg gacaccgttt ggctttgatg gggctgtgtc   30274
ctaggcttga cccaggtggt caggagcctt ccactatgca gtgggatatg ctgcaggagt   30334
agggcggaga aggaagggaa tggccggtgg tgaacagctg ccatgcccca ggcatttaat   30394
tttgaccgca gtgctggggg gccatacccca gtaatacaga tgaaggactg agactcaagg   30454
gtcagtgctt gctcagagac ccacagtgaa gagtggggcc atcgtgttgc atgtgtgtgg   30514
ctgggcccca tccccctcct tctacagcac caccccctcta ttccttatca agttcacctt   30574
taaggctcct ttgcccctca ctggggcagt catgagggga gcagaggcct cggatctggg   30634
catggatgag ggtagagccc tggctgtgtc ctgcaggtga cacgtacaga gcagaaggtg   30694
atgctggaac catccgccag ggaagggctg tccaggaaga ggtcacagcc tgaacagagg   30754
cgaggtggag agagagtgct cgtgtgtggg gactggtggc agctcaggag ggcaagactg   30814
tgacttgcag gctgggaacc agggaggctg caggtgatgg aggccccatg ggtctcatgg   30874
ggcgggctga ggagcgtggc tcctcccctg cagctggagg ggccaggaag ggctttaagc   30934
catggagtga gggaccagag ttgggtttac aagggtcact gtggtgtcgg tgtggagggg   30994
cttgaaggga ggagtttgga gggaggggct gtagcaatgt tgagattccc taatcacttt   31054
agtgtttcca tgcatgaggg ccccgaggtg ctttttttcca gagcctgcac tgaggttccc   31114
tgttggcgga ttccctcagg ctgctggaac ccccttttcc tgtgcacctg cagagctgga   31174
ggttactgga aactcatgtc ctctgccaga gtcagccctc acccagtcac tgacaggtgc   31234
```

```
agtggtataa ataccccagc tccctccctc ctgatcagga cactttgaga tgggacctac   31294
actgtcccca gagctcccat gggactgagc tcaagtcgca ctccttgaga tttttcctgt   31354
tatcacaccc cacttggcct ccttcatgtc ctggccccac ttccctacac ccttcctggc   31414
tttcccagca acacttccta atcacttcca gaaaaatgtt ggcctcaggg tctgcttctg   31474
gagaacccag cctagcagag ggcagcaaag gtgttgaggc actaggagaa acatggtgag   31534
atacagactc aggcggcgtc catcagctat gccaggaggc tctgagacgt gccagtcagg   31594
gagggaggtg ctgaggccac agcaaactgg gggccagaag taagcaccac agacagcacc   31654
aaggctgcca gggtccatca tcttgggtct cccaattggt tgggtccaga gaccagcctg   31714
ctggggttta cagagccagc atgttacatc tctctgtgtc cccactgctg aaagcctctg   31774
gtcagtgcca tggtgctgag ggagcttggg cctcccttag aggttgctaa gagcccccca   31834
cacctgccct gtgagttgtt ggcccccaggg gactctgagt ttccctgttt ctggtttttcc   31894 tgctcatggg attgggagtc tgacctgagc ttgctgagac agataactga tcattcagat   31954
acaaaactct aaaggttaga actcttttct gataacttaa atagaaaatg aattcatgca   32014
acatgtactc atctgtccat ctgcgcatgc atccaacatg tatgtatctc agttgatggt   32074
tgtttccatg ccaggccttg gggatctaga gatggcttgg tccctatggt catacccatg   32134
tgaagggaga tagaggtgga cagaaagaca accataatgt cattttgaca aattctggga   32194
aaagatgggc cacccagcct gtgagacctg tatgtagtga tggagggatg gggaacggtg   32254
gaggtgtcag ggaagctccc caggggagct gttccttgag gtggttttaa gagcttagca   32314
agagttttct acgcagtgaa gtgaagacgt agggcaggtg gagtggaggg ttggcaccta   32374
aaggtcctga aaaggaatgg tgttgcaaga ggcagcaaat agcatggggt gggctaagct   32434
ccagctggtt gagtttgggt cagaagtgtg gacttggttg gtaaggactc ctgagagtgt   32494
catgtccagg cacttggact tgatgctgaa aatacagcca ttcaacagag aagtatgtat   32554
gtctgagtgt gatgtggtta gatctttagt ttaggaagat ctctctgttc atggtgggga   32614
gagtggatga gatggggtg gactggaggc agaagagcag aggagaagag cagactttct   32674
aggagacgaa gcgggagggg ctgctcccag ggcctggctg tgagtggtac tgaccagagc   32734
catccatcag cccagatcat gtctccctaa tttagaagaa aatgagagga aagagccttt   32794
tcatctctgc ctcttctggg atggaaatga gctattttga atcacgctaa agttagattt   32854
ctagttttcc ttttaatccg tgtctcattt agagcattag aaactggaaa agcaccccg   32914 tatgaatgta gtgtcataaa tcagtgcacg tcacaaactg cagaaggagt catttctaca   32974
agagtgtgca gccttgcatt tatgataaat ctaatgcttt atcttttgg gcttcagact   33034 agagtaatta gtcatttctg ctgatactgg caaaccattg catgtgcagt gttaatggag   33094
agcaaatgta tttgaactgc ttttgcaatt gcttgtgagc attgctgtgt atctcttcta   33154
cctgttctta gaggggaaac atcctatata tttcattctt gcctattcta ggaataggtg   33214
tggtaatagt atcaggtaac acttactggg tttcttccac atctctggca ctgttcagag   33274
attcaataag aaaggatcct ttgtccaaat ggaagctgcc gtgtgtgtgt tgaggtcctt   33334
gggtcaatct gatcatgctc tgtctcctgc tctgtgcccg cactgtgtca gggaccacct   33394
ggataccact catgtattat tcacctaata ggtttcttta aatgttggcc ctctaccata   33454
aatggaaaac cagcaaatca ggccaaaaat agaagtaacc aaagacaagc acaggtgttt   33514
ctgctctaat gaaatagaga catcctgaga aacttctcat tctgcaaaat cccaaacaaa   33574
tgacatcaga gctgatggac agaatggggt tgggacagat gactggaagt ctatgcagtg   33634
```

```
tgtcaccaga cacccataaa aatattaagt tttagaaaaa tctggcacaa tgaaagaaaa   33694
acatattaat tcctgttaaa gaaacattcc aaccattata caatcttatc ttgaaggaaa   33754
aagtgaaggt catttaatgg aaggggctga aagggaggga gctgaattat ggctgggaca   33814
tggcctgggt acagagggag acccgtccac caaactcttc caaactgagc taagaggtag   33874
gtgcgcaggg aatgagtcta ttctcttggg ccacattcct ttgaggcttg atgttcagcc   33934
attagtgtat tttgcattca gttgcttcct ctggctggca caaaacatta acacactgag   33994
aaaggctgcg tttgaaccaa cctaacttttt acattatact gacatcattc ccctatgtac   34054
aaattgcata cgacctactt tgcaaaggca atggtcatag taactgtacg atggtgagtg   34114
gggttgttaa atgcagacca gatactgctg taatagggct gtgactcagg actatcattc   34174
cagttgcctg atatgaaaaa ggacatgaag gagaaggttt tatgagaact ctggcaaaga   34234
cccatgaaac cactcttctt tgccctccag aaaacctggt aaaactgaaa gtaagccagc   34294
agccccacgg gtttgggatt gatccagaag actgaaggaa taaaaacaag ctaatatatt   34354
tctatcccct cccttctaag gcctgtagtt ggttccatta tgatgagaca gcagccgatg   34414
cacgtaaaaa cagaggccat gcatctacac aggggtgttg aggattgaat gagattaggt   34474
ctgaaagaac acacagtgga gacagtgttg tcattgtggg gacaaagatt cttttcaca   34534 atttgagtga cacttgtcat ttctataggc agttaagaga caataactgc atactgttgg   34594
ccgctgtacc tttcctgtgc actgagtccc tgagcatatt cgtgagtctt taaaagtaca   34654
ttctagtcaa tgtagaaaac agatagtaag ggacatgact ctacctagat taagctcagt   34714
tttgaagcag ggcctagagg atttagaagt gacagagtcc tggattaggt gacatttgat   34774
aagagctcta tccctaactt cctcttaatt ctggacaagc cactccccgc tctggctgta   34834
gttcccccat ctttaaaatg aaacagttga atcagacaac tacaaaagga cttgccaggc   34894
cttctgtctc agatcctgtg ttgttgaagg gatgtctgag gccagagatg cagtttactt   34954
ctgagcaatt acagttgtat ttcttgtgtt cagcctagcc ctttaccaag ctttgttgaa   35014
gaaatggagc aagatcctg tccttttgctt cggtggtttt taaaacttgg atgcctaaag   35074
aaaccaggaa ggtcatatca gtgagcaaag tacaaaatgt ataagcaaga cacagtgcac   35134
catgacgctg agagtggcaa agtaacagtc caaccatgca tcagggagtg gtggggactg   35194
tggcgtgctg gcaagcatag ccttgtggga ttctgcattg gacagctctt acaatttctg   35254
gagagaaatc agaaattcag gtctacatgt tgaatctttt aatattgaaa tgttcacttg   35314
gcaatgtgta aacatcattt gggtcaaagc ccatctgtga accaagttag tcaaagacaa   35374
cttgggcatt tggacctcag ctttatagtc tatataaggg ttggtaaact atggcccaca   35434
tgctaatctg acccacctcc tgttttttgtg aataaagttt aaatgaagat gcagtcacac   35494
ctatgtgttt aggtattgcc tgtggctact ttcacactac aacagcaggg ttgagtagtt   35554
gtgacggtag ttgagacagt gtgggccctgt atttattctc tggacccttta tggaaaaagg   35614 ttgctgaccc ttggttcatg tcaatgactc atatggagca gcaggaaaca ttctgaattt   35674
ggagctgaat gaccagggtt tgacgcctgg ctcaggaaac tctagtaaca gagtagagag   35734
tgtttctctt ttctccttttt ggaaatgatc ctgaagcaac aaatggaaca aatggaaatg   35794
caaatgccat ctttgatgga accatagctt ctggaacctc atatgtgggg aagtgcagta   35854
aaggtcaaaa atgggtgcag gatgtctcca aagggaaata aaatgcccat ggctgtaaag   35914
ctcagacaga gcaaacaaag cagaattttc tacaccttct gtggtgggct cagatggcaa   35974
gacctatagt tcctctcatg gagcaataag aacaagtgca ttggctggtg tcttagtctg   36034
```

```
ttcatgctgc tatagcagaa taccatagat tgggtggctt gtaagcagca tacttttatc    36094
tctcacagtt ctggaggctg ggaagtctga tacccaggtg taacagattt ggtgtctgct    36154
gaggacctgt tttcttgttc atagatggtg ccttcttgct gtgtgcttgc gtggcagaag    36214
gggctaggga gctctctgag atctctttta taagggtact aatcccattc atgagcactc    36274
caccctctaa gacctaatca gttctgaaag acgttacttc ctaagaccat cacattgggg    36334
gctaagattt ctatatatga atttcggggg acacacatt cagaccataa caactggtgt     36394
gggagccttc ccagatctag ttttgcacaa agtgaaatca gggaagtctg gggtgaacaa    36454
ggtctcacat ggacaagcta tattttcaaa aagcagtcta ctagagaggc aaagtggaga    36514 aaagggctg tgttatgtgc cagcctgtgg catctgatct taacaagaaa gaagtaaagg     36574
ccaaaagaac tgactctcac tcacaagcct gttttctaag aactagatta ctcttttgga    36634
cactctggtg cacgaatctt gtataaatag atggttcagg aagaactcat cacattcaga    36694
gatgagtaat aattagtaag gaccagtgca agctctatct caagatcctc caaaaatgaa    36754
gaaagtaaca gatgaaaaat atgcgcaaga aaacatttgc cataaatcag atgaaaatgt    36814
caacagtaca taatgccttg gactaaggaa aaaaataatt gagcaatcac acctctaaac    36874
aagagtataa agttgagata caagaactca ggagaggtgg taacatgaca gaagagagtg    36934
aaacctgata tgatgagctc cacaaagtag atagattaac aaataaaccc atctaaaaag    36994
tgaagtatgc aatggaatga ttatgacagg gaacacagaa aacacagtaa gagatatgga    37054
agatgagatt gggaaaagca agataaaatta atgtaaagag agagagagaa atattagaac   37114
atgatacaga ggacagataa ggggatccaa catacacata attggtgtcc ctggagataa    37174
gaatgaaaat aattaaataa aaaaaattta aggcacaatt ccagaacttt ctaaaaataa    37234
gatttgaatt tatggactga aaggaagtac agtgagtggc tgagaaaata ttgatatggt    37294
gaggtcaaca gaaagacata gagaagtact aatttcctca taaatcaaga accccccaaaa   37354 aaattcaata gaagaatgga taaggatgt gatgaggaga tggtttacat aaaaggaaat     37414
agaaatatct tttaaacaca taaaaactca acctcactca taataagaaa actccaagtt    37474
aagatactgt tttttatcta tcgtataggc aaggactaaa atagctgata ttaccatgat    37534
ggtgcaggta tgagggaaac aagaactctc agaaacatgg ctatggattt cacttctaat    37594
ccttgtctga tggaagtaca caagtaagag gccaggtgtg gtggctcatg cctgtaatcc    37654
cagcactttg ggaggccgag attggcagat cacttgaggt gaggagtttg acaccagact    37714
ggccaacatc acgaaacccc atctctacta aaactacaaa aattagccag gcgtggtggt    37774
gcatgcctgt aattttaggt acttgggagg ctgaggcacg agaatcgctt gaacccagga    37834
ggtggaagtt gcagtgagcc gagatcacgc cactgcactc tagcctgggt gacagtgtga    37894
gactctgtct caaaaaaaaa aaaaaaaaaa agaaaagaaa aagaaatac gcaggtgaga     37954 aatgacattt atccacattt gtcatagcat tgttggtaat gggaaagaat ggaaatatct    38014
gtaatggcca tcacagggga ctgtttacat aaattattcc agagcgtgat agtggatagc    38074
aatgaaaaga atgtgacagc tcagggtgcg ctgatgtaga atgatgttta agattcttta    38134
ggtgaaatga gcaaggtgca aaatagtgga tgatccatga catgctttat gattaaaaca    38194
tggtatctta tgactgcttg tgtgtagact ccttctggta ggatgatgca cctgaaagtg    38254
ctcatagtgg ttgccactag acaggagagc tgagtgagtg ggagaagggc ctaagggaga    38314
cttattttca ctgttagctt ttttgtgccc tttgcatttt atactcattt cttaaccaaa    38374
ggctgcacag cttaggttgt gaccataagc tctagagtca gctgttcgag ttcgaacct     38434
```

```
gactgggctg cctactcgct gtgtgacctt ggacaagtta cttcacctct gtgggtctca   38494
gagttgtcag atggatgtaa caatggtgcc tatttcataa gttgttgagg atgaactgag   38554
tcaattcaag ggaaagaatg aggacagaac ctggcacaaa aaaatacagt caaattagct   38614
attatagtga ctgcatgtat agttgaaccc agggtctgga tttggaaccc gtatgcttat   38674
tggcccaatg gggggatga cttggccaca gaacagccac agccaggcag taaagggcac   38734
agggaggggg ccttagcctg gggcttcagg gaagctgccc aggggaagtg atgctgctgg   38794
gtcttacaga atgatgggaa aacttggcgg caccgtttca ggcgacgcta cttagatctg   38854
caaaactgtt gatgtcttac aataccaagt gtagggcggg gctggagaaa tggaaactaa   38914
tgccaccact ggaaatggat atgaaagcaa accatttgca aagtcatttg ccaatatcca   38974
gatatgtcca agcagcccct ctgttcccct tctaggtaaa tagcagggaa gccttcagct   39034
gtgcacagag agccattcag caacagagca gaccctcgaa caacacgggg ttgggggagc   39094
caaccccctg cacagtcaaa aacccacata caacttttga ctccccaaaa acttaactaa   39154
tagcctcctc ttgattggac ttccaaaaac atgaacagtt gataaacata cattttgtat   39214
gttatatgta ttatatactg tattctaata agtaagcta gaggaaagaa acatcatta    39274
agaaaatcat aaggaagagg aaatatattt tctgttcatt aagtggaagg ggatcactat   39334
aatctttatc ctcgttgtct tcatgttgag taggctgagg agaaggaaga ggacgggttg   39394
gtcttgcagt ctcaggggta gcagaggcga aagaaaatca tgtataagtg accctcacag   39454
ctcagctcat gtttgagggt caactgtgtt ctaaaatcca agaggctctg aaagcctaaa   39514
gatttttcc taacttattt ggcagtgaaa cccaacctaa attgatgtga aaccatttat    39574
agcccttctc tatccctgta gtgtgaagtt tcatatgtta tgtacagaaa tagaaatgcg   39634
tatgcgtgtt gtcccagaag cccttggggg tgacagatgt cctaggtgac ctgtgcacca   39694
tattactgta cagtccaaat cctctatcct gaaatactgg gcccacccct tgggatttgg   39754
gagatgacag tgaagctggt gtgtgttcag ggaattccag gttgttgaag gtgctggagt   39814
agaggggaga gggggaaacg aggcagcagg cgctgggtcc cgacggtcct ggacaccta    39874
ctgaggatgt gggtacaaca cttctttcat ccctggggct cagagatgtc tgctgaatca   39934
gtcgagggc cttcagtcca ctgtgagccc cagaaggcag agctgtggcc tcctccgact    39994
tgtttctcag aaaggtcact tgggcagcag gtgaacatgg ctcaggagag gcaagggagg   40054
gtggggacag gtaggaagca gaagccactt actgggcaaa gaccatagcc atgaggatgg   40114
ggagggactg agtagccaga gaggcgctca tcaaagccta ctgctgtcgt ctgaaggtct   40174
ggtttctccc aaattcgtat attgaaatta agccttaaga tgatgtgtta agaggtgggg   40234
cctttgggag gtggtcaggt catgaagatg gagccctcat ttatgggatc agtggcttta   40294
taaagggacc ccacagtgag aagatggcca tctatgaact atgaagaggc cctccccaga   40354
cactgaagct tctacacctc gatcttggac ttcccagcct ctagaactgt gagatgtaaa   40414
tggctgttgt tataagcccc ccgagtctgt agtattctgt gggagcagcc ccaaatgact   40474
aagtccacgg cccatcctcc acccactgag gccataccac tggaagggt atcagaggca    40534
gggttgggt cttagaggtc cagggtctct tgtccaggct ccccagaggc aggccccgag    40594
gtgtggacta gagtataagt ggtttatcaa ggaagtgtac ccaggggagg tccagataca   40654
agtaggaggg gctcaagcac agaggagcca gggaaggggg ggctctggac cgaaaccatg   40714
tccccctccac ggctttggac ttagccccctt ggggacacag acgtggctgg ggatgggtca 40774
caaagtaacc agggtgactg ccagcctgaa ctctgggctc tccagacttc tggggaccgt   40834
```

```
agtctcagcc tgagcagctt tctccaagga gggtcctgga aacctggggc ctgcccctga   40894
ttttgtcctg ggagcagggc ccctccatgg tgttctggag ccccctcatat agctttttga  40954
ggttgattgc ttaattttca gtttggagag ccagcagaca tcttgttggt agtttgaaat   41014
tggccagggc aggggtattt ataccatgga agctggcagg ggctgccttc cagaacctct   41074
ctccctccag gtgcagggaa acacggacct gcacaccctg gtggctttca caccttcccc   41134
tcctcaggcg gctcgtcccc ttgctcagtt atactgatcc ttgggcttgc aggcagaacc   41194
atctctgtca tccagaatct ccctagtaac cccaacccca aaagtgggct gccggaagag   41254
gcagatggca gtgtcccagg gctatggaag ccactgataa acatcttcca acaaacagga   41314
tcagggatct gcaaagtttt ttttttttgt tgttgttgtt ttttgagac agagtcttgc    41374
tctgtcgccc aggctggagt gcagtggtgc gatcttggct cactgcaacc tctgcctcct   41434
gggttcaagt gattctcctg cctcagcctc acaagtagct gggattacag gtgcctacca   41494
ccacaactgg ctaatttttg tgtttttagt ggaggcggtg tttccaccatg ttggccaggc  41554
tggtctggaa ctcctgacct catgtgatcc acccgccttg gccccccaaa gtgctaggat   41614
tacaggtgtg agccaccgtg cccggctgga tctgcaaagc tgttgaaagg aggagtggat   41674
aggattacaa agttggcctg attctgctaa atgaacattt caacatgttt ccctcgtgc    41734
accgaggagg catgcactct cctctgaggg tctgaggctt cttcacgga gctttgtaa     41794
accacttctc cccagcactc tggagtgggg gagtcacgta gggaagtcat ttctctcctc   41854
ttggacctct cagtccccctt tggcttctcg ctgataccag gcagtcaggt ggatcagaga  41914
agacatggac tctggagctg gatgtctggt gcaggcagtg tggcttcagg caacttgctt   41974
tgcctctctg ggcctcagct tcctcctgga aaatcatgat gctcatacct agggtttcat   42034
gggggtcagg caggacagtg caggtgcagg tatgagcacc atcccatcaa ggacatagtc   42094
ctggctgctt tcagtgatct tggtgctggg gaaaatgggg ctgattctca tggaagagga   42154
aatggattca tgtgcccact tcttaaatgg aaattcaagg ccttgatcgt ggcccactta   42214
tgaggtgggg actagtgagg cttcaggtgg tgtcctaaga ttagaaaact ggagcattca   42274
gttgggagtc agacctctgc tgatgtgctg tgtgacgttg ggcaaggtgt gtgacttctc   42334
tgggcccttgt gttcagtaga agcaggtcat ctttcaatag acctccttcc cagaccctct  42394
cggatgctgt gggcatccag ctggccccca tgccacacct ggcttctcgg ggactggcct   42454
gcattctcac acccgttctt tctgcaacg atgggcattt gtttctcccc tgccagcaaa    42514
ctcctttgga ccaagaattg atgccatggt gttagcatac aataaagctt caaggagctg   42574
gtgaaacact ctgagacggt cataaaattg gcttttcatc cctgtcggag ctttcttatt   42634
acagacaaca agcagtgtca gggagcagca cggtagatgc tgcttaaccc agcagcaggc   42694
gagactgagg gggtctcgtg ctgtttgtca ccaccgcctc tctgagatca tccccaaccc   42754
atactgttga cattcactgg gatacctggc tacctgtttt gggtttcctt acaattttt    42814
catttgttta atagtttttta tttttcaaag tcttaaaaaa cacaagtcag tgaaagtttt  42874
ggtctttgtt actgtcttcc taccaggtac gagggcctga aagtcactgt taattgatta   42934
ttgattatct gattagaacc gtacatttac tttttaagga aatgtgaaaa ataagcctag   42994
aaatgaaatc aaaagtgcgg tgttgaagtt agaaatggca gcgtcacggt caggaattaa   43054
agctgctgct tctctgtcac atggtatacc acagggggtg gtagctacag cccatgggca   43114
aaacttggcc cagtgcctgt ctttgtaaat aaagtttgat tggaacagag tcatgccat    43174
gtatctacac attgtctgtg gatgcctttc tgctataatg gcagagttgc agagttgcca   43234
```

```
aagaggacat atgtcccacg aagcctaaaa tattggctat ctggccctttt gcagaaagaa    43294 tttgctgacc cttggtatag aggaaagtta gtggcacaag tttagatcgc ctatagtgaa    43354
agaccttgca ggaccaggag tcaggcagac ctggggttcga aacccgctct gccacttcct    43414
ggttgtgact tcaagctgct tgccttttcc tctcagggtt ctgtttctgt ctctgtcaaa    43474
tgcagccaaa tactgcccag tttgcacagc tgttttttgga gacagagaca ctcagcaagg    43534
ggtccagccc ctggtgggtg gtatcccaat gtcactgttg gcatttgcag tgtcagtgat    43594
gtctggctta ttcatcaggc cctcttgagt ttgccccaaa cgagtcaacc ctccagggct    43654
gtgaaacttc tgctgccttg atacgatgtg atttccgaac cagaaaaatg gaggaggccc    43714
tggcccctaa tgcttaagtc acaggtgact ctgtgcaatt ggtttcttcc ctgtctcctg    43774
tccctctaaa aagaaccacc tgagctcccg gactgtgcta tatccaggcc taaaggctgg    43834
tggaccagga cacagtcacc agcaatcagc tttcatcgac ttggctggac cttggaaact    43894
taaggcttgc cctgccctgg cttcttgcgg tgagcaggtc ttatggagtt gctctaacca    43954
ctgtccatcc aggccggggt tagaggatcc aaacacagcc atgttgatgg aacctggag     44014 gcaaatagag ggcatgagac cctcctctcc tgaaaccttt ctggccttct tattggatac    44074
ccaccaaaca gtcttgatct taaaactttg tgcaaagcaa taggatgaac ttgtaggaca    44134
tgcataaaga ggaaggtatg gattgtgaca tgaggctctt agggatgctc ctcctacagt    44194
gctgagtgac cctcctcaga ggcacaggtg tgggcacagc ttgttctttc aaatcctggc    44254
accccagctg ttctgctgtc tagctcgttc cctcattgac aaaacaggaa taacagtgcc    44314
cacctccttg ggctgttagg ggatcaactg agatgctaag tcatccagga gggggagcct    44374 cttttcccaga gtcctgcctg tgcccggtgg ctgtgcagac ctgatacccg cagccatcta    44434
cctctacacc tcatgtgtgt tagagaacac cactctgatt tcagcctctc agactggggg    44494
ttcagtcact ggctgctaaa agcttcctaa agccaaggcc tctccttgcc tccaggggct    44554
ccgtgtctgt tagatgtgta aacagatcca tcaccgagca tactgatgag tcctggccta    44614
gggacaagca tggccacaaa tgaggtgtct ggaaagggct cacaggggaa ggagccactg    44674
aggagggcaa gaagaaggct tggccaggaa gatggggtag ggctcattcc tggcaggtcc    44734
agcctatgtg aagcccagag acccagtgag gggcttgccc atcctttggc cttgctggag    44794
ccaagggtgt gaaatgggag ctgagagtag gatgttagta gcagtggctt cctgggaagg    44854
gcccccacat gggagcctct ggcctggttg caaatggcag gaccaaggag gtggttgttg    44914
agttagttgg aaggcactgt cctgccagga tttcccacgt cctcgtttga gcattgagat    44974
gctgaacgtt aaactgtcct tcattctcca gctcagttct tttattcatc caacaaacac    45034
agagtagcta ctgtgtacca gatactattc taggcactgg gcatacagtg gggcccccag    45094
ctcgtcctgg cctccagcc cagtgggtgt ggagcagtga gcaggaggac ctcgagtgtc    45154
acacttgctc cccttggtac acattggcac atggcgttgc caggtcagat attctcttct    45214
tggggttcac cagcatcccc cttggatgtg ccctccgtgg tatgtggccg cttccatctc    45274
agtctcaggc cgatggaaga tattttcaaa attaacttag cttttggaat tggttcctcc    45334
ccatgttggt gctcaaagac tccccagtga gacagctgcc tccttgagct ctgtgtgcaa    45394
aacttgggga gcaagacttg cttgagccag tgtttggcct ggcccaagct gttgggcctg    45454
cagagcctca cctgcccctg tggctcaggg cttggtgtct gaagtggatg gaggcagctg    45514
aactggtttc tccagggccc catccagcct gcgtttccca ggctgctgtc ccagctctgc    45574
tccacccaag tctactctgc cgtcccctga tactgacact gagtgtgttt ctgaacactg    45634
```

```
caggggggtga ggaataaggt gggcatattg tagcttcagg aggtgatgct tgtgtctgaa    45694
atataaggac cacaattgcc atgcaggtgt aaatatctcc agtgattaca catttccctg    45754
caccgaccga gtggctgcac ccagtctggg gctctgtctc tcctggtcag tctgttcttc    45814
ctgaagccag gaacacagga gggcaagttt ctctccatcc ctagtcccac cctggagcca    45874
gcacacagta ggctgcagga agtgctcgtg gaacaaacac aggcagcaat ggaagaatcc    45934
ccaccactgg gattttcagc agctgatcgt agaagggagc tggactgcaa ggccgtctcc    45994
gaccgcctcc ctctcactgc ccagctggct agggtgatga gtatggacga ggatggaggc    46054
aggctgtggc tgctgtctca tccaagtagc cttttcctga caccccaagg ctgggcagag    46114
ggactgagtt ggtcccaggg cggagcctgc tgggaaggaa ggctgttagc cgctgccttg    46174
caggtgccat agcaatgcca ggcagcccac ctgctccttg gattagatgg gggatcagag    46234
ccgtgaggga agcaggcctg tacccaggaa caggctcatc ccgcccctgc cctggcccgg    46294
tactgatgga cctggagcca tagagtgcct ctccccgcaa cacacatgca catgcatgca    46354
cgtgtgcatg cacacacata caccacatac acaccacaca cacacacccc acacatacac    46414
acataacaca cacaccacac acacacacac acacacacag ccaagcatcg attctgggcc    46474
ctgttctgta tgcacaccaa ttttcctgaa cagactctcc ttgtcttcta gcacccggga    46534
ggattcagaa gtgtcctggc tgccctgtgg tgatggggat ggcagggacc tgcattttg    46594
tgagttcctg cacgtgatga aggggaaatt gcaactgccc aggcagcctg tgcaaaaagg    46654
cagtgggttt caagtgtggt cataaaccaa aagcctcagg ttcacacgtc atgggggagg    46714
ctgagggaa cacacagcct ctgagctgtg ctctcgggct gattctgagc tcgtgctggt    46774
ggggacaccc ccagacttcc agcagcactg gatgtccctg gatcctcaca tgactcatga    46834
ggaggggctg gcatgttcct gaacttcagg tgttgactct gcagtgaggc gatttggatc    46894
agagagactg tgcaggtgcc caggacacat agcaggtgag gtgcacagcc aggcttggct    46954
agcaattggg ctcttaatga tgctcacact ggacgtgtca gagtgcctgc tcctgggcgt    47014
gcacagcctt gtgggagggg ccgacaggtg gacaggggaat tatagggtgg ggggacaggg    47074
agctgtgctg gctgttgtgg ggacaccaca gggaaggccc cctgactctc atgttccagc    47134
attgccactt cctgtcatcc tctcggcaac cctatatgaa tgggaatagg agtaagtgct    47194
ctgtaaagac tcctctggct gccaggcacg tgctaagctc tttgcccaca ccactcaggc    47254
attcttcatg atggccctaa aagtagagac tcttgtgtcc ccatttttaca gagtaggaaa    47314
gtgaaccta aagaggctgc ctgctgttct gcggccacgc agctgggcag tggcggcatc    47374
gggatttgaa cccagaaact ctggctgtac ggtcttagcc ttggctcact ctcacctcca    47434
agaaatagac tctgagcagt gaggtgacgt gtcccaggtc tcatgggggc tgagggatct    47494
gggaagggtg atttgccccc acccctgcat ctcccacacg gtcccatccc tgaacccttg    47554
cacacacggc ccctctgcct ccatgccctt ccctcactt tgtcaaaccc cagcagctgt    47614
tcagcaggca caccacagcc gcctctggag gaggcattgg ctggtctcct gtgtcaatgt    47674
atcgacactg cctggcgagg tctggctctc cggcctccct gtgtatccac aggtctccc    47734
agctctgcaa tccctttagg gcaggctcag gtcagtcatg ctatggtcac ccctcagtgc    47794
cccgacatgc tcagcagtg tccggtggct tgaatggagg accacaaact gtcctctctc    47854
tgcagagggg ccccaggtca tatctgctga cttagcaccg cctataagat ttaaagacca    47914
ctctgttttc acctggagga accgtcagct cacgcaggat ggcaggtggt tttcagggc    47974
tccacagtga ggtctccagt tcatcttttg atgagggtga tgatgggaca gtggccctga    48034
```

```
aagcacatgg ctctagagtg cttaggagcc tggtgacctg ctgctgtgac ttcctctcca   48094
gagctggagc tccaggggct gaggttcccc ttccctgggc agcccttcc tcctaatccg   48154 gctttccctg tgaggaagag cctcctggcc ttaagccaca tccttagcag cttctgccgt   48214
ggcccttcct ccagccgggg accctggcag aatgcatggg caggaggagg tgccttggcc   48274
ccaggacagc caggtgggca gtgaatggac gaaatcagtc tgtgcaggag ggaaacacta   48334
acactaaccc taaccctaac cctaacccta acacattctc aaaacatttg attctaactt   48394
aaaacacaca agggcactcc tttccatggc cctactacat gatctggcct gacctgcctt   48454
tctggcctct gctcatacca ctacctccct gatctttcag ttcctcaaac acaccaagct   48514
ggttcctacc ctctagctcc ctcccactga ctcctcctca ccctgagatc ctcctcagct   48574
tatcaaaaaa agattccccc attttctcac ttcaacccctt tgttcatttc ctccaaagta   48634
ctgtattaca gttaatgatt attttttggg tctgtttacc tgtttgggct tcgcctcccc   48694
agtggtatgt aagatcttta agggcagggt gcatgtgtgt ttcttgcttt ccaaaatatc   48754
cctagtgggg gccgggtgtg gtggctaatg cctataatcc cagcactttg ggaggctgag   48814
gtgggtggat cacttgaggt caggggttcg agaccagcct ggccaatgtg gtgaaacctc   48874
gtctctacta aaaacacaaa aattagctgg gcgtggtggt gtgcacctgt agtcccagct   48934
acttgggagg ctgaggcagg agaactgctt gaatccggga ggcagaggtt gcagtgagcc   48994
gagattgcac cactgcactc cagcctgggt gacagagtga gactgtcttg aaacaaacaa   49054
acaaaaaact aaaacaagaa aaccccccaaa atatctccag tgggtagcac agagcctgac   49114
acacagtagg tctgcatgaa tatttgttga aggaatgaaa cagtgcctgg atgagtgtat   49174
tgcagcccct tccaggtagg gcacagccat cggggagcca gcgtgacaga tgtgagtgct   49234
gtggccctgg gatgcgatga caaccccttc tcactggggt gtaccctgga ttggggtggt   49294
gcatgtagaa tatatggcat gctgctggca cttggcaggt gctctgtcaa ggttagttgt   49354
tgttacttaa aaactctaat caagtaagca tgacatatac tgaggtccta ctgtgttact   49414
gttatgggct gaattgtgtc tgctccaaaa ctcacatgtt gaagtcctaa cccccagcac   49474
ctcagaatgt gactgtgttt tgagacaggg ttttcacaga ggtacctaag gttaaactgg   49534
atcattaagg tgggccctga tccaatatga ctgtgtcctt ataagaagag gagattagga   49594
cagagacaca cacagaagga caactgtgtg aagcacagg gagaagacag ccatctgcaa   49654
gccaggagag aggcttcaga agaaaccatc ctgctgacac cttgatcttg gacttccagc   49714
tccagaactg tgaggaaata gatttctttt gtttaagtgg cacagtctgg ggcactttgt   49774
tatggtggca ctagaaatga atacagttac caaatttaat ttttcaagct ctctctagca   49834
gcaaagtatt tcccccatat aaaaaaatga ggacgctgag gctcagagag gtgaactcgt   49894
ttgccggagc cacagggctt gctggcgggc gttggcactg atagttgaac cctggtccac   49954
tagtgtgcct ccagagatgg tgcaggccac gccgtctgcc ttggtctcac gcaagtggcg   50014
gctaagccca gaggcacttg tctccatttc agtgccctgc tattggctgg ttagaaagtc   50074
aatattttat ggagcctcat caacctccca agtcttgggt ctcaattccc ccttttggtg   50134
tgagcctctg aagactggtt gagcatttgt gagaaacaaa gttttgacta ctcaagactc   50194
tagttaaaaa aaaaaaaaaa ttgcaccaat gtgccatccg gctgcagcgt ctcagggca   50254 tgattcggtt tttgcaacag ggagtagctc ttcttgaaac attatgggat ttcttcctt   50314 agttgacttc acttacattc tgctcagcac atgcaaagca tttggttatc gggaggcaga   50374
gtaagatgac aaccctatta ttgaaggtaa gcagacctgg cctgttcaca aagcccttt   50434
```

```
tacatcttgt ttcattctgt taccaacagg gtaactgtga agtgggtggg caggaactgt    50494
gacttctttt caagtctcag aagatgtcag tcccccaggg aggctggcct ccgagtgcca    50554
gtgcaggtgg ctcccccteg gccgtcctat gccacgtgcc ctctcctcgt cattctcagc    50614
cccctcgcgt ctggagtcac ctcgctggtt tatcgtcttg tggtccatct gcccgtgagc    50674
attccagcca ggtctgtggg cttcgttttc acggccgcca ttttggctgc ccgcagagtg    50734
cctggtgcaa agcggatgac actcagtatc tagagcggca cttccgggta atccacaaac    50794
atttatcaaa cacttaggtg tcacttgggg tgctcggaat tgcaaacatg aggacaaacc    50854
ctcactccat ttggggcctg cagattcagc aagagtggaa aaaccagctt tttaaaatgg    50914
cagcctggga atcccagaat taggaagcac aagcttgtct ttggcaggcc aggccagctg    50974
ctgacccgca cggccttcag gggccagcca gtgcgaccat gattgaatgc acagccctga    51034
ctcctttgtg gcattggctc ctgggtccag gtgggagcat ctgattggcc cccactggtc    51094
atgtgctaac caggaagtgg tgtgtgatgg gctgagccta gggctcatac ctgcatgtgt    51154 tttggggggaa acagagagaa aggtgtggcc tctccacttc tgtggacacc caaatagga    51214 agaagggtgc acacaaagca ccgcttcctc cacgaagccc tcctcaggca catcgaggag    51274
aaccagctgc ccaagctctt ggctgctgcc cttctgaggc ctgcctggta ggtggcgtag    51334
gaggaggctt ggtaagcaga tgatgggaca tcatctacca catcccatca gtaacatcca    51394
acaagtgtgt gtgccagcac agacctgggc actggcatgt cccagccgtc attccatgtc    51454
aaatacttat ctgtgccgtc atcgtcgagg tctggttttcc aactctatgg ctccattgtc    51514
tcaggtttaa ccagtcctct tattgggcat cagcttttcc attttttgctc tgtgagaggt    51574 tgttgagtta gttggaggac caagcccata atttcctgga tgacagttcg tgtcccgcag    51634
atagagctta accaacagtg gttcccttttc cagacctaag caggtgggag tcagagatga    51694
gcatagagaa agggtgaagg ggtgcctctg gattcccaag gcagggacat agctggggga    51754
gctgcctccg gactcgcaag gcggggggtgt ggcagacact ttgcagaaaaa agtacatctg    51814 tccttggggc gagaggccgc acatgcagcc ccaagtccct ggacctgtga tcctggct    51874 gcctgctgtt gatagaacgg gacaggtggg gggatgcttt tgattcatgt acggtgaatg    51934
atcttattct cacctttatc actggtggca cattctgatg gaaggagaca ttggcagtgg    51994
gactgggcaa gaaacaggtc atttgtcatg gctgtgtgcc agcctcctgt cgttgcacag    52054
cctgtccttg ggaagtcttg ctcacctgtc atgtggagta gttgtatgtg tgtgagtgtg    52114
tgtgtgactg agagagacat acacatatgc acacacgc agaagtgtct gtacctctga    52174
gaatatagtt ctccagagga tgcagaaaaa ttggggattg cagactgtcg tgcgtttaaa    52234
tgtgtccttc tctcaagaat aatgtccact tggaacctca gaatgtgacc ttatttgaa    52294 atagggttct tgtgtatgtc actagttaag ttgaggtcat attggattcg agtgggcctc    52354
aagtccaatg gctggtgtcc ttctaaggag aggacacaca gagacacagg gagaggaagg    52414
ccgtgtgatg acagaggcag agattggggt gatttatcta cacaccagaa gccaggaggg    52474
agtcagggag cggctcctcc ctcagagctt ccagagggag ccaggcctgc ccacgctgtg    52534
atgtcacatt cctggcctcc agaactagga gaggataaag ttcgattgtt ttccagctgt    52594
ctgtgtgtag taatatgtta cagcagccac aggacactga tacccagaca catcccaggc    52654
cctaacatcc cagaagagga gtccctgata ctcctctttt gcaaaatgag gtgtgggctc    52714
agagcaagtt cgattttctg tgaagggcct gatagtagat attttagact ttgcaggctg    52774
tgtaaatctc tgttgcatat ttttctttttc ttttctcttc ttttctttttc ttttctttct    52834
```

```
tttttagac agagtctcac tctgtcgcct aggagtgcag tggcagtggc accatctcag    52894
ctcactgcaa ccactgcctc ccgggttcaa gcgattctcc tgccttagcc tcccgagtag    52954
ctgggattac aggcacatgc caccacgctt gcctaatttt tgtgtgtgtg tgttttagt     53014 agagatgggg tttcaccacg ttggccaggc tggtctcgaa ctccctacct caggtgatcc    53074
gcctgcctca gcctcccaaa gtgctaggat ctgttgcaca ttttctttg tttgttttgt    53134 tgtcatttgt ttgttgtttg tttcacaacc ctttgaaaat gcagaaaaca ttcttagctc    53194
ttgggctggg tgtcactgag tttgccctag gggaaccctc accgcatgcg aagctgagtg    53254
ggcacggttt cctccgctgt caacgggaat attgatggtt ccctgagtg aggacccagg     53314 ggaagcactg ggctggtgcc cgcctcctgt ctctgtgccc aggcctactg tctgcttcac    53374
actttactcc ccagaaccag gcatggcact tagtacaggg caggccgagc tcggggaga    53434 tttgcttgaa gaatgaggaa cgtttctgga agcctctctg accacccagc aggcaggggc    53494
aggtcttcct ctgagaccca agtcctctat gcttccctcc atcctagcag tgacttccat    53554
gacacaccat tgtcccttg ggagcacagg actctggctg agtcatctct gaagtgaggt     53614
gaacccagca cagggactga tggcttggga agagcagctc agcctatgtg ggggtgttg    53674 agggtgccca ggcccagggg cgatttgatc ccaccctacc ctagcgcagc cagaatgctg    53734
gggccgaggt tcacctggga gatgcaggag tttagagaag aggaggagga tgtttaagcg    53794
tgcgagctgg tgataggagc gtggagttgg agctagaccc agacttgaat tctggctttg    53854
ctgcgtggca gcagctgtgt ggcccttgat gagtgtctta accttgctgg gctttggctt    53914
cctctccagg agggcatagc aagtcctgcc tgttagggcc atcctgagga tggggtgacc    53974
agagcatgag cagccgggtg cccagggcac ctgggcaaca gccctgtggg taggtgggtc    54034
tgaatggttg agccccacgt tttagtcaag accactctcc ttgcagagca gttcatgtcc    54094
acttgcccac atccttcctg tcccagcacc gtctgtaggt tgctatgatc acccatttt    54154 acagatgagg aagcacatgc ccaaagaagc aagtgacttc ccaaggcggc aaggcaaggt    54214
gaggggcaga atgaggaccc caacccagtt ctccccaccc cctccttccc ttccagagcc    54274
cctgcctgct ggaggcattg tcccagcggc agagggtcag gccacatctg ccagagctaa    54334
ggggagtctc cgtcatctca aatcattggg tcaaatgaca gaaatctgct ggcatgctgc    54394
cttttgaggc tcggcgactt ctctgaggct ttcctgatgg ctgctctggg tgtctggaat    54454
gagctgtgga cgagggccgt cctctgagtg accatgcccc ccacgcagcc gaggttcccc    54514
tctgcctggc tcagtgcggg ttctgagaaa gcctgcctgc cctcactgga ggcacctctg    54574
actcactgct gcaaggatgt ggccatggac tggggtcccc ggggccccc gaaagcctca     54634 gcaggagaac atgtttatcc agaagcctgg gcaacaccca gagggtcctg gcatgggtgt    54694
gccaggcaga ctgggcatgg aaacatgccc cgtgatgtct ttgggatcct gggagcctga    54754
ggcttgttct cagtgtgtag ggcaggggct gggtgccacc caaggggggc aaactgaggt    54814
cacagagagg gaggcagtac ccccagaaaa ggtgattctt ctcattggaa gattcccaag    54874
gcccaaggcc tgggtcagca gacagtggaa caagggtaat ggtcatgtcc ttaattcacg    54934
taaccccgag gtgggtccct gtgaaaatcc cgtggatggg gcctggtgat ggctacactt    54994
atattctcag aagcagcatt accacctgga cccttccctt ttctcttact ccctcctcct    55054
cgtggggtct gcaaggggt ctggtaaatg gcatccccct ccccgcccag gggctggacc     55114
cgtggagcat aagccaaaag gggcggcaaa gagagacacg gaacctcact gccactgccc    55174
agctgccggt gctgcaggac ctggcttagg ttcaggggcc cggtgggctt ccccagtgct    55234
```

```
ggaccccagc aggcaggtgt ggagggagca gggggtagtg gagcagagta cagtggcccc   55294
tggctgttct cccccaggaa gagaggagag gcggggctgg actctttccc atctccctcc   55354
ccaatactcc agcgtcagtc agtctccccc cgacaggggg aagggagaga ggccaggagc   55414
cttcccctgg ggcacacaca gagagcccag caggcttgga agaagtgtct ccctcctcct   55474
ccagccctgc cagatggtcc cagccctcct gcagggttcc cgaagtggaa ggatctggac   55534
tcagagccca gtgctgctgc ttggcatctg tggtcccggg ctggagggcg tgttggcagc   55594
tcatgcctgg ccagcgcatc ggggtggctg cagcagagga tggggagggg gagcagggac   55654
aagaggagcc tgcaggctgc tgggtgcagc cagggcttct gcttcacccc gggggtcaca   55714
gctgctttct gttgggaaag ctcccactgg aggtatgggg taggcagtgc tggagaccct   55774
ggtggcaagt gctgagctgg ggcacaggtg aggatcagga ggagctggga gggacatccg   55834
caggttgtgc tgatggactg cctctgagta ttttcacggg atggtggaaa gaggctttga   55894
gtcagacctg ggttcgaatc ctggctccta ctcttggtag cagtgtgact ttatgtgacc   55954
tttctgaacc tcagttttct ctgttgtaaa atggggaaaa ccacacatcg tgggggcngt   56014
tgtgtgcacc taaggaagcc accccagggc tgggcacacg ggtagccgat tgtcatatcc   56074
ttgttatgga aggttgttat ccttgttagg ctggtgggca ggggtggtag aggagtaggt   56134
tgtttttgga aaatggtgga cttagtctta gacatgttgt gtttaaattg ctcatgagaa   56194
atccaaatag aaagacccag ggtgacagca gggactgcta ggaacttggg ataaaaaatt   56254
ggtcctgggg tgctggtcac tgatcctgtg gataaaggag ttggggtgct ctgtttgggt   56314
ccagctggca gagttggacc agttgagaga aacttctagg aggaaggttt agaagaagaa   56374
tgctttcacc atcagagcta tcttaatagc tgtgtaatgt ggtagtgagc tccccatcgt   56434
aggaggtatg tgagtcatgg ctggaggact acttggaggt ctgttgtaga aggattcaga   56494
caccagagag ggttagactg gatgaccttc agttcccctc ctgggtgacc acagctcttc   56554
aaagcccctc actgctgccc gcttctgcag gattcagggt tgaatgtcag aagtctgctg   56614
gaatgctgtc gattgaggca cggtgacttg gccaagcctt tcctggtggc tgctctggta   56674
tctggaatga gctatgggtg agggccgtcc tctgagtgac cgtgcccccc tcacagctga   56734
ggttcccctc ggcctggatc agcgtgggtt ctgagaaagc ctgcttgccc tgactggagg   56794
cacctggagg tggttttcaa agtgtcactg tcaccgtgac ccagacatgc ttgagcccca   56854
ggctgggaaa gcttttttttc tttgctttaa aaaagcagaa acagtgaagc aagcataaat   56914
ttgcctttga aataagaggc tgaatgtctg ccaaatgcaa atggattgaa atggccggtg   56974
gtctgacctt gggatgttcc attggtagtt tcagaggggc tctgagcccc caggccggct   57034
gtaacagtgg acatgctggc gctggccagt ttgatcccct tgaaagcccc ccgatattca   57094
cctccaagag agaaggccct ggcaggtcct ccagcatgcg gacgaggcgc atgcactgtg   57154
aggcagcggc tctgtgggag gacgggggcct tttgtccact gtcctggcat tccatggccc   57214
tgtgtcccca gatatccgca cctgttcctg acaccatccc ttcctgtcgt gtgagcgaga   57274
tgctcttctg tggaacctgg gttcctatgg tcactgggag ggtgaccctg agttcacaga   57334
gaaaggggag caggctgttc aggaaaacta agcacatgtg gtgagcatcc acaggcggct   57394
agggatggaa ggcttttcat ccgggctttc agatgaggcc cctgaagctc agagggtta   57454
ggcaattggc ctgaggttgc acagccagga aggagtgatg gcgtagtgat tcccattggg   57514
ctctcccacc ccctgttcct ccctccatcc agcccaggcc ctcgtggata cattaggagc   57574
ccaacaagag ttcccctccc ttctccttg cttctctgag cctcggtttc cccatccata   57634
```

```
taccaggagg aacccoctgc ccatctcnta gggctctttg acatggtgaa atgagatcca   57694
gatactggct gtctgtgtca actgtaaagt gctgtcctga gtgaccagtt gttgttggtg   57754
cctgtagcca tccttgaggc taaaagagac tgctgcttgc ctgatgctcc tcccgccagc   57814
ctcctgcttt ctgcgtgact tccctcgccc cagcaatgaa ccctggagcc acctgcaaat   57874
gggaaagctc ttttgttagt ttccacagaa tgcccaccgt gcacatgatc agagagtttg   57934
cgagcctagc tcaggtcagt ggaactggtt cttttcgtac atgtaggaag taatgcaggg   57994
tgctgccgaa taaatccact gcctgcctgg cctctgatga acttaccagc tcacgccagt   58054
tctagctcca gccaggagga ggaaaaaggc atactaggcc gtattttgtt tctttcaatg   58114
tttatttacc tgtacacaca cacacacaca cacacacaca cacacacaca cacatacaca   58174
ggcaaaactt atgttactgt cccatgcata attctctaga tttgggccac atagatctgg   58234
ttttggccat tgactggcaa catggcagta gccaactgca gagccaccag ggagcagcct   58294
cattctgatt gagtataacg aagacgctga tgggaaagag agacacgggt gagcaggggc   58354
tgtggggcat catgagagtt gggagggtcc ccatcgtgga gctggccagc cctgagtggg   58414
agccccggca cagtcctctg ctagctgtgg cctttggcca gtctccactt ctcagagtct   58474
cagtgacccc agctgccacc accaggattg ttggggtgtc caagaatgaa aatagggtc    58534 atccctggcc ctcaggggat atgtgggctt cccctcatc atgaatggaa caggtgagtg    58594
ctgtggtgca ggctgagagg cggcagggtg ttctctcaca gcagggtcgg gtcttgctct   58654
gataactgca ccaggacaaa catccccagc ctctgggatg cacacccacc agcatctgcc   58714
cggcaggttt aattaccggc tgagatgggt tgtgttgggc tcactaagta tgctccataa   58774
gtgatgaaat tggcaagtt ctcacctctg gaggctctga ccccgagtag ctttgaccct    58834
gagtagctga aggaacaggc agttcagcct ctgcttatgg gctgtgtgtg cacacatgca   58894
cgagtatgag agtgtgtcag tgtgtatcgt gtgaatatgt gtgcaggtaa gtgtccatgc   58954
atatgtgtaa gtacatgaca atgtgtgtgc gagtacatga ctgtgtgttt gtatgtacaa   59014
ctgtgtgtgc acatgtatgt ccgagcacat tggcgtgtgt gtgaatgtga gtgtgagagc   59074
gtgtgatttc atgactgtac atgttcactc tgtttattct cggggaaat agcaggcaat    59134 ctgtaagaaa atgactgtgt aagtttcatg ggtggaggct tatgatactg ttagagtcta   59194
tcttagtctg ttggtgctgc cataacaaag ataccataga ctgggtgatt cataaacaac   59254
agaaacattt ctaacagttc tagagctggg aagtccaaga tgaaggtgcc agcagtttcg   59314
gtgtctgttg aaggccctat gcctggttca caggtggcga cttcctgttg tgtcctcaca   59374 tggggaagg ggcaagggag cttttgtagg cccttcttct aagggcacta atcccattca    59434
tgggggctcc accctcatga cctcatgacc tcccaaaggc cccacctcct aacaccatta   59494
tcttggggtt agggtttcaa catatgaatt tgagggaca cagccattcc atctgtgacc    59554
gtcctcaatc agccttctcc ctgcagggct gcaaatgagg gtgctgccgg attcataaga   59614
gaagatacat tgtaacatcc acagcacaca ggcactaggt tgggagcctt ttccagcact   59674
cagatcaggg ttcaaaccct aactgtgccc ttcaggagct gtgtgacttg ggcattcctt   59734
cattttttat tcaagcacac agctggcatc tacatgcctg ctgtgtgtca gggagataga   59794
aatagagggg tgagccctg tgatattagg caggcagctt tccttccag ggtctcattt    59854 ttctcactgg tgaaatgagg gcaggggctc ctcccctggg gttactttga ggggtcagta   59914
aggtgaacag ttcagtctc ttgcacagcc cctgaacgtt gtttagaagt caatactctg    59974
ttccatccca tcagcttcct cttcccttgt tttgactggc aaatagtcat caccttctga   60034
```

```
agtcattaag agaaggtctt tttaaactat tatgatgcca tcaaaactga cttttgatcc   60094
aaaatatctt ttaaacaagc tgaccattca gtgaggattt gccaggctcc tttgtgatcc   60154
atccttttgg ggccagggtc tgtgggccc agagctggac atcatggaac tagctctgag    60214
gagctcatgt tcaggtggga cacagtctcc tggaatcaca gttctaagca cttttccaact  60274 attaactcat ttaatcgtta attactacca tttcccagat gatgcaccag ggatgttaag   60334
taaccaagga atatggcagg gccactggga tagtgggctg ttagaaaagt cagggtggag   60394
gccgggcncg gtggctcatg cctataatcc cagcactttg ggaggccgag gtgggcggat   60454
cacgaggtca ggagattgag accatcctgg ctaacacagt gaaacccgt ctctactaaa    60514 aatacaaaaa attagccagg tgtggtggcg ggcgcctgta gtcccagcta ctcaggaggc   60574
tgaggcagga gaatggcgtg agcccaggag gcggagcttg cagtgagctg agattgcgcc   60634
actgcactcc agcctgggcc atagagcaag actccctctc aaaaaaaaaa aaaaagaaa    60694 tgaaaagtca gggtggagta cagacacaaa ttagagaact taagaggcac caacaagagt   60754 atggcagta taggagaaa tggaattagc acggagcagg ggcttcctag ggaggaatga     60814
tgggaggaga caccctcctt ctgctgctcc tgctgtgtgc cagcctgggc tgggagcgtc   60874
acgccatcag ctccagtatt cattccagcc ctgtgaggct ggcagcaggg tcctcctagt   60934
ggggctgaaa ggtgcaatgg tgaggaggag gattgcaggg gctggagtcc tggccccacc   60994
acttcctggc tgtgtgactg tgggcacgtt actcaccctc tctggccctc catttattca   61054
tcattaaaat gggattaggg gccaggtact ggtggctcac acctgtaatc caagcncttt   61114
gggaggctga ggtgggtaga tcacttgagc tcaggagttc aagaccagcc tgggcaacat   61174
ggtgaaactc catctctaca aaaaatacac aaattagcca ggtgtggtgg catgcgcctg   61234
tagtcccagc tacttggtgg ggctgaggtg ggaggattgc ttgaacctgg gagggttgaa   61294
gctgcagtga gcagagatcg caccaccgca cttcatcctg ggtgacagag tgagactctg   61354
tctaataaat aaataaataa ataaataaat aaataaataa ataaaacagg gggaatagta   61414
gtccctactc catagggctg ttgtgaagat ctagtgagat caatgttcat gaaggacttt   61474
ggcgctgcac acgtttctga gaaagggtga cctggccagg ctcactgggg tggtaagtgg   61534
cagggatggg cttctccacg tctcccctgt gatattaggc aggtgtatgc agttgcttca   61594
cgtccagcca caccccctca cacacctgca gaccagccag catggcacac cagacacatt   61654
tctgctgcac cttccccac acagtaccta ccacctggcg tgcctctctg cccatcccca    61714 tcttttgat attttacctt ccacctaaat ccgaactgaa atcccagacc tcactagctg    61774
gtgggtgcat ggggtctctg ctctgccact tctggagctg ctcctagtgc atgcccagt    61834 tactcactcg tggccaccac cccccgagtc aggggtcgag agtccccttt gtccatgatg   61894
ggtgacgagg gcatacccgg aacagagggc taattaaatc acacgctgag gtttgtagaa   61954
catgggacgc ttcattaggc tctgtgtgaa caagtgcgcc cagcctgctc ccactactcc   62014
agcagactcg agcctggtat aatcacagct cacactctgc ttcatcagct cgctgaggct   62074
gtggggaggg ctcacacctt tgggctctaa agagagtggg cctgaggtgt gggatcctgc   62134
ttctgagcag gggtgtctgc cccgagccag cttgcccagt ggtgtggagc tggagccccc   62194
tctgcttaag taaaggcctc tgaggacac atgtcatgca gatgatgaca ccagactggc    62254
tcctcacttt aaactctact tcctgagagc agaaggcagg gaaggcctca gttggaggtg   62314
aaaatggaac tttcatccac cagatgttag ataaaagata ggaagggtgt tccaggcaga   62374
ggggaaagtc tgggcaaagg cttggaggat aaaagggcac cgcatgtttg gggagcgggg   62434
```

```
catgttccct ggggccagag acctgagttc tcctcttggc tctatcccca gctccaccca    62494
tgacttgggg tgagtcctga accccgacca accttagtgt ctccagggct gggatatggg    62554
ggggtggcag cctctgatct gtggtcacag ggagtctcag ctgtggtgct cctgtgcctc    62614
cctcttgcta ctctctggcc agtgacgatg gcactttact ctcctgcaga gacctgtccc    62674
cagtgcctgc ctcctccagt cctcttcctc atgggctggc tgctctgggc acatctcagg    62734 gcagcccag aaggtgggct gagctgttat ttggggcgtg gggttctcgg ttcctccgct     62794
ccatgctggt gggcctggtg cctggcacca ctggcccgtc ttccaggaag ctcactgaca    62854
ccatcctgga tgggccttgt tttctctctg gcctgggagt cagctgcact ctcgcaggtc    62914
ctaggccaag gtgacctgct tgtttcattc ttgtctttct cctttgcttt atggtatatt    62974
tttaagcata agatatattt atttgtaaaa taaaagttca ttataaaatg atgccttaat   63034
taccttcctg caatataaca attatttggt tgtatagttc ctgttctccg tattttgtgt    63094
aataaaatgg acccaatggg tgctcacaa tgctgggtgc cacagggaac acacactgct     63154
gttttctcct ggatttttaa aatttttaatt ccagcatggt cctttttatat gtgctttcac  63214 tctagctgtt tgcctacatc tccacagttt tgattgtcca gggtggtgaa taaaatgcaa    63274
cacttggcat cttttaatgt ttaaaaaaat caacaagtat tttatttaaa ataaaatgtg    63334
aatatctgta atcctaaaaa aaaaaaaaaa aaagccacag gatccttgag aggccctctg    63394
agacagtgac accctgacc agctgcagcc ccctgtccac tccccaggct ccattctctc     63454
tacccactgc ctctgcatcc tccgcccttg gagtttctca gggtgccccg cagatcacct    63514
gtggcccaag tgctcaggga cttgtttaaa attcagattc ccaggccccg cccaggcttg    63574
caggcagcca gggccaagga atccaaatac taatcaagcc cactgtaatt gccctgcatc    63634
tgaggtctga aatcactcgc ctgctctgga ttatctgtgc tccagggtgg cctcagttta    63694
caccatccta cctccccatt gaaaccttac tgctcacgat ggcccaggtt cccacccatc    63754
ctgggagaga aagatgattg gctcagttct ctgggaggcc tggtgattgg ctgcctctag    63814
gagggtgtgg ctacctcttg atccaatcag tggagggcag catggggatg tgatcatgca    63874
gtgaagaacc tgtaccgggg gtagttaggc gccagggaag gggaggagga gaaaccagtt    63934
ctactgttag tatcagctca tctaacattt ggccctggt gggggttttt gcatcctttt     63994
gggggtctag gtctcttctg ccattttgtt ggcactttaa tttcttgtta acaaacccaa    64054
gagcacatac aacttaattt ttaaattccc aataatttcc agcatcctct aagttagtgc    64114
tgagcgatag aaatgtaacg gaagctgtac gtgtagtttt aaaacttctg atagccaggt    64174
tatgcacgta aaaagaaaca ggtgaaatta attgtaataa tttgtatatc caaaatagta    64234
taaactgtaa tcaatctaaa gtaattgaga cattttcat tctgttttc atattaaatc      64294 tttaaaattc ggtgtgtgtt ttatgcttac catacatccc agctcagact agccacattt    64354
caagggttca ttagccaccc atggctgtg gtccctgtac tggatagcgc agcactaaat     64414
gatggcttta ctttgtatcc ttggggaagt atgtatttt gaatccattt tcctcacttt     64474
tgaatagttt aagaacttcc cagtccattt gtctaagggt atttgacttc taaatgttgg    64534
gtttcttggc cgggctcagt ggcttacacc tgtaatccca gcctttggga ggccgaggta    64594
tgcggatcac ttgaggtcag gagtttgaga ccagcctggc caacatggtg aaaccccgtc    64654
tctactaaaa atacaaaaaa aataattagc cgggtgtggt ggcgggtgcc tgttgtccca    64714
gctacttggg aggctgaagc tggagaatcg cttgaaccca gcaggcgagg ttgcagtgag    64774
ctgagatcgt gccaccgcac tccagcctgg gcagcagagt gagactccat ctgaaaaaca    64834
```

```
aacaaacaaa aaaaccagtt gggtttctag caataaatgc tcataaaatc tgctggagtt   64894
ttggaggatt agtccattca tcctgacttg tgtcctgttt ctgctgggtc attgttgact   64954
tcccccactt gcctcacact tgtaaggcca tgtggcacac catcaacatt catctctgat   65014
taaggagctt gtttcttgta gtggctgcca taacatatta tcacacgttt ggttgtttaa   65074
acagcagaaa cttacactct tcctgttcta cagtccagaa gtccaaaatc atggtgtccg   65134
taggcctacg ttccctctgt agcctgcagg ggtggatcct tccttctcta gaggctgcca   65194
gcatctcttg gctttatggc cacattactc taagttctgc ttcggttttt acatcacctc   65254
ctcctctttc ccccatgtct tctcctctgt gtgtctctta taaagccact tgccactgca   65314
tttagggctt actcagataa ttcagaatga tcttctcatc tcagaatcct taattatgtc   65374
ttcaaagacc ctttttccaa ataaggtcac attcacaagt tccagggatt agagtgtgga   65434
cataccttt gttttttatt ttattttatt taatgtattt atttattttt gagacagagt   65494
tttcccctgt ttccctggct ggagtgcagt ggtgcgatcc cggctcactg cagcctccgc   65554
ctcccaggtt caatggattc tcctgcctca gcctcccgag tagctgagat tacaggtgcg   65614
tgccaccata cccagctatt tttttttgg cttttcttt agtagagaca gggttttcat   65674
ccaacagatg ttagataaaa tgttgcccag gctggtctcg aactcctggg ctcaagcgat   65734
ctacccgcat tgggctccca aagtgctggg attacaggcg tgagccctgc acctgccaa   65794
gagtgtgtac atatcttttg tggggcacca ttcaacccat tgcagtgagg tgtcagtgtt   65854
ttgacaggaa gaagcagcaa agaagacaaa tcagcacttt attttctaa gctttgaaat   65914
tcttaaaatg atagtgggtt aagaaagacc aacttcccca tggaaggtgc tggtccacac   65974
tggctgggtt tagatccctt tggctgaggt ttagatccct ttggagggga gtcaatttga   66034
agaagaagca catcagacac attcaggaag gcaaacccaa agacagcaga aaggcaagaa   66094
tgtctcaaat tgttcaaaaa taaatacgtt agttcttgta acgtgctccg aatagggtga   66154
ggctcaacat gagcacttaa taaatgctca gtttaattgt ggtaattgta attctcattg   66214
gtatatattt atgtcctgat cctatacctc tgttattaat gagactgata ataggtaagt   66274
gaagggaaaa agagaccccc ctgctgccag gaaacaaaac aaagtatcga gccaaatgcc   66334
aaatccataa gtcaccaaga tgggttttga tgacaaaacc tttctttctg gactcccct   66394
gcccctccgc gaagccgttc cccatggcca cgcttgtccg tggctggctt tataggccca   66454
tccttctttt atatgatcat caagatggca ctaatttggg tttgcaaatg aggttttcgt   66514
gatgttgtca tgtcagcatc tggattcaag aggggctgct tcccagaccc tgaccctccc   66574
ctgtggcctg ggagcaggcc cagcccctcc ctccatctaa tcactcccca ggaacctggg   66634
ggatttgcta atgggcccag gaagccataa agagtaatga aagtgctgtg tgactgctct   66694
gcacggggtt gcccttgggg tcccttcctc ataattaaat tcggaatcct ccttctgcct   66754
ttgagctgga agagagggtt ttatcctccc tgtggtctgt tcatcccttc ttcccccat   66814
tcatttgttc agcacttatt atccagttat ttgtttatca agccacagtt gaatgcctgc   66874
tgagagccgg tttagggcac tgagcttcct gttctcaaca ggcagaggtg ggagcagcca   66934
ggctgctgtg ggaagagcag agtggctatg gagccgccct gagccagctc tgctgtgcgg   66994
gagttctgcg acctggggaa cccgctcgct tggcttcctc atctgtaaaa cggggagact   67054
aatataatag cagctaccct ccagggggc tgtgagaatt aaaggggacg atggatataa   67114
actcccacac actgtcgggc acagggcgtt aatagcagcc ctcagtctca tgtcccactt   67174
attttgtgcc cgacacactt ctgagcatct tatgtctatt cactcattta atttgcccag   67234
```

```
taactctagg aaggaggtca cgtccatggt tcttattttg ctgatgaggc agttgaggta    67294
ggcagaggtg cggtgccttg ctcaagatgg cacagtggaa ggacacgggg cagggcggac    67354
ctgaccgcag ttggccctcc cttgcctgcc tcttagcacg catgcagccc cctcgcctgc    67414
tctgcccgtt gtgtctcaga atctccactg ccatttgcgg gtgccctgaa tccacctcgc    67474
ttttccgtgc ctccctgctt ttgtgcttgg tgcagacccc tgcttcctca tgggcacctg    67534
cctccttaga acccccttg gaatctgtta actacagctt cctgggccca caccagcatc    67594
cctctgcaac tcagaatttc cagggcccat aatttcctac aggcccctcg ggtgattgct    67654
ttctcagtag gcaacttagg gccgtccctc caaacccttta gagtgagaag cgtgctacct    67714
gggtgcttca taactgatgt tgcaaatgtt caaccaagtg taggaagtga acacactttg    67774
tatctgcaaa gtgctgtgca tacaagcgag gtcaggagca gctggcaccc gtccccaagg    67834
gtttccatgc ctctggcgag atagggtagg agtatctgca agtagctgcc ttcttggcca    67894
tggaagaaca agttcaacag ggcgcctctg tgtgcctgcc ccttgctgtg tacaaggacc    67954
ttgcacttca gggacatcaa ggcaccttca gccgggcttt ggggaacttg tgtatgggag    68014
gggggggacct ctaaggacct ttcctgtccc aaggagctcc ccagaagcct gttgcagtgc    68074
ccagcacccc agcctcatgg ttaaggtagg cagtccccag gagtccccttt cctgggacat    68134
caactctcct ggtgggaaca aatgctgagc acctcagcat gagatgggta cagtcaggga    68194
ctccacaggc aggtcatgtc acagacaagg tcacacagct aggtggtggc aggttggaga    68254
gagagggcag tccctgact cccatcccag tgctctttc tcccatgaca gtgacgggtg    68314
aaatggcaca gtgtatccct gtcaggcagg aggggatttg ttgtacttttt ttttttttt    68374
ttctgaggcg gagtttcact ctgtcaccca ggctggagtg cagcggcgca atctctgcac    68434
actgcaacct ccgcctccca ggttcaagcg attctcctgc ctcagcctcc tgagtagctg    68494
ggattacagg cacccaccac cacgcccagc taacttttgt attttttagta gaggcgggggt    68554
ttcaccatgt tggccaggct ggtcttgaac tcctgacctc aaatgatccc cctgcctcgt    68614
cctcccaggt tgtatttttta atcctccaca actaaatact catgtcagtg aaaggttcc    68674
aagctcttta aagacagcct ctgccagcgt gctcccaggg gaggccaggg aaggctttgg    68734
gaagcctccg tgggggtggg gacctcctgc aaccccctggc gcacagcctc accccgctgt    68794
aaacagagct gggattgaag tgcgatttcg gtttctttttt cttttttttct aatcaaataa    68854
aaacacctag ggggcaggaa gcgaggagga agaggccagg gagtaattct tgttgccaaa    68914
ccagtttcta aggggctccg ctccgctccc agcatttctg tctctgaggc tccgacctct    68974
gagatgatca atcctcccat ttcagccaga tgagaattgc tgtgggccct gccttttctt    69034
aatattttgc atgagagcga cagcccgcc agcggcagta atctcccacc cacgtgggga    69094
ggcacccact gtcctgccat gtgcataatt gaagtcttca gactgctcag tggttctaat    69154
tagcccaaag tggccccttc tggcctcagt ggaaattact gccctcctgc cgcctggtct    69214
tactagctga tctttgaagg tgtgagtgag ccgggagacg tgcagagcct agcactccct    69274
ctgctgcatt ggtctttctt ggcaggcctt catggctttg cagagggcgg gcagttgagg    69334
cctctgtctg ccgttgaggt cctgcctccc tcctctctgc caccactctc catgggacag    69394
gtgctccagc tgggcgcatg catgcccctc tcacctgaat gcctcccact agcagtgtct    69454
ctgctctttc tgacccttca ggttatgcag tgcctcctcc tccaggaagt catccctgat    69514
ccccaggctc ggccctcaga atccccatgt ctccctccat cgcagccctg gccatggcat    69574
gtggtgcttg tttacatcca tgactgcccc atgagactgg gagcccctag ggggcagaag    69634
```

```
ccgctccatg tcccacctac tcctggccta gcgcggtccc ataggacatg tctacgaaaa    69694
tggagggcgt gagggtggga ggaaggaagg aaggcaagaa ggaaagaagg aaggagaagg    69754
aaaaaggaga agagagaaaa gagggaggt gggcaggtag caccatgccc attttgcagg    69814
tgagaacact gaggagacat aaccgggaag tggcagggcc aagcacaccc ttggcagctc    69874
attatacttt cccttcagcc tagcaaagct actgttcgat ttggggaaat ggggccgctt    69934
gtatgaagag ccgcaggcaa agtggaaagt gccgagggct ggaagtcaga tgggtgtggg    69994
tgcgcagcct tcctgtgtac ctgtgggcac cacttacctg ctctgtgacc ctgagcaggg    70054
cacctttgcc ttcgaaactt gaagatcaca gtcgtccagg tggattcaag gcgatgaaca    70114
gcaacagcgc atgctcttcc caaacagtat tcttcttatc ctcactgaag ccccagaagg    70174
tagttgatcc ttaccacatc attaacctca atgcgcagat gaggatgcca aagcacagag    70234
aggttgagca actggcccaa agtcacacag tgcgtgagtg acagagccag gatttgcgcc    70294
tgggttcttg gctctgatat tagtgccatt gactccactc tgttgtgtga ggtatgaagg    70354
catccagtac agtgtctggc atcggcaggt agcttccatg gcagataccc cccctctccc    70414
accagattct gccctttgag cgacaggaag ataaatagcg ctgttctcca gtgtcacttg    70474
tgactttcct ctgtgagttc attgtcaggg tgctcctgag ctgagctgtg gccaccactc    70534
attggtgtgg tccctggaga cacttggata aaattgtgat gacagagggc tctcaggctc    70594
atgagatcac acagaggagg gtggagctca aagggctatc tcagaccggg atgctccaga    70654
ggttaggtct tggtgctgtg tttggcccccc agctgctctt tcaggccttg gtcttgccct    70714
tgcccttggt ctctggaagg ctgaatagct gcatcttgtt catctggaaa ctctctggga    70774
tgagtgactt tagcatctcg gatgttgcca tcgtagccca tgtgcataac aacttattgt    70834
gcaagcatgt acagtcatat tgaaaataaa tgtagaagtg aaggaggcag tccaaagacg    70894
gttcctgaca atactcggaa acagcttcat taggtattgg ccagagcttc tatttgtggg    70954
ttgctttggc gaaactgctt ccttaccatt aaccatatcc aggagatgga ggggaaagtc    71014
ttcacctggg ttggtttttc tcagagggc aggcaagctg aataacggga gtactaacat    71074
ttccaagaag attaatgatt aaaatgttga atacaatttg agacttgttt tcatgttcat    71134
attttatagt ccagaagttc tttctataat gtcctcataa atattttatt tggccttagg    71194
ttaaatgtca gtttccatgt cctgccacgt gccacttgac caacgtgtgt gggaacgtct    71254
ctactttgga cacactgtct atatgaatgg aggcccttct acccttgaa atgttcctca    71314 actcccagct cagtttccct tccgcatccc tttgactgca tgagcggaag cgaggcatta    71374
cagagaggtt tgaggagcca gccagcaagc tagcaacggc ttcagttcat ttctgagatg    71434
tttgcattca ggggtcccat tggccaacct taacttctcc tttgagctct aggcatcttg    71494
tgatgaatgg cataagcctt agaacatggg agaggcttgg atgggccagg agctccaaac    71554
actaaggaat gttgcttaca tcaatagacg ccttagttac ttaggtcaat agataccta     71614 gttgcttaga tcaatagatg ccttagtaga tcaaacaccc aaatcaccca atgtactttt    71674
agggcaatgg ttgccaaact ttttggtctt aggaccccctt tttacactct aaaaattat    71734 tgtggctccc aaagaggttt tgtgtatgtg ggctatatcc ttcaatattt gccaactttg    71794
aaattaaaac tcagacagtt aaaaagattt atatgaattc attgaaaaat aaaaagtgta    71854
aacccattac atgttaacgt aaataatatt ttttttggaa aataactgtg ttttgtttta    71914
aaaagtgaga agagtggcgt gtgtatcaat ctctttaatc tctagcttaa tagatgatgg    71974
ttggattctc acatcagctc ctgcattcag tctgttgtga tacattgttt ggttgaggta    72034
```

```
ttgtcgaaca tctatcctca aacagatatg tagttggaaa agggagaacc ccacaatccc   72094
ctgaaaacgt cttggggtcc cctggaggta cttagaccac agtcttagaa ctgctgattt   72154
aggtgatggg tgaaactcaa gatgaagaca aaagagaaaa catttcaacc ccaagagact   72214
tcaatgcatt cacatgcatt gactcaggat cattaaagct ctaactgaac ccaacatgga   72274
gacagagcag gaaacacagc catggctggc ttgacttcag cctcccatca aagaccccca   72334
tctttggctc aactgccccc agtggtttca atcagccaca gacttccctt gtccagctgg   72394
actggacgtt ctgcatttga ctgtctgtcg gctgcccact gattttcagg ctgctgaatt   72454
acccattagc tcacctgaac ccctaatgcc acatctaaac ggtcctcact ctgccttttct  72514 cagcatccga gaatgtccta taaaaggctt cttccatgga ggtgggcagc cttgggcctc   72574
tcctagggtc agctcaggct gcccacgctg gctatggctt cctgctggcc cctggaagct   72634
gtgtacacct gggagagtga ggtgaatgtt aatttattca gcatgcaatt aatgaattct   72694
accctgtgcc tggcacgact catttctcat gccaaagcta gggtggatca gaccaccttg   72754
gacaaatctg gatgggtgaa cttgtggatt gatcaatgat cttagttgat gaaaaatgca   72814
ccaaatgact gttccttta atgcgattgc ttgggtggtg gactcgatta cgttgagggg   72874
attaaattag cagcttgctg ggtttcagat gagtgcaggt ggctgctggc acttcctctc   72934
ccctcttttc tttctttccc ttttactgca aacgaagact tttcaaagct ttactaagta   72994
caataaatgc catcccctta aagtgtagac ttccatattc ttagaattgg caagctatgt   73054
atatgtttgt gaaatcaccc ccataattaa gatttggagc atggccttca cccacaaaac   73114
gtttcctgtt ctctgtgtgg tccattccta tctctgccct gcaccctggg tagccagtga   73174
tttgcctttg gtcactgtag gatagtctgc acttcaaga atttcatatg aatagagtca   73234
tagatgcatg cattttttgg tctggcttct ttcactcagt gtgggtattt tgaacttccc   73294
cctggttgct gtgtgtgtca atgatttgtt ccttttcttt tgaggagaat tctgttctgt   73354
gaatatgcca tgatttattt attccttccc ctgctgatga atatttgagt tttttctaat   73414
tctgagctac tgtgcagaaa gctgctatga acacgtacgt atgcaccttt gtgagtttgt   73474
gagctttcgt gactcttggt tacaaggatg gttggttcgc atggtagacc cgtgcttatt   73534
ttcacgcttt aagaaactgc cttgctgttt cccacggggc tctatcgttt ttcattcccc   73594
cagcagtgtg tgaggggctg tttgctccac ctcttcacca actccatatt attagtcttt   73654
ttaatgttcg ccactctgat gggtgtacac tggtatctcg ttgtgatttg catctgcgtc   73714
ttgtgatgac tgatgatgtt aagcccttg ccatgtgctt cctgaccatt cttgtatttt    73774
ggtttgggaa gtgtctgccc aaatcttttg cctattttaa atcaggttgc ttgtgtttat   73834
attattgagc tgtaagaggt ctttatacat ccgggctaca agaggtttac tagatacatg   73894
tactacgaat atttctctc attccatgcc ttgccatttt cttttcataa cagtttcttt    73954
cacatagcaa aggtttaagc tttgataaag ttcagtttgt ccatttttg ttgttttca     74014 tgcttttgt gtcttgagaa atcgaagttg caaggagttt cttctataat gtctcctaga    74074
aggctcatgg ttttagcttt tatgtttagg tagatgatgc atttcaatgt cagtttgtca   74134
gatggtgtaa gagttgatat tcattttgcc cccagtcatt tattggaaag actgtgcttt   74194
cctcgtggaa tcacctgagt gcctttgatg acaatctgag ttcaccacag acttgtgggt   74254
ctagttctgg attctctgtt tagttgtatt gatccacatg tctgtccttt taccaggacc   74314
acactgtctg tatcactgta tctttatatc agctggggta aatcctccaa ctgtgttcct   74374
ttatttattt atttattgca aagtcatttt ggctattcta ggtcttgttc taacaggaac   74434
```

```
atattttcgc ttatttaatc cttaggaccc tctgaagcag gtgtgaatat taagcccatt   74494
ttatggataa ggaaactgag gttcggagag gatgagtaac tttcccaggt aactgaggag   74554
gaagtgagcc ttgcccctgg taggtctggc agctgcactt gcccttagcc tctaggcagg   74614
ctgcactgcc ctctctgtgg gttccaacca ttcctggtac acacccctag ccaagaactt   74674
gtgaggttct tggaacctca tgcaagaggc tcttgcatga ggcctctttt ccaacttctg   74734
tttatcctgt cccaaagagg tcagtgaggg acccccaggg ccgcctctgt tccctcaccc   74794
tgcaccttgg ccgggagacc cccgcagcgc agggagcatc cctccggatg tttcttccca   74854
ggcaacaata ttctgtttat caagccaggc cccgaggctg aggcctcccc ctggcctggg   74914 gtgattttg gttggtggtg agaagcagca ggggtgcctg ggggcctggc tgtcatcgga   74974
gccagctccc tgtcctggtc tctgctgtgc gggatggcat gggtagggc tttgtgcagg   75034 atgagggtcc tgccgactgg gacgtgggct ttggaagggc cacgcttctc ttacaggggt   75094
gcccttgtgg ctgtatgagg agtccaagct ctgaggttga acactgggat tgaaggattc   75154
ctgccagggt gcacttaggt ggctcacttg gcccagagtg agccagagct ggctcgcatc   75214
agtgcgcggg agtcaatagt tacattttta ggaattttt gagccagttg ttaaactgtg   75274
ggtagcatgg aaatcagccc tggcttgagt aggctcgcat cagtgcgcgg gagtcaatag   75334
ttacattttt aggaatgttt tgagccagtt gttaaactgt gggtagcatg gaaatcagcc   75394
ctggcttgag tattcatgcc acggacttgg caaatgccgc aaatcagggc cttctctcta   75454 cccccctccca gccccaaccc gaagacctga ttgttaactg cactggcaaa cccctggctc   75514
tgcctcctgg agcctcaggt tccttatctg gaagcgggga gaataatgcc cacaccttaa   75574
ggcatcatca acacccttaa atgagatcat gggtatgaaa tgcttgtgaa tagttttgag   75634
tgtgatacgc aagtgtgagg ggtgctcacc accctggcca ttgccattgt cctcctcatg   75694
gcagcagctg gacaatgtgc ccaggctggg agttggtgtc tccaggaaaa actggaggaa   75754
aggagcccga taacccatgg gcagcagctg ggttagggag ggctccagac ctgcctatct   75814
ccgtcagccc tgctgaatgt gcctctgttt gctcatcttt ataatgggtg cactgatccc   75874
agctgagagg ggtgtggtgg gctttggggt acaggccaca aggtacaagg catggcctga   75934
ctgcagctcc gtcactctca tggctcaggt gcatggctgt cccacagtgg aaggaccagg   75994
ggctggcctg atctgcactt catggcatca agagcacagg ccctggagtc caccaggcac   76054
agagaagcag cctgctcctg ggtggagtac aagttcaacc ctcgggagtt gtggtttccc   76114
catgtggaag ctggcagcat gccacgcacc tgccagggct gccgcgaggg ttcgcacaca   76174
ctgtgtgtaa tgctcctgtg tgagttcccc ggtgacccag gtcccactgg ggtggccggc   76234
gtgtaaccag gacaggaaca tctccaaagc cactccttgt ttgctgcctg gtggctcaag   76294
cagaacatct gtgcctgcag ggggcccata agccttaatg ccctgcagag aggggcctg   76354 ggggaggctg ggactcacac cagctgggga acaaggcctg cagctggggg ctaccaggga   76414
tgctccttgc cagtaaagag ggtcctcagg agatcagcca cagctcaatc aggagggtct   76474
gcccatttca caggggagga aagcgagcct ctggaggctg agctgccagc agtcacgggg   76534
ccagcgcaca gccagagctg accactctgt atgactggcg ggtctgcgcc cttggcatac   76594
cacagcagct ctcacaccaa cagaggctgg acctgctgat cagcccccgc tgtgggggt   76654 cccgcctctg cccacaccct accccacacc ttcacagggg tggactgtca ccctctagca   76714
gactgtcctc cagagaccga gacacggagc ctctccacaa ggagggagga aagggaggtg   76774
gaaaccagcc ttaccctgga caccgggtgg tccttgctgc atacccaacc ctcattggtc   76834
```

```
agactggtct gggagggcct ggacatgccc gcggggtccg tttctgaatt cccgttgcct    76894
ggcataagct ctggcactta gtaggtcctc agttaatact tgtcagataa ataaatggcc    76954
tcctttgggg aaatgaagaa tgtccaggct ggccacgggg aagggcagt gttaggagtg     77014 gagagcgaga gggtgagcca ggcagatggg acctttattc aaagggcagt ggggagccat    77074
ggaaggtttt agggagggcc atcggatgag gttttcattt tagaaaagtc cttctggctg    77134
ctgggtggat ggggtcaaga tgaagacagg aaatccagag aggaggcggc tgcaggctcg    77194
cgggtgagag gtgaccatgg ccaggccagg gcggaggcag ggaggtgggc ggagggggc     77254 tgctggctct gccaactgtg accccagcac ccagctcagg gaattatggc cagagacaaa    77314
gcagcttaga gcctgacccc tgccctggag cagataggcc tgggaagggg gctgatggac    77374
acgctgatgt gatgggacct gagaggtgtt cttgtcacca ggccagtttg gccccatcg     77434 cccgcctgcc ggctggggtc taaaaggctg gctgtagccc cagcagagag acagggcct    77494 gtgggacccc aggtgctggg agcacagaag ccagccaggc catctggccc ggctgagact    77554
caagtgatag gtccgcatca gtgtcaggcc tccatgcccc ccatcctggg atgggaacag    77614
cacatcacag tttgcagagc cctgcggcag gggtgactct tattgccatt ttgcaaatgg    77674
gaaaactgag acttagagtc tctctgactc acataagcag gacaggagac agtcgaacca    77734
ggtcccccag ctgcaattta ccacatctca aacccttttc ctctctctgt cattgattaa    77794
tctttgcttc aatgtccaca tagttctgtg atttgctttg ggtacatagt agcaataatt    77854
atagcaacaa tttctagcag tttcttggtg ccagacactt ctgtctttgt tgcctcgttg    77914
aatcttcacc atcaaccttg aatatgaaac ccattttaga gattaggaaa ctgaggctca    77974
gagactgttt ataacttact gagaatcagg cagccccact gaggtgcttt accagtctcc    78034
cctttaccag tggttctcaa accttggcac accacaggaa aacctgtcag aatgcagatt    78094
ctaggcccca gcaattctgg tcctgtccgt ctgggcagag ccttggcaag cttcgtcttt    78154
aggagagaag cccaggtgac tgggggtggg gctttccgga gcctgtgttg caagaaggaa    78214
ggcagggagc atgtgatctt ctctcggtct ccctcacctt gaccctgtcc caaggccagc    78274
tgctggcctc aggctgcctg gttgcctttg aaggtccatg gggatccgat ggagggttgg    78334
tcgtgctgaa gccaggctgg gtgtcatcct ggctctgagc acagtccagc ctggctagag    78394
tcaaacccag cagcttgacc ggatcctgct gaccacagac aaatccacaa ctaccccgtc    78454
cacctccccc aggcccatct gcctctgtgc cagccaggct ggcagacact ccatcgggcg    78514
ggccccacct ggcttggcca gggagaaact ggcagccaca gcccctggcc tccccgatcc    78574
ctgtcccttg tgcactgccc atgggagggg cagtggcctt ccacgctggg tctggctcct    78634
gcagtagcag agctgggtgc agacacgggt tggaggccgg ggccatgggg gcattcgtag    78694
gctcatgagt cccttctcac tctcttctgg ggactgggtt tctgctggaa gagaaaggga    78754
ccagccttaa aagacatcgt gattaaaatg gaattattat ttcagcctgg aaaaggaatg    78814
atgtactgat ctgtgtcaca acatggatga accttgaaaa cattctgcga agtggaagaa    78874
gccaggcaga ccccaaaggc cacgtgctgc tgtatgattc tatttatgca aaatatccag    78934
agtaggcaaa atccatagaa acaggaagta gatcagtgat ttccggggc tggggagagg      78994 aggggatagg gaatgctgc cgacggatgt ggggtttctt tttgggtgg tgggaatgtt       79054 ctgagtttct ttttggggcg gtgggaatgt tctggcatta gactgtggtg atggttctag    79114
aattctgtga atctgttaaa atccaatcaa gtgtacattt aaaagtggtg aatttcatgt    79174
tatgtatatt gtacctcaac tttagaaatg ctaaaataga aacaacaaaa tcatcatgat    79234
```

```
gcaacgcctt tcctcataga cctggagcga ggcctgagag agaagccata taaggcagat  79294
gaggggtggg atggagagct tcctttcatt cgctgcctgc ccagtgaggg tctgcttcct  79354
ctggcactta cttaacaaac ccgagagtca cccatgtgtg aggcatgggc tgggcacaga  79414
agggtccacg cccacccctg aaagtgctcg tccatgctag aaagacagaa ggatggggtg  79474
gtcattgaac ctaagtcaga ccgtggcttc ccagctcatg cagaataaaa tgctcaggcc  79534
tctcccggcc tgctgggtgc aggaccccgg cccagcccac ctctctgagc tctgagctca  79594
tgtcctgccc catccctctc acacgcacac tggcctcctt gctggcctgc aacagatcaa  79654
actcacccta cctcagggcc tttgctcgtg ctggtcacct gatatctgtg aggctccctc  79714
tctcacatcc ttcaggtctc tgctcaaatg cgtctccccc aggaagtctt ccctggcctc  79774
cccagctaaa acagccctc ccaccctcc catgccattt accatactat agttttcatc  79834
ttagcccta tatctccctc caagagctat ttattgacat gaaatttgc ttattggctg  79894
tctctcccat tcgagagtgg gcttctctg gggagtgtgc actgctgaat ttccagtgta  79954
tgcaacagtg ctgaggagag ggtaggtgct cagttaatgc ttttaatta aattttctat  80014
tgtggtagaa tatacatgac atagaattta ccatctgaac cattttaaa tgtacaatca  80074
atgtcattaa gtatattcac gttgctgtgc acctgtcacc accatccatt tctgggactt  80134
tctcatcatc ccagacagag actctgtacc tgttaaacaa gaactcgcca ttcattaata  80194
ttcttttgaa tgactaattg aatgactaag tgtatttcct gtgtgtcggt cacaagctag  80254
gtgatgagcc agtaaacctg cgcgcctcgga gggtgtgtgt tcccgtatct gtctcggaga  80314
tggacagatc gactcagaga ggtgtgaagg gcttgtgccca aggtcacaca gctggtcagg  80374
gtgggattca aacgcaggtc tttccccctt tccacacagt ggcagttctg ggggatcact  80434
gcatgcaaag ggcatagcca tggcacctcc aggcctccag ccccacccag ggcttccct   80494
gctgccgctc cccaagggt cactgtgtcg gccacatgtt cctggtgtcc tcggctctgg  80554
caggctgacc accagtcaca ggcacgtctt gggaccacac ttggaggttt cagcttccca  80614
tttcacctgg tgctcttggg gtggaggccg ggatcatgga atccttttc catgcctttt  80674
aacacaaatc aatactgtgc ccagtttaaa tgtttatgta actcatcatc tgccggctct  80734
gctattacgg tgtgcttttc tttttataaa ccaagctcag gggaggtgat attaagtcca  80794
ggacttgcct ggcgaggccc agcgcgtgtg cagaggattc aatgtggcaa taagggcgag  80854
ttccctgcac agcgcctgcc atggctcgtc ccagcctcct ccctcatctg cttgtgtcct  80914
ctacacggta gggaggaggg agaggtccag agagggagg tggcttgccc agggtcacag  80974
ccacaatgag gtggaacagg gattgtttcc aaggtgtgtg tgggggtggg acccaggctc  81034
ctgccagagg ccagggcggc agagcccga caggcagatc ctgggttcct gggtgtccag  81094
gttacgtggg tgggcaggtg gcagctggca cccacccat acagacactc tctgacaccc  81154
cccaaaaata ctcccaccag cccccttcaca ttttcctcca gccaagtgac caaagcacag  81214
ctcagggccc attttgccctg gccacactgt ccccactctc cccacccaac ctctgaccac  81274
aggcctggga gctgccccat ctccaccaag ttcaggctgc aggaggaaac gtctcaccag  81334
gcccgctgga aggtggggtg gtgatgaaat gtggggttc ttcagcgaga gtggaattca  81394
gtaataaggt gatcatcact gccggcggt gcctggactc atgatgagcc aggactaggt  81454
gagtgcagag ggctggtgag caggcctgat ctgtgacccc ggtggccctg cggctctcag  81514
accccctcaca taaatccca tcagggatat tccgttccct ggcccggaat gaggtcttcg  81574
tctttctgat cgcccttgga gagcccaacg gccttccgtc actcactcag tgctgatgtc  81634
```

```
cagtcccggc aacagtctga ctccgcccag acttggcgct tccctccca tgcgcccgcc    81694
gcccggcgtg ctccctgctg gagggtgaca tggggagggg cctggctgca gcccttttca    81754
ggcagctctt gttggctggg aagggagcct ggggatgggc cgccttctac ctgccggtgg    81814
ctgtgcccac tctgagtgtg cttggtgggt gattacagct gctcacagct gtcaggagtc    81874
cttcacaggg cagtctggaa gtttcctgta gagctgtctc ctgcagagtc cttacctagg    81934
gagacccgc tgtatgtcct gtggccagta gcatcctgtg gctttgctca atcccccagg    81994
cacagtgtgt gcaccccag cctccctctg ctgtgttctc cacgcccctc tgggcagccg    82054
gcactcagga cctaaggtgg tcctaagcag ctctcccctg tcccctggaa gtacgtggag    82114
gtaaaagctg catccctggc agaatcagac cccaaactcc agacccttt gctgtgagtc    82174
tcaggctagg gtctcccacc tgcaggaatc attttgggcc ttttgagggt ctctttcata    82234
gacgtgggtg gggcgtctgc tcagcacctg ctttctcctt caccaactcc tcagcctccc    82294
atctctgacc ccataaacgc tgagaggaga accaggcctg gggggcaagt tcaaggactc    82354
aggaggcaga ccgctggaat ccaatctctc ccctgccctt actagctgag cggctgttgg    82414
caagttgtct tctctgtgct tcagtttctt catctgtgca atgggggtga taacagcaca    82474
caagaacatc ttggagttgt taagaagatt cagtaatagg tgtaaaatgc taaagctggg    82534
gcctggctcc caggaagtgc ccagaaggtg tactgtgata accacagacg ccacgtcacc    82594
ccgctggacc tggactccgt gaggaggggg ctccccatct ccttatccca gtgtcagccc    82654
gctgctgggt aaattcgctc gccaagccca taccaggtgc taatggctgc aggagcctct    82714
tcctctccct gacatttccc ttcggcagca ggcggacccc tccttcctcg cccacctcca    82774
tccttagcag ccctgatacc tctgacaatg ctaattaaat gcaacaacct catcagaagg    82834
ctcgagctgg gcttgcctaa ggcccctct ctgccctgag ccctgatgga tcattaatgg    82894
tgtcagcagc acttatggtg atggacgagg ggagcaagtc ccccgacgtg ctggggagga    82954
agtccgtgac gagcatcttc atctcctgtc tgcaggcctc ggccagagtt tccagggaac    83014
gtcctagtcc acagaatcgt ttgaatttca catttaccct gggagaacca tggccaggca    83074
gggatgtcaa ttcccattgt atccatgagg cagtcagggc tcagagaggg caagagattt    83134
gggtgagggc acacagctgg taagtagtgg ggctgggact ggattaccac ggctttgatg    83194
aaagctgcag ggggcatctg taagatccaa gggcgatgtc tcccccaggt ggcacgtgga    83254
gaagaaagcc agcaagtgcc accggcttgg gggtagccca gttctcgggg gctggagcct    83314
gcacactctc atctcagctc tgtgtcagtt tcctagggaa gctgtgacaa agtgctacaa    83374
actgcgtggc ttaaaacaac cgaaatttgt tctctcacag ttctggaggc cagaagtctg    83434
caatcacgat gctggcaggg ctgggctccc tctgacggct ccaggagga ctctgttcca    83494
ggcctcccca ccagcttcta gtggtggctg gcaatccttg gcatttccgg gcatttccag    83554
gcattgggag gcccggctcg gcccccaaa gtgctgggat tacaggtgtg agccaccatg    83614
cccgtcctgc ccttcattct tgatgcctcc cttcagcctc tgcctctgtc tccccatggc    83674
ctcctccctg tatctgtgtg tgctgtgtct tcatatggac ttcttatcag gataccagtc    83734
cttagatcta gggcccacca taatccagta tgaccgcacc ttaacttgat catctgcaaa    83794
gactctattt ccaaataagt tcccattcat aggtaccagg ggttaggatt ttaacatctt    83854
tttgtgggat gcagttcaac ccacgatacc atctttgccc atctctggct ctggcgtgca    83914
gggacctgtt actgggcggg tcactaggga taccacctct cacctctctg gcacccatt    83974
ggtaggcctg tgctgtgccc agcaccaggg ggctggctga ggcctccttg tycagtggct    84034
```

```
cctgtgtgcc tctccacttg ggggttgccc tagagctgcc caggaaggga ggaggcacct    84094
caggggggga aggacagcat gagtttccat gggcttctcg tcacccacac agagtgactt    84154
ggaataatgc acccagtggc tgatctgggg ccctgagctc gaggctgcag ccagtggcag    84214
ctccaggccc tgcagtgtgg ggacagcgat ggccaaaaag agcacatgcc aaaggccctg    84274
ccacttaggg gactttggga aagtttgacc aagtttcctt gtctctaagt aaggaatgat    84334
aattggtcga tgggattgtt ctgagatgaa agtgctggtc cttgggaaag cttcagctga    84394
aatgtctttt tattttgccc ttcactcttt ttttttttc ttcactgttg tcgcccaggc    84454
tggagtgcaa tggtgcaatc tcggctcatt gcaacctcca ccacctctca ggttcaagca    84514
attctcctgc ctcagcctcc cagatagctg ggattacagg cgcccgccac catgcccgga    84574 taatttttt gtatttttag tagagacagg gtttcatcat gttggctagg ctggtctcga    84634
tctcctgagc tcaggtgatc cacccggctt ggactcccaa agtgctggga ttacaggtgt    84694
gagccactgt gcccggcctg cccttcattc ttgacgaata tttcgactga attcagaatt    84754
ctgggtttcc aggttttaac attttctttc ggcacattaa aagagtcttc tgggtgccat    84814
tatttctgct gacaagtcag cagtctctga gtcctggtgt ctctgaatgt aatatgttgt    84874
ttttattcta gctgctttaa cattttctca ttatttcagt ttccagtagt ttgcagtttg    84934
accaggatgt acctgggtat aattttcctt gtgcttatcc tgcttggagt tagctaagct    84994
tcttaaattt gtaaattgat gtcttttacc aaattgagga attttcggt cattattttt     85054 ttatgtgttc tttttagtat atcttctctc tccctccct ctacaactcc aatcacatgt    85114
gtgttgaacc ttttgatatg caacaggtct ttgaggatct ttttcttttt aaaaaaattt    85174
tttttctctc tattcttcag actgggtaat ttcattgaa atcatcttca agttcactaa    85234
ctcttctatt ttctcagact ttctgttaag caatttctgt taaggtgtga tttttttct     85294 gtctcagaca tggtattttt aagttataga attttcattt agttctttt taaattgttt    85354 atatttctct gctgagattt attctttcat gaagtatgag ccaattttct ttacgtcttt    85414
taacacagtt atcatagcaa gtttaaaaat ctctatttgc taattgcagc ggccagcaca    85474
tttcaggtga gtttccactg actgtctttt atattaagta tggctggttt tcctatttct    85534
ttgtatatct tcatataatt ttggatgata tcctgggtgt tgtgaatgat agcataagag    85594
cgactctaga tttttgttac ttctccccaa agagcatttt tgttttgctt tgtatttgca    85654
agcagttaac ttggctgaaa gcaactgtaa accatctgca gtcgtgagtg gtgggcagtg    85714
gcaggagcct ctgttcactt cttctagccc tggctgggtt gcagctgctg gaagtctgtc    85774
ctgtgtgtgt gtggtttggg gtcagcccaa gacatgggca gagtttattt gcccctctg    85834 gggatctgtc ttggtggctc tcttcattcc agaatttact cccacatttt tccagctgct    85894
gcgagtgtct cagactctgt ttgctgctct atcaagccag tgagactctg gctttccgtc    85954
tgagttctgg cagccctatg acacaggctg ggacttgtcc tcaggctgtg aaagccatga    86014
gaccaggaaa gccaacgccg gctgttcctc ccaattgctg accgcctgca gcatctgctg    86074
cggcctcacc ctccgatgcc ttcagagtgt cattttgttg ttgttttttc aagggtttat    86134
agtctatagt tatctgtgag agagttgctg cactaggagc tactaggcta ttaccggaag    86194
catttagagc agggcctggc agacagtaat cacttaagaa atgtgagtta atgtggtcaa    86254
ccatagtgcg gcgctgtttc ctctggtcaa ggctagagac aacgtggaca cagacagcac    86314
catgcaggaa gtgtcagtac ctagtgaaga gcacacaatg gccttaagac tgcacttgta    86374
ggccgggcgc ggtggctcac acctgtaatc ccagcacttt gggaggtcga ggtgggcaga    86434
```

-continued

```
tcacttgagg tcaggagttt accaacctga ccaatatggt gaaacccat ctctactaaa    86494
aatacaaaaa ttagctgggt gtggtggcag gtgcctgtaa tcccaactac tcgggaggct    86554
gaggcacgag aatcacttga acctaggagg tacaggttgc agtgggccaa gattgcaccg    86614
ctgcactcca tcctgggtga caaagtgaga ctctgtctca aaaaaataaa taaataaaat    86674
aaaagcctgc agttgtagga gagaccactt aactggggga gggggaaagg ggactatcca    86734
ggaaggcttc ctggaggagg tggtattgga gctggaaatg tcagataatc caagatgaga    86794
agatggactt tcttcacaga ggtggctgcc aaaacaacca attttatggc cttactgatg    86854
agaatttctg gcactcaaga gaggcaactt ttcctaaggc aaatcctgaa gacatttacc    86914
tataaaaatg agtagacatt aaacatccac tagctccttc atgggccaga ggaagcagtg    86974
ctcaggcaag aggggatctg aggtctggtg gtggttctgt agatgtttgc agggagcgac    87034
tggcgggact ggtaggcggg accatccaca gtgaggttgg gcgcccagat ccatcgccac    87094
attgcagagc ttgtggctgt caattctgtg gcagccagga gcacaggtga ccgggagctt    87154
tagtttctgt ccagtacatt ttggtgattc attattcctg gagtcctcgt cttctcttcc    87214
tccctcccag accctctcac ctccttgtct cacttgaacc tctaatcctg ggaaggctcc    87274
accataagca cactacagat aatgaaacca aggctcagag aagttgtgtg gcttacccaa    87334
gaccacacag ctgaagcact ggagccaaga ctccaaccag cacttctgtc tgcaaagagc    87394
tcatggcgta gtctctcatg gagggagcct ccatctcctc tgctgccaaa tggaaatcac    87454
agtagtgtct cccgcagggg ctggcgtgag gttaaaggag gtagcagata tgaaaatgac    87514
atataaattg taaattgccc acagacatta gtgtgtgttg cctggtaacc acccagcatt    87574
tgtggactgc atttacttgg gatagcaata gttatattgg cattttaatt taatagcatt    87634
gttatgttcc catcataaaa ataatataca ctgtgtgtat gcccaccctc atcaaattat    87694
atacattaag tatgtgcagc gttttatata ttgattgtac ctcaatacag ctattaaaaa    87754
atgatgtaac ttcattatag aaaatctaga aaatatggac aagttgaaag aggaggaaat    87814
attattttgt tccagctacc ctaaagctac ctccgttcac attttggaga attctcttcc    87874
agcttttttc cccactgccc agtttctttg cttatttcac atggctataa tcactgatgt    87934
agatcattac aagcatttta tacccaattt tatatcccgt tccttcaccc tcagggggtt    87994
ttaatatgaa atagcaagaa ccagcgcccc atcggggacc ctagcacagc tgggctgggt    88054
ggttctggct tctgcccaga tgtgtctggg tgtccctggg ccaggcagg ctgccccacg    88114
gagggacaat gtcaggacag ctgggacctg accctgttct gactccatgc ccggtgggcg    88174
tttccgtgtt cccacagagc tgcttttctt atcttgtctt tttaagttca gtgacatgtg    88234
catctgtctt gatggatgga tggatacgtc cagcccgtca tcccacttct aaccaccctc    88294
tctcaatctt ttctgttgcc tcaaagctgg cattgactca tggctcagaa ggccagggca    88354
ggccaggagc tgtcctaaaa ggcccagact ggaaaaagaa aaggcatttc ttggatagat    88414
atctctggcc tggctactgc atacaggcac catttgaagc cgtgaattaa gcctgaggct    88474
cctgccctca tgaagtttac gttctggcca ggaagagagc ctacagatga taaaagcctt    88534
tacagaaaga aaaacatcag attaggttgg ggcagggatg tcagggtgt cctgtatgag    88594
ggtgctgggt gcagacagc agtttcagca aggtgatcca agctgtgctc acgggaaggc    88654
agcagtgggg cagaattgga agaataggaa ggagccatgc tggtacccag ggaaagccac    88714
tgcaggccga gagagcaggt cttgggacag caggtggcca ggactttggg gaaagggcaa    88774
ggagcctggt gtttggaggg gaataagcag gtggagagca gtagatgagg ctggggaagg    88834
```

```
ggaggaggta cctttttgctg agttaaaaac acgagacccc gtgcatacaa cagtaaatgt  88894
tttcatcatc ttgcatctgc gattctgtgg tctgggcttg gctgggcttg ccctgctctg  88954
tgggtcagtg gggccctgct ggaggctggg cttggccggg ggttggggggg gttcttctgc  89014
acccactctt cctcctcccc ctcaggggcc agtgggccag cctgcgcagg tcctgctcct  89074
ggtaccgcca gaggcgttga tggcaacccc cagtacctaa gcccctttgc atctctgttt  89134
gcggcttgtc gaattgccgt tctgcaggcc aaagcaaaac acagggacaa gcccagaatc  89194
aaggtggggg gcagagaaca ggtcacctgg cccaccatgg gaggggtgaa ggtttggctc  89254
cagatgcggc ccacctgggc ctcggcaggt ggggggctgcc tttagaacac tctgtgcttt  89314
tctctgagta cacaatggga gccgctggag ggttttgagc aggggagtgc caggatcagt  89374
cctgggtgtt accagcctct ctgctgccag tctgttgagg ctacgtcata gccagggaga  89434
aagagctgtg gcagtcatcc agtgagaggt gggagagtgg ctggcatccc gatatgctgt  89494
gaaggctgag caggcaggat tggatgtggg gtgtgtgtgt gtgtgtgtgt gtgtgtgtgt  89554
gtgtgtgtgt gagagagaga gagagagaga gagagagaga gagagagaga gagagagaga  89614
gagaacgaga aactccaagg cttgggcctg agcaagtgaa caatagagct gtcatcacct  89674
gagactgggg aagctgcaga ggatgaggct gaggagggat cagaattcag ttatggtgac  89734
caatgaaggg tttttgaatag agggacacag ggatgcactg gctcaggagt ttggtcatca  89794
cgttggccgc cagagggaga acagaggctg ggacagggaa ccctgtggag tgtcctctct  89854
gtggctacag ggagcaacgg tcagatctgt ggctggtttg aaagtagatc cattttgcta  89914
aaggtggtat cacagatttt ggagactaca gaatccaggc caggagagca aagaacgaca  89974
gaggtcccat tcacagcagc gggccatccc gggctcctac tagcttttgc tgcttgggcc  90034
tatggggatg gtattctaga actttccatc ttccaagaca tactggaaat gtggattttt  90094
ataggaaatc ttctactttt caaatattaa gaatgacttc aaattaaaag taataatcat  90154
tttgggggctg cagtaaaact tgttggtgga gcaggcctca ggcttcaggt tggtgagctg  90214
tcctccagtg ggggtttctc ttccaggcta gggccttgtc ctcccctgct ctccccccact  90274
cccagggctg gccacccaga atgtgcaggc cactcatctc tgtgactcgt agaacctgag  90334
aatgttggtg atggaagggg tgttccccta gttcccacat gcaaaaagtg gggcctggag  90394
atggggctgt ctttttttctc caaacacttg cccatccagg aaggccagcc ctgggcattg  90454
aagactccag gtatggggt gactccataa ggagaggttc ctgagtgacc tgaagaaaca  90514
tggttgggat gaagtgcagg gagggtcagg gcaggcaggg ctgagcttcg cttctgcgag  90574
cagagattag agagcgatcc cagaggcctg cctggaggtg gggccacaga gcaggagtct  90634
gaaggagagg gggtaattca cctctgtcct actgtgtggg aagccctgag tgggcccta  90694
gcagagggtt gccttgcgct tatctatgga gatattggga agggcttccc tgacccaggt  90754
tgctggagca tgggggcctg ggtggcaggg gtaggtgtgg gagattcaag acaggaggat  90814
gaggccacat ccaggtggct tcagatacca ccgtgagtcc catagagtgt ccagttacta  90874
taaagtctgc cagccactgt ggtcgcccca ggcctgtgcc aagtcccgag atctctgccc  90934
tgcagccagt gcagagggaa gaggagggca ggagggaca ggttggtggc ccctcgccga  90994
tgctcctgac ccctcaggct ccctgctgcc tcctgcccag ggctgtgggg cctcggggag  91054
cggggagctc gccattgctg tggcactgtt gagcacccgg gagaggcggg ttctgacagc  91114
cacccctttcc cgtcttgctg ttcccctccc a gct gac atc atc tct acc gtt  91166
                                   Ala Asp Ile Ile Ser Thr Val
                                    25                  30
```

-continued

| | |
|---|---|
| gag ttc aac cac acg gga gag ctg ctg gcc aca ggt gac aag ggc ggc<br>Glu Phe Asn His Thr Gly Glu Leu Leu Ala Thr Gly Asp Lys Gly Gly<br>35 40 45 | 91214 |
| cgg gtc gtc atc ttc cag cgg gaa cca gag gtgcgaagcc ctgggtctgg<br>Arg Val Val Ile Phe Gln Arg Glu Pro Glu<br>50 55 | 91264 |
| tgggaggtgg gaggggtggg gagcagagtc aggtgggagg cggcatggt gggaggggat | 91324 |
| aaggataagg gggataaggg gtgatgcggt gagaggtggg aggggactat actccaaccc | 91384 |
| acaagagggc ttttaactga caggaggtgt ggggtgtctt gcctggatca catctcccag | 91444 |
| gggcatggat tccaggggtg ggaatgggat gctttggaat gccgaggtgg gagtggcggg | 91504 |
| cggtggtagg gggagtgcac tgggtgggct ggcaaagcca ggttctgagc cccctgccct | 91564 |
| cagccgatgt ttgcggagag ctgcctgcat cccatgctct gtcctagacc ctggatgaat | 91624 |
| ggtcaggatg tggcacaggc agctgctgcc ccagcttgtg ccttcagtga aaccttcctc | 91684 |
| tgcctgggtg acctgcgttg tcctggccag actggggagc gggaggactc cactcttgcc | 91744 |
| cagctgtcac agccctcaga ctgagctagg tggttttttgc tcaggcctgg gcccttgtcc | 91804 |
| tcacccctgt cctcaccccc accccgggg gcttgttgtc cagcagaact ctgggtaaga | 91864 |
| cagcagtggc ctggacaacc tgcccaggac cacgtttctg gaacactgaa agagcctcgg | 91924 |
| gacaaaagcc catttactga gaacacttgc taagtattct ggagttgctt ctggtttact | 91984 |
| ctgcactgct cacctccgag ggccagatcc acacccctgt gacagatgcg gaaactcaga | 92044 |
| gaagccaccc agctagtgaa cagcagacct ggctgcccga cgccaggaca gtggccagca | 92104 |
| acgtcacaca ccacccggcc tcagagaggg cgtctccccc cgcaaacacg gactgtgcct | 92164 |
| ggaattagat gcagaagaca tccaggaaac caaggaggag ggaggagggg atggagcagg | 92224 |
| agaggcaggg gaggggaggg gaggaggaga agagaaggtg gagaagggga ggtaggaggg | 92284 |
| aggggaggaa gccgggggtg aagagaggac ctgcggaatc atctttcccc cgattcactc | 92344 |
| ctgagcatgg cccacgaact gaggatcctt gagtctgact ttatcttggt ggctcacata | 92404 |
| accctcctca cggtgaccct gtgggtgtag tgcagtgcgg ctactcccct cattttacag | 92464 |
| aggaggagcc cagagtgcag agggttaaaa tagttgacaa ggggcacatc ctagctgcca | 92524 |
| atcagttcct caaacacagc actcggccag cacctgtggg cttcaccaga tgcacctgtg | 92584 |
| gggtgtccca ccaggcactg cgaagctcag ccttctttttt gccaagctgc agaaagagat | 92644 |
| cggattggtt gatgcgattt tcttcatttt gaattttct cctttagtgt tttcttcctt | 92704 |
| ctagtcccac tgacctttgt catagcgagt gctcatggga agtgaagtga attagaggca | 92764 |
| aaaatattgg agaacttcta agcttttcaa aagcaagaca gggatagaaa tatagatact | 92824 |
| taaaaaaatt accaggaaat cttgaaattg ttctgggttg aatgtctccg tttctccctg | 92884 |
| gttgggtttt cgtgttgtcg tatgagttga actctctcct gggaacgtgg tccctggcgc | 92944 |
| acacagtgga ctcaccacct gactatgctg ggagctccac ggtcaagggt ctttattaga | 93004 |
| aggagctctg ctgcctaaac caggccaagc actgctgagg aaagccgggg acagattcca | 93064 |
| atccaggtct gacattgcca gacattctgt cccaatgtta aagtctgctc ccaaattcat | 93124 |
| ttattcctca agtcaggcct gagttggaca cgtggaatcc aggagcaagt cagggcccaa | 93184 |
| gacacgaggg tggccagagc ctcaagcctt ggcgtcaggc aggcctcggc agaggggtgc | 93244 |
| tcgccggaga gtgacctcac ggctctggga agtcacttcc cctctgagtc tctgtttgct | 93304 |
| ggtctgtgaa atggggagag tcgtggtgct caagcagagg aggcctggag ggtagaatgc | 93364 |
| gatggtgcgg ggaggactta gtggggtgtc cagcttgtag caggcgctgg ggaacattcg | 93424 |

```
cattagcaag ttagccggct cgggtgtgag tgtttcatgg gaccgcacgg gagcggggct        93484
tgtccctggc acactgcaag tcatgggccg gttaagctgc agagagtttc atttgaccct        93544
cgaattggat ccctggcacg gctcggcact tggtcccacg gccggccctg ctgggtcccc        93604
ggaggtccta gccgtcgccc tgcaggtcac ggtgctcagg cccttctcc gggtttccct         93664 gcag agt aaa aat gcg ccc cac agc cag ggc gaa tac gac gtg tac agc        93713
     Ser Lys Asn Ala Pro His Ser Gln Gly Glu Tyr Asp Val Tyr Ser
          60                  65                  70 act ttc cag agc cac gag ccg gag ttt gac tat ctc aag agc ctg gag        93761
Thr Phe Gln Ser His Glu Pro Glu Phe Asp Tyr Leu Lys Ser Leu Glu
             75                  80                  85 ata gag gag aag atc aac aag atc aag tgg ctc cca cag cag aac gcc        93809
Ile Glu Glu Lys Ile Asn Lys Ile Lys Trp Leu Pro Gln Gln Asn Ala
         90                  95                 100 gcc cac tca ctc ctg tcc acc aac g gtgaggcgct gcccggcctc                93854
Ala His Ser Leu Leu Ser Thr Asn
    105                 110 gcttgcatgg gcacaggccg tagatgtttc taccaaatgc tggtttgtat ttcacttata       93914
ttgtgagcat ttttctatgt cttcagaacg cctagaaaat aatatccttt ttgagcagca       93974
tataaatccc atgagtgagt atgccagacc ccctcagacg ctccctgtgt ctggacacag       94034
ggctgccccc cttttgagc agcatgtaaa tccatgagt gagtatgcca gaccctctca        94094
gaagctcccc atgccagac acagggctgc cccctgctgt gaatagagcc atccgagcca        94154
tctttgtagg cctttgcttt ggggtgaggg agtgtgatgg acaaggatgc aggtcgcaga       94214
cacgggggat atttgacaca aagtgaaccc ctcctcccca cgccgaatcc agacccctag       94274
actggggctg tcaccgcggc cttgcggggc agtgggagga gccttggttt aggacccegg       94334 ccggcctctt aatcctcttg cctcagggag gagcatgtac ccctcaggca ccggaggctc      94394
tcggcctgac gcctgcttcc caggctccac tctgagggag tggctggggc tgtcctgctt       94454
ggctcaccat gggcctgggt cccccactca cgcccctgc ccatcctcct tcacctgggc       94514
cccctgcgga cccaggcagc ctggggtcgg gtaggacaca cctggattct ttttttctt        94574 tttttgagag acaagagtct tgctctgtca cccaggctgg ggtagagtgg cgcgatctct       94634
gctcacggca acctccgcct cccgggttca agcaattttt ctgcctcagc ctcccgagta       94694
gctggaatta caggcgtcca acaccatgcc cagctaattt ttgtatttt tagtagagac      94754 ggggtttcac tacatgttgg ccaggttgat ctcgaactcc tgacctcggg tgatccgcct       94814
gcctcagcct cccaaagtgc tgggattaca ggcatgagcc actgtgccca gccaggacac       94874
acctggattc tgtccctgcc ctgcctccct tgggcagtga ccttgctttc ctgagcccca       94934
gcagggtgga cacatctccc ttctggggtc cgtgaaatgg tgcccactca accccctgag       94994
aacagtaacc gctgcacaag caccagccag gcttcgaggt gctgtcccca cgccttcccc       95054
gaggacgtcc acgctcctca gcggggcctc caaggctctc ccgaacatgg ctaggcgcag       95114
cttctgccag cccgcctgtg cctgaaggct atcctcgccc tgtacctggc caactccctc       95174
ctcatcccat aagccttgct gggtgcccgc cttttctgac ctctccactg agccaggcat       95234
ccctcctgtg acaccctggc tcctcttaac tccggttcac ccctctctg ggcacctgct       95294 gttctgatgg tgttctcccg ccatgcacct caaaggcagg atctgtgtcc cctaagggc       95354 cctgcccagc aaatctgtca cctgagccag cagagcatga gagatcctcc cgaagggcag       95414
gccctggggg acaggagcct cgtcctgtcc ccatgcacct gctcctttg aaaatattta       95474 agaaggacgt gtcagccaca tgcggtggct catgcctgta atctcagcac tttgggaggc       95534
```

```
tgagatggat ggattacttg agcccagaag tttgagacca gcctgggcaa cgtggtgaga    95594
ctctatctct acaaaaaaat aaaatattag ccaggtgtgg tggtgagagc ctgtagtccc    95654
agctactcag gaggctgaga ttgaaggatc atctgagacc ggtaaagtca aggctgtagt    95714
gagctgagat ggtgccactg cactccagcc tgggtgatgt gagtgagacc ctgtctcaaa    95774
agaaaaaaaa aaaagacat gtcactttct tcctgcctct ctacagaaaa ggtcatcttt     95834
cagcactccc tacactccgc tcccctcaaa gcttcccacc tgggtttgaa tcctggcttc    95894
actctttcct aatggcaggg ccttgggtac ctttcagatg ctccactgac cccagttctc    95954
agttctcttc ccagttcctt ctcatcaaca tggtgctatt tgttttgact cctgtagtag    96014
tcagggttct ccagagaaaa agaatcagta gggtatgaga gtgagaaaga gaaaggggga    96074
tttatttttaa ggaagtggct cacctgactg cggaggctgg ccgttccgaa atctgcaggg   96134
aggccgaagg ctggaggcct cgagacagag ctgcagttct ggtccaaagc cgtctgttgg    96194
cagaaccccc tccttcccca ggaggtgcct catgatttca ccttctaaag tggatcttct    96254
cttccatccg gctgcttaat tatgtgactc gctttatttt gttctgtttt taaag at      96311
                                                             Asp
aaa act atc aaa tta tgg aag att acc gaa cga gat aaa agg ccc gaa      96359
Lys Thr Ile Lys Leu Trp Lys Ile Thr Glu Arg Asp Lys Arg Pro Glu
        115                 120                 125
gga tac aac ctg aag gat gaa gag ggg aaa ctt aag gac ctg tcc acg      96407
Gly Tyr Asn Leu Lys Asp Glu Glu Gly Lys Leu Lys Asp Leu Ser Thr
    130                 135                 140
gtg acg tca ctg cag gtgagctccg gtgaggggga agcaggcaca cgcctcttta     96462
Val Thr Ser Leu Gln
145
ttacacctga ggattttagg gctggaaaag cctttgagat ttgagccaga gtcaggtgca    96522
gaccctggtt gggctgctgg ctgctgggcg gccacgggcg tcttcctgcc ccttgcctca    96582
gtttcctcac cagcagcata cagatgacca cgtttcttct aggcttcttg tgagcatgca    96642
ggggtggtgt atggctgtaa agtgcttttc acctatagct gagggtggag agcaaggcag    96702
ataatcccctt gttataagaa gggggaaact gaggcccaga gagagacagc aactcaccta   96762
aaactgctca gctgagtgag taggcagagg cagaaagaga atgggtcagc agagctttgt    96822
ggctcctgag tccttactg agggcagaag gaagcctgga ccgtgtgagg ccttcagcat     96882
ctacaaaggc ctgaaacaga catacccctga aacagacaca cacgtgccca gcatccagtg   96942
agccgccata aatataaagc agtagtcagt gctcttcctg agaagaagaa ataaatgttt    97002
aaatacattg gcctaaatga ctggcaaatt gcacaaataa attctgagga agtgggcagc    97062
cgattagctt cgatgttgag taatgagggt gctggtgccc cctgccccac ccccgtccc    97122
aagaaagttt atgagggttt catctagagg gaaggataca gcgatcacat cttgatcacc    97182
ctggtgtttg gggcagagcc agtggccttc ataaaaatcc tgtttatgtc cctcccagcg    97242
ttggagattt ttctctgtaa gtcacacaca tcccaagaca cttaactgtc actgagaacc    97302
tgggtgccct ggtctgtcct catcctgcct ctcaccttgt ttgcttccga tttcacccac    97362
gccacgccaa ccctgcacag cattctaccc accctgcgca gttcacactg gaggcagctg    97422
tttactgagg agctgctcca cgctaggccc cgggctagcc cttggggccc tagaggtgag    97482
caaggttcaa ctcagtacct gtccccaaag tgtccccagc cccaaggaa acagacatgg     97542
aatcgccatc acactggcgc tcagtgcggt gacagaggaa cacagagagg ccgtgggcac    97602
cccaggaggc ctttctctac tttgtcaatt tggtgaactc ccatacatcc cataaaaccc    97662
```

```
tactggcctt cacctctgta aagcctttct gcgcaggcca gatgacaatt gtgatcttc      97722
ctgtgtcccc tcttgccttt tggatccgac actgtctgtc cttagtgtct gtatcttcct     97782
tgcccctcat cttgactaga ctgtggcttc tgcggaggca gcatgtttta ctcatgaaac     97842
ccccaaacct tcagggaagg tttcctttct ctcttcttct ctttactaaa aaactggttt     97902
tgagctctgg tttggtggat ggcagcaaat ggctggagca ctggatgaac tgggtcccaa     97962
ggccgcctgg agaaaacaga aagcaatgtt gccggaagga agcaggaggt ggactgagat     98022
gccaagactt tgctgggcca gtgatgctct gcccttctcc agagcagctg ggctccctct     98082
ctctcctgag agtccaggga tccccagggt gggcagtggc tgcaccccga aggaagggaa     98142
ggttagcagc atagctaaaa tatctgacac aggaatacgt gcagggagga tgccttggag     98202
gagtnnnnnc acactaacac caactcccag gcacacaacc tagaagcaaa gacacagagg     98262
caacaatgca agaaccaccc agagccaggc tgtcactcac accggtgctg cgtgcacaca     98322
cacacacaca cacacacaca catgcatgca catacacgta tactcagtca tgcatgcaca     98382
ctcacatgca cactcatatg cacacactca tacatgaact ctcagccatg cacactccca     98442
cacacacagg ctgggtgccc tggtgtgtgg gaaaatttaa cgtgggctgc agagctgcct     98502
ctgctccaaa ggagctcagt gcttgtcact ccgactgcag caccgaggct gtcacctccc     98562
atctcagctg ttccctgaga gctcagggac acagcccatt cattcattct ctcacacatt     98622
cactcattca ctggagagtc tctctgctag gccttggact gagcgctaga gagatggaga     98682
gataaacaag aggtgacgcc ttgctcccgt agctgatccc tagtccactg ggaaagctga     98742
tgggaccagt tgacagcctc agggttggtc agggctgtgc aagggacctt cagggctgtg     98802
aaagctcagt gtctgatgcc atggcaagga ctcctcgcac caactgtctg agatgaaagt     98862
tcgtatgagt caggctaact ccaccgctgt aacaaaacaa caccagcagt ccagggccga     98922
gcacggaaat gcatttctca ctatgggaag gttcgatgtg gatgtgctgg ttgggacaca     98982
gctctcctgc aggatccttc catccccatc ccatgagtct cagtccctaa ggcttgggtc     99042
ctcaccttcc aggtggggaa ggtgctcccg ctgcttagct gcatcagggc caggtatcac     99102
tttgctcaca tcccattggt cagaactagt catgtggcca tgtctgggca caaaggctgc     99162
tgggaaatgt agtccacatg tagacagctg tttcccagtg acagcactgc attgcaggag     99222
gaggtgagga ggcctggcag acaattggct ggctctgcca cagtatcttt ttgtttcatt     99282
ttagagttga ggaaattggg gtataggagg gttcagccac ttattcacag acccacagca     99342
ggtaagcatc catgcctctc ttgcagggct ggtgggcggc gggcatttgc catctgtcac     99402
tgcctatttc agaccacgga ggatcaggat ggacgcccac cctgtgttc cagcctccgg      99462
ttgggatcac atgctcacgg catgctatgt cctgatgcca ccrcctggcc ttcacctctt     99522
ccctgcctcc tcatcctctg cag gtg cca gtg ctg aag ccc atg gat ctg atg     99575
                           Val Pro Val Leu Lys Pro Met Asp Leu Met
                           150                 155 gtg gag gtg agc cct cgg agg atc ttt gcc aat ggc cac acc tac cac        99623
Val Glu Val Ser Pro Arg Arg Ile Phe Ala Asn Gly His Thr Tyr His
160                 165                 170                 175 atc aac tcc atc tcc gtc aac agt gac tgc gag acc tac atg tcg gcg        99671
Ile Asn Ser Ile Ser Val Asn Ser Asp Cys Glu Thr Tyr Met Ser Ala
                180                 185                 190 gat gac ctg cgc atc aac ctc tgg cac ctg gcc atc acc gac agg agc        99719
Asp Asp Leu Arg Ile Asn Leu Trp His Leu Ala Ile Thr Asp Arg Ser
            195                 200                 205
```

```
ttc a gtatccttca ctgtggcctn ggccagtgcc tcccacgggc agagtagctt    99773
Phe
ccgttgggtg gtgggtttgg tttgattggc agacagctgg tttggggatg gctgcattgt  99833
ttaacttctt cagtgaggca cctctggctc ctagtatgcg tgtgaggccc agatacaaaa  99893
tcatgtcacg tctgtttctg aaaaccgcaa agtcgtggtt gctgagcatt gcacccatcg  99953
cctcctccag catggccatg atcccctcat cctagggcct cacaagggc caggaaggag  100013
acagagttca gggttcagct gctctggacg agggactgct ggccttgctc agcgtccact  100073
gaaggcgcct cggggccctc cccactggga cccaaggcag gctgtgttag cataggagga  100133
ccagcactgg ggccccggcc agggcttcgg gtgacaacca gggtgtcaga agcccagctg  100193
ggttggggtc ctgagggccc cctgctcggt gttctcctgt gtcagggcaa gctagggaa   100253
gcagcagcat tgacgattcc cgccgactgc tgggaagaga gctggtgatg acatgagcac  100313
cagcctgcag gcagggcgag gcttggcctg ccgggggct ggtgggcggg caggcaggtt   100373
gctgtgatgt cactattctg catacaacca atgataataa taattataat aacacacagt  100433
gagactctgt gtgccaggct ctgtgactaa catcaacaag cattcatttt aactcatttc  100493
accttcacaa caaccctatg aggtaggtac tattctaagt ctcctttaca gatgaggaaa  100553
ctgagtcaca gagcactcaa gttaacttgc tcaaagctca cagccagcaa gtgtcaaagc  100613
tgggcctgaa acccaggccc tcaggcccca gagtccccgc ttctaacctc ataccacac   100673
tgcccttttgt ggaggatgcc acccaggtgt gtcttggaag gggtgggaag accctcctga 100733
gagcctccat gcaactggat ggcctcccga ctccaggcag cctgggcacc cagcagtggt  100793
caggagtggg ctgtgtccct cggagcagta aagccggga tagctgtggg gagcagggga   100853
ggcagggagc attccaggaa gggtgaaaga gagtaacaaa tggcttttgt ggtctgagat  100913
ccaggcacag ccagagaccc ctgggcaggg agaccctttgg aaaacagcgg gaagggaaca 100973
gagcaaagcg ttggatgtcc cctgagccag ccagagggtg cggggcacat gtgtgggctt  101033
cggaggcaga aagtctgttt gggtctgact gccaccttca agctttgtga ccctgggtga  101093
gtacactcac ctccctctcc gagactccgt cttttcaatc atgcctcctc atagacctgt  101153
ggggtgccgt cagtgagccc ctatgtgtga tgtgccgaac cctaagtcag cacttggtgg  101213
gtatcaggaa gcatcagcat ctctctccct tctcttgtcc caaaggcatg gagtgcccag  101273
agctgggagg ctggattggg ccagccagga aggttccagg aaggattggg acctgagctg  101333
cttttgaaggc ttgaagctca gatttctctg gacatagagg gctgggctgg acatctgtct 101393
gaccctccac tgaagccgaa aggacatcgg gccccaccag tccacagtgc tcatagcagc  101453
agttggttag actcttttctg ctgcacgagc atgtttgatg tggataactg taagagagct 101513
gcgggccagg tggcttcagg ggctggagca tcgtgggtga tggctctctg ggctgattgc  101573
ctctgctgtc ttctgtgttt caatctcagg tgccagtagt tggggcccca ccctcccaga  101633
ataaagtcca ggagaaacga gaccagttct ctctgaactg tcccactagg accctaaatg  101693
gcatcttgtg ggctctaatt gggggtgaat gccttgttgt gattggccag gccggactcc  101753
tgtacctctc cctggtgctg gagggagtca gctccgcccc caaccctgg atgtggggga   101813
ggggcggtct cctagcagga gctccaggtc tgcaaatggg gagggtgtgg ggctcactga  101873
gcggcctgga ccgtaccgta cagtttacaa atcagcctgc cgttcgttgt ctcacttggt  101933
gctcagagac agtggtaatt tgatgatcac cccatttcac agatgaggaa acggaggctg  101993
ggggagatga gggactggcc cagagtcccc agttggcagg ggcagagcca gagctcatgc  102053
```

```
tcgggcctcc atgcctggtc cagggctttt gccctggcct cggcctgccc cctgcagccc 102113
tgggacagtg gcagccaccc ttctcgagca cctgcttcct tcctgccgga cttgggtggg 102173
gatggtaatt gctgctcggt tttcctgtct gggctgctgt gaggattccg tgacactatg 102233
gatgccgaaa cccttctaa agaaccataa agccctagag tatggaaggg atgctgcttc 102293
atttcattta ttcaaccatt cattcccac gcctttctac tcccaggccc acactgagcc 102353
ctagggacat ggggatgaat gggagaaact caacccttcc ctggagggct caggggctgc 102413
tgggggacac agccccgcca tggcagtgga agtgagggag tcatccttgc tgtagcccag 102473
ggtctggaca agctgctgtg ggggccgcca aggaagccag agaaggaatt tcggtaggaa 102533
gctccctggg ctcgaggagg ctgcctgagg gcatgggtgt gcaggaggcg gatgcatgag 102593
gaggcagaag gtgccggagc tgtggcactg tggatggtgc aggcagggg ctttctcttg 102653
gggtaggggc cccgaatgcc agtcattcac aaaaccccc acagctgtgc ctgcctccac 102713
atgccacgtg tgcttcctt tacttttccc atttaaaaaa aattgttttc tttaagtcaa 102773
gttgctttat ttttgccgaa gtaatttttct tttgaaaggg aattgaattt caccatgata 102833
agttaaagta tcacatacca taaataggag gtagcctcaa ccataacggc tgtgcacaca 102893
aaatggtggg aataaaatac aggctcagcc ctgtctgttg aactttctg tggtagtaga 102953
ctgcttcgtc tgcactcatg gggcggcagc caccagcccc atgtgcctgc tgagtgccta 103013
aaacgtggct tggtgactga ggagcgacat cgttaatttg atttagttcc agttaatcat 103073
acttcaaacg aaatagccac atgtggccag tggctactga acaaggacgc tgcagcctct 103133
ctccaggttg cccttagacc ctgaagctgg ttctctctga aaagatggag gtaaacatgt 103193
gcttcaatgt taaggggag agtgcaaaac agagacatcc cccttcattc atcagaagga 103253
ttgaatcctg tctccccgtc tgcatctata ttacattact ggaggctgtg ccgacttccc 103313
acctgcctgc ttccagggaa cgggaaacta tgaagctatt gatgtactgt aaacagggc 103373
gtgtcactag ccagctttgg aggtgtgtat gtcgtgggtg tgtgtcgtgg gtggattgga 103433
ttccagcaga caaggctggc ggcttgggaa ccagcaagga gacccgggga gagagagtga 103493
gaggcagggc cagagcgtgg ccacgggtgg gaggcggtgg aggaatgaga ttgtaaggat 103553
ggaggtgtca tagatttgga ttgtatcata accagttttg gatcggggtg gccacaagac 103613
attcagacag gttggctgta aagaagaaaa gggggttggt tcatcccagg actgcaaagt 103673
cctccctggc cgttaccgtg agccttgcct cctgtcccgt cccgaacaca cagattgtgc 103733
cctgtccgca tgttgcagag cacaccattt accagcaggt atttattaag cacctactgt 103793
gtgccagccc tcttgggtga tgctggaact agataaagat tctgcctcca ggagtggaca 103853
cgtgataaac cattggtaaa ataccccgca ttggagcagg tggtccgtgg gtgctacagg 103913
gagtcggtgg cccagccagc gcagccgtgt acatttctct ccagccacgc ctgctgctgg 103973
ctgcaggcct caggtcggtg gagggtaagc caggggtgtg gttttgcca agtgaggatg 104033
tagacacgga gctgatggtg tgtgcaagag agtgaaaata atgattattg accaagaat 104093
ctgagccagg tgagggacag tgacaaggga ggagtgtcag cagatcgggg gcccctgtgg 104153
atcctgggaa catccctggc cgcacaccct gccgtgtaac tcagtgtcag atctctgtgt 104213
aacttcccat tctgtgaaaa tgattattaa ttcatcaaaa cataaagcac cctgccctta 104273
gtgatagagg agtgtgtgtc tatagcatga acaagattct gagctgggct tgaggcagcc 104333
ctgatagggc aacttaggca tttggcagga gttgagtgga gtctccaggg gcacatggtg 104393
gccatggaaa cctcccccgat tggatctatt cattggggaa cctcagtgca cctggtgctc 104453
```

```
cccatggcct gttgccgctt ggctccccat ggggtgctgc tgcagtgaca agacacagat  104513
ccagggctca caccacagag agaagcctta cttggcagag aaagtgtgag gactgtgggc  104573
tgcaggtgct gcgatgagga ctgatagcag ccgagtaatg agaggaggcg tttcatttct  104633
gacatgggag gaggccagaa aggcagctga gacccccatgc ggagctggga attgctctga  104693
atgtttgaga taccttctaa gcaagtctca gtggggtgga ttctggctgt cagagggtga  104753
cagttctgat gagtcctgac aagaaaaacc cagggtcagg aggcctgtgt ccgcgcagag  104813
ccaggggaag gcttgggctg gacttggggt ttgcatcctt ctgaccctg ctctctgggg  104873
tcctcactcg gcccgatgac actgttcagt cctccgtgcc cactggaggt tttccaccat  104933
gtcgcatctc ctaagtccaa tcactaacac ttcccgtctc agcaaaatgg acttttagta  104993
accatatcaa gagaaaggaa aatgtttctt agtaaaggag aaaaagaggg cattgctttg  105053
actattggac aatgagaaag gtgactcaga ggacatctct gctggaggga gggagcctgg  105113
tgatactgag gctctgtgac ctgtctcggt gtagtcacca aggttcaagg aagaggagcc  105173
ctcccagcct cctccctctc tctcacccctc agaatggaaa gaggtgccca gccctctcta  105233
ctctccccag acacttgcct gaatcccgcc ctgtcctgcc cagagccttc tgcacagctg  105293
tgaaattggc tcatcggaac ctctggtctg accatgtcag ccccccttaa aactctcacg  105353
ggttcccctc tggcttctgg aggaagcctg agccctcca cagtgccctg tgcctttggt  105413
gaccagcccc tgcccacctc tcgggtcaca ctggctcact ccttcagctg ctgggtccct  105473
ggcatggggc agggtggggt ggagcactgc catccgccat cccttctcct gaccatgcca  105533
tctgcctctt tggcctggct gactcctgtt tgcccacttg cagcatctca cagcccatta  105593
tctgggacag cctctgacct gtccctgcca caccctcct aggctggtca gagcccctct  105653
aagcctgcgg ctccttggct gccccggtc acactgagtg ttttgttact gtgacagcct  105713
cctccatttt atggtggaag ccctgagatt aggaacccag ggtgaggcct ctctgcatcc  105773
cctgctccac ataggacttg gcgataggag gtacttatga acggttgtag gtggagtggg  105833
ctggaagttc accacttcca tgtggtctta ggatacagac acctcctttt tgatctgggc  105893
gcctggggaa tcagagaccc cagaccctaa agtgcaggag aaggagcccg ggctttgggc  105953
cctggcgggc ctgggctgag acccattgct cagcctgctg ggccatcagc ttccctgaat  106013
ataaaatcag aaaattccct tttataagga tatttgtaag gaataaagaa atctttcaca  106073
taaagagcct ggtgcctaat tggagcccag caagaggatg gtttattttg tctcttaaac  106133
aacagcccctt caaacattta agattggttc tcataaaatc cctgcatctc tgatggttaa  106193
aactccgttt tccacggtgc agtttcaacg tctgtttaag caacctctcg cgtcctttaa  106253
taccaacatt ttgagactgt taacacagca ctgggtgatt tttcttgagt ctgatgcatc  106313
ttaaaggtaa caaattgcac aggaggtctc agcggatgga cctctgcttt attttagca  106373
cccagagaat ttaaaagacg gttcgattga ttttctctc ccttagtgat ttctcacggt  106433
gggaactggc atcacaccaa gcctcggcct ggagaatttc taattcccat ttacagagca  106493
ggtccgcacg gccaggtggg ctggagggg gtgcagccat tcaccgcagg aggctcagaa  106553
ccttcatcag cccatgcctg cctgaagact cagcttgtct tctgtgcaga gaacaaagga  106613
gggagcagac acagtccctc tgcatgcaga ctctgtgctg ggccaaggga ccctgagccc  106673
aggctctacc cctgcctctg ccactgaccc tgatcagtca ctcagtcttt ctgcaccccc  106733
tttatcccat gggagtgtgt ctcctttacc aggagctgta aaggtggaat ggccgatgag  106793
tatggggcct ggtgccgtgt agacaagcaa ccctcaccag cacatgaccc actgtcgggt  106853
```

```
accttacagg ccacctcttc ttcctgccct tggtgctaat ttacagagaa ggaaactggg   106913
atgccctgct cagaaatgct ctgttcacgg catgtcagat acataccact gatggctggg   106973
agtctggacc cctgggttct tactccagct ctgccactac ctgcccacgg ttctgtgcat   107033
tcattggttg attcagcagc attggccgag agtcttctct gtgttgagca ttggacttgg   107093
tgctagggaa gcagacaggg tctctgccag ggcctgcgag tacagttgta tgggttgtct   107153
gctgcccaaa agaggtgatg atccaagcca agcaccttgg gaagaaggga cttttttgtt   107213
tttcagttct gcaaggaaga gctgtctttt cataattggc acaaaggcac tttctgagtg   107273
aatgggggatc ctgatgctat ccaggtgaac tttctaggtg agcaaaaaga tagtcttctt   107333
cttgctcaag cctcgatgag tcctgtgatc ccatcgtcca aatgcaccca gagcccacct   107393
gcctgtctgc ccccagcatg tgtttaggcc actgtctcac tctgatcatg atggtgacct   107453
gactggcctc ccttcttagg tctaggagcc agactgccag ggctcagacc ttggccccaa   107513
gacatagggga ctccgcggcc tcgggcagct cacttgggtt ctctgtgcct cagctcctca   107573
cctgtaaagc gaggaaaagc ccctgctgac accatacggc tgcttgagga ctgggtgcta   107633
cgatgacatc tgggaagcct ttagggcagt gcctggcaaa tcaccgagct gcagcatcat   107693
tgcttcatta gctgtgtttc cccaggtgtc tccttacagt ctgttctcct acaacatgag   107753
aaaaaaaaaa acgacaagat catgtcactc cttgctcaga acccttcagc aacttctccc   107813
aactggaagt aactccgccc cttctctgg cctccaaggc cctgcaggag ctggccctgg   107873
cccctccctg gcccacttcc tcctctctcc ctttgctccc tgggctcagc gttcccggcc   107933
ccctgctctt caccatattt ccagccatct cctgcagcag agccattttg cactggctgt   107993
tccctccgcc tgtgaagttt ctccatcctc atccactcag tggacacctt cttaaagagg   108053
cnttccttga ccagtctgtc ggaactagtc catcccctcc atgactccct cgagcccctt   108113
ccctagaggc ttggcctcta cctcgttccc tgttcatttc ccgcctctcc ctcctggact   108173
ggcagcttct tgagagcagg gaccttgttt gatctacctg gaataatgcc tggtccagag   108233
tagatgctca aataatggaa ctagtgtaat acagtgagat gggtgttagg ataaggtggg   108293
gaggaccccg gcctccttag aaagtccttg atggaaaggc attgacactg aggcttctgt   108353
tctggacctg ccacgtggtc ccctggcagt ttgcttcacc ttcctggaca ccagtttccc   108413
cttctcttgg ctggactggt gtcctgaaac tggctttcat ttagacagtt gggctatcct   108473
tgccgggtct cccttgatct ggctatgtgt gaccttgtgt cttgccagct gctagcatga   108533
cacaaggtca cacacagctt gtaacagcca ggtgtgcaca tctcttccca aatccatgtt   108593
catggacatc tctttggcag cttgaatttg ccatggtgg tagtatttct ttcttttct    108653
tttctttttt tttttgagat ggagactcac tgtgtcgccc aggctgaagt gcagtggctc   108713
aatctcggct cactgcaatc tctgcctccc aggttcacgc cattctcctg cctcagcctc   108773
ctgagtagct ggggctacag gtgcccgcca ccacgcccgg ctaattttt gtattttta    108833
gtagagacgg ggtttcaccg tgttagccag gatggtctcg atctcctgac ctcgtgatcc   108893
acctgccttg acctcccaaa gtgctgggtt tacaggcgtt agccaccgca cctggcctgg   108953
tggtagtatt tctacagata tctacaaaca ctacaaaatc aatctctccc ctccccagaa   109013
gagagggtat tgttcaagtt accagcacac aactgctctg gggccttcac aaggccaggc   109073
agttggtcag tcagcctcca ncatgactga gggcttcctg cgtgccatgg cnctgtccat   109133
ggtgctgacc ccgttgtgag ccattgcgtc gaggtcagca tctccacctc ccacccccact  109193
gtcactactt gctgtgtcac acggtgttct gagcacgctg ccgatgttaa ctggttgaat   109253
```

```
cctcccaaca acactatgtg gtaggcgtta ttaatatccc cctttacag atgaggaaac    109313
aaagccacag taagtttcag taatctaccc aaagtcaaag gggaaagggg gtgcaggga    109373
aaggggtgc cagggctggg attcagattt aagctgtctg gatgcagaac catgcactta    109433
actgtcatgc tacaccgcct ctcagtcatg atggtaacaa ccccagttgc agcctgcctg    109493
gtgctggggt gaacaaatgc aagatgccgc tgttgcattt cagtctcatg accactcgcc    109553
aggtgggggc tgtcactgtc ccaactcagc agaagtggag atgggcactg agaggtgggc    109613
tcccttgccc aaggcccctc tgagccaagt gtccttctga tggcctgccy agctttgttg    109673
agacagccgt atttcttggt tcttgcttta ggtcctgtgg aaagacaggc ccaattgcag    109733
gatagatggg aggttgtttt gctatgagca tggctgtcag tagctgtatg gcagtcctca    109793
cgtttgccct gcaggtggca tggtagaggt gtgcgaccct ggcctgcctc ctgtcccttc    109853
ttgacagacc tccctggcat ttctagaact cgctccctgt taaaatcctc ttgacccag    109913
gcctgagccc agacctttg gcctgcttcc ctcttcagga tgggtcctgc cactcccagc    109973
cttatgtcag gaccectcca ccctcatagc tcatactcca tcaccctgga gcctctccct    110033
ccctcttaga actcctctcc ttttggacag agcctatgct ccctctgagt tctgctggcg    110093
ccgcatcctc tccagcctgg ctctcaccct ctctgcctcc ctccctcatg ctcagccacc    110153
cagcctctca cacctctgag ccttgcactc ccctcttca acccctcac ccctccaac    110213
acacacacac cccaaacatt ttcccaccca ctagctctgc cgggataatt cctactcacc    110273
atgggcttcg gagggccctt ccctgactct gcaccatctc agggcctcgt tataaatctc    110333
tgacatgagc acctgtgtct ctcttaggcc atcgatcgat catggagcta aatctgcttc    110393
cctgccaggc tgggagcccc agcagtcagg gcggggtctg gtctgctcct tctcagtgct    110453
gtgggggtac agctgcctgg gtgcacatcc cagctctgtc caaccttgga ttcccctct    110513
cagttcttgg aaaccaaggc atgccattca ccacagaccc tcctagtcct cccaggggt    110573
gacaagcact gtacctttg catcctgctt agctgtatgc tttttttccca gagggagaga    110633
aagactctgg gagttctaat ttaactaaat tcaatttaac tgtagccatg tgctgggtct    110693
tttgacatat gtcatctggt gaaatcctca ttacagccct gcaaagcaga agttatcaac    110753
ccattctaca gataagaaaa gcagagcaca gaaaggctga gttttcaaga gatcacacag    110813
atgttaggca gtggggctgg actttcaagc tctgggtttt gtgattcaga agtcaggact    110873
ttcttccttt ttcatagctt ggttgattcc tttctaagca cttatgaatc acctgaggtg    110933
ggctatggca gagctgtgaa gatggactca ccacacagag agcgtgcagg gctcagtggc    110993
ttgtgcagtg agcggtgaaa tagaacagca ccttttcctac ggttccagca agctgggttc    111053
tgctccctga gaggaattgc ataatcatta aggtgttccg agtggagaag gaaggaggc    111113
tgttacaggc tagattgtgt ctcctccatc cccattcata tgttgaaacc ctaactccca    111173
gaacctcaga atgagactat atttggagac agggccttaa aggggtaatt aagttaaaat    111233
aaggctggca gggtagaccc taatccaatc tgactggtgt tcttataaga agaggtgatt    111293
agaacccaca gagagatgtt aagatgcagg aataagaatg tgaggacaca aggagaaggc    111353
agtcaccttc aagccgagga gacgggcctc agaaggagcc agccctgcta acaccgtgtt    111413
attggacttc ggacctccat agctatgaga aacacatact gtttaagcca ctcggtctgt    111473
agcattttgc tatggcagcc aggaatcctc ctgtaggatc tgacatgcct tggtctgagt    111533
gcttgcagct catgtttgta gtcaggtcat cttttggaga tttgctgaaa aagcagtttt    111593
tcaagatgaa ctccatgtgt gggaggcctt ctagggcacc tccgcatccg gcgtccctgg    111653
```

```
tgagctcatg cgtgagtcct tttgtggctc ttggcagggc tgcctccatc cctaactccg  111713
gtggctgctt ggttgccatg gcgacagctt cctccatcct gagagcaggc tcctgccgag  111773
acatctggat gagcctcact gtgctcggtg aaatcggtgg agcccaaggc tgcagccctc  111833
tttctcatgg atccctgctc tgcacccagc atccccttg ctgaggacac aagccagtcc  111893
agccagcctg gcatcagggt ccttggggtg cccaccccat ggggaaagct gcagatggtg  111953
tggaaatgcg tttactccag aacagtggga ggaacgctga ctggaagtta gggagccagg  112013
atttcagtcc ttactctgcc agggctctgc atgtggccct gggcaaatca ctgcccaccc  112073
tgggcctccc tctcctcctg ggtggggttg gcacatgggc agttcctgcc tgcaggggtg  112133
gactatttga ctggtctgtg ctaggcatgg ctctctgggg ttattaccat gtctcaaagt  112193
tcaattactt gctgtggttt ttagattagc ttgtcgtggg atctccactg gggcccatca  112253
tgaggtgaac cagtatttgc acactgcttt tggcgtttgt ggagtgcttt gcatacttgc  112313
ttctctcttg agctccttgc cagaaccaac cagtgatgct tcttcatttc acatacctgg  112373
ctatatttcc agtcagcaga gatttgccct gtagaggagc gagcagccct tggttcctgt  112433 gcccaccttta caggagagga cgaccggggg gcagactggt gcagcttagc tgccatggct  112493
cctggaggtg cagccacctc ctccagcctc acgtggggct ggtgtggctg agctcgcgtg  112553
gctgggctcc aggagagcag gctgtgcctc tggtagcagg agatgaagga gtttcttttt  112613 tttttttta caggtgaaat aaattttaat gataaaatta ttttagtaat aaaaatctta  112673
ataataaaat gtatttaact aaatataccc gaaatattat catttcaaca ttggcactag  112733
ctacatttca agtgcttttt ttgttattta agttctaggg tacatgtgca caatgtgcat  112793
gtttgttaca taggtataca tgtgccatgt tggtgtgctg cacccatcaa ctcgtcattt  112853
acattaggta tttctcctaa tgctatccct cctccattcc cccactccat gacaggtcct  112913
ggtgtgtgat gttccccgcc ctgtgtccga gtgttctcat tgttcacttc ccacctatga  112973
gtgagaacat gtggagtttg attttctgtc cttggaatag tttgctcaga attatggttt  113033
ccagcttcat ccatgtccct acaaaggaca tgaactcatc ctttttttatg gctgcatagt  113093 attcaatggt gtatatgtgc cacatttct taatccagtc tatcattgat ggacatttgg  113153
gttggttcca agtctttgct attgtgaata gcgccgcaat aaacatacat gtgcatgtgt  113213
ctttatagta gcatgattta taatcctttg ggtatatacc cagtaatggg attgctgggt  113273
caaatggtat ttctagttct agatccttga ggaatcacca cactgttttc cacaatggtt  113333
gaactagttt atagtcccac caacagtgta aaagcgttcc tatttctcca catcctctcc  113393
agcacctgtt gtttcctgac ttttaatga tcgccattgt agctggtttg agatggtatc  113453
tcattgtggt tttgatttgc atttctctga tgaccagtga tgatagcatc ttttcatgtg  113513
tctgttggct gcataaatgt cttcttttga aaagtatctc ttcatatcct ttgcccactt  113573
tttgatggtg ttgtttgatt tttttttgt aaatttgttt aagttctttg tagattctgg  113633
atattagccc tttctcagat gagtagattg caaaaatttt ctcccattcc gtaggttgcc  113693
tgtttgctct gatggccatt tttttttttt ttttgctgtg cagaagctct ttagtttaat  113753
tagatcccat ttgtctattt tggcttttgt tgccattgct tttggtgttt tagtcatgaa  113813
gtccttgccc atgcctatgt cctgaatggt attgtctgga ttttttttcta tggttttctt  113873 ggttttaggt ctaacatttta agtctttact ccatcttgaa ttaatttttg tataaggtgt  113933
aagggaggga tccagtttca gctttctaca tatggctagc tggttttccc agcaccttt  113993 attaaatagg gaatcctttc cccatttctt gttttttgtca ggtttgtcaa agatcagatg  114053
```

```
gttgtagata tgtggtgtta tttctgaggc ctctgttctg ttccattggt ctatatctct   114113
gttttggtac cagtaccatg ctgttttggt tactgtagct ttgtagcata gtttgaagtc   114173
aggtagcgtg atgcctccag ctttgttctt ttgcttagga ttgtcttggg aatgcgggct   114233
cttttttggt tccatatgaa ttttaaagta gttttttcca gttctgtgaa gaaagtcatt   114293
agtagcttga tggggagatg aaggagtttc tataaaaacc tctgcatgcc cgaggactat   114353
acgggaggcc tgtgtggatc acacctcctg tgtcctcgga agggatggct gcagacttca   114413
ctcttgggtg gaagaaaccc cgctttgctg actccccag gtgcaggttc tgagctcaca    114473
ggggtggtct gaacagctgg gggcacccag caccccctacc cccacccacc agggtgagga  114533
gctccttgta ctgtggatgg gggaccggga taggcccacc tgtccctcca gggctgcact   114593
tgctccatct gacattgaac ctgggcctgt gtgcagtaaa aagggaggc tgtgtgaccc    114653
aagcaagact gcatcgcctc ctgtaggcct ggggctgtgg gcggcagggc aaatccactg   114713
tgcgtggggc tttctgtgca catagccatc ctttgtttag ctagcacctc tggctggttt   114773
tctgttacaa cagcagagtt gagtccttgc agtttcgata gaaatcctac gtctggctag   114833
gcctgaaata ttgactctct gactctttgc agaaaacact tgccaacacc tgtgaatgtt   114893
ggcactggaa ggaaaagggg gtccatttca agacatgggg ggctgaagcc agacaactgc   114953
caggtccccg ggcccctcca gggacctgac agccctcct tgcccagcac ctcgctgtcc    115013
ctgtctcatg cccatgactg cagctgtgac tttctcctcc tgctccctga gcctcagatg   115073
acacagagtc cagagaggct gagactgacc cgaggtgcca cagcagatga aaggggatt    115133
tgaggctggg acccagggtc ccacctgaca gcctttccct gcccagcacc tcgctgtccc   115193
tgtctcatgc ccatgactgc agctgtgact ttctcctcct gctccctgag cctcagaaga   115253
cacagagtcc agagaggctg agactggccc gaggtgccac agcagatgaa aggggattt    115313
gaggctggga cccagggtcc cacctgacag cccctcctg cccagcacct cactgtcct    115373
gtctcatgcc ggtggctgca gctgtgactt tctcctcctg ctccctgagc ctcagatgac   115433
gcagagtcca gagaggctga gaggctagcc cgaggctcca cagcagatga aaggtggatt   115493
tgaggctgga acccagggtc cctggcagcc aggcagaaca ggccgcagac cttctcagca   115553
gctcacctac agagcgccca ctctgagcct ggtcctgttc tcagcgcttc acgtggacta   115613
ccttacccca tcctcatctg ggagctgcag agtgcaattg cccttctgaa gttggggaaa   115673
ccgaggcaca gagaggttca gaaacttgcc caaagacaca tagctagcaa gcggcagagc   115733
tggagccacc cccagatggt caggggggcaa ggattgcact ctggagccac ggagggcgta  115793
tggaagactc tggagcccaa ctgagtccca ggcctggtct gacccttctc tccttgtccc   115853
tgagcaattg gcttctcctc gccgagcctc tgtttccaat gtagaagggg cacacctcac   115913
tcatggaagg cagaggggat tggatgagct acagatgcga agctagtccc acccagccag   115973
ccggccgcac gtgttagctg cgacaggtac taggtgcttg gctggggttt ggggatata    116033
aacagtagaa caactttgcc tagtcaggtg aatgacacaa gcaggtcagc cagtatttgc   116093
aacctaaaaa gatctcgctc atgggccttg gagcaggtgc agtggagacc agaggaagca   116153
gtgtaggaac aagttcttcc tgatggactt cactggaccc gcagcacgtg tgacgtgctt   116213
cccagaccac agtgctcttt ttttttttt ttttttttc caggcagagt ctcactctgt     116273
cacccaggcc ggaatacgtg gcacgatctc agctcactgc aacctctgcc tcccaggttc   116333
aagtgattct cctgcctcag cctcctgagt agctgggatt acaggtgccc actaccacgc   116393
ccagctaatt ttttttgtat ttttagtaga gtcagggttt catcatgttg gctaggctgg   116453
```

```
tctcaaactc ctgacctcaa gtgatcctcc tgcctcagcc tcccaaagtg ctgggattac 116513
aggcgtgaac caccatgccc ggccagcaca gcactcttgc gtttgtaccg cagcagcaat 116573
actttcaaca cgctgcaggg ggacggctcc tttgaatggc ctttgtcagt gacgatccac 116633
tcctaaaaaa cccctcacac cctggggcct ccttgaccat gcctcttttt tttttttttt 116693
tgtgctttct gtggctttct tttttctttt ttttattata ctttaagttt tagggtacat 116753
gtgcacattg tacaggttag ttacatatgt atacatgtgc catgctggtg tgctgcaccc 116813
actaactcgt catctagcat taggtctatc tcccaatgct atccctcccc gggagttgaa 116873
caatgagatc acatgacac aggaagggga atatcacact ctggggactg ttgtgaccat 116933
gcctcttatc tcaactttaa cagctgcttc cccttgagat ggtttgcaac ctcctgcccc 116993
ctgagccctg atcagagggg accacaatgg gctgattcat tcattcagtc agcaactact 117053
tactaaacac ctactgtgtg ccaggcactg aaggtgcagc agcaatcctg acaggcaggt 117113
ccctgccctc gctggggaca gatagcaaca aacaggccaa taatgtaata agcagtgatt 117173
aatgcttgca aaaagagaaa gcagaaaatc tataattaaa caaggtaaaa taaatgttta 117233
ttttgagggg cagaggagat ttacaggagg ttactttgtt aaggagcatt gaggcaggga 117293
tctgaagggc atgagtgtga gggccctgca gtgggaatgt gcccaacacg acctgggttg 117353
attggacacc tcctccgtgc gcacaacctg cagcttcttc taaggggcaa tggggcctgg 117413
ctgtgggggg ctgtgggcgg aggaacccaa gctggattcg caatcaygca cccgggctca 117473
ggtatcagct ctgctgctca ctgactgtgg aaccctctga gcctgtctct ggacctaagg 117533
aaagcaaagt ggagcaccag ctgccttctg caccctgtta gtgtgtgttg gggtgggggt 117593
ggggggcaaa tgaccgtgaa cagagtttct aaattggaag ggctgttccc agggaaaggt 117653
tcagagtcgt ctccccatct aatatttgcc cacggatcag tcatgcagcg aacatgtccc 117713
aggcaccagc tctgggcagg tcgtgtgtga ggggtgtggg ggcacggagg tgaatcagga 117773
ggtggagctg gccctggagc cgactgcagg gcgggacaga tggtcacata cacagcacaa 117833
tggtcctgag gatgagcaga cgggtaaggc cttgccttgg tgttcaggca gagactagga 117893
atgctccggc aacttcgaac tgctggatat ggctggcggg tatggaggga gaagcggcca 117953
aggtgagact gaggaagagc aggcaggggc agcacgctgg gcaagtccga cctcctcggt 118013
ggggtgggag aggccaacac gcagggtggt ggggagtccc gcagctgttt gaggaagttc 118073
actctagctg agcttgggca cggaccccca tggggacaga gatgctgatg gcctgggctg 118133
aggggcatag cgcaagggt tcagatggag gaacccagg acctgaaggc tggctggaca 118193
agggaagggc ttataatgag gaataagccc cctgatgcct ggcttggtgc cccaaggctg 118253
gggatgagga aatgggagtt ctagagaagg agcggtgtgg gggctgttgg tgtgggggc 118313
tgtcggtgtg ggggggctgt cggtgttggg ggctgtcggt gttggggct gtcggtgtgg 118373
gggggctgtc ggtgtgggc ggctgtcggt gttggggct gtcggtgttg gggctctcg 118433
gcgtggaggc gctgttgtct taacgcccctt tcgttctaac cgcccttctg ttttcaccgc 118493
cctgggctct aacaccccta tctctccaac ccctctgga tccccccccc cactcttttc 118553
ctcgcccccc taggcaacgc cttcttaatg tgcccaaagc ccccggcccc cctgcttggt 118613
tccccaccct ttttatgag tcatatctta ttctcttctc tccaaccctc tctttctttt 118673
ttttctctgc ctccctccct cctcctccct cctactcctc tctcttcttc tctctccttt 118733
tctcttttcc ttttctttcc ctcttttcct ttctttctta ctcctctctt tccctctcc 118793
ctccttttt ttcccttccc ctttctccct ctatctcttt tttttccttc tttctttttc 118853
```

```
tcttccctct tcctttcttc ttcttttct ccttttccc ctctttnttt ctatctcttt  118913
ctctctctct tattatttct ttctctcctt cctcctccct ttctttcttt cctccatctc  118973
tccttctcct atccctctct ctcttctcca tcttcttctc attcttggct nnnnnnnnnn  119033
nnnnnnnnnn nnnnnnnnnn nnnnnnnnnn nnnnnnnnnn nnnnnnnnnn nnnnnnnnnn  119093
nnnnnnnnnn nnnnnnnnna cnnnnnnncn ggcgtaggtg gtagatagtt cttaggtcag  119153
tcgcatgtac tagcggtggt gtctagctgg tcgtggttgt gtcggaggga ggcgtcgtag  119213
atagtgttat gtatacgagg tcgaggtcgt cggtgctggt aggtgcgatg ttcgtgctcg  119273
ttgtgctagg gatcaagatg tattagtggt ctactggtgg gcggtagtac tagaggtgtc  119333
gcacggatgt gggttcgtgg tggatttgtg agaatgagac tggtgtgtgg cgggagttgg  119393
ttaagttgtg gggtgtgtaa tggataaggc gtctggctgt aggagtttgt gtgtcggttg  119453
cgtgggggcg tgtctggttg aggggcggg ctgtgcgtgt gtcagggta gctgtggttt  119513
gtgtggggt cagttctgtg tggggtgggt tgtcttgttt tgtgggtgat ctgtgcgta  119573
ataggggtg tgttgggttt tggtggactg ttggagtgga ggggcgtggt tggtgtgtgt  119633
gggggcttga gtgtatgggg gggcgtttgc tgttggggat ctgtcggttt gtgggactgt  119693
tgatgctgtg gagtgtacgg tgtgttggtg cacttggtgt tggggggtg cctgtatggg  119753
ggggttgttg ggttttggg gtctgatgcg tgttggggc tgttggtgtg ggggtcggg  119813
cggtgtgaag ggctgtcagt ttgggggtc tgtcggtgtg gggcggctgt cggtttgggg  119873
gggccgtcgg tgtgggggc tgtcactgtg ggggggctgt tggtgtgtgg ggctgtcggt  119933
gtggggggct gtcggtgtgg ggggttgttg gtgtgggggg gctgttgggt gttggggct  119993
gtcgggtgtt ggggctgtt ggtgtggggg ggctgtcggt gtggagggct gtcggtgtgg  120053
ggggctgtc agtgtggggg ctgttggttg ggggctgtc agtgttgggg ggctgtcggt  120113
gttggggtgc tgtcagtatg ggaaggctgt tgggtgttgg gggctgtcgg tgtggggga  120173
ctgtcggtgt tgggggggctg tcggtggctg cccatagcac tggcattgcg tctgctctta  120233
tttcccaact cccaggaagc accttgggtg ggttagtgtc ctgtggctgc tgtggcaaat  120293
tgccataacc ttcatggctt caaaatacag atatattctc accgtcctgg gggccacaag  120353
ttctcaatcc aggtgttggc agggccgtgc tctctctgaa ggttctaggg gaggaggctt  120413
ccttgtctcc tccagctccg gggctccaga tgttcctgta gccatcgctc ccatctctgc  120473
ctttgtctcc acatggcctt ctcctctggt gtctcctctt ctgtctctta gaatgtcact  120533
tgtcattgca tttagggccc acctgggtaa tccagggtga tctcatctca agatctttaa  120593
ctacatctgc aaagacccctt tcccaaatg agatcacact ccacagtctc tggggatcag  120653
gatgttatgg acacatgcta tgctgatgta tttgtggggg ccattattca acccactgca  120713
gtggagaaaa atagtctgtg ctcagttgag gcatatggga ttgaagagcg atttttaccttt 120773
ctctccttt catcctctct gcataacttg ctcctctctc tggaattcct acctgtgtct  120833
gacaaacttt tcttgcaggg aaaatgactc ttagatgcta gagtgtgatt ggaagggaaa  120893
caaatcccac cagacagttg gagtggaatt agatgggaaa acagaagatg aataattcaa  120953
gcagctttgc caggggaaag gggactctta aatgagccta attatgcttg ttcccaaggg  121013
aggccagtcc tgaaatgaac cttgtgaagc agttttcaa gcaggattta ggcgggatc  121073
atgaagctgg ggtggggcca cctgcggtta gtcctggaaa ggaaagggcc caggccctca  121133
ttttgcagat ggggaaagca aggcttgcag aatggaaatg atgttccagt aacagccaag  121193
accagacgcc cagccggggg ccccgagtga cagccaagac cagacgccca gccggggcc  121253
```

```
ctcagcttct gacctggtgc tggtcctgcc taagttaaag ccaccgagtg tggtcactgg  121313
gccaaatgct tcaaagtcta cacacggggg agggcatggt gtgggcaga aagctgtgtt  121373
cacggtagct gagtttgggc ataattctcg tgctccggag gcttctccca cagctacttc  121433
ccttgtcagg agtccatctt cagggccctg tgttatgatg gattgaggga gcaccaacag  121493
gggccacccc acttggtaat taattccttt tgtaaagggc tgggctgcag gcccgggtag  121553
gtcctatggc cacctgagcc aaggtcttgg agaggcggtc gcacggacca ggtgaccatg  121613
gacccagccc ggtgcccaca ccgtgaaggg tgctgtgctg cccagaggtt ctgggcacgg  121673
ctctgggccc tgggattcag aggctcggga ctgcttgcct ccccacggag atcttaccgt  121733
ggggaccctg ttgtggaggg cctgccgcat tggccgtgac agtgattttt ctccttctgc  121793
agggtgatgt ggatgcaggg cctctgtgtc tcacatggtt gtttcacagc agccaccgta  121853
tccgaagaca gagagaaaga gcaggagaga ttccctgtg atggctcccc catgggtcct  121913
gacccaggtt tgggagactt tatctcccca aagccaggcc ctcgatccct ttgcctttgg  121973
ggactctgtg tccccagcct atacatgggg tgctcgattg agtgtccgtg ccctcagcc   122033
ggccctgggt tgccgtggct cgggtgtgtt gccacaggg ctacagacct aatggagccc   122093
tgcatacttt tattaattaa ttaattaatt tatttattta ttttgagat ggagtcttgc   122153
tctgtcaccc agtctggagt gcagtggcgc gatctcagct cactgcaacc tctgcctccc  122213
cagtcaagcg attctcctgc ctcagcctcc caagtagctg ggatttcagg catgtgccac  122273
cacgcctggc taatttttt ttatttttta ttttagtag acacggggtt ttggtatgtt   122333
ggtcaggctg gtctcgaact cctgagctca ggtgacctgc tcgccttgac ctcccaaagt  122393
gctgggatta caggtgtgag ctctggtgcc tggcctccta catactttga aaagttctga  122453
aacatcccca ggtgggaaag gaaagagcgt ttgggtggac actgaacctg tcaggggggct  122513
cacgttttgc agtggtagca aacaacctga aggtctccaa ggcctcaaac acccacttca  122573
caccteccac tcacgctgca agtgtggccg tcacaggctg gctttggtgc gatctcattg  122633
cggagggaac agtgtcacag cagaccacgt gctggctctc aaaacttcag cctgaggtg   122693
acatgcctca cttgtctatt cattggcaga agcaaccagc ctctggccac tctgggttct  122753
gaaaggccga aggagaggtc tcccctggg agagaacctg gaatgttcag agaacccct    122813
gggtgtcagc atttgacttc atcccaccga gtcctcctgc acccactgcg ccccatgagt  122873
tataacccca ggaaatacaa cgagaatgag tgtcctgatg acgcaaacag aactcctgtg  122933
ggactcacgt tcctgggcgc ttctgttgcc accaagcctc ctgtggcttt tgtgtgtctc  122993
agggtgtgca gagagaatgt agcccctctc tgccctgcct ctctactgca cattatccat  123053
gggccgtcgc actaatgtgc gtgacatttc atcagtggcc gcactttttc tctgatccc   123113
actttagtga agttcagtaa ggacctgaga gctgctccga gcgggcagcg tgtcctggaa  123173
agccatggga ggcattcggc ctggggaggc tgggctgcca ggtggacgct ggagaaatca  123233
gcatggcagg aggagggctc ttttcttgct tggccttcag tatcattttt cattatttaa  123293
tcgctgcttc ttttcatact ggaaaactgt agtttcctgg gaaaccagcc aggcagtgat  123353
gccttaactc attttccct ctctttctat ttttatgtga ttctcagttt gtggttaatg   123413
acgtgcttcc gggaagcaag atttgagcac gagcacagag accctttag gtgctttctg   123473
actgcacaga tcagccattt ttttccctgg cattttataa accctcgggt ttagagaggt  123533
cagaaaatac tgcttgcttg cttttttttt gacagagtct tgccctgtca ccaggctgga  123593
atataatggt gcgatctcgg ctaactgcaa catccacctc ccaggttcac gtgattcccc  123653
```

-continued

```
tgcctcagcc tcctgattag ctgggactac aggcatacgc cactactaat tttttttttag  123713 tagagatggg gttttgcaat gttggtcagg cttgtctcca actaatttct ttttgtattt  123773
tagtagagac ggggttttac tgtgttggcc agaatggtct cgatctcctg acctcgtgat  123833
ccgcccgcct cggcctccca aagtgctggg attacaaata ctgctttctt actgagagag  123893
gcagcagctt gggtggagga agagggaggg cagatggatt tcagagtttc agtcagtatt  123953
ttccagatag aaaataataa aaatggaaac tgacattcat tgagctctgc aacgcatcag  124013
gcagtgtgtg aagggctttg cctctgatga tcttcacagc gaagtgataa ggctatactg  124073
ctgactcatt ttacagatga ggaagctgag gcatggatag ctgggaactc actcagggtc  124133
acacagccag gaggtgacag agctgggatt caaaccccag accttccaac tccagggctc  124193
acatgcacct gaagagtcag agggaacaga ccgtgcaaag ccccatgcag ggccggggag  124253
accggagcct gaggtcattg ctgtgagagg ggagagggcc tttctgtcag ggtgatgggt  124313
gggatctgaa gctggaaagc cggagagaag ctcgggggtg ccagtccttg catgctccaa  124373
gagattctga tctgctgctg ggcagcaggg aagggatagg aaaagagcag gtgctggggc  124433
cggggaggtt gtgaggctga atccagcctt accaatcaca cctgggccac cccggacgag  124493
ttgctcatct tctctgtgct ctagtgtaac agtcagggat actgcctttg caagcagcaa  124553
agttcttgac tctaaacaaa aaatggacat ttattggctc ccacatttag cagtctgggg  124613
ggaatggctt caggtgcagc ttgatccagg attccaatgg catcaccaga tctttctctg  124673
cactctttcc actgtctgcc ccaccctcaa gctccagggt ttctccttgt cctggcagca  124733
gatagaagct ccttctttct acaccaccca gcacagcagg ggtgaccaag ctgcatccca  124793
gccttttcag tattccaagt cctggggtct ggagagcaca gatcagagcc gaggtggggc  124853
cgacccagaa acccagaaga acctttgccc aaaggagaat ctccatactg tggtcagaag  124913
aaggggagca ggtgccgggg gcaggaaggg gagctcccag atgcccacac actcaattcc  124973
agacacaatt tgaaaaggga ccgggaagac ttgaaatcat tcaccaatag catccactgc  125033
ccagcatgca gtcggcacaa tataaatgct ctttttcttc tgcttggcaa ccaacagggg  125093
aaggaaggca gaggagaggg gctccacagg tcagtgctat gtgtggctgg aactgatgca  125153
ccctcactgg ggtggggtgc aggtgagggg ggccgcaggt caggagggaa gtggtgggtc  125213
cagcttcatg ggaacagggg acaggcacct agaaggggta gccagcaggc agttcaccat  125273
gcaggtctgc agctcagggg gacgcatttt gagggtctca ggaacagaga ggcagctcag  125333
acgcgagggt ggacggtttt gcctcgggag aggtgtcaga aacctccggg aaggcggagc  125393
attgagggcg cccttcactg cccctttcctt gaccgcactg cccccag ac  atc gtg   125448
                                                         Asn Ile Val
                                                             210 gac atc aag ccg gcc aac atg gag gac ctt acg gag gtg atc aca gca   125496
Asp Ile Lys Pro Ala Asn Met Glu Asp Leu Thr Glu Val Ile Thr Ala
            215                 220                 225 tct gag ttc cat ccg cac cac tgc aac ctc ttc gtc tac agc agc agc   125544
Ser Glu Phe His Pro His His Cys Asn Leu Phe Val Tyr Ser Ser Ser
        230                 235                 240 aag ggc tcc ctg cgg ctc tgc gac atg cgg gca gct gcc ctg tgt gac   125592
Lys Gly Ser Leu Arg Leu Cys Asp Met Arg Ala Ala Ala Leu Cys Asp
    245                 250                 255 aag cat tcc aag c gtaagtgccg gtgcctgggg gtgggggggct gtgcattggg   125645
Lys His Ser Lys
260
```

```
caggcgggcg ggtgggatgt cctgtcctgg tgcagctgct gcaggggtgg tgggtgtggg    125705
atgagcatgt cctggactgg ccaaggtggg tgggcccatt gctgcttcag cgctggctgg    125765
tcggggagcc tggtcttgcc acctgctgcc ccccagagtc cctgcacagc caggaacagc    125825
ccagctttta gggttcaggg ctctagggcg agggtcaggg catccagaag gtaaggaggc    125885
accaaactta aatgtcacct cctgtaggaa agcttcccgg cctcctactt tagatctgga    125945
tcctcctctg tggccctgca gcccccaaag cttccctctt ccaaaactag ccacacccag    126005
caaacttgct gtgggctgcc catcttctcc ggctccttgg agcagggtct gtaacatgtc    126065
ccctcatcct agaacccacc acaggcctgc tgtgggggtc ccacagggt atccgtggag     126125
gtctggggct gaacgagttc caggggacat tttgtgacac agcagccccc agcataacag    126185
ctcacactga acactcactc tgagcccagc ccttaccaag gctttacct gtgaactcat     126245
cgaatcttca cacaagcccc aggagatgct gttcagaaga ggaaacagaa gctccagtta    126305
ttggcccaag gtcacccaaa ttcaatcgtg cagagctgg gctgcctggc actgggttgt     126365
ggccatgggc tgcacactgc cacagccatc ccagaggccc ctgaaggcga gggatcaggc    126425
cacggcatcc tccttcccag acagccctgc agggctagca aggggccagg caggaggtgg    126485
ggtgtccccc aggcagaggg cagggacttt gcttatctgg ttcccctcac tgtctgtccc    126545
cagcacctac cacagtgtct ggaaataaac acttgttgaa taaacccag aggacccctga    126605
ctgaagcctg ggtgccggcg gcagagggct gtttgggagc gatggggcca cactgttccc    126665
ttagggtgtc tggttttgct gggcagtcag agacagggtg cacaccagcc ccaggactca    126725
ggctcagggc ccaccaaaac ctccagcttc tgcctccttc cttggccaag ttctggcccc    126785
cacatccacc ccctcatctc ctctgggttt gtccacgctc cgtgtgtcac gctcagccat    126845
ccaggcattc agtaggcgcc tattcctggc atgggtgtgc agcagaggcc caccgtcggg    126905
agctggcgtc tgcggggag acagacagtg aacacacacc tgacgcatgt cagggcatgg    126965
tgagcaatgg caccaacacc cacaaagtca ggtacaggga cagaggggt cagggagggc     127025
ctccctgaag agaccacagt ggaacggaca ccctgagggg gtgggtggtg ccgatctctg    127085
gggaagaatg ttcgagaagg agggcactgc agtggccgtg actccacaca ttgcctgtag    127145
gtcaagggag ggactgggtt ttgttctggc tgagctgaga atgagaagct gtgggttgtc    127205
acgagattgg gacttgagga ggaagaggag acgccgcaga gggtccccgg gggagcaggc    127265
gtcagaggtc gctgcagggt ctgcaggaag aaatggtgac cccactgagg gggttgttgg    127325
gaggtggggc agggctcacc tggctgcccc ctctggatgt tgcttggagg tcgagctttg    127385
ccttgtgggg cgtgactctg tggttggttt gagctgtggg tgaaggtggg gccgtggcct    127445
ggaacaacag ggggtgccag ggaccagcag gcaggtttca gacccgcgag cctgaggccc    127505
gtattgggtt ccaaggaaat gggtcgagta ggcagccaga tatccaggca gtaatgccac    127565
ctggagataa gtgtggagtt agtggccgtg gactgatggg aggctggaga ccagctgaga    127625
ttcccggggt gcaggggct cggggctgcg tcctgtgcgc cacaacaaag gaccacacac     127685
ttggtggctg aaaacagggc atatgtatag tctcagtccg cagtcccaca gccagctcac    127745
tggccataat gaaggtgcca cgggctggta ccttcgggag gctctgggga gcaccgtttt    127805
ccctgcctct tctggcttct agaggcgctg cgttccctgg cacgtggccc ctcccccatc    127865
ctcccagccc acagcggcca agcctctctc acgtctctga ccctcctgtc tgtctttcgc    127925
gtataaaggc ccttgtgatc gccttgttcc tgccacccct aatgatccag gatgacttcc    127985
tcatctcaag gttggctgag ttgcgtcctt gatttcatct ttggccttat tttgactttg    128045
```

```
ccgtgtagca taacatagtc acaggtgcta gggatcagga cgcagccgtc tctgggggcc  128105
gttccaccgc ctactacagg acactgcccc cccacctacg cctcccgccc attcactcag  128165
gccacatgtg cctccagctg tgcctgtgta cagccaggtc tgggtccgaa tggaatggga  128225
gaatattggg gaagagaggg ggttcttcct gctcctggtc cgctgctgac cccgtgtgag  128285
ccctgtggga aggaggatgg ggcttcattg gcaccctgtt gtttataggg gtggaaatcc  128345
agaaacatcc tcaatatccc aatcttaaat gctaagatta ttcaactctt ctgaaatgag  128405
tgaggcagct ttttgtttct ttttctggaa ccgttggtgt aatatatctg ctccttgaag  128465
tattaggaaa acttgtgtgc aaatctattc ggcgtccttt tgagggagag aaggaaaatt  128525
ttaagcaacc agtttaaaat gccgagaaaa tgatgtcgac agtgatgaca tccatgtact  128585
agaatattgt tcggtcatgt cagctattgt tttagaagaa tttttaatgc cacagggaag  128645
tgattatgtt gaaagattta ggggataaca aaataaggct atgaccacca gaaaagtgga  128705
aacagagaaa actctggaaa gaaatacact aagttgtccc tgagtggtga gctataagaa  128765
actgatggaa tattttcttt ttatttttct gtgtatttt actttcatga tggatttgaa  128825
ctttgaatca gaaaacacat gtgtgtgcag gaagggtgga atttagagag cacagagacg  128885
ggcataggac agttttgtgc acccctcaat gtttgtgtga cattttcag tgggctagag  128945
ggggcagtca gacccccttt ggctcccgaa gcctgtgcta tccggtttcc cagggcagaa  129005
gcagcggtca catataccttt gcacatttcg tgagtccaag cacagacaca tccatttcag  129065
ccacgtaatt tcatatgcct gatgatgtat gagccttgtg tgaatcagcc aatgaactca  129125
acagtgcgag aaatatgagt gttttcgatg actcaattca atttcattct tcaccccag  129185
ctcccagggc tgcagtgaac gttaacttt agggcctcgg cagattccac tcctctccgg  129245
attgcactga ggttccagaa ggctctggca ggccgaggtg cggagagagg gacatggtgt  129305
cttccaggcc actgaggact tttgattgtg cctgggcgac cttggggcca ggtccttgct  129365
gacaaatccc caagggcctg ttggctgtgc tcagtgactc acctgggagg ttggcaacat  129425
gctgacctct ggcggctctt gcccgcacca gtgatcccaa gtctgtagac agggtggggc  129485
tgcctgtgat gtactaaggt tttatgtatg cttttgcac acacagtcat aggtgaagtt  129545
ggtttataat tttcttttct tatactctct tgcccaatt ttaagattat tcaactctcc  129605
taaaatgaac tgggcagctt tttcttcctt tttctggagc agttgatgta atatatctgc  129665
tccttgaaat cttaggaaaa cttgtgtgca aatctatttg gtgtcctttt gagggagaga  129725
agaatttttt tcttttttt tagacagaat ttggctccat caccctgaca cgatcttggc  129785
tcactgcagc ctccacctcc tgggttcaag ggattctctc acctcagcct ctggagtagc  129845
tgggattaca ggtgtgtgcc accatgcctg gctaatttt tttgtatttt tagtagagac  129905
agggttttgc tgtgttggcc aggctggtct cgaactcctg gcctccagtg ctgggattat  129965
aggcatgagc caccatacca ggccaagaga agaaaaattt taaacaacca gcttaatttc  130025
ttttttgatt attgatttat gcaaatttta tttaaatttt ttctagaata tttttcatta  130085
tcaaactcaa tatcctgtac ggaaactttc tctttcgtgc cagcaaaaag attgcgcagc  130145
agtttttagc atgcttttac agcttccatt tctcctcatt taatttgccg cacattgggg  130205
cgagtggctg aagtgtctgt ccttctgcat gccttgtccg ggctgtgttt ttgctctgtg  130265
gctctcatgg gaaatcaagc acgcagccgc tttccaatta gcaggtggcg gctgttttta  130325
atctgaacac aaatggctgt tatttgagct aattttttaa aagggatttg gggattagga  130385
ttagttcttc acctcccact tccatccatg tatccaatta ctgctcaaaa ctcagggagt  130445
```

```
ggctgatagt gacaccccag agatgtgctc acagcatcat tttcctaaca gaatcagacc   130505
gcgaatgaag agcgtcctgg atgcaggaag gtgagcattt ctgccattgg acagatgagg   130565
agaccgaggg tccgagaagc tctgtgactt ccctggaccc ctcctctatc agggcagagc   130625
tgggggcaca caggccactc tgttccctct gcagcttccc acctttctcc gaagcactgg   130685
aaatccgcgt cttgtgactg cttggcagtg tgacagggta accgtggaaa caaccgtaca   130745
tgagtcctca aaatagacag ttacttctgc ttatgacagc acagagcctg cggaaagaaa   130805
gggccgtgcc cggaacactg ggatttctta gaattggggg tgatgatggc tgagaccctg   130865
atttcttaga atcggggccg atgatggcca agacccttca taggccccca acgacgtgcc   130925
tggcccggtg ttgggtgaaa taataaccgc agctcattct ttgcacacct agtgcaaaca   130985
catgctgttt tcagtttata tctcattaaa tactcagcac ctatgatggg tgtgttatag   131045
tattcatcct acagatgagg aagttgaata cacttgaccc tggaatgatg tgggagttag   131105
gggttcagac agtgcctgaa tgcagttgaa agtacatgct taactttga ctccctcaaa    131165 acttcactcc taatagtcgg ctgttggtgg ggagcattac cagtaacatc aacagctgat   131225
gaacatttga agagactgat gtctacgtgg attttatgca tttgtgacat acctaacttt   131285
ttcttttctt atatatatat gtatgtatat atatgtatgt gtgtgtgtgt gtgtgtgtgt   131345
gtgtgtgtgt gtgtgtgtgt gtgtatcgtg gcagatctcc aaaatgtttt cagtatattt   131405
actgggaaaa tcgcacatca ggggacctgc aggttcaagc ctgtgttgtg tgagggtcaa   131465
ggggcaactg tatacgcact tctcattgct gcgggaacaa ttgccatgag cttagtggct   131525
caaaacaaca caaaagactg ttgtacattc tggaactcgg gctaaaatga aggcgtcagc   131585
tggcctgtgt tatctctgga ggctgcaggg tgggctgtt ttctgatctt ttccagctac    131645
tagaggcttc tagaggctgc ctgcactcct cagctcatca ttccaacctc tgcttccatc   131705
atcccatctc tttcttccat cttttgacctt ccttcttcct cctatacaga cccttgtgat   131765
gacattgggc ccatccagat tatccagggt cacctccgta cctcaaggtc cttcacttaa   131825
tgacatctgc aaagccctt ttgccatgtg agataacagg tgcacagatt ctagggtgga    131885
ggatgtagat agacgccttt aggggtcatt gttctctgct acattgaagc acagagagat   131945
taagacattt gcccaaggtc acacagctaa gtagagccaa gatagagcct cagagagtct   132005
catgccttca acctgcactc ttttttccctt tctcatcaca gaagccttga gaactaaaac  132065
tcttacagga attgtgggtg agctgggttt tttttttttt ttttttttgaa atggagtctc   132125 attctattgc ccaggctgga gtgcaatggc atgatcttgg ctcactgcaa cctccacctc   132185
ctgggttcaa gcaattctcc tgcctcagcc tcctcagtag atgggattgc aggtgccggc   132245
caccacaccc gactttttgt attttttagta gagacaaggt tttgccatgt tggccaggct   132305
ggtctcaaac tcctgacgtc aggtgatctg tccacttcgg cctcccaaag tgctgggatt   132365
acaggcgtga gccaccgccc cccacctgag tgggttcatt taaagggct gtgtgggctc    132425 aactcccagg gctcactcta gtaatggatc tgctgcagaa agaccagcct cagcccagac   132485
cctgcagctc tccaggtgca ggaccagggc aaagctcccc aacagtggga acagcccatg   132545
tgagggccct gtggctggat acagaggctg gagagaggag gtgaggtcag agaggtgtgt   132605
ggctggagga ggcctcacag gccagagcaa gagcttcggg tttcctctga aagggacagg   132665
aaccacaagg ccgtctgagt agggagtggg ccagcctggc catgtgttca caggatccct   132725
ctggctgccc agtggggaat aagctgaggg gtgaggtaga agtgggggct ggctggggc    132785 tagcgtgttc acgcaggtga gagacgctgg tgcgcagagt gagtggccgg tgcaggtggg   132845
```

```
gaaggtggtg ggccctgccc cccatggcag gtggggcctg ctggatttgc tgctggattg    132905
gatggagagg gagggagggt cggggatggc ttcaggctct gtacagagac caggctcccg    132965
tctgtgtgga gctttgtgga gggaccacag aagggact agtaaataag taggtgcatt      133025
ggagtgggaa ggtttccatg aagggcatca ggagccctct gatgcattgc acctcagggg    133085
tcaggagagg tgtccctgga tgagaaagag cctgggaatg ggggcggggg tgccccaccc    133145
cacagtagtg tctgagagga acctggctga cgtcaggacc cgtgtggctg gaacaggtgg    133205
agggtgggc tcttgtgtgc aaagatgggt taagggagag cgtgccggg cctgggggcc     133265
acagctgggc ttgagttttt tgtttgatgg ggctcgatca catggtgctg ggcagggagt    133325
gacaactgtc atctcttcat cagtgagcat tcattgtgcc cacctgtgcc attgtaggaa    133385
ctccctgctc cctccccact gtgtacagcc tcagggatag ggaaagaggc cgaacaggag    133445
gcccctcccc aaacagtggc atcacctgga acccaggagc aagccagtgt ccaggggtgc    133505
tcggggatcc ataaccccca tcgtccttct tctgcttctc ggaccctcca agctcctcct    133565
ggagcgcggc ctgaggtgag gccagctggc ccaggccact ccaccctcgt ggatggcctt    133625
gtatcccatc agatcacagg agggaccccgt ggcagggta gccaggggcg atcactgccc    133685
aggaccccat aggcccctcc cctccaggc cacctcctcc catgtttccc acctccaccc    133745
acctgcaggt ccctcccacc ctcatctgtt tctctggagg cctcactgaa ctgcacttgt    133805
ccctgaatgc atggctcaag cccatgcatt tctactgtgt gaacccaatc ggcctccacc    133865
ccagccccag aggagtgtcg tccacacact gacaacgatg ggggtggggc acagcaggtg    133925
ctaccaagag ggccacagag caagtgccac gggcacacag gggccacccc caggctggct    133985
gaggcttctc tgccaggcct ggaaactgca gtggaaccac atcaggttgg ggaagaaaga    134045
tgtcagtgag gggctggagc agaaacggca ggcagctgca caagcttctc tctgctcagg    134105
gagcagggcg gggccatgag gcagggtctg tgctaggcag gggcgccaag atgatcagtg    134165
actaatgacc aaggcaggac ccctggccca agggagctta cagccccatg aggggaccct    134225
gccctcctgc cagtgccaca ggagaaggta cccagcggct tggggcagc agagggtaag    134285
cacaggattt ctttagagag catgtgaaca atatgcacag aaagcagggt gtgagcctgg    134345
ggttctagag gatgtatagg agttggtaag aaagaccagc taaaaatggg aaagggatct    134405
cagggagaga aaatgatgtg aaaaataact ccaggaatcc ctccgtagtt ttattgagca    134465
gctactgcaa gccccacact gggccatcgc ctccaggcat gacctctgaa gatcccatcg    134525
tgctccttct ccagatgagg gaagctgggc tcagagagga ccaggccctt gcctgaggtc    134585
acacagagca cgatgcattc tgctctctgc ccagcacatg gcggggcagg ggctacggga    134645
ggcaggggga gatgcctagg gctcaacatt gaggagacac ccaccccag agcctttgag    134705
tggatgcagt gccctagggg cccagcagga aggggctgg agtgtgcggc agagggaac    134765
ttgcgtgtgt gaggcagcag cagcaggctg gttgggaccc attgagaagg agctggtcag    134825
ctacaggtag gagcctaaac cttgatcctg tgggcactgg ggagccaagg agggcttcaa    134885
gcagaaggag gtgccgtcgg ctctgtgtga ggctggaaag gaaggtgggc acctgctctc    134945
aggcttcacc tcctgttttcc tttgattcac aggtccgtca gagccgcccc acaccttggt    135005
tgggctcccc aggtcccctc caccttggcc tgagccaggg atgggggtgg ggaaggctct    135065
ctgtggccac aacaccgtgc aacacccagg gaggaagagg atgtggttgt cagggaaccg    135125
gctcgagcca tgagaccct aattatgcaa aatcattaaa aagaaacagg atggagattt     135185
cggctgattg agagctctcc aacttttaaa taattagggt gtgggggagt gggtggagat    135245
```

```
gggactgggc ccatcacaag tgatgggggc tttgagacat gtttctttaa acccatggca    135305
ggaataatta ctgtgaaatg tccttagcga ttcagtcaat tagaggggag accccttatc    135365
tcttgttagc gctctgaagg tggtgcagcg gggtgtgtgt gtgtgtatgt gtgtgtgttt    135425
gcgtgcgtac tcgggggcag cgattgatat ggaatagtag attccactat cttttggaaa    135485
aaaatctatt gtatcaaaaa tttcatagaa acgtctaaaa agaaaaagag gaacttttag    135545
gaatggtttt tcaggcttat taatatccct tccgatctat cgtttgcatt cctgttcctt    135605
gtgtccttaa aaaccctcag aaatgcccga gtacagccag cagtggggcg acaagggcca    135665
gcgccgtttg gctttgtttc cactatcgat tcaattgttc tctcagcctt tgatctttgc    135725
ggttttcct gctggaggct ggtaggatac ttggccactc gttctgccct gtgacaccca     135785
gcaccggtgc cccctgtgat tctggctgaa tccacccgca agtcctgctg ggaacctaga    135845
ccagccctca aggtctgggg gagtctggtc tgagagaccc ctgagcaggc gaggggtac     135905
taaggccact ccggaagtca gcctgtgaga ggccgccctg gctcagtttt ggactcacct    135965
ccgcctcacc tccaagtgac agaaagccta gttcaggcca gacagggttc ccgccactca    136025
cctgggcagg tgctggggc caccaggtcc cgctgagatt ctcttccttg tttccatcca     136085
tttagccacc gggggtccct cttctctcaa gccctctccc tgcttctccc aaatatgagt    136145
ctctacccac tgctaatgga aaggcagcac aacatcaccc ctttagggaa tcaagcgttc    136205
gaagtgattt tctttacggt aggcatcaga gagaaaggg aactgtggtt gatccttctt     136265
tggcttaaca agaaaaaact acaaatatat atatatatat atatatatat atatatatat    136325
atatatatat atacacacac acatacagaa acaaagatgc caatttaatt attattatcg    136385
gggcacaaaa cattatcatg tgagatgacc aattagaact cagaggttca gaagctcaag    136445
gtgactccca gggagatttt actacccta ccgtacccat cctcctccac aggcagggag     136505
gggttggagg gctcacagga gggagcatta gggccagggc ctcctccatt tttatggttc    136565
ggaaatcaca tcgtatcaag gcagcataag tttgcacagc cctggagggt tgactcgttt    136625
ggggcaaact caagagggcc tgatgaataa gccagacatc actgactctg tgaatgccaa    136685
cagtgacatt gggataccac ccaccagggg ctggacccct tgctgagtgt ctctgtctcc    136745
aaaaacagct gcgcaaactg ggcagtattt ggctgcattt gacagagaca gaaacagaac    136805
cctgacagga aaaggcaagc atcttgaagt cacaaccagg aagtggcata gcgggtttcg    136865
aacccaagtc tgcctgactc ctggtcctgc aaggtctttc actataagcg atctaaactt    136925
gagccactta cttttctata taccaagggt catcaaattc tttctgcaaa gggccagata    136985
gcccatttt tatggtttcg tgggaacata tgttctcttt gggcaaagtt tgccaacttt     137045
gccattttta tccaaaaagg gttttcacat aacaatgtgt tggattcctt gggggatgac    137105
ttcttttccc aatcaatact tttttttaca aaaacctggc tcttgggcca aattttgtc     137165
ccatggggcc tgttatctta ccctccccct tgtgggtttt accttgttgg aacaaaaaaa    137225
accatccatc tttgttattt ttttgccccg ttgacacctt tctatttat ttaaattta      137285
acaaaccgat ccttttggga attcatattt tggggcttt ttgttttaac gattgtcgct     137345
ttaaaaattt aaattggtgc cggtggcttc catcctattt atatcaatca tattaatttt    137405
aagcaagctg atcttcgga ggcccttctg gtcccttggt tgtggaaata actgttttct     137465
actataccaa agtatctttt acttgggcgg gttgggtttt ttaaaatgt tttgggaaaa     137525
atataaaatg agagagaaag agaaggagag agacggaag aaagaagaaa ggagagagaa     137585
tagagaggga agaaggaaga ggggggata gtggagtagg ggggagggga agagagagag     137645
```

```
aagaagggag aggagagaaa agaagagagg agagcgagga agaggagaaa gagaaagaga  137705
gaggagggaa ggaaggagga gaaagaagag gaaaggggga gagaggagaa gagaaagaag  137765
agaagagagg aagaggagga gaaagggaaa gggaaaagaa agagagagag aaaagaaaga  137825
agagaagaag agaagaaaga gaaaggagag agggagggag gggagaaaga gaggagaagg  137885
aggaggaaaa gaggaggaag gaagaaggga gggggggggg gggaggaaga gagggaggaa  137945
ggaagaagga aaggggagag agaagatggg aggaggggga aaaagaaaga ggatagaaaa  138005
aaaaaaaaaa aagggggga gagaggaagg gagtgtgtga agagggagag gagaagaagg  138065
gggaagagga aaggaaatga ggaagggaag aagaagagaa aagaggagag gagagagggg  138125
ggaggaagaa ggaaaagaga ggagggagga gagagagaga gagagggaga ggaggaagag  138185
ggagagagag gaggagaaaa aagaaaaaaa agggaggaaa ggagggagga gaaaaaagga  138245
gttcgttaag aagggaggga gggagggaag taagtcagta gggctgcagc actcatcgtg  138305
cactgggctc actctgtaca gcatctttgc tgcctgcggc cctgcctgta cccagggtgg  138365
tgccaggcct ggctgcaacc ccctcctcct gccccttcct gaaaagcgcc cttggctcct  138425
gttgtaggga ggagcaaggc cagggctcag ggaggtgaag gcgttcaagg ccacacgagg  138485
ggctcgggga ttgagaccct ggcagcctgt tctctcccag ctccctctgc gagcggcctc  138545
acccttcctt cccatggtgc tgattttctt tctggtcctc ccttcaatgt gcccttgtgg  138605
aaagaggaaa gctcgggcca ctgagaaggg cgcccctgtg aacgatggag ggagattgag  138665
gtcgcaggca ggcctgggga ctgggggcgt gtggagggggt gggttgggct cctggaaagg  138725
gaggcgccta ctgtcagttt tgagtttcgt taaacacctg ccagcctgat agcattctaa  138785
ttccaaaata tgacaccact tattagtgga taaactaggc tccctccctc cttcctgatc  138845
ttgacgccag gactggaagg agcgaccacc tgccctcagg atacccggtg cagtgccatg  138905
gctttgaggg cagaggtgtg gggttgaagg ctgccactgc tcaccagagg ctgtggagag  138965
gctaaggaca gggatataga tctcctgagc ttcagggtc tgcttcagag acaggtgttt  139025
ggaggccttg ctctcaagag aggtgggggg gaccttcctc ctgctgcctg ctctgatttg  139085
gggggatacc agaggcatga acataaacgt gggagccttt tcctgccctg taagcagctt  139145
cccctcccct cctctcacct cccctcacct ccctgcatgc agtggcctgg gatcaggatg  139205
gtgacacctg ggctctgcag ccctggccca ccgggtgctg gaacttcctt cctccgtcgg  139265
gagggactc cagcctcctg cctgcccctc cctacctcct tgactcagat ttcatcctcc  139325
ctgtctctga accctcagtg gctcccgttt ccctaatggt gacttcctca cccctctccg  139385
tggcccatga gatcctgcgt gggtggcccc ttgcgtccct gttccccctg ctcactcctt  139445
tctctgcctg cacggccctt ggcgtgtccc tgcctcaggg cccttgcgtg tgccgtccct  139505
tctgcccagc acacccctct ccaggcatcg ccaccaatct ctccccaact tcactcagac  139565
cttggtcaaa cagcacctcc cacgaggcc ctgttcacct aaaactaccag cccccagcac  139625
ctatctgcct gctggctctt cctccccagc acttgctgct ccctggcggt ggagggcgcc  139685
acttagtttt attgtctgta tctgcaagga gaatgttggc tgcacaggaa cagtggcttt  139745
atgctggtca ctgcatcatc ccagggcctg gcacagagta ggtgctgttt gcattggttg  139805
actgagtgaa taaatgaatg aatgaatgaa tgagtccatc agggcatcca gtgggccctg  139865
cagaggggag ctggacagga gttgtatttc tggagaggca gtggccaggt acagtgtcca  139925
ccttggacag gagggagaat gggtgctgc catttcccat gaggggataa ggggctggga  139985
cagacctggg aggcaggaca cgagcccttg tggctgagag gggccagcag ggaggggcct  140045
```

-continued

```
ctcgggagcc tcagggtgct gtgatcagct ctgcttccct gtttctgggg tagagaccag  140105
agcaggccag caggcaaggc tgccactcag ccggtttcca tggggacagc tggacaggtt  140165
gtcataggtt taggtatttc cagattggct ggtgaatggc tgtcaactcc accaccctgt  140225
tctcttccca tcgttccctg ggtctctctg tggcccaggt cctagggagt tagtgcctgg  140285
cccaacaggg gtcctagtcc ccacgctact cagccccag ggtcactgct accagtgaga  140345
cagataccag cagaaatgag cttagagacc ttgtcccact ttgggaactt ctgcagctca  140405
ggaaggccag gttatggggg cagtggggag gggacactgt ctggggagtc ctcattgccc  140465
actctgtccc agtctataat tgtccaggtg ggcagcaaac cgttgccttt agggaccaga  140525
taagcaactt cctgtgcaga gcaggtgctc caagaaaaaa ggagatggtc agtggatggc  140585
atacaggaga ctgtaccaac tctgtggcag tcagatttga ttttgttaca aaccccatgg  140645
caatgaaaca aaacccacct ataagtaggg ctcagccatg cctgcccagg acaccatgaa  140705
cagagataac tactggccca aggtcccagg gccagttagt gccagagcca caagcagtgc  140765
ccagtctggt agaggacatt gtccagcaca tttgagaatg tcaggacacc tttgcaatct  140825
ggcattcagc atcaccagta gggggcagta gagggcagca catcaagtat agctttggct  140885
tcaaatcccg actctaccac cttcttccag cactgactcc ccaggcatgg gttttagcca  140945
gctgctcctc cattttcttg gctatgaatg gggatagtaa tggctatttc tgcacagcac  141005
agaatcttac caggcttgtt ccctggtaag tgtttagttc taggtttgag gaatgaatga  141065
atgactgaat aaaacagagca tgggcccagg tgcaaaacag agtcatccgt cgtgccaacc  141125
ccatgggcgg gagcagcgca gtgacggcca ttgcttctct gtctccacag tc  ttt      141180
                                                        Leu Phe
                                                            265
gaa gag cct gag gac ccc agt aac cgc tca ttc ttc tcg gaa atc atc   141228
Glu Glu Pro Glu Asp Pro Ser Asn Arg Ser Phe Phe Ser Glu Ile Ile
            270                 275                 280
tcc tcc gtg tcc gac gtg aag ttc agc cac agc ggc cgc tac atg ctc   141276
Ser Ser Val Ser Asp Val Lys Phe Ser His Ser Gly Arg Tyr Met Leu
        285                 290                 295
acc cgg gac tac ctt aca gtc aag gtc tgg gac ctg aac atg gag gca   141324
Thr Arg Asp Tyr Leu Thr Val Lys Val Trp Asp Leu Asn Met Glu Ala
    300                 305                 310
aga ccc ata gag acc tac cag gtgggcacca cagcaggaga ccccaatcc      141375
Arg Pro Ile Glu Thr Tyr Gln
315                 320
cgggtctttt ttccctatgc tgagatcccc atggaggggg ccttcctagc caggcgtggc  141435
tttcatatgc ccggtatgta ggtgaagaca cggaggctga agaaatccag caactcatcc  141495
ccacacgtag cttggcagag ggcaggagtg ctcagtcttg cctcacaggg agctttggat  141555
gtccctgagc aaggcctgca gtccagggcc caggggcctc aattccaggg aggaaagaga  141615
tgtgggaaca gagatgagcg tcaggctggg ccccagtgga gcatgtagac gatggcttnc  141675
cctccccact ccctgggagc ctgcatcgga gctgtaccat taaagagggt taagcgttgc  141735
cctcccaggg tgcatccgta agcagtgcac gcagaggtga actgagcaca tgtttccttt  141795
ccagatcctc agcacaggcc tataagcctg gagtctaggt gaagcctggg cccttcttgg  141855
acagtattat ttattatctt gctattatca tccattcaga tatgttaggg ggtagacaac  141915
aaaactcatg tgatgttaaa ataaaatgtg gacttgaaag aaatgtggga tggcttcaaa  141975
gctggttcca gttaggtggg gagatcaggg aggcttcttg gaggaggtgg catttgtgct  142035
gggccttgaa ggatgggtaa gatctggncc gtgcaaacat gggtgggaaa acaccccacc  142095
```

```
agaaacccca gccggttcct caccgtgtca ctcctcacac angggtgcc acgtgcttga    142155
catctgtcac ctccattctt tactgtccgg tgacaaggag ccatcatcct atttggtgga    142215
aagggaactc gggcactgag aggtaggag atgaggagg tgtctctcgg ctgggcggtg    142275
acagattcag agcccaggct cagagcccta cgctttcctt tcctccgtgc gaagacctag    142335
taggaaagcg tcctgggtgg cgcaggcctc gctgggaact ggtgcagagc tcagagggtg    142395
ggctgctctg atctgacctg ggccccagag gaacagctca cgctcctgga agccacacac    142455
ccacaaggac cgctatgggg accgcctgtt tgtcagccac gtgtgtttac ttgagttctt    142515
gcgactgccc cagctcctcc ctcaggcccc ctcctcacac tgcacacccc aggcaggact    142575
cagccctcct ctgtccctgt gggaatggca gagacccag actaggagag gacaggata    142635
agcccggctc aagcctgcag gagcaactct ctggctccct ctggaggcag ctcagggaaa    142695
tgaacatttc caaccccctc cggcccctg tccggtcact tacctccatc cctgaggtca    142755
gcaaaggccc atgaacccct gaaactacgt ggaatgtgtt ctatgagcat tttcaggggg    142815
aggggacac agctttctga aattctcatg aaggacccca cgaaggaggg gaatgactgt    142875
tctggagcgt gaggccgtaa gctgggcact tggcatctgg cccagctgac ctattgatgc    142935
taaaataata gcaataacta cataaaagca gnacaacaac caacatttttt tggtggcttg    142995
tgatgtgcta gaaattgtgt gtagcaggac tcgttcggc tggtgtgcgg tgcttaacaa    143055
atcgggcta tttttctccc anaacaggga gtctggagag ggcagtccag gaaggtgggg    143115
gggctccatg accccggcag cgccacagtg gttccttctg tgatccagtc caccatcatt    143175
tgggcgttgg ttttccacct tcacatgtgg tacctcatgg tggcaaagtg gctgccacac    143235
ctccaagcac tttgcctaca ttccaggcag gaaataggaa atgcactaga tctcacccct    143295
ggggtctgtt gcgtgtttca ctgtgattgt aaaatcttcc ccagaatgct tctcagaaga    143355
cttcttacac ctcattgtct agaatgggtc cctggcagcc accatagtgg ctgggaagat    143415
taatggttta acagcctctg tggttgaaga aggcaagggt gaaggggctg gggacggttg    143475
ttgaatgagc cacactgagg taagtccata ntatgctttg cctcatctaa gcctcccagc    143535
tgtcctggga ggtggggccg gtattctccc catcccattt tattggaaga cnattgagtt    143595
aaatggcaaa tctgtgacag agccagcaag cagnggacct tagattgaca gtctttctcc    143655
agagctcttc ctcacccctgc cactagaggg caggagatgc ttagtgcacg gcagagaaa    143715
cagcatgcgc atttggacgc gtgcatcacc aaggctgctg ggagctgagt aaggaggaca    143775
cacaaaaatg cagagccggg ggtgggacac gaacactaaa acctgctgcc attcatcccc    143835
cttgattttta gttgttacac atactgagcc agtaccctgt gcccaacaca gtgctagacc    143895
ctggacccag agagaaggaa gaacctcggc ctcaccctcg agggtccag acagacagga    143955
acacagtgac cctcagcttg gtggggctgc agcccagggg cccaagggga aggcaagggt    144015
caccaggagg acacggggc tggggaggga tgagcagggc cccaggcggg agtcaggtag    144075
ccttgtctaa ccatcctgtg tgcagtgaat agcaggccct tcctcccaat cctgcttccc    144135
ctagtgccac tctgttttcc tgtgtagtcc ttgccaccat attagtcaga tggctcgag    144195
aaacagaacc aacaggatgg ggatagagac tgagaaagaa gggagatttg aaggaattag    144255
ctcacgtggc atgttctaaa tctgcagagc aggcgggcag gctggtgacc caggggagag    144315
tgactatgcg agcccacacg catctgttag cggaatcccc cggtcctcag ggaggtctgt    144375
cttttgttcta tcagggcctt cgactgattg gacaaggccc cccacatgat ggagggcagc    144435
ctgctttact cagtatatca gcttaaatgt taacctcccc tacaaaatgt cttcacagaa    144495
```

```
acaccaagta tctgggtacc ttggcccagc caagctgaca cacgaaattg acgttcacac    144555
cacccttcac attttctgtg ttcgttggag ttgttaattt caactcctgg gagttgaaac    144615
caggctccat ggcacccagt taccttccct tccgcaccca gagggcagag cccgtgccct    144675
gttgtcctgg cagctccagc ctcagcagag ggctggcact catgcggccc tccgggtaca    144735
gggcttgtag gaccggctgc agtcaggtgg atgcaggtcc tggggtgtca ccctctctcc    144795
tgtggggtac gggaatcctg gggaagggtc ctggtcagcc tcttagaggc tgtgtgaccc    144855
tgtgagcctc agtgcctcgt gctgtggatg gatgagaaac ctctgtgggt tccctcttcc    144915
cctttcttga tggccgccac cctgtgttct cggagatcat taccctcaaa aggcctgccc    144975
tgcacttaat gccagaacca ctgtgaggtt cgccctctta tcactttaag tttgaagaaa    145035
ctgaggctca gagagatgaa atcacttgtc caagatcaca cagctgggag ggcagagcca    145095
ggatctggac cccaggtggt cctggcccct gtgctgtgag cgttctgttt gtcacagtgg    145155
actctgctcc ctggtgctac tcccgtctct ggccacagct cagaggtcag ccgtgtgcct    145215
ggtcgtgggc ccccgataag atgagcaggg ctgtattggg ctgtgtcacg gtggaggtca    145275
gccgtgtgcc tggtcgtggg cccccgata agatgagcag ggctgtattg gctgtgtca    145335
cggtcggggt cagccgtgtg cctggtcatg ggcctcccga tgagatgagc agggctgtgt    145395
cgggctgtgt cagagcattc agaccctcgc tgagatgagc aggtctgcgc tgggccatgt    145455
cagggcatgc agaccctcgc tgctctttga gaccttcctt gtggaagggc caggatggtc    145515
gggacgcccc gtccactcac ctcatccctt atcccaccag gtc cat gac tac ctt        145570
                                             Val His Asp Tyr Leu
                                                              325
cgg agc aag ctc tgt tcc ctg tac gag aac gac tgc att ttc gac aag        145618
Arg Ser Lys Leu Cys Ser Leu Tyr Glu Asn Asp Cys Ile Phe Asp Lys
                330                 335                 340
ttt gaa tgt gcc tgg aac ggg agc gac ag gtaagccctg acctcagccc          145667
Phe Glu Cys Ala Trp Asn Gly Ser Asp Ser
                345                 350
gcacctcacc tcaccgtagg gagggtttct gccctgcagg ggtctgggct ggattccgg       145727
tgacccgcag catggggcta ctcagcctca atgggtccag gtgtctgggt gaagcccacg      145787
cttttccagag caggtccaac tctcagcgct cagattcaag gggcaggaca tgaaattctt    145847
catcttctgt cactgaacct cacagccacg ttggcgcctg ccctatgggc agtagtggga     145907
acatgtttag ttaattcagg gtccccggtg atgtgctccc ctctcccagc ttgtcggggg     145967
cgagggctat agcccagcac ccggtcacca tcatccatcc acacctgtat gtcctgagac     146027
agccctgcac ccctgtggct ttgaccatcg gtctactcac ccctcctccc atcaccacta    146087
ctgtctccct ctcttcctgg tgacacccca ctcgggcccg ctgaggctca ggggcacctt    146147
ggagctccta caccctccag ggcttgtcac aatccacaag tccagccgtc tctcaacccc    146207
acctgcctgg aaagtggcgc cccagtgcca gaagtgagtt cctgtgtctc cctagcctgg    146267
gctcagccca gggcgggcat ggacaagggg gctgtggcag ggctcctga cctgacctct     146327
acccgtgggt ccttacctct gtgtctcttc tctgggattc ttcctccatt ctggaggtgg    146387
gaaaatccct cttctgccct cccaaatcac atcagctttg tgctcagggt cctgccaggc    146447
gtaagattct gaaatggaca agcctactct ccatctgtga gtttcgatct cagaagctga    146507
gaggtggcct ctcagtgtct cctacagctg cttcctcaag gacaggatgc ctctttgtcc    146567
agccgcccag attcagaagt gggtctccag atgatacaca gtgtggagat aaagactaca    146627
ctggctgcta gatcagaata ccacctgtca ggagcccatg tactgtcacc tcctcccgc     146687
```

```
agtcctgtcc agtgtggtgg gcaaggaggg tggagtgaga gccagcagcc ctgacttggg   146747
catcacctgg tgggggggctg tccaccctgt ggatggcatc agtcaacatg acaggtctgg   146807
gctctcccag acctctgagg gtggctggca ctgtggtggt catgtgagag ctgccgcact   146867
atgactctct gtggctctgg gcatagggct gggaccatca gggttggtgt gtgggatgag   146927
gggagggctg gacatggcag agacaggacc aggaggggagc cccctggaag cagggctgga   146987
tccaagtggg gggccaagtc attgtgtcca gggaaggaga tttctgagag agttgccaac   147047
atcctggagc tcccccagcc cgcagggggtc tctcagcaga gcccgagctc aggcaagggg   147107
ctggcatggt gatcacaggg ggccactaaa ggatgcttag aaaaccagga tggaggcccg   147167
acccggggct gggctggcac agctgggtca gcaggacaca ggaccttctc tctaggccct   147227
gcccccagat agatcccaga caccccccagc agacagggct cctcccatgc tgctgagctg   147287
catttggggt tccctggtgc agtgggtccc aagagggtct atccaaatcg gacgagaggg   147347
acctgcagct gtaacaagct gattccagct tttatgtgcg ttttgcgggg taggtccccg   147407
ctggctgcga cccactgccc gtccttcctt caagctgcca ccaggggggca cccgcggcca   147467
ggtgatgcct gctcccagga ctggagaagc cgccaagcat ccccaggctg acagtggtgt   147527
ctaggcctgg gctctcctgt cctgcctccc acccgccact tcctgcgtgc actttacacg   147587
ccagccacgc cctgtcctag tggtccccca cccgcctcac tgtctctcgc tccacactg   147647
gctctgctct gcccggctgg aacctctgtc cttgtttgcc tcccgcaatg ggtggggtgc   147707
cctgggggggc tactatgact caacctgttc tgagcccttc actggggacc tcaggtgtgt   147767
ccagtggctg tgggtgtttc tagaaggcat agaggtgtgc cacctcccag ttcactttga   147827
gcactgttct gagaacaaca tgccccatgg tcagggggtcc caagataaac agaccctggg   147887
tcctgccttc cagggcctca gaggctcagg agagaagcaa ggattccccc caggttccca   147947
catccttgca gaccaaagca aactcgaatc ctggcaggct cccagttgct gccctcttat   148007
tcctggtgac cccctctgac agttggtccg gcccgcagag cgccgctgct gccgcgtggt   148067
ggctgcccga tggcccctgc cgtgggggctt cctagcaccg gcagaacgca gatgggcagc   148127
gtgctgtgga gaggcagcag ctctcctgct ggactctctc agtctctggt ccacattcta   148187
ccctcgccac cgtgtgcttg aggaagcccc taagtcagct cggctggaaa gtggttctag   148247
gaaactggcc ttcgtggccg cttttgggat gagaccatgt gtgatgcctt cagcaagatc   148307
ccagttcgta tgcgcagggg tgccgcagtg atcctgcgtg gactatccta ttggcaggcc   148367
tgcccttccc caggttacct acccggagga atccgcagg ccctcccaca acaggcttca   148427
acgccccctc ctccatgaag ttctccttga tctgtcctgc ctgggggggag agatttgtgc   148487
cagccgagcg tgctcgggtg cgggagtcaa acacacctac acttgctctg aggagtcctg   148547
ggcaaggctc ccccagggggc ccatgctgta tcccctagggc tgtttttttc tctccggccg   148607
ttttcttctc tccatgcttc cccatctccg ctcctccctg cttcttctta cacactggcc   148667
tcatcctctc cctcttcaga gatgaccccc aaatcattcc cctttccatt atcctcagcc   148727
agccaacccc tccaggggac tgtgtaaaac tctcatggaa ggatctgatt ggctctgtgt   148787
gggtcacttg cccactttt gcaccaatca gcatggacag ggatatcaca tgcccaagtt   148847
ggccaggcca aggggcgagg agagcactgt gattgaccgc tcacagggat agggagtgca   148907
gtggcgccat ctcggctcgc tgcaacctcc gcctcctgga gtcaaacact tctcctgccg   148967
cagcctccca agtagctggg attacaggcg ccacggggtgg cgaggggcagg agccttttctt   149027
tccccaaagg aaagaggagc ggagcactgg ggctgaaagc agccggcgtt gnggtccac   149087
```

```
atgcagatga ggctaggaga ggtgaagcag ctcccctgcc cttttccctg ttaagggaac   149147
cttctggaat ttaagaaacc tgcctgaatg tgaggaatgg ctctcatggt ggtgcggcct   149207
ggtgctctag gatgagaggg gcccctccct ctcccccaga gcacgtgtca gctgaattcc   149267
acacccgaac aggggagga tcaggaactg tgtgggttgc aaatgacttt aattatgtcg    149327
ctctccttcc actaaatgga tcagaagaac cagcattgtg tgaaatcacc caggttcatt   149387
ctgtgaactg ttccctgaag aacaaagggg gctgcctccc cactgtgctg gcgcggggag   149447
ggtgtggcct cccccagtca gcctgtggcg cctgggcagg gcccttctgt gggactcgtt   149507
cacccggccc cctcgcatg ctgcttccct tgtcccaggc tctgagtcac atataaagcg    149567
ggtgcggctt tggtcacatg gacgattagg atcgaggagt acctggtaaa taacaagaag   149627
caaagtgcct caagcccagc actgtgcggg gtgttcagcc tatgtcccct gattcacgct   149687 caccagggc tgcgttccct tgttgatccc agttcttata gaaaactaag agagtgcgca    149747 tgtcaggta gggcagagct gggatccgga cccaggcgga ctggccagag cccaagcccc    149807
tgactgcagt gccggagctc acgtgtgagc ttttgtcctc tgtgcataac ccctggagac   149867
ccagggatcc acctggttct gtcacagagc agtgtcaccc tcaggaagcc cagctcagct   149927
tccaaaagga aacaggattt cctccctgaa gagccttcag caggacaact tctttatggt   149987
cgcttttcgt aacatcctct tcctccccag ttacctgca cctcacagct gctccagggc    150047
cctgcagagg ccaaacccca aaaccctccc tctgggcgca ggcccacaga actgtgcttt   150107
ctctcctgcc tcttactatg tggatgaact taccccttcct cccaccggca ggaaccctt   150167 ctccttagga gcagggagag cagagaaatg gtgtggaatt ctcttagcg ggacggtgag    150227 ggcagcgagc ccctgcacgt cagcactgct cgccccgacc ctcatggcga tgcatgtttg   150287
tttattcgcc cgagtcctcg ggacaggcgg gcccctggag ggaagcaggg cctggtggtt   150347
ttctgtccca gctgcttcca tgtctacctc ctgctgtggt tgcacagtct gtttggaagg   150407
ccagagcttt ctctcctgga ctaacagaaa ttacaggagg gtcttttctt ttcttttctt   150467 ttctttttc gagacggagt tttgctctta ttgcccaggc tggagtgcag tggcgcgatc    150527
ttggctcact acaaccttgc ctcctggatt caagcaactc tcctgcctca gcctcctgag   150587
tagctgggat tacaggtgcc caccaccatg tccagctaat ttttgtattt ttagtagaga   150647
cagggtttca tcatgttggc caggctggtc tcaaactcct aacctcaggt gatctgcccg   150707
ccttggcttc ccaaagtgct gggattacag gtgtgagcca ccacgcctgg ccaggagggt   150767
attttcatga tgattgggc agaggataaa aaggatctta gctcctggcc ccaaagtctg    150827
catgttggtg gcagctgaca tgtgagggg tataagagac cccaagatac aggggaatag    150887
aggcaggtgt ggtttccctt tccagggagt gatggctctg taggctctgg gattgctttt   150947
tcatttgttt gttgttttgg gacagagttt tactctgtca cccaggctag actgcagtgg   151007
taaatcacag ctcactgcag tctctgcctc cccaggctca ggtgatcctc ctgcctcccc   151067
aggctcaggt gatcctcctg cctcaacctc ctgaatagct gggactacgg tcatttttaa   151127
tttttttttg tagaggtgga gtctcgctat gttgtccagg ctggtcttga actcctaggc   151187
tgaagcaatc ctcccaccgg ggcctcccaa agtcctggga ttatgggcgt gagccccac    151247 acctgggctt atttctcgag aagggcttg tgctcctcct cacctgatgc ctctccttct    151307 cccaccag c gtc atc atg acc ggg gcc tac aac aac ttc ttc cgc atg       151355
           Val Ile Met Thr Gly Ala Tyr Asn Asn Phe Phe Arg Met
           355                 360
```

```
ttc gat cgg aac acc aag cgg gac gtg acc ctg gag gcc tcg agg gaa    151403
Phe Asp Arg Asn Thr Lys Arg Asp Val Thr Leu Glu Ala Ser Arg Glu
365                 370                 375                 380 agc agc aag ccc cgg gct gtg ctc aag cca cgg cgt gtg tgc gtg ggg    151451
Ser Ser Lys Pro Arg Ala Val Leu Lys Pro Arg Arg Val Cys Val Gly
            385                 390                 395 ggc aag cgc cgg cgt gat gac atc agt gtg gac agc ttg gac ttc acc    151499
Gly Lys Arg Arg Arg Asp Asp Ile Ser Val Asp Ser Leu Asp Phe Thr
        400                 405                 410 aag aag atc ctg cac acg gcc tgg cac ccg gct gag aac atc att gcc    151547
Lys Lys Ile Leu His Thr Ala Trp His Pro Ala Glu Asn Ile Ile Ala
    415                 420                 425 atc gcc gcc acc aac aac ctg tac atc ttc cag gac aag gta aac tct    151595
Ile Ala Ala Thr Asn Asn Leu Tyr Ile Phe Gln Asp Lys Val Asn Ser
430                 435                 440 gac atg cac tag g tatgtgcagt cccggcccc tgccacccag cctcatgcaa       151648
Asp Met His
445 gtcatccccg acatgacctt cacgaccgca atgcaaggag gggaagaaag tcacagcact  151708 gatgaggaca gctgcagagg tggcagtgtg tggacacagg aagtttgggc ccctccctg   151768 ccccagcttt cctaggccag aattgtgttt ggcagtaatt gtctgtttaa aaaaataaaa  151828 ag                                                                 151830

<210> SEQ ID NO 38
<211> LENGTH: 447
<212> TYPE: PRT
<213> ORGANISM: Homo sapiens

<400> SEQUENCE: 38

Met Gly Glu Asp Thr Asp Thr Arg Lys Ile Asn His Ser Phe Leu Arg
1               5                   10                  15

Asp His Ser Tyr Val Thr Glu Ala Asp Ile Ile Ser Thr Val Glu Phe
            20                  25                  30

Asn His Thr Gly Glu Leu Leu Ala Thr Gly Asp Lys Gly Gly Arg Val
        35                  40                  45

Val Ile Phe Gln Arg Glu Pro Glu Ser Lys Asn Ala Pro His Ser Gln
    50                  55                  60

Gly Asp Tyr Asp Val Tyr Ser Thr Phe Gln Ser His Glu Pro Glu Phe
65                  70                  75                  80

Asp Tyr Leu Lys Ser Leu Glu Ile Glu Glu Lys Ile Asn Lys Ile Lys
                85                  90                  95

Trp Leu Pro Gln Gln Asn Ala Ala His Ser Leu Leu Ser Thr Asn Asp
            100                 105                 110

Lys Thr Ile Lys Leu Trp Lys Ile Thr Glu Arg Asp Lys Arg Pro Glu
        115                 120                 125

Gly Tyr Asn Leu Lys Asp Glu Glu Gly Lys Leu Lys Asp Leu Ser Thr
    130                 135                 140

Val Thr Ser Leu Gln Val Pro Val Leu Lys Pro Met Asp Leu Met Val
145                 150                 155                 160

Glu Val Ser Pro Arg Arg Ile Phe Ala Asn Gly His Thr Tyr His Ile
                165                 170                 175

Asn Ser Ile Ser Val Asn Ser Asp Cys Glu Thr Tyr Met Ser Ala Asp
            180                 185                 190

Asp Leu Arg Ile Asn Leu Trp His Leu Ala Ile Thr Asp Arg Ser Phe
        195                 200                 205
```

```
Asn Ile Val Asp Ile Lys Pro Ala Asn Met Glu Asp Leu Thr Glu Val
    210                 215                 220
Ile Thr Ala Ser Glu Phe His Pro His His Cys Asn Leu Phe Val Tyr
225                 230                 235                 240
Ser Ser Ser Lys Gly Ser Leu Arg Leu Cys Asp Met Pro Ala Ala Ala
                245                 250                 255
Leu Cys Asp Lys His Ser Lys Leu Phe Glu Glu Pro Glu Asp Pro Ser
            260                 265                 270
Asn Arg Ser Phe Phe Ser Glu Ile Ile Ser Ser Val Ser Asp Val Lys
        275                 280                 285
Phe Ser His Ser Asp Arg Tyr Met Leu Thr Arg Asp Tyr Leu Thr Val
    290                 295                 300
Lys Val Trp Asp Leu Asn Met Glu Ala Arg Pro Ile Glu Thr Tyr Gln
305                 310                 315                 320
Val His Asp Tyr Leu Arg Ser Lys Leu Cys Ser Leu Tyr Glu Asn Asp
                325                 330                 335
Cys Ile Phe Asp Lys Phe Glu Cys Ala Trp Asn Gly Ser Asp Ser Val
            340                 345                 350
Ile Met Thr Gly Ala Tyr Asn Asn Phe Phe Arg Met Phe Asp Arg Asn
        355                 360                 365
Thr Lys Arg Asp Val Thr Leu Glu Ala Ser Arg Glu Ser Ser Lys Pro
    370                 375                 380
Arg Ala Val Leu Lys Pro Arg Arg Val Cys Val Gly Gly Lys Arg Arg
385                 390                 395                 400
Arg Asp Asp Ile Ser Val Asp Ser Leu Asp Phe Thr Lys Lys Ile Leu
                405                 410                 415
His Thr Ala Trp His Pro Ala Glu Asn Ile Ile Ala Ile Ala Ala Thr
            420                 425                 430
Asn Asn Leu Tyr Ile Phe Gln Asp Lys Val Asn Ser Asp Met His
        435                 440                 445

<210> SEQ ID NO 39
<211> LENGTH: 19
<212> TYPE: DNA
<213> ORGANISM: Artificial
<220> FEATURE:
<223> OTHER INFORMATION: primer 99-24169/139

<400> SEQUENCE: 39
ctggctgagg cctccttgt                                                  19

<210> SEQ ID NO 40
<211> LENGTH: 19
<212> TYPE: DNA
<213> ORGANISM: Artificial
<220> FEATURE:
<223> OTHER INFORMATION: primer 24-257/320

<400> SEQUENCE: 40
gtccttctga tggcctgcc                                                  19

<210> SEQ ID NO 41
<211> LENGTH: 19
<212> TYPE: DNA
<213> ORGANISM: Artificial
<220> FEATURE:
<223> OTHER INFORMATION: primer 99-24175/218
```

<400> SEQUENCE: 41
caagctggat tcgcaatca                                                        19

<210> SEQ ID NO 42
<211> LENGTH: 601
<212> TYPE: DNA
<213> ORGANISM: Artificial
<220> FEATURE:
<223> OTHER INFORMATION: amplicon 30-4
<220> FEATURE:
<221> NAME/KEY: allele
<222> LOCATION: (301)..(301)
<223> OTHER INFORMATION: polymorphism 30-4/58
<220> FEATURE:
<221> NAME/KEY: allele
<222> LOCATION: (301)..(301)
<223> OTHER INFORMATION: biallelic marker 30-4/58

<400> SEQUENCE: 42
tgaagccgac gttgtcgccg ggcagagctt cgctcagagc ctcgtggtgc atctccactg      60
acttcacctc agtggtgatg ttcactggcg caaaggtcac caccatgccc ggccgcagga     120
tgccggtctc cacccggccc acgggcaccg tgccaatgcc tgcagagggg aggggtgtg     180 aggggaaggt ggggcccgag gggatgctgg ggcaggatat cggggacag agcctggaaa     240 ccaacaaagc ctgggactgg atcccccga caggcctggg ggttggggcc acatgggcgg     300
rgtgcagggg aagggaggcc agggacaagg gcagacacag agattccaag ggaagtgggg     360
gctctcccac ccagctgggg aaataagagg ctgagcagca gagctcccag gaacccacgg     420
aaaagccaca gggacagaga agcgggagga tgggcagaga ggggctgtct gaacctgggg     480
tcccatcctt gcccccggag agcactttcc ctcaaaggag gcactatggg acccctcctt     540
tgtctgagga ctcctccctg tgagtgtggg cggggcgact gactgcttct gcctggggcc     600
t                                                                     601

<210> SEQ ID NO 43
<211> LENGTH: 601
<212> TYPE: DNA
<213> ORGANISM: Artificial
<220> FEATURE:
<223> OTHER INFORMATION: amplicon 30-2
<220> FEATURE:
<221> NAME/KEY: allele
<222> LOCATION: (301)..(301)
<223> OTHER INFORMATION: biallelic marker 30-2/62

<400> SEQUENCE: 43
gctaacagga gaaagcacct gcacactagc tccccgacgc tggaacaggg ccatggccct      60
gcgccccaca ctccagctcc actctccaca ggaaaaggct cccagaatcc agccactcag     120
tgtgtggggg caggggccct gctgacttag aaacaagtgg cacattgatc cgcattcaaa     180
cttgccagcc aatcaaccac agccccgcgc acagactctc ccaggtggga ctgaggggt     240 ctcccctgtc cttggcaggg gcgtctcccc cacgcacccc cagtcccgtc ctctccacag     300
rctccagatg cccacatccc cagaacactc aatgggacaa ctcagagcag gttacagaga     360
aagaaaagcc acacaagctc accagggca cgctatttca gaagtgcctt ctcctcctgg      420
aaatgtcgac cccaaagctc tcactgggaa acctctggcc tggccccggg aagcgacagg     480
cgcaggtttg gggctgaggc cgtcccagca gctctgtggc ctgccagacc tcagagcact     540

```
cccatcaggg gccacaagag cagagagctc ttcagcccca tgttctcctg gacgaattaa    600
a                                                                   601
```

```
<210> SEQ ID NO 44
<211> LENGTH: 601
<212> TYPE: DNA
<213> ORGANISM: Artificial
<220> FEATURE:
<223> OTHER INFORMATION: amplicon 30-17
<220> FEATURE:
<221> NAME/KEY: allele
<222> LOCATION: (301)..(301)
<223> OTHER INFORMATION: biallelic marker 30-17/37

<400> SEQUENCE: 44
caccacccgc cacctgcctc caggagcact gcagcctcgc cagtcagccc actttgggct    60
ctgtctccag ggatataggg gctggatgga cccgtctcct gaggccagca gaggctccac   120
gccagggtcg gtggcagggc tggcacaggg gaaccaggag gcgccgctgg cttcaccatc   180
ttagctacgg cagcccattc ccctgagcct cctggcctgg gcaacagtgg ctcgcatggc   240
cagcccaccg tgccctccag ggtcagtagc gtctattctg gcggccagca gggctggaga   300
rtcttgggac tgttgagacc ctcccccaac ctccctgagc ctccgggcac agatgtgaaa   360
agggtgccca ctgcagtcag cactcaaccc ccacagcgtc cagggaggga gaggggccac   420
cgggggctga cccctgccca ttctgcagac aaagccacca ccctgccagg gctcaagagg   480
gaagaaaatg gggaggggc catttgagca aatgagccca ccgtgagca aggtggaggg    540 acagcacagt ctggcaggat ggggtctcgg tcactggggg gcctggggcc cctggaactc   600
a                                                                   601
```

```
<210> SEQ ID NO 45
<211> LENGTH: 601
<212> TYPE: DNA
<213> ORGANISM: Artificial
<220> FEATURE:
<223> OTHER INFORMATION: amplicon 30-7
<220> FEATURE:
<221> NAME/KEY: allele
<222> LOCATION: (301)..(301)
<223> OTHER INFORMATION: biallelic marker 30-7/30

<400> SEQUENCE: 45
gccgagatcc cccgagtccc gaggcgtcgc gtgcttgggg acgtcaggag ccgatggtac    60
aggctcgctc aggaccccag tcctgagtcc acaccctgc actgcctgag gccaacacac   120
cgtgcccatg ggggccaggg gtgctcagag tcctggtgct gtgggtgcct ctgtcccaac   180
ggcctctggt cccatcccca acaacaaaag cacaggtggt cggggagaac cggacggggg   240
ccaggggagc acatgggcac aggctcagcg ggactcctgg aatgttctct ctttctccac   300
ygcacgagcc atttcaaagg caagaatagg cccctcctga ccccgctcag gcaggcctca   360
gggcaagtgg gagtcactgg aagactcaat tcctctctct gcgtttccac ccgaggcagg   420
tccagtcacc agagagagaa gcagccacct cctttctcac ggcagctggc aaagcaccgg   480
gtggaggaca gagccggtcg gcccaactgt agcttcgggg ctgcccttgg ctggtctctg   540
ggcagagccc ggtgctgagg gcttgcagtg ggaaaggcac agcttgagga atgggcatca   600
g                                                                   601
```

```
<210> SEQ ID NO 46
<211> LENGTH: 601
<212> TYPE: DNA
<213> ORGANISM: Artificial
<220> FEATURE:
<223> OTHER INFORMATION: amplicon 30-84
<220> FEATURE:
<221> NAME/KEY: allele
<222> LOCATION: (301)..(301)
<223> OTHER INFORMATION: biallelic marker 30-84/37

<400> SEQUENCE: 46
tgtgctaaaa catagtggct taaaaataat gataaccatt tatcgtctca gtttctgcag      60
ctcaggagtc ggacggcacg cagccgatct ccactcccaa cgtgcagggc ctctgccata     120
agccttgaag gcactcattc actcacgcat cggggctag tacaggctgt gacagaggcc      180
tgagctggaa ctgttgacca ggacacacac atggccatgt ggcctctggg cttcctcaca     240
gcatggtgtc tggattccag gagttggcat cctgagaaac aaccatgcag aagcagccct     300
rtggatcctg gcctggcctt ggagtcaggc agtgtcactc ctgtgccttc taacctgggc     360
ccccgggccc aaggggagga atggagacc ccacctccca gtggagggaa ggcaaggtcc      420
cactgtgggg gtagcacatg ggatacaccc atgtggctgc cgctggagac gttagtttgc     480 cacaccgtt tcttctacgt gaacatttgc ctgcatctca ccttctaact cctgggtgct      540
gtttgtccat tttcactaca ccaggggccc ccacagtata tgcagaccag gtttcctggc     600
c                                                                    601

<210> SEQ ID NO 47
<211> LENGTH: 601
<212> TYPE: DNA
<213> ORGANISM: Artificial
<220> FEATURE:
<223> OTHER INFORMATION: amplicon 30-15
<220> FEATURE:
<221> NAME/KEY: allele
<222> LOCATION: (301)..(301)
<223> OTHER INFORMATION: biallelic marker 30-15/54

<400> SEQUENCE: 47
gatgctgaat aagccaggaa gaagatccgg ctaaatgttg gcacattcta aagtctacgt      60
gaggccagtc tgaccctggg aacctccatg aagacatggg cgtggagggt ctgccttttg     120
cagggcccac caggggctca caggaaaggt cgtggaaaat tacaagaaat cttccctctg     180
gcactagcgg gtgaggggaa tggaagccac cgccagacag caccatctcc tcaccctcct     240
gtgaagcaca agactcactt gcagagggaa gagcgcagaa accgtcaccc caggacgctg     300
mggttgaacg agaggaagcg agaatggaga agccctggcc ctggggaaca ggatggaaaa     360
cgcttggctc agctccgtgg ctgcgaagga accggcgcgc tcgcggaggc cacaccccga     420
gacccgagga cacagtgcct gcctgagatg gagccagaaa cattctccac cctttcacgc     480
aagactaaca agggctccat gaaaataaaa ctggaagagc tgaaagagaa gcattctccc     540
tgggtgtgaa accaagaaaa gacacaaagc caaggaaaag ccattgagaa aacacctggc     600
a                                                                    601
```

KCNQ2-15 POTASSIUM CHANNEL

CROSS-REFERENCE TO RELATED APPLICATION

This application is the U.S. national stage application of International Patent Application No. PCT/EP2003/050246, filed Jun. 20, 2003, which claims the benefit of U.S. Provisional Patent Application No. 60/391,359, filed Jun. 25, 2002.

The Sequence Listing for this application is on duplicate compact discs labeled "Copy 1" and "Copy 2." Copy 1 and Copy 2 each contain only one file named "G-194US03PCT-Subst-Seq-List.txt" which was created on Jun. 22, 2005, and is 264 KB. The entire contents of each of the computer discs are incorporated herein by reference in their entireties.

FIELD OF THE INVENTION

This invention is in the field of mental disorders such as bipolar disorder, schizophrenia, depression and other mood disorders. More specifically, this invention relates to three novel potassium channels subunits, KCNQ2-15bx, KCNQ2-15by and KCNQ2-15bz. The invention also relates to the use of potassium channels comprising KCNQ2 subunits for screening for modulators, and to the use of said modulators for treating said mental disorders. The invention further relates to the use of biallelic markers located in the KCNQ2 gene for diagnosing said mental disorders.

BACKGROUND

1. KCNQ Potassium Channels

Malfunction in ion channels, due to mutations in genes encoding channel proteins or the presence of autoantibodies, are increasingly being implicated in causing disease conditions, termed channelopathies. For instance, dysfunction of potassium channels has been associated with the pathophysiology of a number of neurological disorders both affecting the central and peripheral nervous system (e.g., episodic ataxia, epilepsy, neuromyotonia, Parkinson's disease, congenital deafness, long QT syndrome). Potassium channels, which demonstrate a high degree of diversity and ubiquity, are fundamental in the control of membrane depolarisation and cell excitability. A common feature of potassium channelopathies is a reduction or loss of membrane potential repolarisation. Marketed potassium channels openers include for example flupirtine, an analgesic drug used for treating pain.

KCNQ polypeptides belong to the potassium channel family. KCNQ polypeptides associate to form homomeric or heteromeric potassium channels, each polypeptide corresponding to a subunit of the channel. Currently, five different members of the KCNQ family are known: KCNQ1, KCNQ2, KCNQ3, KCNQ4 and KCNQ5. Heteromeric KCNQ potassium channels can be comprised either of different members of the KCNQ family, or of KCNQ polypeptides associated with other members of the potassium channel family. KCNQ potassium channels underlie the M-current, an important regulator of neuronal excitability. Both their amino-terminal and their carboxyl-terminal extremities are located on the intracellular side of the membrane. These extremities play an important role both in interactions with other proteins and in modulation of the channel's activity.

KCNQ1 is expressed in heart, cochlea, intestine and kidney. It assembles with either the product of the KCNE1 gene or with the product of the KCNE3 gene. Mutations in the KCNQ1 gene have been shown to cause one form of inherited long QT syndrome and a form of deafness.

KCNQ2 was first cloned in 1996. In 1998, geneticists discovered that an inherited form of juvenile epilepsy, the benign familial neonatal convulsions, is caused by mutations in the potassium channel KCNQ2 (Singh et al. Nat Genet, 1998, 18:25-9; Biervert et al., Science, 1998, 279:403-6). More specifically, Bievert et al. showed that a five-base pair insertion deleting more than 300 amino acids from the carboxyl-terminus of KCNQ2 leads to impairment of potassium-selective currents in vitro. It was thus demonstrated that loss of function mutations in KCNQ2 causes the epileptic syndrome. Wang et al. showed KCNQ2 to be expressed in brain, and to be associated with KCNQ3. In addition, they showed that the KCNQ2/3 heteromultimers underlie the M-current (Wang et al., Science, 1998, 282:1890-3). In 2000, Main et al. showed that KCNQ2 is the molecular target of retigabine, a potent anticonvulsant compound, and that retigabine acts as a KCNQ2/3 potassium channel opener (Mol Pharmacol, 2000, 58:253-62). Biervert et al. determined that the KCNQ2 gene has at least 18 exons, occupying more than 50 kb of genomic DNA (Genet., 1999, 104:234-240). Until now six different isoforms of KCNQ2 produced by alternative splicing have been described (see, e.g., SwissProt Accession No. O43526).

KCNQ4 is expressed in inner ear, and it has been shown that mutation in the KCNQ4 gene lead to a form of inherited deafness.

KCNQ5 is expressed in brain and skeletal muscle, and can co-assemble with KCNQ3, suggesting that it may also play a role in the M-current heterogeneity. It has been suggested that KCNQ5 deficiency leads to retinal degeneration.

The activity of KCNQ channels has been shown to be modulated by Protein kinase A (PKA) and by the c-Src tyrosine kinase (Src). Schroeder et al. showed that currents generated by heteromeric KCNQ2/KCNQ3 channels can be increased by intracellular cyclic AMP, and that this effect is mediated by PKA. PKA stimulated current intensity by 66% (Schroeder et al., Epilepsia (2000) 41:1068-1069). Gamper et al. showed that coexpression of Src with KCNQ2/KCNQ3 heteromeric channels resulted in a 4.5-fold reduction of current density and a 2-fold slowing of activation kinetics at 0 mV. However, Src had no effect on currents generated by KCNQ2 homomultimeric channels (J. Neurosci. (2003) 23:84-95). In view of these results, modulation of KCNQ channels by kinases and phosphatases is believed to be important for control of neuronal excitability.

Studying KCNQ channels in humans and animal models is of great importance for the understanding of how M-channels control excitability at the cellular, network, and behavioral levels. A better understanding of the physiological role of KCNQ channels is a promising way of finding of new targets for novel diseases, thus leading to the possibility of novel screenings of drug candidates.

2. The PP2A Phosphatase

The PP2A phosphatase is an intracellular serine/threonine protein phosphatase constituted by two or three subunits. PP2A phosphatases comprise of a catalytic subunit (PP2A/C), a scaffolding subunit (PP2A/A) and eventually a regulatory subunit (PP2A/B).

Regulatory subunits are thought to confer tissue specificity, subcellular localization and developmental regulation to PP2A. More than eleven ndifferent regulatory subunits are currently known, and PP2A/Bγ is one of them. PP2A/Bγ is encoded by the PPP2R2C gene that was mapped to human chromosome 4p16 between markers D4S2925 and D4S3007 (Hu et al., Genomics., 2000, 67:83-6). The PP2A/Bγ protein can only be detected in brain and is enriched in the cytosolic fraction of the cell. Furthermore, PPP2R2C is developmentally regulated.

3. Mental Disorders

Mental disorders encompass a wide range of CNS disorders. Mental disorders include, e.g., mood disorders, psychotic disorders, anxiety disorders, childhood disorders, eating disorders and personality disorders, all these terms being defined according to the DSM-IV classification (Diagnosis and Statistical Manual of Mental Disorders, Fourth Edition, American Psychiatric Association, Washington D.C., 1994). Mood Disorders encompass bipolar I disorder (mania with or without major depression), bipolar II disorder (hypomania with major depression), cyclothymic disorder (numerous brief episodes of hypomania and minor depression), dysthymic disorder (prolonged minor depression without mania/hypomania) and major depressive disorder (major depression without mania). Psychotic disorders encompass schizophrenia, schizoaffective disorder, schizophreniform disorder, brief psychotic disorder, delusional disorder and shared psychotic disorder. Bipolar disorder, schizophrenia and depression are three particularly serious and widespread mental disorders.

3.1. Bipolar Disorder

Bipolar disorders are relatively common disorders, occurring in about 1.3% of the population, and have been reported to constitute about half of the mood disorders seen in psychiatric clinics with severe and potentially disabling effects. Bipolar disorders have been found to vary with gender depending of the type of disorder; for example, bipolar disorder I is found equally among men and women, while bipolar disorder II is reportedly more common in women. The age of onset of bipolar disorders is typically in the teenage years and diagnosis is typically made in the patient's early twenties. Bipolar disorders also occur among the elderly, generally as a result of a neurological disorder or other medical conditions. In addition to the severe effects on patients' social development, suicide completion rates among bipolar patients are reported to be about 15%.

Bipolar disorders are characterized by phases of excitement and often depression; the excitement phases, referred to as mania or hypomania, and depressive phases can alternate or occur in various admixtures, and can occur to different degrees of severity and over varying duration. Since bipolar disorders can exist in different forms and display different symptoms, the classification of bipolar disorder has been the subject of extensive studies resulting in the definition of bipolar disorder subtypes and widening of the overall concept to include patients previously thought to be suffering from different disorders. Bipolar disorders often share certain clinical signs, symptoms, treatments and neurobiological features with psychotic illnesses in general and therefore present a challenge to the psychiatrist to make an accurate diagnosis. Furthermore, because the course of bipolar disorders and various mood and psychotic disorders can differ greatly, it is critical to characterize the illness as early as possible in order to offer means to manage the illness over a long term.

The mania associated with the disease impairs performance and causes psychosis, and often results in hospitalization. This disease places a heavy burden on the patient's family and relatives, both in terms of the direct and indirect costs involved and the social stigma associated with the illness, sometimes over generations. Such stigma often leads to isolation and neglect. Furthermore, the earlier the onset, the more severe are the effects of interrupted education and social development.

The DSM-IV classification of bipolar disorder distinguishes among four types of disorders based on the degree and duration of mania or hypomania as well as two types of disorders which are evident typically with medical conditions or their treatments, or to substance abuse. Mania is recognized by elevated, expansive or irritable mood as well as by distractability, impulsive behavior, increased activity, grandiosity, elation, racing thoughts, and pressured speech. Of the four types of bipolar disorder characterized by the particular degree and duration of mania, DSM-IV includes:

- bipolar disorder I, including patients displaying mania for at least one week;
- bipolar disorder II, including patients displaying hypomania for at least 4 days, characterized by milder symptoms of excitement than mania, who have not previously displayed mania, and have previously suffered from episodes of major depression;
- bipolar disorder not otherwise specified (NOS), including patients otherwise displaying features of bipolar disorder II but not meeting the 4 day duration for the excitement phase, or who display hypomania without an episode of major depression; and
- cyclothymia, including patients who show numerous manic and depressive symptoms that do not meet the criteria for hypomania or major depression, but which are displayed for over two years without a symptom-free interval of more than two months.

The remaining two types of bipolar disorder as classified in DSM-VI are disorders evident or caused by various medical disorder and their treatments, and disorders involving or related to substance abuse. Medical disorders which can cause bipolar disorders typically include endocrine disorders and cerebrovascular injuries, and medical treatments causing bipolar disorder are known to include glucocorticoids and the abuse of stimulants. The disorder associated with the use or abuse of a substance is referred to as "substance induced mood disorder with manic or mixed features".

Evidence from twin and adoption studies, and the lack of variation in incidence worldwide, indicate that bipolar disorder is primarily a genetic condition, although environmental risk factors are also involved at some level as necessary, sufficient, or interactive causes. Aggregation of bipolar disorder and schizophrenia in families suggests that these two distinct disorders share some common genetic susceptibility. Several linkage studies of bipolar disorder have been reported, and several susceptibility regions have been identified. The regions that are associated with bipolar disorder include 1q31-q32, 4p16, 7q31, 12q23-q24, 13q32, 18p11.2, 21q22 and 22q11-q13 (Detera-Wadleigh et al. (1999) Proc Natl Acad Sci USA A96(10):5604-9). Some of these regions, like 4p16, 12q24, 18p11, 21q21 and 22q11 have been repeatedly implicated by independent investigators. Furthermore, some regions that are linked to bipolar disorder such as, e.g., 13q32 and 18p11.2, are also implicated in genome scans of schizophrenia, confirming that these two distinct disorders share some common genetic susceptibility. However, the genes underlying bipolar disorder and/or schizophrenia have not yet been identified.

3.2. Schizophrenia

There are an estimated 45 million people with schizophrenia in the world, with more than 33 million of them in the developing countries. In developed countries schizophrenia occurs in approximately 1% of the adult population at some point during their lives. If there is one grandparent with schizophrenia, the risk of getting the illness increases to about 3%; one parent with Schizophrenia, to about 10%. When both parents have schizophrenia, the risk rises to approximately 40%. Most schizophrenia patients are never able to work. Standardized mortality ratios (SMRs) for schizophrenic patients are estimated to be two to four times higher than the general population and their life expectancy overall is 20% shorter than for the general population. The most common cause of death among schizophrenic patients is suicide (in 10% of patients) which represents a 20 times higher risk than for the general population. Deaths from heart disease and from diseases of the respiratory and digestive system are also increased among schizophrenic patients.

Schizophrenia comprises a group of psychoses with either 'positive' or 'negative' symptoms. Positive symptoms consist of hallucinations, delusions and disorders of thought; negative symptoms include emotional flattening, lack of volition and a decrease in motor activity.

A number of biochemical abnormalities have been identified and, in consequence, several neurotransmitter based hypotheses have been advanced over recent years; the most popular one has been "the dopamine hypothesis," one variant of which states that there is over-activity of the mesolimbic dopamine pathways at the level of the $D_2$ receptor. However, researchers have been unable to consistently find an association between various receptors of the dopaminergic system and schizophrenia.

3.3. Depression

Depression is a serious medical illness that affects 340 million people worldwide. In contrast to the normal emotional experiences of sadness, loss, or passing mood states, clinical depression is persistent and can interfere significantly with an individual's ability to function. As a result, depression is the leading cause of disability throughout the world.

Symptoms of depression include depressed mood, diminished interest or pleasure in activities, change in appetite or weight, insomnia or hypersomnia, psycho-motor agitation or retardation, fatigue or loss of energy, feelings of worthlessness or excessive guilt, anxiety, inability to concentrate or act decisively, and recurrent thoughts of death or suicide. A diagnosis of unipolar major depression (or major depressive disorder) is made if a person has five or more of these symptoms and impairment in usual functioning nearly every day during the same two-week period. The onset of depression generally begins in late adolescence or early adult life; however, recent evidence suggests depression may be occurring earlier in life in people born in the past thirty years.

The World Health Organization predicts that by the year 2020 depression will be the greatest burden of ill-health to people in the developing world, and that by then depression will be the second largest cause of death and disability. Beyond the almost unbearable misery it causes, the big risk in major depression is suicide. Within five years of suffering a major depression, an estimated 25% of sufferers try to kill themselves. In addition, depression is a frequent and serious complication of heart attack, stroke, diabetes, and cancer. According to one recent study that covered a 13-year period, individuals with a history of major depression were four times as likely to suffer a heart attack compared to people without such a history. Depression may also be a feature in up to 50% of patients with mental disorders such as Parkinson's disease and Alzheimer's disease.

3.4. Treatment

There are currently no cures for mental disorders such as bipolar disorder, schizophrenia, depression and other mood disorders, so the objective of treatment is to reduce the severity of the symptoms, if possible to the point of remission. Due to the similarities in symptoms, schizophrenia, depression and bipolar disorder are often treated with some of the same medicaments.

3.4.1. Treatment of Bipolar Disorder

Depressive episodes may be treated like depression. However, most antidepressants can cause swings from depression to hypomania or mania and sometimes cause rapid cycling between them. Therefore, these drugs are used for only short periods, and their effect on mood is closely monitored. At the first sign of a swing to hypomania or mania, the antidepressant is stopped. Most people with manic-depressive disorder are given drugs with a mood-stabilizing effect such as lithium, carbamazepine and divalproex.

Lithium has no effect on normal mood but reduces the tendency toward mood swings in about 70% of the people with manic-depressive illness. A doctor monitors the level of lithium in the blood with blood tests. Possible adverse effects of lithium include tremor, muscle twitching, nausea, vomiting, diarrhea, thirst, excessive urination, and weight gain. Lithium can make acne or psoriasis worse, can cause the blood levels of thyroid hormone to fall, and rarely can cause excessive urination. A very high level of lithium in the blood can cause a persistent headache, mental confusion, drowsiness, seizures, and abnormal heart rhythms. Adverse effects are more likely to occur in the elderly. Women who are trying to become pregnant must stop taking lithium, because lithium may cause heart defects in a developing fetus.

Newer drug treatments have evolved over the past several years. These include the carbamazepine and divalproex. However, carbamazepine can seriously reduce the number of red and white blood cells, and divalproex can cause liver damage (primarily in children). With careful monitoring by a doctor, these problems are rare, and carbamazepine and divalproex are useful alternatives to lithium, especially for people with the mixed or rapid cycling form of manic-depressive illness who haven't responded to other treatments.

3.4.2. Treatment of Schizophrenia

For schizophrenia, antipsychotic medications are the most common and most valuable treatments. There are four main classes of antipsychotic drugs which are commonly prescribed for schizophrenia. The first, neuroleptics, exemplified by chlorpromazine (Thorazine), has revolutionized the treatment of schizophrenic patients by reducing positive (psychotic) symptoms and preventing their recurrence. Patients receiving chlorpromazine have been able to leave mental hospitals and live in community programs or their own homes. But these drugs are far from ideal. Some 20% to 30% of patients do not respond to them at all, and others eventually relapse. These drugs were named neuroleptics because they produce serious neurological side effects, including rigidity and tremors in the arms and legs, muscle spasms, abnormal body movements, and akathisia (restless pacing and fidgeting). These side effects are so troublesome that many patients simply refuse to take the drugs. Besides, neuroleptics do not improve the so-called negative symptoms of schizophrenia and the side effects may even exacerbate these symptoms. Thus, despite the clear beneficial effects of neuroleptics, even some patients who have a good short-term response will ultimately deteriorate in overall functioning.

The well known deficiencies in the standard neuroleptics have stimulated a search for new treatments and have led to a new class of drugs termed atypical neuroleptics. The first atypical neuroleptic, Clozapine, is effective for about one third of patients who do not respond to standard neuroleptics. It seems to reduce negative as well as positive symptoms, or at least exacerbates negative symptoms less than standard neuroleptics do. Moreover, it has beneficial effects on overall functioning and may reduce the chance of suicide in schizophrenic patients. It does not produce the troubling neurological symptoms of the standard neuroleptics, or raise blood levels of the hormone prolactin, excess of which may cause menstrual irregularities and infertility in women, impotence or breast enlargement in men. Many patients who cannot tolerate standard neuroleptics have been able to take clozapine. However, clozapine has serious limitations. It was originally withdrawn from the market because it can cause agranulocytosis, a potentially lethal inability to produce white blood cells. Agranulocytosis remains a threat that requires careful monitoring and periodic blood tests. Clozapine can also cause seizures and other disturbing side effects (e.g., drowsiness, lowered blood pressure, drooling, bed-wetting, and weight gain). Thus only patients who do not respond to other drugs usually take Clozapine.

Researchers have developed a third class of antipsychotic drugs that have the virtues of clozapine without its defects. One of these drugs is risperidone (Risperdal). Early studies suggest that it is as effective as standard neuroleptic drugs for positive symptoms and may be somewhat more effective for negative symptoms. It produces more neurological side effects than clozapine but fewer than standard neuroleptics. However, it raises prolactin levels. Risperidone is now prescribed for a broad range of psychotic patients, and many clinicians seem to use it before clozapine for patients who do not respond to standard drugs, because they regard it as safer. Another new drug is Olanzapine (Zyprexa) which is at least as effective as standard drugs for positive symptoms and more effective for negative symptoms. It has few neurological side effects at ordinary clinical doses, and it does not significantly raise prolactin levels. Although it does not produce most of clozapine's most troubling side effects, including agranulocytosis, some patients taking olanzapine may become sedated or dizzy, develop dry mouth, or gain weight. In rare cases, liver function tests become transiently abnormal.

3.4.3. Treatment of Depression

Several types of antidepressants are available. These antidepressants belong to four main categories: tricyclic antidepressants, selective serotonin reuptake inhibitors, monoamine oxidase inhibitors and psychostimulants. Tricyclic antidepressants include, e.g., Amitriptyline, Amoxapine, Bupropion, Clomipramine, Desipramine, Doxepin, Imipramine, Maprotiline, Nefazodone, Nortriptyline, Protriptyline, Trazodone, Trimipramine and Venlafaxine. Selective serotonin reuptake inhibitors include, e.g., Fluoxetine, Fluvoxamine, Paroxetine and Sertraline. Monoamine oxidase inhibitors include, e.g., Isocarboxazid, Pargyline, Phenelzine and Tranylcypromine. Psychostimulants include, e.g., Dextroamphetamine and Methylphenidate.

All these antidepressants must be taken regularly for at least several weeks before they begin to work. The chances that any given antidepressant will work for a particular person are about 65%. However, most of these drugs have side effects varying with each type of drug. For example, the tricyclic antidepressants often cause sedation and lead to weight gain. They can also be associated with side effects such as an increased heart rate, a decrease in blood pressure when the person stands or blurred vision.

Thus, for mental disorders such as bipolar disorder, schizophrenia, depression and other mood disorders, known molecules used for the treatment have side effects and act only against the symptoms of the disease. Consequently, there is a strong need for new molecules without associated side effects that are specifically directed against targets which are involved in the causal mechanisms of such mental disorders. Therefore, there is a need to identify proteins involved in bipolar disorder and schizophrenia. Providing new targets involved in bipolar disorder and schizophrenia will allow new screenings for drugs, resulting in new drugs that are efficient in treatment of these serious mental disorders.

Furthermore, there is also a need for diagnostic tools. There is increasing evidence that leaving schizophrenia untreated for long periods early in course of the illness may negatively affect the outcome. However, the use of drugs is often delayed for patients experiencing a first episode of the illness. The patients may not realize that they are ill, or they may be afraid to seek help; family members sometimes hope the problem will simply disappear or cannot persuade the patient to seek treatment; clinicians may hesitate to prescribe antipsychotic medications when the diagnosis is uncertain because of potential side effects. Indeed, at the first manifestation of the disease, schizophrenia or bipolar disorder is difficult to distinguish from, e.g., drug-related disorders and stress-related disorders. Accordingly, there is a need for new methods for detecting a susceptibility to mental disorders such as bipolar disorder, schizophrenia, and depression.

SUMMARY OF THE INVENTION

The present invention is based on the identification of novel splice variants of the KCNQ2 potassium channel.

Therefore, in a first aspect, the present invention is directed to an isolated KCNQ2-15b polypeptide selected from the group consisting of:
a) a polypeptide comprising a span of at least ten amino acids of amino acids 589 to 643 of SEQ ID NO: 2;
b) a polypeptide comprising amino acids 589 to 643 of SEQ ID NO: 2;
c) a polypeptide comprising amino acids 545 to 643 of SEQ ID NO: 2;
d) a polypeptide comprising SEQ ID NO: 2;
e) a polypeptide comprising SEQ ID NO: 4;
f) a polypeptide comprising SEQ ID NO: 6;
g) a mutein of any of (a) to (f), wherein the amino acid sequence has at least 50% or 60% or 70% or 80% or 90% or 95% or 99% identity to at least one of the sequences in (a) to (f);
h) a mutein of any of (a) to (f) which is encoded by a DNA sequence which hybridizes to the complement of the DNA sequence encoding any of (a) to (f) under moderately stringent conditions or under highly stringent conditions; and
i) a mutein of any of (a) to (f) wherein any changes in the amino acid sequence are conservative amino acid substitutions to the amino acid sequences in (a) to (f).

The present invention further relates to a potassium channel comprising at least one KCNQ2-15b polypeptide.

The invention further relates to a purified KCNQ2-15b polynucleotide encoding a KCNQ2-15b polypeptide or a polynucleotide complementary thereto.

An expression vector comprising a KCNQ2-15b polynucleotides, a host cell comprising an expression vector comprising a KCNQ2-15b polynucleotides and an antibody that specifically binds to a KCNQ2-15b polypeptide are also within the present invention.

Further, the present invention pertains to a method of making a polypeptide, said method comprising the steps of culturing a host cell comprising an expression vector comprising a KCNQ2-15b polynucleotides under conditions suitable for the production of a KCNQ2-15b polypeptide within said host cell.

The present invention is further based on the finding that KCNQ2 is associated with the onset and the development of mental disorders.

Therefore, in a second aspect, the present invention is directed to the use of a KCNQ2 polypeptide as a target for screening candidate modulators.

The present invention further relates to the use of a modulator of a KCNQ2 polypeptide for preparing a medicament for the treatment of a mental disorder.

The invention also concerns a method of assessing the efficiency of a modulator of a KCNQ2 polypeptide for the treatment of a mental disorder, said method comprising administering said modulator to an animal model for said mental disorder; wherein a determination that said modulator ameliorates a representative characteristic of said mental disorder in said animal model indicates that said modulator is a drug for the treatment of said mental disorder.

In the frame of the present invention, biallelic markers located in the KCNQ2 gene have been identified and validated.

Therefore, a third object of the invention consists of the use of at least one KCNQ2-related biallelic marker for diagnosing whether an individual suffers from or is at risk of suffering from a mental disorder.

The invention further encompasses the use of at least one KCNQ2-related biallelic marker for determining whether there is a significant association between said marker and a mental disorder.

The invention also relates to a method of genotyping comprising the step of determining the identity of a nucleotide at a KCNQ2-related biallelic marker or the complement thereof in a biological sample.

The invention further pertains to a method of diagnosing a mental disorder in an individual comprising the step of genotyping at least one KCNQ2-related biallelic marker using a method of genotyping comprising the step of determining the identity of a nucleotide at said KCNQ2-related biallelic marker or the complement thereof in a biological sample.

BRIEF DESCRIPTION OF THE FIGURES

FIGS. 1A and 1B show an alignment between the full-length KCNQ2 polypeptide (KCNQ2-fl, SEQ ID NO: 7), KCNQ2-15bx (SEQ ID NO: 2), KCNQ2-15by (SEQ ID NO: 4) and KCNQ2-15bz (SEQ ID NO: 6). The box shows highlights the amino acids that are unique to KCNQ2-15bx, KCNQ2-15by and KCNQ2-15bz compared to KCNQ2-fl.

BRIEF DESCRIPTION OF THE SEQUENCES OF THE SEQUENCE LISTING

Figure 2:
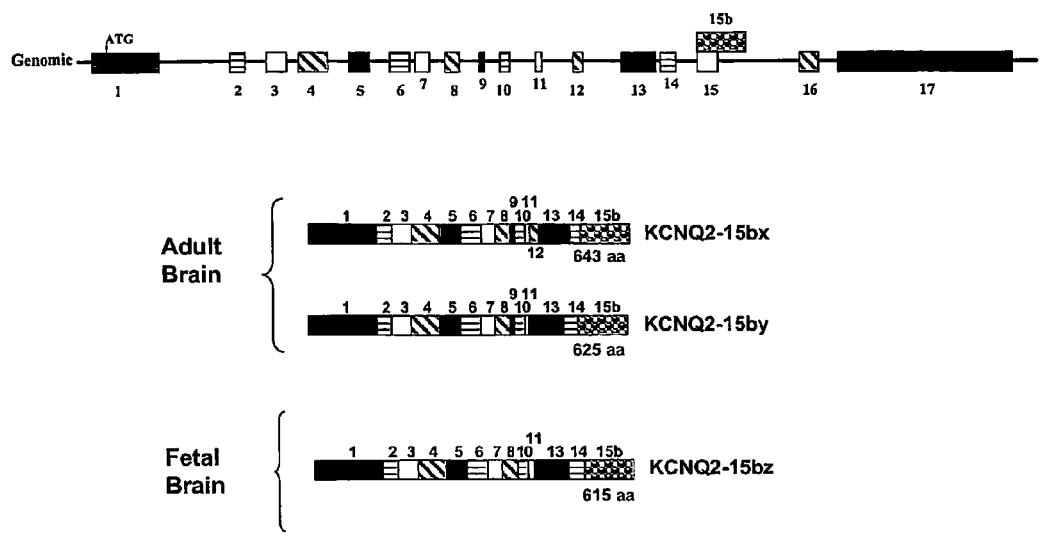
FIG. 2 shows a sheme of the structure of the KCNQ2-15bx, KCNQ2-15by and KCNQ2-15bz cDNAs.

SEQ ID NO: 1 corresponds to a polynucleotide consisting of the CDS of KCNQ2-15bx
SEQ ID NO: 2 corresponds to the KCNQ2-15bx polypeptide.
SEQ ID NO: 3 corresponds to a polynucleotide consisting of the CDS of KCNQ2-15by
SEQ ID NO: 4 corresponds to the KCNQ2-15by polypeptide.
SEQ ID NO: 5 corresponds to a polynucleotide consisting of the CDS of KCNQ2-15bz
SEQ ID NO: 6 corresponds to the KCNQ2-15bz polypeptide.
SEQ ID NO: 7 corresponds to the KCNQ2-fl polypeptide.
SEQ ID Nos. 8 to 36 correspond to primers and probes used in Examples 1 to 4.
SEQ ID NO: 37 corresponds to the PPP2R2C gene which encodes the PP2A/Bγ subunit, on which PP2A/Bγ-related biallelic markers are indicated.
SEQ ID NO: 38 corresponds to the PP2A/Bγ subunit.
SEQ ID Nos. 39 to 41 correspond to primers used for microsequencing some of the PP2A/Bγ-related biallelic markers.
SEQ ID Nos. 42 to 47 correspond to regions of the KCNQ2 gene, on which KCNQ2-related biallelic markers are indicated.

BRIEF DESCRIPTION OF THE TABLES

Table 1 presents the structure of KCNQ2-fl, KCNQ2-15bx KCNQ2-15by and KCNQ2-15bz..
Tables 2A and 2B present the location of the primers used for amplification of genomic DNA by PCR in PPP2R2C and in the KCNQ2 gene respectively
Table 3A and 3B present biallelic markers located in the PP2R2C and in the KCNQ2 gene respectively.
Tables 4A and 4B present the the primers used for microsequencing biallelic markers located in PP2R2C and in the KCNQ2 gene respectively.
Tables 5A and 5B present the p-values for biallelic markers located in PPP2R2C and in the KCNQ2 gene respectively.
Tables 6A and 6B present the genotypic odds ratios for a biallelic marker located in PPP2R2C and in the KCNQ2 gene respectively.
Tables 7A and 7B present the risk haplotypes for two sets of biallelic markers located in PPP2R2C

DETAILED DESCRIPTION OF THE INVENTION

The present invention stems from the cloning and the sequencing of three novel splice variants of the KCNQ2 gene, KCNQ2-15bx, KCNQ2-15by and KCNQ2-15bz. These splice variants all display a novel exon (exon 15b), corresponding to amino acids 545 to 643 of SEQ ID NO: 2. Data showing that KCNQ2-15bx and KCNQ2-15by can assemble as functional homotetrameric potassium channels are provided. In the frame of the present invention, it has been demonstrated that these novel splice variants interact with the Bγ subunit of the serine/threonine protein phosphatase 2A (PP2A/Bγ) both in vitro and in vivo. Furthermore, association studies are described in example 15, and it was shown that both the KCNQ2 gene and the gene coding for PP2A/Bγ are strongly associated with bipolar disorder. Novel validated biallelic markers located in the KCNQ2 gene and associated with bipolar disorder are provided. In the frame of the present invention it was further shown that KCNQ2-15bx, KCNQ2-15by and KCNQ2-15bz are (i) dephosphorylated by PP2A; and (ii) phosphorylated by the PKA and GSK3β kinases. Moreover, the phosphorylation of KCNQ2-15bx, KCNQ2-15by and KCNQ2-15bz is inhibited in the presence of lithium, a known mood-stabilizing agent.

Accordingly, the present invention provides novel KCNQ2 polypeptides and means to identify compounds useful in the treatment of mental disorders such as bipolar disorder, schizophrenia, depression and other mood disorders. The invention further relates to the use of KCNQ2 polypeptides as targets for screening for modulators thereof. The use of said modulators for treating mental disorders, and the use of biallelic markers located in the KCNQ2 gene for diagnosing mental disorders are further aspects of the present invention.

1. Definitions

The term "treat" or "treating" as used herein is meant to ameliorate, alleviate symptoms, eliminate the causation of the symptoms either on a temporary or permanent basis, or to prevent or slow the appearance of symptoms of the named disorder or condition. The term "treatment" as used herein also encompasses the term "prevention of the disorder", which is, e.g., manifested by delaying the onset of the symptoms of the disorder to a medically significant extent. Treatment of the disorder is, e.g., manifested by a decrease in the symptoms associated with the disorder or an amelioration of the reoccurrence of the symptoms of the disorder.

The term "mental disorder" refers to diseases characterized as mood disorders, psychotic disorders, anxiety disorders, childhood disorders, eating disorders, personality disorders, adjustment disorder, autistic disorder, delirium, dementia, multi-infarct dementia and Tourette's disorder in the DSM-IV classification (Diagnosis and Statistical Manual of Mental Disorders, Fourth Edition, American Psychiatric Association, Washington D.C., 1994).

The term "schizophrenia" refers to a condition characterized as schizophrenia in the DSM-IV classification (Diagnosis and Statistical Manual of Mental Disorders, Fourth Edition, American Psychiatric Association, Washington D.C., 1994).

The term "bipolar disorder" as used herein refers to a condition characterized as a Bipolar Disorder in the DSM-IV. Bipolar disorder may be bipolar I and bipolar disorder II as described in the DSM-IV. The term further includes cyclothymic disorder. Cyclothymic disorder refers to an alternation of depressive symptoms and hypomanic symptoms. The skilled artisan will recognize that there are alternative nomenclatures, posologies, and classification systems for pathologic psychological conditions and that these systems evolve with medical scientific progress.

The terms "comprising", "consisting of", or "consisting essentially of" have distinct meanings. However, each term may be substituted for another herein to change the scope of the invention.

As used interchangeably herein, the term "oligonucleotides", and "polynucleotides" include RNA, DNA, or RNA/DNA hybrid sequences of more than one nucleotide in either single chain or duplex form. The term "nucleotide" as used herein as an adjective to describe compounds comprising RNA, DNA, or RNA/DNA hybrid sequences of any length in single-stranded or duplex form. The term "nucleotide" is also used herein as a noun to refer to individual nucleotides or varieties of nucleotides, meaning a compound, or individual unit in a larger nucleic acid compound, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064, the disclosure of which is incorporated herein by reference. However, the polynucleotides of the invention are preferably comprised of greater than 50% conventional deoxyribose nucleotides, and most preferably greater than 90% conventional deoxyribose nucleotides. The polynucleotide sequences of the invention may be prepared by any known method, including synthetic, recombinant, ex vivo generation, or a combination thereof, as well as utilizing any purification methods known in the art.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., polynucleotide as defined herein) which can be used to identify a specific polynucleotide sequence present in samples, said nucleic acid segment comprising a nucleotide sequence complementary of the specific polynucleotide sequence to be identified.

The terms "complementary" or "complement thereof" are used herein to refer to the sequences of polynucleotides which are capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

The term "polypeptide" refers to a polymer of amino acids without regard to the length of the polymer; thus, peptides, oligopeptides, and proteins are included within the definition of polypeptide. This term also does not specify or exclude prost-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

As used herein, the term "exon" refers as well to the portion of a DNA that codes for portion of spliced mRNA as to the amino acids encoded by said part of a DNA.

As used herein, "splice variants" refer to different mRNAs produced by alternative splicing events and translated from the same gene. The term splice variant refers as well to the mRNA as to the corresponding polypeptide.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

The terms "trait" and "Phenotype" are used interchangeably herein and refer to any clinically distinguishable, detectable or otherwise measurable property of an organism such as symptoms of, or susceptibility to a disease for example. Typically the terms "trait" or "phenotype" are used herein to refer to symptoms of, or susceptibility to bipolar disorder; or to refer to an individual's response to an agent acting on bipolar disorder; or to refer to symptoms of, or susceptibility to side effects to an agent acting on bipolar disorder.

As used herein, the term "allele" refers to one of the variant forms of a biallelic marker, differing from other forms in its nucleotide sequence. Typically the first identified allele is designated as the original allele whereas other alleles are designated as alternative alleles. Diploid organisms may be homozygous or heterozygous for an allelic form.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A polymorphism may comprise a substitution, deletion or insertion of one or more nucleotides. A single nucleotide polymorphism is a single base pair change. Typically a single nucleotide polymorphism is the replacement of one nucleotide by another nucleotide at the polymorphic site. A "single nucleotide polymorphism" (SNP) refers to a sequence polymorphism differing in a single base pair.

2. KCNQ2-15b Polypeptides of the Present Invention

The term "KCNQ2-15b polypeptides" is used herein to embrace all of the polypeptides of the present invention.

Preferably, the KCNQ2-15b is selected from a peptide, a polypeptide or a protein selected from the group consisting of:

a) a polypeptide comprising a span of at least ten amino acids of amino acids 589 to 643 of SEQ ID NO: 2;
b) a polypeptide comprising amino acids 589 to 643 of SEQ ID NO: 2;
c) a polypeptide comprising amino acids 545 to 643 of SEQ ID NO: 2;
d) a polypeptide comprising SEQ ID NO: 2;
e) a polypeptide comprising SEQ ID NO: 4;
f) a polypeptide comprising SEQ ID NO: 6;
g) a mutein of any of (a) to (f), wherein the amino acid sequence has at least 50% or 60% or 70% or 80% or 90% or 95% or 99% identity to at least one of the sequences in (a) to (f);
h) a mutein of any of (a) to (f) which is encoded by a DNA sequence which hybridizes to the complement of the DNA sequence encoding any of (a) to (f) under moderately stringent conditions or under highly stringent conditions; and
i) a mutein of any of (a) to (f) wherein any changes in the amino acid sequence are conservative amino acid substitutions to the amino acid sequences in (a) to (f).

KCNQ2-15b polypeptides of the present invention all comprise an amino acid sequence of a span of at least 10 amino acids of SEQ ID NO: 2, wherein said span falls within amino acids 589 to 643 of SEQ ID NO: 2. Preferably, KCNQ2-15b polypeptides comprise amino acids 589 to 643 of SEQ ID NO: 2.

In an embodiment of the invention, KCNQ2-15b polypeptides comprise any of SEQ ID NO: 2, SEQ ID NO: 4 or SEQ ID NO: 6. Preferred KC NQ2-15b polypeptides consist of SEQ ID NO: 2, SEQ ID NO: 4 or SEQ ID NO: 6. As further used herein, "KCNQ2-15bx" refers to a polypeptide of SEQ ID NO: 2, "KCNQ2-15by" refers to a polypeptide of SEQ ID NO: 4 and "KCNQ2-15bz" refers to a polypeptide of SEQ ID NO: 6.

In a preferred embodiment, KCNQ2-15b polypeptides are capable of binding to the Bγ subunit of the PP2A phosphatase (PP2A/Bγ). In other words, said KCNQ2-15b polypeptides bind to PP2A/Bγ when the binding is tested by any suitable assay. Such assay s encompass, e.g., the yeast mating test described in example 9 and the solid phase overlay assay described in example 6. As further used herein, the term "KCNQ2-15b binding activity" or "binding activity" refers to the capacity of the KCNQ2-15b polypeptide to bind to PP2A/Bγ.

In another preferred embodiment, KCNQ2-15b polypeptides correspond to a subunit of a potassium channel. In a more preferred embodiment, KCNQ2-15b polypeptides correspond to isoforms of the KCNQ2 polypeptide that are produced by alter native splicing events. Such KCNQ2-15b polypeptides may associate either with other KCNQ2-15b polypeptides or with other potassium channels subunits to form a potassium channel. As further used herein, the term "KCNQ2-15b biological activity" or "biological activity" refers to the activity of a potassium channel comprising the KCNQ2-15b polypeptide.

A preferred embodiment is directed to a potassium channel comprising at least one KCNQ2-15b polypeptide. The potassium channel may be a homomeric potassium channel comprised of several KCNQ2-15b polypeptides. Alternatively, the potassium channel may be a heteromeric potassium channel comprised of a KCNQ2-15b polypeptide associated with other KCNQ polypeptides and/or other potassium channel subunits. The KCNQ2-15b biological activity can be measured by methods well known by those skilled in the art such as, e.g., measurement of the M current.

As further used herein, the terms "KCNQ2-15b biological properties", "biological properties" and "activity" encompass both the biological activity and the binding activity of the KCNQ2-15b polypeptide. KCNQ2-15b biological properties further include, but are not limited to, e.g., KCNQ2-15b-specific antibody binding, binding to KCNQ subunits and modulation of potassium channel activity.

In further preferred embodiments, KCNQ2-15b polypeptides comprise the novel exon 15b. The term "exon 15b" refers to the amino acids at position 545 to 643 of SEQ ID NO: 2. Preferably, exon 15b is the most carboxyl-terminal exon of said KCNQ2-15b polypeptide. KCNQ2-15b polypeptides may further comprise any combination of exons 1 to 14 of the KCNQ2 gene.

The present invention is also directed to fragments of at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 or 610 amino acids of KCNQ2-15bx, KCNQ2-15by or KCNQ2-15bz.

Further embodiments are directed to muteins. As used herein the term "muteins" refers to analogs of KCNQ2-15bx, KCNQ2-15by or KCNQ2-15bz, in which one or more of the amino acid residues of a natural KCNQ2-15bx, KCNQ2-15by or KCNQ2-15bz are replaced by different amino acid residues, or are deleted, or one or more amino acid residues are added to the natural sequence of KCNQ2-15bx, KCNQ2-15by or KCNQ2-15bz, without lowering considerably the activity of the resulting products as compared with the wild-type KCNQ2-15bx, KCNQ2-15by or KCNQ2-15bz. These muteins are prepared by known synthesis and/or by site-directed mutagenesis techniques, or any other known technique suitable therefore.

Muteins of KCNQ2-15bx, KCNQ2-15by or KCNQ2-15bz, which can be used in accordance with the present invention, or nucleic acid coding thereof, include a finite set of substantially corresponding sequences as substitution peptides or polynucleotides which can be routinely obtained by one of ordinary skill in the art, without undue experimentation, based on the teachings and guidance presented herein.

KCNQ2-15bx, KCNQ2-15by or KCNQ2-15bz in accordance with the present invention include proteins encoded by a nucleic acid, such as DNA or RNA, which hybridizes to DNA or RNA, which encodes KCNQ2-15b, in accordance with the present invention, under moderately or highly stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC.

The polypeptides of the present invention include muteins having an amino acid sequence at least 50% identical, more preferably at least 60% identical, and still more preferably 70%, 80%, 90%, 95%, 96%, 97%, 98% or 99% identical to a KCNQ2-15b polypeptide of the present invention. By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (s o-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at world wide web site ncbi.nim.nih.gov) and FASTA (Pearson W R, 1990; Pearson 1988).

Preferred changes for muteins in accordance with the present invention are what are known as "conservative" substitutions. Conservative amino acid substitutions of KCNQ2-15bx, KCNQ2-15by or KCNQ2-15bz polypeptides, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g. under thirty, and preferably under ten, and do not remove or displace amino acids which are critical to a functional conformation, e.g. cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |

TABLE II-continued

More Preferred Groups of Synonymous Amino Acids

| Amino Acid | Synonymous Group |
|---|---|
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of KCNQ2-15bx, KCNQ2-15by or KCNQ2-15bz, polypeptides for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

Preferably, the muteins of the present invention exhibit substancially the same biological properties as the KCNQ2-15b polypeptide to which it corresponds.

In some embodiments, KCNQ2-15b polypeptides and muteins or fragments thereof have biological activity or binding activity as defined above. In other embodiments, KCNQ2-15b polypeptides and muteins or fragments thereof do not have activity as defined above. Other uses of the polypeptides of the present invention include, inter alia, as epitope tags, in epitope mapping, and as molecular weight markers on SDS-PAGE gels or on molecular sieve gel filtration columns using methods known to those of skill in the art. Such polypeptides can be used to raise polyclonal and monoclonal antibodies, which are useful in assays for detecting KCNQ2-15bx, KCNQ2-15by and KCNQ2-15bz expression, or for purifying KCNQ2-15bx, KCNQ2-15by and KCNQ2-15bz. As a matter of example, a further specific use for KCNQ2-15b polypeptides is the use of such polypeptides the yeast two-hybrid system to capture KCNQ2-15bx, KCNQ2-15by or KCNQ2-15bz binding proteins, which are candidate modulators according to the present invention, as further detailed below.

3. KCNQ2-15b Polynucleotides of the Present Invention

The present invention is further directed to KCNQ2-15b polynucleotides encoding any of the KCNQ2-15b polypeptides described above, and to sequence complementary thereto.

In a preferred embodiment, said polynucleotide is selected from the group consisting of:
  a) a polynucleotide comprising nucleotides 1776 to 1929 of SEQ ID NO: 2.
  b) a polynucleotide comprising nucleotides 1632 to 1929 of SEQ ID NO: 2.
  c) a polynucleotide comprising SEQ ID NO: 1,
  d) a polynucleotide comprising SEQ ID NO: 3,
  e) a polynucleotide comprising SEQ ID NO: 5,
  f) a polynucleotide complementary to the polynucleotides of (a) to (e).

The invention encompasses a purified, isolated and/or recombinant nucleic acid comprising a nucleotide sequence selected from the group consisting of polynucleotides encoding a KCNQ2-15b polypeptides, including splice variants as well as allelic variants, and fragments of KCNQ2-15bx, KCNQ2-15by and KCNQ2-15bz polypeptides. Preferably, said fragments comprise nucleotides at position 1776 to 1929 of SEQ ID NO: 2. More preferably, said fragments comprise nucleotides at position 1632 to 1929 of SEQ ID NO: 2.

Preferred KCNQ2-15b polynucleotides of the invention include isolated and/or recombinant polynucleotides comprising a contiguous span of at least 8, 12, 15, 18, 20, 25, 30, 35, 40, 45, 50, 60, 70, 80, 90, 100, 200, 300, 400, 500, 600, 700, 800, 900, 1000, 1100, 1200, 1300, 1400, 1500, 1600, 1700 or 1800 nucleotides of SEQ ID NO: 1, SEQ ID NO: 2 or SEQ ID NO: 5.

In a further preferred embodiment, the purified KCNQ2-15b polynucleotide has at least 70, 80, 85, 90, 95, 96, 97, 98 or 99% nucleotide identity with a polynucleotide selected from the group consisting of SEQ ID NO: 1, SEQ ID NO: 2, SEQ ID NO: 5, sequences complementery thereto and fragments thereof.

Another object of the invention relates to purified polynucleotides that hybridize under moderately stringent conditions or under highly stringent conditions with a polynucleotide selected from the group consisting of sequences complementery thereto and fragments thereof.

Most preferred KCNQ2-15b polynucleotides of the invention include polynucleotides encoding a KCNQ2-15bx polypeptide, a KCNQ2-15by polypeptide or a KCNQ2-15bz polypeptide. A KCNQ2-15bx polynucleotide corresponds to a polynucleotide encoding a KCNQ2-15bx polypeptide. A KCNQ2-15by polynucleotide corresponds to a polynucleotides encoding a KCNQ2-15by polypeptide. A KCNQ2-15bz polynucleotide corresponds to a polynucleotide encoding a KCNQ2-15bz polypeptide.

In some embodiments, said KCNQ2-15b polynucleotide comprises or consists of the coding sequence (CDS) encoding the KCNQ2-15b polypeptide. In other embodiments, said KCNQ2-15b polynucleotide comprises or consists of the messenger RNA (mRNA) encoding the KCNQ2-15b polypeptide. In further embodiments, said KCNQ2-15b polynucleotide comprises or consists of the complementary DNA (cDNA) encoding the KCNQ2-15b polypeptide. Preferred KCNQ2-15b polynucleotides are polynucleotides comprising a CDS having the sequence of SEQ ID NO: 1, SEQ ID NO; 3 or SEQ ID NO: 5, mRNAs comprising these CDSs and cDNAs comprising these CDSs.

The present invention also encompasses fragments of KCNQ2-15bx, KCNQ2-15by or KCNQ2-15bz polynucleotides for use as primers and probes. Such primers are useful in order to detect the presence of at least a copy of a KCNQ2-15bx, KCNQ2-15by or KCNQ2-15bz polynucleotide, complement, or variant thereof in a test sample. The probes of the present invention are useful for a number of purposes. They can notably be used in Southern hybridization to genomic DNA. The probes can also be used to detect PCR amplification products. They may also be used to detect mismatches in the KCNQ2-15bx, KCNQ2-15by or KCNQ2-15bz mRNAs using other techniques. They may further be used for in situ hybridization.

Any of the polynucleotides, primers and probes of the present invention can be conveniently immobilized on a solid substrate, such as, e.g., a microarray. A substrate comprising a plurality of oligonucleotide primers or probes of the invention may be used either for detecting or amplifying targeted sequences in the KCNQ2-15bx, KCNQ2-15by or KCNQ2-15bz gene, may be used for detecting mutations in the coding or in the non-coding sequences of the KCNQ2-15bx, KCNQ2-15by or KCNQ2-15bz mRNAs, and may also be used to determine expression of KCNQ2-15bx, KCNQ2-15by or KCNQ2-15bz mRNAs in different contexts such as in different tissues, at different stages of a process (embryo development, disease treatment), and in patients versus healthy individuals.

Methods of cloning or constructing KCNQ2-15b polynucleotides are well known by those of skill in the art. For example, the methods described in the examples may be used to clone or construct the KCNQ2-15b polynucleotides of the present invention.

4. Vectors, Host Cells and Host Organisms of the Present Invention

The present invention also relates to vectors including the KCNQ2-15b polynucleotides of the present invention. More particularly, the present invention relates to expression vectors which include a KCNQ2-15b polynucleotide. Preferably, such expression vectors comprise a polynucleotide encoding a KCNQ2-15bx, a KCNQ2-15by, a KCNQ2-15bz polypeptide, a mutein thereof or a fragment thereof.

The term "vector" is used herein to designate either a circular or a linear DNA or RNA compound, which is either double-stranded or single-stranded, and which comprise at least one polynucleotide of the present invention to be transferred in a cell host or in a unicellular or multicellular host organism. An "expression vector" comprises appropriate signals in the vectors, said signals including various regulatory elements, such as enhancers/promoters from both viral and mammalian sources that drive expression of the inserted polynucleotide in host cells. Selectable markers for establishing permanent, stable cell clones expressing the products such as, e.g., a dominant drug selection, are generally included in the expression vectors of the invention, as they are elements that link expression of the drug selection markers to expression of the polypeptide.

Additionally, the expression vector may be a fusion vector driving the expression of a fusion polypeptide between a KCNQ2-15b polypeptide and a heterologous polypeptide. For example, the heterologous polypeptide may be a selectable marker such as, e.g., a luminescent protein, or a polypeptide allowing the purification of the fusion polypeptide.

The polynucleotides of the present invention may be used to, e.g., express the encoded polypeptide in a host cell for producing the encoded polypeptide. The polynucleotides of the present invention may further be used to express the encoded polypeptide in a host cell for screening assays. Screenings assays are of particular interest for identifying modulators and/or binding partners of KCNQ2-15b polypeptides as further detailed below. The polynucleotides of the present invention may also be used to express the encoded polypeptide in a host organism for producing a beneficial effect. In such procedures, the encoded protein may be transiently expressed in the host organism or stably expressed in the host organism. The encoded polypeptide may have any of the properties described herein. The encoded polypeptide may be a protein which the host organism lacks or, alternatively, the encoded protein may augment the existing levels of the protein in the host organism.

In one embodiment, the expression vector is a gene therapy vector. Viral vector systems that have application in gene therapy have been derived from, e.g., herpes virus, vaccinia virus, and several RNA viruses. In particular, herpes virus vectors may provide a unique strategy for persistence of inserted gene expression in cells of the central nervous system and ocular tissue.

Another object of the invention comprises a host cell that has been transformed, transfected or transduced with a polynucleotide encoding a KCNQ2-15b polypeptide. Also included are host cells that are transformed, transfected or transduced with a recombinant vector such as one of those described above. The cell hosts of the present invention can comprise any of the polynucleotides of the present invention.

Any host cell known by one of skill in the art may be used. Preferred host cells used as recipients for the polynucleotides and expression vectors of the invention include:
  a) Prokaryotic host cells: *Escherichia coli* strains (I.E.DH5-α strain), *Bacillus subtilis, Salmonella typhimurium*, and strains from species like *Pseudomonas, Streptomyces* and *Staphylococcus*.
  b) Eukaryotic host cells: CHO (ATCC No. CCL-61), HeLa cells (ATCC No. CCL2; No. CCL2.1; No. CCL2.2), Cv 1 cells (ATCC No. CCL70), COS cells (ATCC No. CRL1650; No. CRL1651), Sf-9 cells (ATCC No. CRL1711), C127 cells (ATCC No. CRL-1804), 3T3 (ATCC No. CRL-6361), human kidney 293. (ATCC No. 45504; No. CRL-1573), BHK (ECACC No. 84100501; No. 84111301), *Saccharomyces cerevisiae* strains such as AH109 and Y184, and *Aspergillus niger* strains.

Another object of the invention comprises methods of making the above vectors and host cells by recombinant techniques. Any well-known technique for constructing an expression vector and for delivering it to a cell may be used for construction and delivering the vectors of the present invention. Such techniques include but are not limited to the techniques detailed in the examples.

Another object of the present invention is a transgenic animal which includes within a plurality of its cells a cloned recombinant KCNQ2-15b polynucleotide. The terms "transgenic animals" or "host animals" are used herein to designate animals that have their genome genetically and artificially manipulated so as to include one of the nucleic acids according to the invention. The cells affected may be somatic, germ cells, or both. Preferred animals are non-human mammals and include those belonging to a genus selected from *Mus* (e.g. mice), *Rattus* (e.g. rats) and *Oryctogalus* (e.g. rabbits) which have their genome artificially and genetically altered by the insertion of a nucleic acid according to the invention. In one embodiment, the invention encompasses non-human host mammals and animals comprising a recombinant vector of the invention or a KCNQ2-15b polynucleotide disrupted by homologous recombination with a knock out vector.

In a preferred embodiment, these transgenic animals may be good experimental models in order to study diverse pathologies related to KCNQ2-15b function. In particular, a transgenic animal wherein (i) an antisense mRNA binding to naturally occurring KCNQ2-15b mRNAs is transcribed; or (ii) an mRNA expressing a KCNQ2-15b polypeptide; may be a good animal model for bipolar disorders and/or other mood-disorders.

5. Methods of Making the Polypeptides of the Present Invention

The present invention also relates to methods of making a KCNQ2-15b polypeptide.

In one embodiment, the KCNQ2-15b polypeptides of the present invention are isolated from natural sources, including tissues and cells, whether directly isolated or cultured cells, of humans or non-human animals. Soluble forms of KCNQ2-15b may be isolated from body fluids. Methods for extracting and purifying natural membrane spanning proteins are known in the art, and include the use of detergents or chaotropic agents to disrupt particles followed by, e.g., differential extraction and separation of the polypeptides by ion exchange chromatography, affinity chromatography, sedimentation according to density, and gel electrophoresis. The method described in Example 4 may for example be used. Polypeptides of the invention also can be purified from natural sources using antibodies directed against the polypeptides of the invention, such as those described herein, in methods which are well known in the art of protein purification.

In a preferred embodiment, the KCNQ2-15b polypeptides of the invention are recombinantly produced using routine expression methods known in the art. The polynucleotide encoding the desired polypeptide is operably linked to a promoter into an expression vector suitable for any convenient host. Both eukaryotic and prokaryotic host systems may be used in forming recombinant polypeptides. The polypeptide is then isolated from lysed cells or, if a soluble form is produced, from the culture medium and purified to the extent needed for its intended use.

Consequently, a further embodiment of the present invention is a method of making a polypeptide of the present invention, said method comprising the steps of:
a) obtaining a polynucleotide encoding a KCNQ2-15b polypeptide;
b) inserting said polynucleotide in an expression vector such that the polynucleotide is operably linked to a promoter; and
c) introducing said expression vector into a host cell whereby said host cell produces said polypeptide.

In a preferred embodiment, the method further comprises the step of isolating the polypeptide. The skilled person will appreciate that any step of this method may be carried out separately. The product of each step may be transferred to another step in order to carry out the subsequent step.

In further embodiments, said polynucleotide consists of a CDS. In another aspect of this embodiment, said polynucleotide is a polynucleotide consisting of SEQ ID NO: 1, SEQ ID NO: 3, SEQ ID NO: 5 or a fragment thereof.

A further aspect of the invention relates to a method of making a polypeptide, said method comprising the steps of culturing a host cell comprising an expression vector comprising a KCNQ2-15b polynucleotide under conditions suitable for the production of a KCNQ2-15b polypeptide within said host cell. In a preferred embodiment, the method further comprises the step of purifying said polypeptide from the culture.

In another embodiment, it is often advantageous to add to the recombinant polynucleotide encoding a KCNQ2-15b polypeptide additional nucleotide sequence which codes for secretory or leader sequences, pro-sequences, sequences which aid in purification, such as multiple histidine residues or GST tags, or an additional sequence for stability during recombinant production. Soluble portions of the KCNQ 2-15b polypeptide may be, e.g., linked to an Ig-Fc part in order to generate stable soluble variants.

A polypeptide of this invention can be recovered and purified from recombinant cell cultures by well-known methods including but not limited to differential extraction, ammonium sulfate or ethanol precipitation, acid extraction, anion or cation exchange chromatography, high performance liquid chromatography, phosphocellulose chromatography, hydrophobic interaction chromatography, affinity chromatography, hydroxylapatite chromatography, immunochromatography and lectin chromatography.

The expressed KCNQ2-15b polypeptide may be purified using any standard immunochromatography techniques. In such procedures, a solution containing the polypeptide of interest, such as the culture medium or a cell extract, is applied to a column having antibodies against the polypeptide attached to the chromatography matrix. The recombinant protein is allowed to bind the immunochromatography column. Thereafter, the column is washed to remove non-specifically bound proteins. The specifically bound secreted protein is then released from the column and recovered using standard techniques.

6. Antibodies of the Present Invention

The present invention further relates to antibodies that specifically bind to the polypeptides of the present invention. More specifically, said antibodies bind to the epitopes of the polypeptides of the present invention. The antibodies of the present invention include IgG (including IgG1, IgG2, IgG3, and IgG4), IgA (including IgA1 and IgA2), IgD, IgE, or IgM, and IgY. The term "antibody" (Ab) refers to a polypeptide or group of polypeptides which are comprised of at least one binding domain, where a binding domain is formed from the folding of variable domains of an antibody compound to form three-dimensional binding spaces with an internal surface shape and charge distribution complementary to the features of an antigenic determinant of an antigen, which allows an immunological reaction with the antigen. As used herein, the term "antibody" is meant to include whole antibodies, including single-chain whole antibodies, and antigen binding fragments thereof. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are from human, mouse, rabbit, goat, guinea pig, camel, horse or chicken. The present invention further includes chimeric, humanized, and human monoclonal and polyclonal antibodies, which specifically bind the polypeptides of the present invention.

Preferred antibodies of the present invention recognize an epitope within amino acids 589 to 643 of SEQ ID NO: 2, wherein said one or more amino-acids are required for binding of the antibody to a KCNQ2-15b polypeptide. Other preferred antibodies of the present invention recognize one or more of the amino acids at positions 545 to 643 of SEQ ID NO: 2, wherein said one or more amino-acids are required for binding of the antibody to a KCNQ2-15b polypeptide. Most preferably, the antibodies of the present invention bind to a KCNQ2 polypeptide comprising exon 15b but not to a KCNQ2 polypeptide lacking exon 15b.

A preferred embodiment of the invention is a method of specifically binding an antibody of the present invention to a KCNQ2-15b polypeptide. This method comprises the step of contacting the antibody of the present invention with a KCNQ2-15b polypeptide under conditions in which said antibody can specifically bind to said polypeptide. Such conditions are well known to those skilled in the art. This method may be used to, e.g., detect, purify, or activate or inhibit the activity of KCNQ2-15b polypeptides.

The invention further relates to antibodies that act as modulators of the polypeptides of the present invention. Preferred antibodies are modulators that enhance the binding activity or the biological activity of the KCNQ2-15b polypeptide to which they bind. These antibodies may act as modulators for either all or less than all of the biological properties of the KCNQ2-15b polypeptide.

7. Uses of the Polypeptides of the Present Invention

The present invention is also directed to the use of a KCNQ2 polypeptide as a target for screening candidate modulators. As used herein, the term "KCNQ2 polypeptide" refers to any polypeptide encoded by the KCNQ2 gene. Thus the term "KCNQ2 polypeptide" encompasses all alternative splice variants encoded by the KCNQ2 gene, such as, e.g., KCNQ2-15b polypeptides and all previously described isoforms (see, e.g., SwissProt Accession No. 043526). As further used herein, the term "KCNQ2-fl" refers to a polypeptide of SEQ ID NO: 7.

As used herein, the term "modulator" refers to a compound that increases or decreases any of the properties of a KCNQ2 polypeptide. As used herein, a "KCNQ2 modulator" refers to a compound that increases or decreases the activity of a KCNQ2 polypeptide and/or to a compound that increases or decreases the transcription level of the KCNQ2 mRNA encoding said polypeptide. The term "modulator" encompasses both agonists and antagonists.

As used herein, a "KCNQ2 antagonist" refers to a compound that decreases the activity of a KCNQ2 polypeptide and/or to a compound that decreases the expression level of the KCNQ2 mRNA encoding said polypeptide. The terms "antagonist" and "inhibitor" are considered to be synonymous and can be used interchangeably throughout the disclosure.

As used herein, a "KCNQ2 agonist" refers to a compound that increases the activity of a KCNQ2 polypeptide and/or to a compound that increases the expression level of the KCNQ2 mRNA encoding said polypeptide. The terms "agonist" and "activator" are considered to be synonymous and can be used interchangeably throughout the disclosure.

Methods that can be used for testing modulators for their ability to increase or decrease the activity of a KCNQ2 polypeptide or to increase or decrease the expression of a KCNQ2 mRNA are well known in the art and further detailed below. Preferred modulators of the present invention are modulators of KCNQ2-15bx, KCNQ2-15by, KCNQ2-15bz or KCNQ2-fl. The assays described herein and known in the art for measuring KCNQ2 activity can be performed either in vitro or in vivo.

Candidate compounds according to the present invention include naturally occurring and synthetic compounds. Such compounds include, e.g., natural ligands, small molecules, antisense mRNAs, antibodies, aptamers and short interfering RNAs. As used herein, the term "natural ligand" refers to any signaling molecule that binds to a phosphatase comprising PP2A/Bγ in vivo and includes molecules such as, e.g., lipids, nucleotides, polynucleotides, amino acids, peptides, polypeptides, proteins, carbohydrates and inorganic molecules. As used herein, the term "small molecule" refers to an organic compound. As used herein, the term "antibody" refers to a protein produced by cells of the immune system or to a fragment thereof that binds to an antigen. As used herein, the term "antisense mRNA" refers an RNA molecule complementary to the strand normally processed into mRNA and translated, or complementary to a region thereof. As used herein, the term "aptamer" refers to an artificial nucleic acid ligand (see, e.g., Ellington and Szostak (1990) Nature 346: 818-822). As used herein, the term "short interfering RNA" refers to a double-stranded RNA inducing sequence-specific posttranscriptional gene silencing (see, e.g., Elbashir et al. (2001) Genes Dev. 15:188-200).

Such candidate compounds can be obtained using any of the numerous approaches in combinatorial library methods known in the art, including, e.g., biological libraries, spatially addressable parallel solid phase or solution phase libraries, and synthetic library methods using affinity chromatography selection. The biological library approach is generally used with peptide libraries, while the other four approaches are applicable to peptide, non-peptide oligomers, aptamers or small molecule libraries of compounds.

One example of a method that may be used for screening candidate compounds for a modulator is a method comprising the steps of:

a) contacting a KCNQ2 polypeptide with the candidate compound; and b) testing the activity of said KCNQ2 polypeptide in the presence of said candidate compound, wherein a difference in the activity of said KCNQ2 polypeptide in the presence of said compound in comparison to the activity in the absence of said compound indicates that the compound is a modulator of said KCNQ2 polypeptide.

Alternatively, the assay may be a cell-based assay comprising the steps of:

a) contacting a cell expressing a KCNQ2 polypeptide with the candidate compound; and b) testing the activity of said KCNQ2 polypeptide in the presence of said candidate compound, wherein a difference in the activity of said KCNQ2 polypeptide in the presence of said compound in comparison to the activity in the absence of said compound indicates that the compound is a modulator of said KCNQ2 polypeptide.

The modulator may modulate any activity of said KCNQ2 polypeptide. The modulator may for example modulate KCNQ2 mRNA expression within a cell, or modulate the M-current generated by a potassium channel comprising the KCNQ2 polypeptide. Further activities that may be measured include KCNQ2 binding to PP2A/Bγ, and to KCNQ2 binding to other potassium channel subunits. The phosphorylation state of a KCNQ2 polypeptide is a further activity of KCNQ2 that may be assessed in order to screen compounds. Most preferably, the activity of the KCNQ2 polypeptide is assessed by measuring the M-current. Methods for testing the above mentioned activities are well known to those of skill in the art, and may for example be performed as further detailed below.

Preferred modulators of the invention are modulators that increase or decrease:

KCNQ2 mRNA expression within a cell;

the M-current generated by a potassium channel comprising a KCNQ2 polypeptide;

binding of the KCNQ2 polypeptide to PP2A/Bγ; and/or binding of the KCNQ2 polypeptide to other potassium channel subunits.

In a preferred embodiment, the activity of a KCNQ2 polypeptide is assessed by measuring the M-current generated by a potassium channel comprising the KCNQ2 polypeptide. Assays for measuring the M-current generated by a potassium channel are known by those of skill the art. An electrophysiologic assay for measuring the activity of the M-current generated by a potassium channel is for example described by Pan et al. and by Schwake et al. (Pan et al. (2001), J. Physiol., 531:347-358; Schwake et al. (2000), J. Biol. Chem., 275:13343-13348). High-throughput fluorescence assays using membrane potential sensitive dyes has also been described to screen compounds on potassium channels. For example, EVOTEC has developed assays for testing the activity of ion channels (see, e.g., the world wide website evotecoai.com). In such assays, the activity both of ho momeric KCNQ2 channels and of heteromeric channels may be tested. Homomeric channels that may be tested include, e.g., homomeric KCNQ2-fl and homomeric KCNQ2-15b channels. Heteromeric channels that may be tested include, e.g., heteromeric KCNQ2-15b/KCNQ2-fl, heteromeric KCNQ2-fl/KCNQ3 and heteromeric KCNQ2-15b/KCNQ3 channels.

In another preferred embodiment, the activity of a KCNQ2 polypeptide is assessed by measuring the binding of the KCNQ2 polypeptide to PP2A/Bγ. The binding of a KCNQ2 polypeptide to PP2A/Bγ can for example be measured by the yeast mating test as described in example 3 or by the solid phase overlay assay as described in example 6.

In another preferred embodiment, the activity of a KCNQ2 polypeptide is assessed by measuring the binding of the KCNQ2 polypeptide to other potassium channels subunits. This assay may also be performed using the yeast mating test or the solid phase overlay assay described in examples 3 and 6.

In a further preferred embodiment, the activity of a KCNQ2 polypeptide is assessed by measuring the KCNQ2 mRNA levels within a cell. In this embodiment, the activity can for example be measured using Northern blots, RT-PCR, quantitative RT-PCR with primers and probes specific for KCNQ2 mRNAs. The term "KCNQ2 mRNA" as used herein encompasses all alternative splice variants translated from the KCNQ2 gene such as, e.g., SEQ ID Nos 1, 3, 5 and EMBL Accession Nos. NM_172107, NM_172106, NM_004518, NM_172108 and NM_172109. The primers and probes may detect one specific KCNQ2 splice variant or detect all alternative splice variants translated from the KCNQ2 gene. Alternatively, the expression of the KCNQ2 mRNA is measured at the polypeptide level, by using labeled antibodies that specifically bind to the KCNQ2 polypeptide in immunoassays such as ELISA assays, or RIA assays, Western blots or immunohistochemical assays. The KCNQ2 antibody may detect one specific KCNQ2 splice variant or detect all alternative splice variants translated from the KCNQ2 gene.

In another embodiment, the activity of a KCNQ2 polypeptide is measured by determining the phosphorylation state of the KCNQ2 polypeptide as described in example 7. In the frame of the present invention, it has been found that (I) KCNQ2-15b polypeptides are dephosphorylated by a PP2A phosphatase comprising a PP2A/Bγ subunit, the gene encoding the PP2A/Bγ subunit being associated with bipolar disorder; and (ii) phosphorylated by GSK3β, a kinase that is inhibited by mood stabilizing agents. Thus the phosphorylation state of a KCNQ2 polypeptide is believed to be correlated with the biological activity of the KCNQ2 polypeptide. The phosphorylation state of a KCNQ2 polypeptide may for example be measured in an assay as described in example 7.

One preferred embodiment is directed to the use of a KCNQ2-15b polypeptide as a target for screening candidate modulators. Another preferred embodiment is directed to the use of a KCNQ2-fl polypeptide as a target for screening candidate modulators.

Modulators of KCNQ2 polypeptides, which may be found, e.g., by any of the above screenings, are candidate drugs for the treatment of a mental disorder. Thus a preferred embodiment of the present invention is the use of a KCNQ2 polypeptide as a target for screening candidate compounds for candidate drugs for the treatment of a mental disorder.

As used herein, the term "Mental disorder" includes bipolar disorder, schizophrenia, depression as well as other mood disorders and psychotic disorders. Preferably, said mental disorder is bipolar disorder, schizophrenia or depression. Most preferably, said mental disorder is bipolar disorder.

A further aspect of the present invention is the use of a modulator of a KCNQ2 polypeptide for screening for drugs for the treatment of a mental disorder. One example of a method that can be used for screening for drugs for the treatment of a mental disorder and/or for assessing the efficiency of an modulator of a KCNQ2 polypeptide for the treatment of a mental disorder is a method comprising the step of administering said modulator to an animal model for said mental disorder, wherein a determination that said modulator ameliorates a representative characteristic of said mental disorder in said animal model indicates that said modulator is a drug for the treatment of said mental disorder.

Animal models for mental disorders and assays for determining whether a compound ameliorates a representative characteristic of said mental disorder in said animal model are described and used. For example, animal models that may be used in the above method include but are not limited to the conditioned avoidance behaviour model in rats, which is a standard behavioural test predictive of antipsychotic activity, the behavioral activity assessment of mice and rats in the Omnitech Digiscan animal activity monitors, the purpose of which is to evaluate compounds for antipsychotic-like CNS effects and a variety of other behavioral effects generally associated with CNS activity, the blockade of amphetamine-stimulated locomotion in rat, the protocol for the prepulse inhibition of acoustic startle model in rats, the inhibition of apomorphine-induced climbing behaviour and the inhibition of DOI-induced head twitches and scratches. A preferred animal model is the STOP −/− mice with synaptic defects and severe behavioral disorders described by Andrieux et al. (2002, Genes Dev., 16:2350-2364).

A further aspect of the present invention is directed to the use of a modulator of a KCNQ2 polypeptide for preparing a medicament for the treatment of a mental disorder. Such a medicament comprises said modulator of a KCNQ2 polypeptide in combination with any physiologically acceptable carrier. Physiologically acceptable carriers can be prepared by any method known by those skilled in the art. Physiologically acceptable carriers include but are not limited to those described in Remington's Pharmaceutical Sciences (Mack Publishing Company, Easton, USA 1985). Pharmaceutical compositions comprising a modulator of a KCNQ2 polypeptide and a physiologically acceptable carrier can be for, e.g., intravenous, topical, rectal, local, inhalant, subcutaneous, intradermal, intramuscular, oral, intracerebral and intrathecal use. The compositions can be in liquid (e.g., solutions, suspensions), solid (e.g., pills, tablets, suppositories) or semi-solid (e.g., creams, gels) form. Dosages to be administered depend on individual needs, on the desired effect and the chosen route of administration.

Such a medicament comprising a KCNQ2 modulator or a gene therapy vector of the invention may be used in combination with any known drug for the treatment of a mental disorder. The modulator may for example be administered in combination with a mood-stabilizing drug used for treating bipolar disorder such as, e.g., lithium, carbamazepine or divalproex. The modulator may also be administered in combination with an antidepressant such as, e.g., a tricyclic antidepressant, a selective serotonin reuptake inhibitor, a monoamine oxidase inhibitor or a psychostimulant. When treating schizophrenia and other psychotic disorders, the modulator may for example be administered in combination with an antipsychotic drugs such as, e.g., chlorpromazine, clozapine, risperidone or olanzapine.

In all the above embodiments, preferred modulators are modulators of KCNQ2-15b polypeptides or of KCNQ2-fl. Preferred modulators of KCNQ2-15b polypeptides are modulators that specifically modulate a polypeptide comprising exon 15b shown at position 545 to 643 of SEQ ID NO: 2. Preferred KCNQ2-fl modulators are modulators that specifically modulate a polypeptide comprising exons 16 and 17 shown at position 588 to 872 of SEQ ID NO: 7.

The present invention further relates to methods for screening for natural binding partners of a KCNQ2 polypeptide. Such methods include the yeast two-hybrid screening that is described in example 1. Identifying natural biding partners of a KCNQ2 polypeptide may be preformed by replacing the CDS encoding PP2A/Bγ with a polynucleotides encoding a KCNQ2 polypeptide. Using a KCNQ2 polypeptide as a target has a great utility for the identification of proteins involved in bipolar disorder and for providing new intervention points in the treatment of bipolar disorder and other mood disorders.

8. Biallelic Markers of the Present Invention

The present invention is directed to the use of at least one KCNQ2-related biallelic marker for diagnosing whether an individual suffers from or is at risk of suffering from a mental disorder. As used herein, the term "KCNQ2-related biallelic marker" refers to a biallelic marker located in an exon of the KCNQ2 gene, in an intron of the KCNQ2 gene, or in the regulatory regions of the KCNQ2 gene. KCNQ2-related biallelic markers encompass the biallelic markers shown in table 3B in Example 12. In one embodiment, a single biallelic marker is used for diagnosing whether an individual suffers from or is at risk of suffering from a mental disorder by determining the genotype of an individual. In another embodiment, a combination of several biallelic markers may be used for diagnosing whether an individual suffers from or is at risk of suffering from a mental disorder by determining the haplotype of an individual. For example, a two-markers haplotype, a three-markers haplotype or a four-markers haplotype may be determined.

As used herein, the term "biallelic marker" refers to a polymorphism having two alleles at a fairly high frequency in the population, preferably a single nucleotide polymorphism. Typically the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). In the present specification, the term "biallelic marker" is used to refer both to the polymorphism and to the locus carrying the polymorphism.

As used herein, the term "genotype" refers to the identity of the alleles present in an individual or a sample. The term "genotype" preferably refers to the description of both copies of a single biallelic marker that are present in the genome of an individual. The individual is homozygous if the two alleles of the biallelic marker present in the genome are identical. The individual is heterozygous if the two alleles of the biallelic marker present in the genome are different.

The term "genotyping" a sample or an individual for a biallelic marker involves determining the specific alleles or the specific nucleotides carried by an individual at a biallelic marker.

As used herein, the term "haplotype" refers to a set of alleles of closely linked biallelic markers present on one chromosome and which tend to be inherited together.

Methods for determining the alleles, genotypes or haplotypes carried by an individual are well known by those of skill in the art and further detailed below.

In all embodiments, preferred "mental disorders" include bipolar disorder, schizophrenia and depression. Most preferred mental disorder is bipolar disorder.

In the context of the present invention, the individual is generally understood to be human.

As shown in Example 15, biallelic markers 30-2/62 and 30-7/30 are bipolar disorder-associated markers. Preferred embodiments of the present invention are thus directed to the use of biallelic markers 30-2/62 and 30-7/30. The alternative alleles of biallelic markers 30-2/62 and 30-7/30 are indicated in table 3B in example 12. Positions of biallelic markers 30-2/62 and 30-7/30 on SEQ ID NO: 43 and SEQ ID NO: 45 respectively are also indicated in table 3B. Other preferred embodiments are directed to the use of biallelic markers complementary to 30-2/62 and 30-7/30, i.e., the corresponding alternative alleles that are located on the complementary strand of DNA.

Accordingly, a preferred embodiment of the present invention is directed to the use of biallelic markers 30-2/62 and 30-7/30 and the complements thereof for diagnosing whether an individual suffers from or is at risk of suffering from a mental disorder. Preferably, the individual is a Caucasian individual. Most preferably, the individual is a Caucasian individual of British Isles origin.

The risk genotypes for biallelic markers 30-2/62 and 30-7/30 are indicated in table 6B. "Risk genotype" means that the probability of having bipolar disorder is higher for an individual carrying the risk genotype than for an individual carrying another genotype. The risk genotype for biallelic marker 30-2/62 is "AG". Thus a preferred embodiment of the present invention is the use of biallelic markers 30-2/62 or the complement thereof for diagnosing whether an individual suffers from or is at risk of suffering from a mental disorder, wherein the presence of a genotype "AG" at biallelic marker 30-2/62 is indicative of said individual suffering from or being at risk of suffering from said mental disorder. The risk genotype for biallelic marker 30-7/30 is "CC". Thus a preferred embodiment of the present invention is the use of biallelic markers 30-2/62 or the complement thereof for diagnosing whether an individual suffers from or is at risk of suffering from a mental disorder, wherein the presence of a genotype "CC" at biallelic marker 30-7/30 is indicative of said individual suffering from or being at risk of suffering from said mental disorder.

The present invention is further directed to the use of at least one KCNQ2-related biallelic marker for determining whether there is a significant association between said marker and a mental disorder. Such determination can for example be performed using methods described in examples 10 to 15 below but using populations that are different from the UCL and the Labimo populations, such as populations having different ethnic origins. The KCNQ2-related biallelic marker may be selected from the group consisting of 30-2162 and 30-7/30 and the complements thereof. Alternatively, The KCNQ2-related biallelic marker may be selected from the group consisting of 30-4/58, 30-17/37, 30-84/37 and 30-15/54 and the complements thereof. The KCNQ2-related biallelic marker may also be a marker that is not specifically disclosed by the present specification. Preferably, the mental disorder is selected from the group consisting of bipolar disorder, schizophrenia and depression. Most preferably, the mental disorder is bipolar disorder.

The present invention is further directed to a method of genotyping comprising the step of determining the identity of a nucleotide at a KCNQ2-related biallelic marker or the complement thereof in a biological sample. Preferably, said biological sample is derived from a single subject. It is preferred that the identity of the nucleotides at said biallelic marker is determined for both copies of said biallelic marker present in said individual's genome. In a preferred embodiment, the identity of the nucleotide at said biallelic marker is determined by a microsequencing assay. Preferably, a portion of a sequence comprising the biallelic marker is amplified prior to the determination of the identity of the nucleotide. The amplification may preferably be performed by PCR. Such a method of genotyping may for example be performed using any of the protocols described in examples 10 to 14 of the present specification. Further methods of genotyping are well known by those of skill in the art and any other known protocol may be used.

Methods well-known to those skilled in the art that may be used for genotyping in order to detect biallelic polymorphisms include methods such as, conventional dot blot analyzes, single strand conformational polymorphism analysis (SSCP) (Orita et al. (1989) Proc Natl Acad Sci USA 86:2766-2770), denaturing gradient gel electrophoresis (DGGE) (Borresen et al. (1988) Mutat Res. 202:77-83.), heteroduplex analysis (Lessa et al. (1993) Mol Ecol. 2:119-129), mismatch cleavage detection (Grompe et al. (1989) Proc Natl Acad Sci USA. 86:5888-5892). Another method for determining the identity of the nucleotide present at a particular polymorphic site employs a specialized exonuclease-resistant nucleotide derivative as described in U.S. Pat. No. 4,656,127. Oligonucleotide microarrays or solid-phase capturable dideoxynucleotides and mass spectrometry may also be used (Wen et al. (2003) World J Gastroenterol. 9:1342-1346; Kim et al. (2003) Anal Biochem. 316:251-258). Preferred methods involve directly determining the identity of the nucleotide present at a biallelic marker site by sequencing assay, microsequencing assay, enzyme-based mismatch detection assay, or hybridization assay.

As used herein, the term "biological sample" refers to a sample comprising nucleic acids. Any source of nucleic acids, in purified or non-purified form, can be utilized as the starting nucleic acid, provided it contains or is suspected of containing the specific nucleic acid sequence desired. DNA or RNA may be extracted from cells, tissues, body fluids and the like.

Methods of genotyping find use in, e.g., in genotyping case-control populations in association studies as well as in genotyping individuals in the context of detection of alleles of biallelic markers which are known to be associated with a given trait. In the context of the present invention, a preferred trait is a mental disorder selected from the group of bipolar disorder, schizophrenia and depression, and most preferably bipolar disorder.

Accordingly, a preferred embodiment is directed to a method of diagnosing a mental disorder in an individual comprising the step of genotyping at least one KCNQ2-related biallelic marker using a method of genotyping comprising the step of determining the identity of a nucleotide at a KCNQ2-related biallelic marker or the complement thereof in a biological sample derived from said individual. Such a diagnosing method may further comprise the step of correlating the result of the genotyping step with a risk of suffering from said mental disorder. Typically, the presence of the risk allele, risk genotype or risk haplotype of the genotyped KCNQ2-related biallelic marker(s) is correlated with a risk of suffering from the mental disorder. Preferably, said KCNQ2-related biallelic marker is selected from the group consisting of 30-2/62 and 30-7/30 and the complements thereof. In one embodiment, the presence of a genotype "AG" at biallelic marker 30-2/62218 is indicative of a risk of suffering from said mental disorder. In another embodiment, the presence of a genotype "CC" at biallelic marker 30-7/130 is indicative of a risk of suffering from said mental disorder. Preferably, the mental disorder is selected from the group consisting of bipolar disorder, schizophrenia and depression. Most preferably, the mental disorder is bipolar disorder.

The present invention is further directed to the use of at least one KCNQ2-2-related biallelic marker for determining the haplotype of an individual. When determining the haplotype of an individual, each single chromosome should be studied independently. Methods of determining the haplotype of an individual are well known in the art and include, e.g., asymmetric PCR amplification (Newton et al. (1989) Nucleic Acids Res. 17:2503-2516; Wu et al. (1989) Proc. Natl. Acad. Sci. USA. 86:2757-2760), isolation of single chromosome by limit dilution followed by PCR amplification (Ruano et al. (1990) Proc. Natl. Acad. Sci. USA. 87:6296-6300) and, for sufficiently close biallelic markers, double PCR amplification of specific alleles (Sarkar and Sommer, (1991) Biotechniques. 10:436-440).

Thus the present invention is further directed to the use of at least one KCNQ2-related biallelic marker for determining the haplotype of an individual. For example, a method for determining a haplotype for a set of biallelic markers in an individual may comprise the steps of: a) genotyping said individual for at least one KCNQ2 related biallelic marker, b) genotyping said individual for a second biallelic marker by determining the identity of the nucleotides at said second biallelic marker. Preferably, both markers are KCNQ2-related biallelic markers. Methods of determining a haplotype for a combination of more than two biallelic markers comprising at least one KCNQ2-related biallelic marker in an individual are also encompassed by the present invention. In such methods, step (b) is repeated for each of the additional markers of the combination. Such a combination may comprise, e.g., 3, 4 or 5 biallelic markers. These biallelic markers may all be KCNQ2-related biallelic markers.

When estimating haplotype frequencies in a population, one may use methods without assigning haplotypes to each individual. Such methods use a statistical method of haplotype determination. Thus another aspect of the present invention encompasses methods of estimating the frequency of a haplotype for a set of biallelic markers in a population, comprising the steps of: a) genotyping each individual in said population for at least one KCNQ2-related biallelic marker, b) genotyping each individual in said population for a second biallelic marker by determining the identity of the nucleotides at said second biallelic marker; and c) applying a haplotype determination method to the identities of the nucleotides determined in steps a) and b) to obtain an estimate of said frequency. Such a method may also be performed for a combination of more than 2 biallelic markers. Step (c) may be performed using any method known in the art to determine or to estimate the frequency of a haplotype in a population. Preferably, a method based on an expectation-maximization (EM) algorithm (Dempster et al. (1977) JRSSB, 39:1-38; Excoffier and Slatkin, (1995) Mol Biol Evol. 12:921-7) leading to maximum-likelihood estimates of haplotype frequencies under the assumption of Hardy-Weinberg proportions (random mating) is used for performing step (c).

EXAMPLES

Example 1

Yeast Two-Hybrid Screening

1. Construction of pGBKT7-PPP2R2C

The full-length coding region of the PPP2R2C gene, which encodes the PP2A/Bγ subunit, was first amplified from a Human fœtal brain cDNA library (Marathon-Ready cDNA, Clontech) with the two gene-specific primers of SEQ ID NO: 8 and of SEQ ID NO: 9. This first PCR product was then amplified with a new combination of primers of SEQ ID NO: 10 and of SEQ ID NO: 11. The amplified fragment encompassed nucleotides 52-1540 of the full-length cDNA, genbank accession number AF086924 extended, respectively, with EcoRI and BamHI cloning sites. The resulting 1503-bp fragment was digested with EcoRI and BamHI, purified and inserted into EcoRI and BamHI cloning sites of the pGBKT7 vector (Clontech).

2. The Yeast Two-Hybrid Screening

A yeast two-hybrid screening was performed to find polypeptides interacting with the PP2A/Bγ subunit. The *Saccharomyces cerevisiae* strain AH109 (MATa, trp1-901, leu2-3, 112, ura3-52, his3-200, gal4Δ, gal80Δ, LYS2::GAL1$_{UAS}$-GAL1$_{TATA}$-HIS3, GAL2$_{UAS}$-GAL2$_{TATA}$-ADE2, URA3::MEL1$_{UAS}$-MEL1$_{TATA}$-lacZ) was transformed with the pGBKT7-PPP2R2C construction. A lithium acetate transformation procedure was done according to the manufacturer's instructions (Matchmaker Two-Hybrid system, Clontech). The MATa transformed cells expressing the bait were then mixed with a pretransformed Matchmaker Human brain cDNA library in the Y187 strain (MAT α, ura3-52, his3-200, ade2-101, trp1-901, leu2-3, 112, gal4Δ, met⁻; gal80Δ, URA3::GAL1$_{UAS}$-GAL1$_{TATA}$-lacZ). Three independent mating were performed with respectively 5.10⁶, 5.10⁶ and 2.10⁵ clones of the Human brain cDNA library. The resulting diploid cells able to grow on SD/-Leu/-Trp medium containing plates were further selected onto the medium-stringency SD/-Leu/-Trp/-His selective medium for the identification of bait-prey interactions. Positive colonies were then picked up and plated onto the high-stringency SD/-Leu/-Trp/-His/-Ade selective medium. Only cDNA of colonies able to grow at the same time on SDI-Leu/-Trp and SDI-Leu/-Trp/-His/-Ade media was retained for sequencing and further studies.

3. Results of the He Yeast Two-Hybrid Screening 494 clones were obtained, sequenced and analyzed. Among these clones, the 2E11 and 1D3 clones comprised partial cDNAs encoding a novel splice variant of the KCNQ2 potassium channel. 2E11 comprised a cDNA encoding amino acids 433 to 643 of SEQ ID NO: 2, and 1D3 comprised a cDNA encoding amino acids 454 to 643 of SEQ ID NO: 2. The full-length splice variants were cloned and sequenced as described in Example 2.

Example 2

Cloning of the Full-Length KCNQ2 Splice Variants

1. Cloning and Sequencing

Poly(A)+ mRNA from Human brain, thalamus (Clontech) were reversed transcribed (RT) using the murine Moloney leukemia virus reverse transcriptase (RT-PCR Advantage kit, Clontech) with a primer of SEQ ID NO: 12 hybridizing specifically with the novel splice variant cloned in 2E11. After a phenol-chloroform extraction and precipitation steps, the products obtained by the previous RT-PCR were directly PCR-amplified using the following gene-specific primers of SEQ ID NO: 13 and of SEQ ID NO: 14. The amplified fragment encompassed nucleotides 127-148 of the KCNQ2 full-length cDNA, genbank accession number AF033348. These primers were respectively extended with EcoRI and BglII cloning sites. The PCR products were digested with EcoRI and BglII restriction enzymes (New England Biolabs), purified and then ligated into the EcoRI and BglII cloning sites of the pCMV-Myc vector (Clontech). The two pCMV-Myc-3H9 and pCMV-Myc-3H2 clones were fully sequenced. The sequence of the insert in pCMV-Myc-3H2 comprises SEQ ID NO: 1, and the sequence of the insert in pCMV-Myc-3H9 comprises SEQ ID NO: 3.

Similarly, a cDNA was cloned from a poly(A)+ mRNA library from human foetal brain. One clone was obtained and fully sequenced. Its insert comprised SEQ ID NO: 5.

2. Description of the Novel Splice Variants

SEQ ID NO: 1 encodes the polypeptide of SEQ ID NO: 2 (KCNQ2-15bx). SEQ ID NO: 3 encodes the polypeptide of SEQ ID NO: 4 (KCNQ2-15by). SEQ ID NO: 5 encodes the polypeptide of SEQ ID NO: 6 (KCNQ2-15bz). SEQ ID NO: 7 corresponds to the full-length KCNQ2 polypeptide (KCNQ2-fl).

As shown on the alignment between SEQ ID NO: 7, SEQ ID NO: 2, SEQ ID NO: 4 and SEQ ID NO: 6 (FIG. 1), the three splice variants display a novel carboxyl-terminal extremity compared to KCNQ2. The 55 carboxyl-terminal amino acids of SEQ ID NO: 2, SEQ ID NO: 4 and SEQ ID NO: 6 are unique to these three splice variants. These 55 amino acids correspond to the amino acids at position 589 to 643 of SEQ ID NO: 2.

Figure 3:
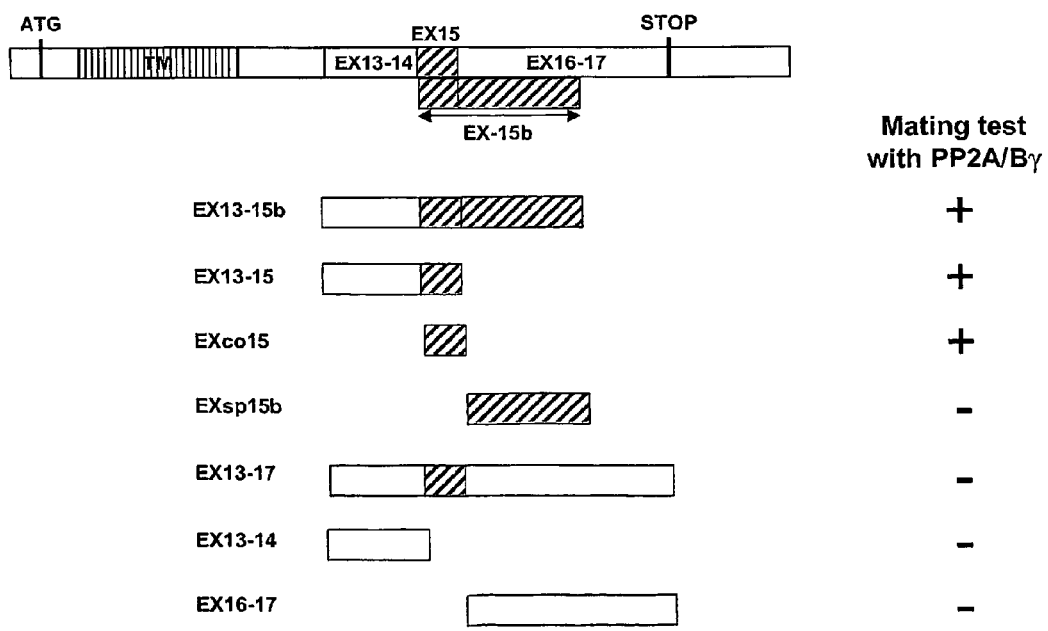
FIG. 3 shows the results of a mating test between PP2A/Bγ and different KCNQ2 polypeptides, as described in detail in Example 3.

The genomic structure of the KCNQ2 gene is shown on FIG. 3 and in table 1. The KCNQ2 gene is comprised of 17 exons. None of the novel splice variants displays the exons corresponding to exons 15, 16 and 17 of the KCNQ2 gene. They all display a novel exon, exon 15b, which encodes the amino acids at position 545 to 643 of SEQ ID NO: 2. The 44 first amino acids encoded by exons 15 and 15b are identical (amino acids at position 545 to 588 of SEQ ID NO: 2). The 55 last amino acids encoded by exon 15b are unique to exon 15b (amino acids at position 589 to 643 of SEQ ID NO: 2). Furthermore, the novel splice variants do not display exons 16 and 17 of KCNQ2-fl. The most carboxyl-terminal exon of these splice variants is exon 15b. SEQ ID NO: 2 further comprises exon 1 to exon 14 of KCNQ2. Exon 12 of KCNQ2 is lacking in SEQ ID NO: 4. Exons 9 and 12 of KCNQ2 are lacking in SEQ ID NO: 6.

The insert of the 2E11 clone, which corresponds to a partial cDNA, comprises exons 13, 14 and 15b.

TABLE 1

| Exon No. | SEQ ID NO: 1 | Encodes AA of SEQ ID NO: 2 | SEQ ID NO: 3 | Encodes AA of SEQ ID NO: 4 | SEQ ID NO: 5 | Encodes AA of SEQ ID NO: 6 | Encodes AA of SEQ ID NO: 7 |
|---|---|---|---|---|---|---|---|
| 1 | 1-296 | 1-98 | 1-296 | 1-98 | 1-296 | 1-98 | 1-98 |
| 2 | 297-387 | 100-129 | 297-387 | 100-129 | 297-387 | 100-129 | 100-129 |
| 3 | 388-514 | 130-171 | 388-514 | 130-171 | 388-514 | 130-171 | 130-171 |
| 4 | 515-690 | 173-230 | 515-690 | 173-230 | 515-690 | 173-230 | 173-230 |
| 5 | 691-816 | 231-272 | 691-816 | 231-272 | 691-816 | 231-272 | 231-272 |
| 6 | 817-927 | 273-309 | 817-927 | 273-309 | 817-927 | 273-309 | 273-309 |
| 7 | 928-1023 | 310-341 | 928-1023 | 310-341 | 928-1023 | 310-341 | 310-341 |
| 8 | 1024-1118 | 342-372 | 1024-1118 | 342-372 | 1024-1118 | 342-372 | 342-372 |
| 9 | 1119-1148 | 374-382 | 1119-1148 | 374-382 | / | / | 374-382 |

TABLE 1-continued

| Exon No. | SEQ ID NO: 1 | Encodes AA of SEQ ID NO: 2 | SEQ ID NO: 3 | Encodes AA of SEQ ID NO: 4 | SEQ ID NO: 5 | Encodes AA of SEQ ID NO: 6 | Encodes AA of SEQ ID NO: 7 |
|---|---|---|---|---|---|---|---|
| 10  | 1149-1217 | 384-405 | 1149-1217 | 384-405 | 1119-1187 | 374-395 | 384-405 |
| 11  | 1218-1247 | 407-415 | 1218-1247 | 407-415 | 1188-1217 | 397-405 | 407-415 |
| 12  | 1248-1301 | 417-433 | /         | /       | /         | /       | 417-433 |
| 13  | 1302-1525 | 435-508 | 1248-1471 | 417-490 | 1218-1441 | 407-480 | 435-508 |
| 14  | 1526-1631 | 510-543 | 1472-1577 | 492-525 | 1442-1547 | 482-515 | 510-543 |
| 15  | /         | /       | /         | /       | /         | /       | 545-587 |
| 15b | 1632-1929 | 545-643 | 1578-1875 | 527-625 | 1548-1845 | 517-615 | /       |
| 16  | /         | /       | /         | /       | /         | /       | 588-629 |
| 17  | /         | /       | /         | /       | /         | /       | 630-872 |

Example 3

Yeast Mating Test

1. Construction of Vectors 1.1. EX13-17, which Comprises Exons 13, 14, 15, 16 and 17.

The pGADT7-EX13-17 plasmid was constructed as follows: a 1414-bp fragment was first PCR-amplified from a Human total brain cDNA library (Marathon-Ready cDNA, Clontech) with two gene-specific primers of SEQ ID NO: 15 and of SEQ ID NO: 16. This first PCR product was then amplified with a second set of gene-specific primers of SEQ ID NO: 17 and 5' of SEQ ID NO: 18. These primers are extended, respectively, with EcoRI and BamHI cloning sites. After digestion With EcoRI and BamHI restriction enzymes, the 1338-bp purified fragment was ligated to the same cloning sites of pGADT7 (Clontech).

1.2. EX13-15, which Comprises Exons 13, 14 and 15.

The pGADT7-EX13-15 plasmid was obtained as follows: a 484-bp fragment was PCR-amplified with primers of SEQ ID NO: 19 and of SEQ ID NO: 20, which are respectively extended with EcoRI and BamHI cloning sites, from the first PCR product of the pGADT7-EX13-17 construction. The resulting fragment was then digested with EcoRI and BamHI, purified, and ligated to the same cloning sites of pGADT7 (Clontech).

1.3. EX16-17, which Comprises Exons 16 and 17.

The pGADT7-EX16,17 plasmid was obtained as follows: a 883-bp fragment was PCR-amplified with primers of SEQ ID NO: 21 and of SEQ ID NO: 22, which are respectively extended with EcoRI and BamHI cloning sites, from the first PCR product of the pGADT7-EX13-17 construction. The resulting fragment was then digested with EcoRI and BamHI, purified, and ligated to the same cloning sites of pGADT7 (Clontech).

1.4. EXsp15b, which Comprises the Region Unique to Exon 15b.

The pGADT7-EXsp15b plasmid was constructed as follows: a 400-bp fragment was PCR-amplified with a primer of SEQ ID NO: 23 extended with EcoRI cloning site, and with a primer of SEQ ID NO: 24 from the pACT2-2E11 plasmid (see example 1). The resulting fragment was then digested with EcoRI and XhoI, purified, and ligated to the same cloning sites of pGAD7 (Clontech).

1.5. EXco15, which Comprises the Region Common to Exon 15 and Exon 15b.

The pGADT7-EXco15 domain plasmid was constructed as follows: a 146-bp fragment was PCR-amplified with primers of SEQ ID NO: 25 and of SEQ ID NO: 26, which are respectively extended with EcoRI and BamHI cloning sites, from the pACT2-2E11 plasmid. The resulting fragment was then digested with EcoRI and BamHI, purified, and ligated to the same cloning sites of pGADT7 (Clontech).

1.6. EX13-14, which Comprises Exons 13 and 14.

The pGADT7-EX13-14 plasmid was constructed as follows: a 300-bp fragment was PCR-amplified with primers of SEQ ID NO: 27 and of SEQ ID NO: 28, which are respectively extended with EcoRI and BamHI cloning sites, from the pACT2-2E11 plasmid. The resulting fragment was then digested with EcoRI and BamHI, purified, and ligated to the same cloning sites of pGADT7 (Clontech).

2. Protocol of the Yeast Mating Test

Yeast mating tests were performed to map the interaction domains between the different partners. The chosen *Saccharomyces cerevisiae* mating partner strains (AH109 and Y184) were transformed separately with the plasmids to be tested in combination with the plasmid of interest. The lithium acetate transformation procedure was done according to the manufacturer's instructions (Matchmaker Two-Hybrid system, Clontech). Transformants were selected on the appropriate SD dropout medium (Clontech). One fresh colony of each type to use was picked from the working stock plates and both placed in one 1.5 ml microcentrifuge tube containing 0.5 ml of YPD medium (Clontech). Cells were then incubated for 24 hr at 30° C. with shaking at 200 rpm. 10 µl of a 1:100 dilution of the mating culture were then spread on the appropriate SD medium: SD/-Leu/-Trp, and SDI-Leu/-Trp/-His/-Ade. After 7 to 15 days of growth on selective medium positive colonies were counted.

3. Results of the Direct Mating Tests Between KCNQ2 Polypeptides and PP2A/Bγ

Mating tests between each of the above constructions and the pGBKT7-PPP2R2C construction described in example 1 were performed. The results are shown on FIG. 2. The sign "+" indicates that colonies grew, thus indicating that the tested polypeptide is capable of interacting with PP2A/Bγ. The sign "−" indicates that no colony grew, thus indicating that the tested polypeptide does not interact with PP2A/Bγ.

EX13-17, EX16-17, EX13-14 and EXsp15b do not interact with PP2A/Bγ. EX13-15b, EX13-15 and EXco15 interact with PP2A/Bγ. EX13-15b interacts with PP2A/Bγ, showing that KCNQ2-15b polypeptides are capable of interacting with PP2A/Bγ. Since EX13-15b, EX13-15 and EXco15 but not EXsp15b interact with PP2A/Bγ, the common region between exon 15 and exon 15b plays a role in this interaction. Furthermore, since EX13-17 does not interact with PP2A/Bγ, the fact that exon 15 or that exon 15b is located at the most carboxyl extremity of the KCNQ2 polypeptide is of importance for efficient interaction with PP2A/Bγ.

4. Results of the Direct Mating Tests Between Different KCNQ2 Polypeptides

Figure 4:
FIG. 4 shows the results of a mating test between different KCNQ2 polypeptides, as described in detail in Example 3.

Mating tests between the different above constructions were performed, and the results are shown on FIG. 4. 4 mating tests were performed for each pair of constructs and the results are shown on FIG. 3. The sign "++" indicates that all 4 colonies grew. The sign "+" indicates that 3 colonies out of 4 grew. The sign "−/+" indicates that 1 colony out of 4 grew. The sign "−" indicates that no colony grew.

This experiment shows that KCNQ2-15b polypeptides can associate and form homodimers. KCNQ2-15b polypeptides can also associate and form heterodimers with KCNQ2 polypeptides comprising exon 15 at their carboxyl-terminal extremity. KCNQ2-15b polypeptides associate with KCNQ2-fl polypeptides at a lesser extent.

Example 4

Expression and Purification of Glutathione S-Transferase Fusion Proteins

1. Construction of Plasmids
   1.1. pGBKT7-2E11

The pACT2-2E11 plasmid rescued from yeast two-hybrid screening was digested with EcoRI and BglII and the resulting 687-bp fragment inserted after purification into EcoRI and BamHI cloning sites of the pGBKT7 vector (Clontech).

2.2. pGEX-2TK-2E11

A partial cDNA of the KCNQ2 splice variants was PCR-amplified from the pACT2-2E11 plasmid rescued from yeast two-hybrid screening using a gene-specific primer of SEQ ID NO: 29 and a primer in the pACT2 vector of SEQ ID NO: 30. These primers were respectively extended with BamHI and EcoRI cloning sites. The 892-bp PCR product was digested with BamHI and EcoRI, purified and inserted into BamHI and EcoRI sites of pGEX-2TK vector (Amersham Pharmacia Biotech). The pACT2 plasmid used for this construction was recovered from diploid cells as follows: a fresh colony of diploid cells was inoculated into 5 ml of SD/-Leu/-Trp (Clontech) and let to grow overnight at 30° C. with shacking at 200-250 rpm. Cells corresponding to 2 ml of the overnight culture were spun down by centrifuging at 4300 rpm for 10 min. The pellet was resuspended in 100 µl of zymolyase (1 U/µl) (Seikagaku Corporation) and incubated 1 hr at 30° C. Then 100 µl of a proteinase K mix (100 mM NaCl, 10 mM Tris-HCl pH [pH 8.0], 25 mM EDTA, 0.5% SDS, 0.1 mg/ml proteinase K) were added for 2.5 hr at 40° C. DNA was extracted by two successive phenol:chloroform steps and precipitated with 0.3 M sodium acetate and 2.5 volumes of ethanol. DH10B ElectroMAX competent cells (Invitrogen) were transformed with DNA and selected on agar plates supplemented with 120 µg/ml Ampicillin. The protein encoded by pGEX-2TK-2E11 was named GST-2E11.

1.3. pGEX-2TK-PPP2R2C

A 1485-bp fragment of PPP2R2C encompassing nucleotides 55-1540 of the full-length cDNA of PP2A/Bγ (genbank accession number AF086924) was PCR-amplified from the pGBKT7-PPP2R2C plasmid using gene-specific primers of SEQ ID NO: 31 and of SEQ ID NO: 32, which are respectively extended with BamHI and EcoRI cloning sites. The fragment was digested by BamHI and EcoRI, purified and ligated to the same cloning sites of pGEX-2TK vector (Amersham Pharmacia Biotech). The protein encoded by pGEX-2TK-2E11 is named GST-PPP2R2C.

1.4. pGEX-2TK-KCNQ2-Cter

A 1393-bp fragment of a KCNQ2-fl encompassing nucleotides 1544-2924 of the full-length cDNA (genbank accession number AF033348) was PCR-amplified from the pCMV-HA-KCNQ2-isol construction using gene-specific primers: of SEQ ID NO: 33 and of SEQ ID NO: 34, which are respectively extended with XhoI and EcoRI cloning sites. This PCR product was digested with XhoI and EcoRI, purified and substituted at the same sites for a 767-bp XhoI-EcoRI fragment of the pGEX-2TK-2E11 plasmid. The pCMV-HA-KCNQ2-isol plasmid used for the construction of pGEX-2TK-KCNQ2-Cter was obtained as follows: the full-length coding region for KCNQ2-fl (encompassing nucleotides 126-2924 of the full-length cDNA, genbank accession number AF033348) was first amplified from a Human brain cDNA library (Marathon-Ready cDNA, Clontech) using gene specific primers of SEQ ID NO: 35 and of SEQ ID NO: 36, which are respectively extended with EcoRI and BglII cloning sites. The PCR product was digested with EcoRI and BglII, purified and ligated to the same cloning sites of the pCMV-HA vector (Clontech). The protein encoded by pGEX-2TK-2E11 is named GST-KCNQ2-Cter.

2. Expression and Purification

Glutathione S-transferase fusion protein expression and purification by adapting the method described by Kaelin et al. (1991, Cell, 64:521-532). Overnight cultures of MAX Efficiency DH5αF'IQ competents cells (Invitrogen) transformed with either the pGEX2TK plasmid or the pGEX2TK-2E11, pGEX2TK-KCNQ2-Cter, and pGEX2TK-PPP2R2C recombinants were diluted 1:10 in LB medium containing ampicillin (100 µg/ml) and incubated for 1 hr at 37° C. Isopropyl-β-D-thiogalactopyranoside (IPTG, Promega) was then added to a final concentration of 0.1 mM and bacteria let to grow for 3 additional hours at 37° C. For fusion proteins recovery using the glutathione-Sepharose 4B beads (Amersham Biosciences), bacterial cultures were pelleted by centrifugation at 5000×g for 15 min at 4° C. and resuspended in 1/10 vol NETN (20 mM Tris-HCl [pH 8.0], 120 mM NaCl, 1 mM EDTA, 0.5% Nonidet P-40) supplemented with 1 mM phenylmethylsulfonyl fluoride (PMSF, Sigma) and one tablet of protease inhibitors cocktail (Complete™ mini, Roche) for 7 ml of buffer. The bacteria were then lysed on ice by mild sonication and centrifuged at 10,000×g for 10 min at 4° C. Aliquots (1 ml) of bacterial clear lysates were then rocked for 1 hr at 4° C. with 50 µl of glutathione-Sepharose 4B beads, which had been previously washed four times in NETN containing 1% Albumin Bovine (BSA fraction V, Sigma) and resuspended (final concentration 1:1 [v/v]) in NETN. The glutathione-Sepharose 4B beads were then washed three times with NETN. For recovery of the bound recombinants proteins, beads were washed two more times with 100 mM Tris-HCl [pH 8.0], 120 mM NaCl and elution was performed in the same buffer containing 20 mM glutathione (Sigma). Quantification of the eluted fusion proteins w performed by the standard Bradford's method (Biorad Protein Assay).

Example 5

In Vitro Labeling of the GST Fusion Proteins

Beads with bound GST fusion proteins corresponding to 1 ml of bacterial clear lysate were washed three times in NETN and one time with HMK buffer without DTT (20 mM Tris-HCl [pH 7.5], 120 mM NaCl, 12 mM $MgCl_2$). Beads were then resuspended in 30 µl of reaction mix (3 µl of 10×HMK Buffer with 20 mM DTT, 10 units of Protein Kinase A Catalytic Subunit [PKA from bovine heart, 250 units/vial, Sigma] in 40 mM DTT, 2 µl of [$^{32}$P]-γATP 6000 Ci/mMole and 24 µl of distilled water) and incubated at 4° C. for 30 min. During incubation beads were resuspended time to time by flicking. Reaction was stopped by adding 1 ml of HMK stop buffer (10 mM Sodium Phosphate [pH 8.0], 10 mM Sodium Pyrophosphate, 10 mM EDTA, 1 mg/ml BSA) and beads washed five times with NETN buffer. Elution of radiolabeled fusion proteins was carried out with 1 ml of freshly prepared 20 mM glutathione in 100 mM Tris-HCl [pH 8.0], 120 mM NaCl as previously described.

Example 6

Solid Phase Overlay assay

1. Protocol of the Solid Phase Overlay Assay

Solid phase overlay assays were performed by adapting the method described by Kaelin and collaborators (Kaelin et al., 1992, Cell, 70:351-364). 100 ng, 10 ng and 0.1 ng of GST and GST-2E11 recombinant proteins were resolved by 9% SDS-PAGE and were transferred by electroblotting onto nitrocellulose membrane (nitrocellulose transfer membrane Protran BA 83, Schleicher and Schuell). The membrane were then blocked in HBB buffer (25 mM Hepes-KOH [pH 7.7], 25 mM NaCl, 5 mM $MgCl_2$) with 5% (w/v) non-fat dry milk, 1 mM DTT, 0.05% Nonidet P-40 for 1 hr at room temperature. The binding reaction was carried out at room temperature in Hyb75 buffer (20 mM Hepes [pH 7.7], 75 mM KCl, 2.5 mM $MgCl_2$, 0.1 mM EDTA, 0.05% Nonidet P-40) with 1% (w/v) non-fat dry milk, 1 mM DTT, 1 mM PMSF and $3.5\ 10^5$ dpm of a [$^{32}$P]-γATP GST-PPP2R2C radiolabeled recombinant protein used as a probe. After 4.5 hr of incubation, the membrane was washed with Hyb75 buffer, 1 mM DTT, 1% (w/v) non-fat dry milk three times for 15 min at room temperature. The blots were analyzed by autoradiography.

2. Results

This experiment was performed to validate the interaction between KCNQ2-15b polypeptides and PP2A/Bγ. In this experiment, the PP2A/Bγ subunit was radiolabeled but not the proteins present on the nitrocellulose membrane. Thus, a signal appears when visualized by autoradiography only if the loaded protein interacts with PP2A/Bγ. GST-2E11 corresponds to a fusion protein between a KCNQ2-15b polypeptide comprising exons 13, 14 and 15b and GST. GST corresponds to the negative control. In the three lines loaded with the GST-2E11 recombinant protein, bands located at a position corresponding to a protein of a size of about 45 kD appeared. This corresponds to the protein size expected for the GST-2E11 protein. Furthermore, the intensity of the bands was proportional to the quantity of loaded GST-2E11. Thus GST-2E11 interacts with PP2A/Bγ. In the three lines loaded with the GST protein, no band appeared, showing that PP2A/Bγ does not interact with the GST protein. Thus the interaction between PP2A/Bγ and the GST-2E11 fusion protein is due to the part of the protein encoding 2E11 and not to the part of the protein encoding GST. This experiment indicates that KCNQ2-15b polypeptides can interact with PP2A/Bγ in vitro. Furthermore, this shows that KCNQ2-15b polypeptides can interact with PP2A/Bγ without a third binding partner, a hypothesis that can not be excluded by a yeast-two hybrid assay.

Example 7

In Vitro Phosphorylation Assay With Recombinant GSK-3β Kinase and In Vitro Dephosphorylation with HTB-14 Whole Cell Extracts 1. Phosphorylation Assays Phosphorylation assays were performed to determine whether the phsophorylation state of KCNQ2-15b is modulated by GSK3β, a kinase that plays an important role in the central nervous system by regulating various cytoskeletal processes through its effects on MAP1B, tau and synapsin 1. GSK3β is known to be inhibited by two mood stabilizing agents used in treatment of bipolar disorder, lithium and valporate.

1.1. Protocol

Expression and purification of the GST-2E11 fusion protein were performed as described above. Beads with bound fusion protein corresponding to 1 ml of bacterial clear lysate were washed three times in NETN and one time with HMK buffer without DTT (20 mM Tris-HCl [pH 7.5], 120 mM NaCl, 12 mM $MgCl_2$). Beads were resuspended in 240 μl of reaction mix (24 μl of 10×HMK Buffer with 20 mM DTT, 40 units of Protein Kinase A Catalytic Subunit [PKA from bovine heart, 250 units/vial, Sigma] in 40 mM DTT, 5 μl of 24 mM ATP and 207 μl of distilled water) and incubated for 30 min at room temperature. Beads were then washed three times in NETN buffer and one time in GSK-3β reaction buffer (20 mM Tris-HCl [pH 7.5], 10 mM $MgCl_2$, 5 mM DTT) (New England Biolabs). Beads were then resuspended in 50 μl of reaction mix (5 μl of 10×GSK-3β reaction buffer, 1 μl of [$^{32}$P]γATP 10 mCi/ml, 50 U of recombinant GSK-3β[New England Biolabs], and distilled water for a final volume of 50 μl) and incubated at room temperature for 30 min. After three washes in NETN buffer, phosphorylated proteins were boiled in 2×Sample Buffer (125 mM Tris-HCl [pH 6.8], 4% SDS, 20% glycerol, 1.4 M β-Mercapto ethanol), resolved by 10% SDS-PAGE, and visualized by autoradiography.

1.2. Results

In this phosphorylation assay, non-radiolabeled polypeptides to be tested are incubated in the presence of GSK-3β, PKA and radioactive ATP. The proteins are then resolved by a 10% SDS-PAGE migration and visualized by autoradiography. A signal is visualized by autography only if the protein to be tested is phosphorylated by GSK-3β and PKA during incubation. In the line loaded with the GST-2E11 protein, which corresponds to the fusion protein between a KCNQ2-15b polypeptide comprising exons 13, 14 and 15b and the GST polypeptide, a band located at a position corresponding to a protein of a size of about 45 kD did appear. This is the size expected for the GST-2E11 protein. Thus the GST-2E11 protein is phosphorylated by GSK-3β and PKA in vitro. Three experiments corresponding to negative controls were performed in parallel. One experiment was performed without adding the GSK-3β kinase during incubation, one was performed without adding the PKA kinase during incubation, and one was performed with a GST protein instead of a GST-2E11 protein. No bands appeared in the three lines corresponding to the negative controls.

Accordingly, this experiment shows that KCNQ2-15b polypeptides are synergistically phosphorylated by the GSK-3β and PKA kinases in vitro.

This result was confirmed by a competition experiment in which CREB phosphopeptides, which are known to be phosphorylated by GSK-3β and PKA, were added during incubation. In this competition experiment, 5 μg of CREB phosphopeptides (New England Biolabs) was added to the kination mix. A band did still appear at a position corresponding to the size of GST-2E11, but the intensity of the band was very significantly lower.

The influence of LiCl on the phosphorylation state of GST-2E11 was further studied by adding LiCl to the kination mix at a final concentration of 0, 8.3, 25, 75 and 225 mM respectively. The intensity of the band appearing at a position of about 45 kD decreased in the presence of LiCl, and the intensity of the signal was negatively correlated with the concentration of LiCl added to the kination mix. In the presence of about 50 mM LiCl, the phosphorylation state of GST-2E11 was reduced by 50%.

This shows that LiCl, a well-known mood-stabilizing agent used in the treatment of bipolar disorder, inhibits phosphorylation of KCNQ2-15b polypeptides in vitro.

2. Dephosphorylation Assays

Dephosphorylation assays were performed to determine whether the phophorylation state of KCNQ2-15b polypeptides is modulated by PP2A.

2.1. Protocol

In vitro phosphorylated GST-2E11 fusion protein was incubated at room temperature for 30 min with 500 µg of whole cell extracts of Human glioblastoma, astrocytoma cell line (ATCC number: HTB-14) with or without 400 µM of the PP2A phosphatase inhibitor okadaic acid (Sigma). HTB-14 whole cell extracts were prepared as follow: cells were washed three times with ice-cold TBS buffer (10 mM Tris-HCl [pH 8.0], 120 mM NaCl) and lysed at 4° C. for 30 min in EBC buffer (50 mM Tris-HCl [pH 8.0], 120 mM NaCl, 0.5% Nonidet P-40). Then the lysate was centrifuged for 10 min at 13.000×g at 4° C. to pellet cell debris. Proteins present in the supernatant were quantified by the standard Bradford's method (Bio-Rad Protein Assay). The proteins were then resolved by 10% SDS-PAGE, and visualized by autoradiography.

2.2. Results

The phosphorylated radiolabeled GST-2E11 proteins obtained from the previous assay were incubated in the presence of HTB-14 cell extracts containing the PP2A phosphatase to determine whether PP2A is capable of dephosphorylating GST-2E11 proteins. In this experiment, a protein that is dephosphorylated by PP2A is not radioactive after incubation in the presence of HTB-14 cell extracts any more. Thus dephosphorylation of the GST-2E11 protein is monitored by disappearance of the signal visualized by autoradiography. One line of the 10% SDS-PAGE gel was loaded with phosphorylated GST-2E11 fusion proteins incubated in the absence of HTB-14 cell extracts, as reference for the intensity of the band appearing for phosphorylated GST-2E11 proteins. In the line loaded with GST-2E11 fusion proteins incubated in the presence of HTB-14 cell extracts, the band had an extremely weaker intensity. Thus GST-2E11 fusion proteins are dephosphorylated when incubated in the presence of HTB-14 cell extracts. When the GST-2E11 fusion protein was incubated in the presence of HTB-14 cell extracts and okadaic acid, a known PP2A phosphatase inhibitor, the intensity of the band was only slightly weaker than the intensity of the band corresponding to phosphorylated GST-2E11.

Thus the PP2A phosphatase is responsible of the dephosphorylation observed for GST-2E11 fusion proteins incubated in the presence of HTB-14 cell extracts. Accordingly, this experiment shows that KCNQ2-15b polypeptides are dephosphorylated by the PP2A phosphatase in vitro.

Example 8

Cell Culture, Transfection, Immunoprecipitation and Western Blot Analysis

1. Cell Cultures

HEK293-H cells (Gibco Invitrogen Corporation) were grown in DMEM medium (Gibco Invitrogen Corporation) supplemented with 0.1 mM Non-Essential Amino Acids and 10% Fetal Bovine Serum (Gibco Invitrogen Corporation), and transiently transfected with 20 µg of the pCMV-Myc-3H9 or pCMV-Myc-3H2 plasmids per 60 mm dish using the Invitrogen calcium phosphate transfection kit and protocols. 48 hr after transfection cells were washed three times with ice-cold phosphate buffer (PBS, Gibco Invitrogen Corporation), scraped and solubilized for 2 hr at 4° C. in solubilization buffer containing 150 mM NaCl, 5 mM EDTA, 1% Triton X-100, 0.1% sodium deoxycholate, 10 mM Tris-HCl [pH 8.0] and supplemented with protease inhibitors (1 mM phenylmethylsulfonyl fluoride, one tablet of Complete™ mini protease inhibitors cocktail [Roche]) and phosphatase inhibitors (1 mM Na$_3$VO$_4$ and 1 mM NaF). The lysate was then centrifugated for 10 min at 13.000×g at 4° C. to pellet cell debris. Proteins present in the supernatant were quantified by the standard Bradford's method (Bio-Rad Protein Assay).

2. Immunoprecipitation

500 µg (final volume: 500 µl) of the clear cell lysate were incubated for 2 hr at 4° C. with 1 µd of rabbit preimmune serum and 50 µl of protein A Sepharose CL4B beads (Amersham Pharmacia Biotech) saturated with 1% Albumine Bovine (BSA fraction V, Sigma). Depleted supernatants were then incubated overnight at 4° C. with 1 µg of anti-Myc monoclonal antibody (Myc-Tag 9B11 monoclonal antibody, Cell Signaling). Protein A Sepharose CL4B beads saturated with 1% Albumin Bovine were then added and the mixture incubated at 4° C. for 2 addtional hours. After five washes with ice-cold solubilization buffer immuno-complexes were boiled in 2×Sample Buffer (125 mM Tris-HCl [pH 6.8], 4% SDS, 20% glycerol, 1.4 M β-Mercapto ethanol), resolved by 8% SDS-PAGE and subjected to 3. Western Blot Proteins were transferred onto nitrocellulose membrane (nitrocellulose transfer membrane Protran BA 83, Schleicher and Schuell) using Towbin buffer (Towbin et al., 1979, PNAS, 76:4350-4354) and an electrotransfer device. After transfer, membranes were blocked, in 5% non-fat dried milk in TBST (10 mM Tris-HCl [pH 8.0], 150 mM NaCl, 0.05% Tween 20) supplemented with sodium azide (0.1%) for 2 hr, and then incubated for 16 hr at room temperature with the anti-Myc monoclonal antibody (Myc-Tag 9B11 monoclonal antibody, Cell Signaling) diluted 1:1000 in the same buffer. After several washes with TBST, the blot was incubated with a horseradish peroxidase-conjugated secondary antibody (Anti-mouse IgG, Fab specific, peroxidase conjugate, Sigma) diluted 1:5000 and developed using ECL Western blotting detection reagents (Amersham Biosciences).

Example 9

Electrophysiological Analysis

1. Protocols 1.1. cDNA injection in *Xenopus laevis* oocytes

The animal was anesthetized and pieces of the ovary were surgically removed and individual oocytes were dissected away in a saline solution (ND96) containing 96 mM NaCl, 2 mM KCl, 2 mM CaCl2, 2 mM MgCl2 and 5 mM HEPES at pH 7.4. Stage V and VI oocytes were treated at room temperanre for 2 h with collagenase type 1A (1 mg/ml) in the presence of 0.2 mg/ml trypsin inhibitor in saline solution to discard follicular cells. The concentrations were determined by measuring the absorbance at 260 nm. DNA corresponding to KCNQ2, 3H2 and 3H9 K+ channels were subcloned in PEKO vector in order to generate the respective cRNAS. cRNA concentrations were measured by absorbance at 260 nM. cRNA solutions were injected (about 50 nL/oocyte) using a pressure microinjector (Inject+matic, Geneve). Oocytes were then kept for 2-6 days in ND96 solution supplemented wirn 50 U/mL penicillin and 50 U/mL streptomycin.

1.2. Electrophysiological Measurements

In a 0.3 mL perfusion chamber, a single oocyte was impaled with two standard glass microelectrode (0.5-2 Mohm resistance) filled with 3M KCl and maintained under voltage clamp using a Dagan TEV200 amplifier system, USA. Electrical stimulations, data acquisition and analyses were performed using pClamp software (Axon Instruments, USA). Current to voltage relationships were obtained applying incremental depolarizing voltage steps (10 mV increment) from a holding potential of −80 mV (equilibrium potential for K+ ions) Repolarizations to −60 mV allowed K$^+$ channel deactivation measurements from the "tail currents".

2. Results

Figure 5:
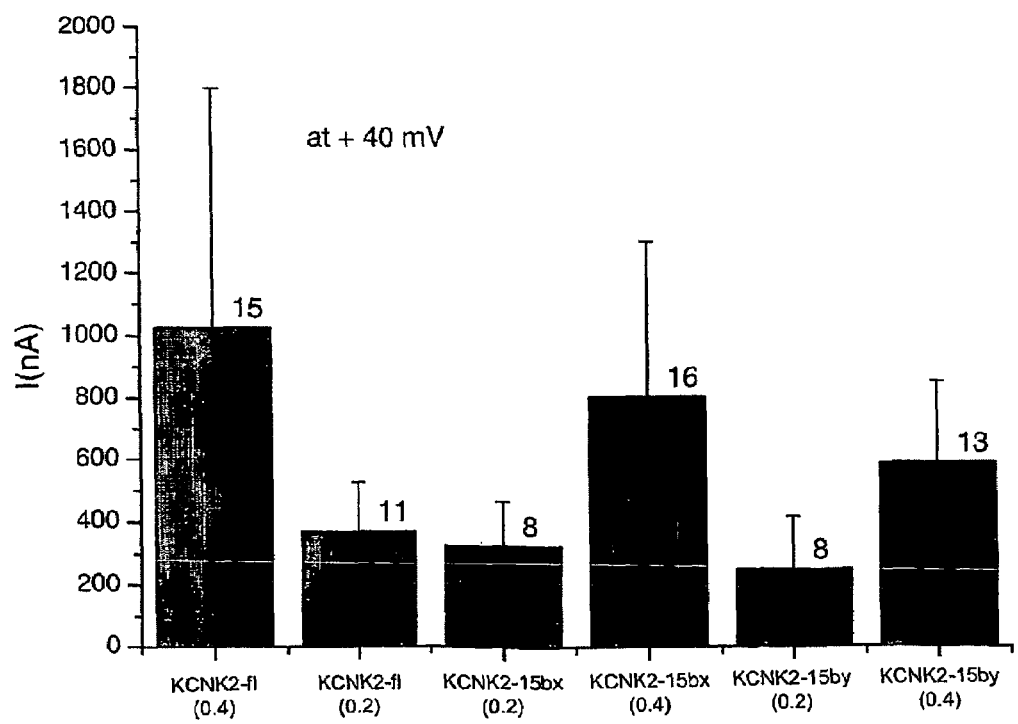
FIG. 5 compares the intensity of the currents generated by homotetrameric potassium channels comprised of KCNQ2-15bx, KCNQ2-15by, KCNQ2-15bz or KCNQ2-fl subunits respectively.

The activity of KCNQ2-15bx and of KCNQ2-15by homotetrameric potassium channels was tested and compared to the activity of KCNQ2-fl homotetrameric potassium channels. 0.2 ng or 0.4 ng of DNA were injected to the oocytes. The results are shown on FIG. 5, on which the intensity of the M-current generated by the potassium channels is indicated. An intensity of about 1 μA is found for the current generated by a of KCNQ2-fl homotetrameric potassium channel when 0.4 ng of DNA is injected. This value is similar to the value reported by scientific literature. A KCNQ2-15bx homotetrameric potassium channel yields a current of about 800 nA when 0.4 ng of DNA is injected, and a KCNQ2-15by homotetrameric potassium channel yields a courant of about 700 nA when 0.4 ng of DNA is injected. Thus the KCNQ2-15bx and KCNQ2-15by splice variants can associate as functional homomeric potassium channels in vivo.

Figure 6A:
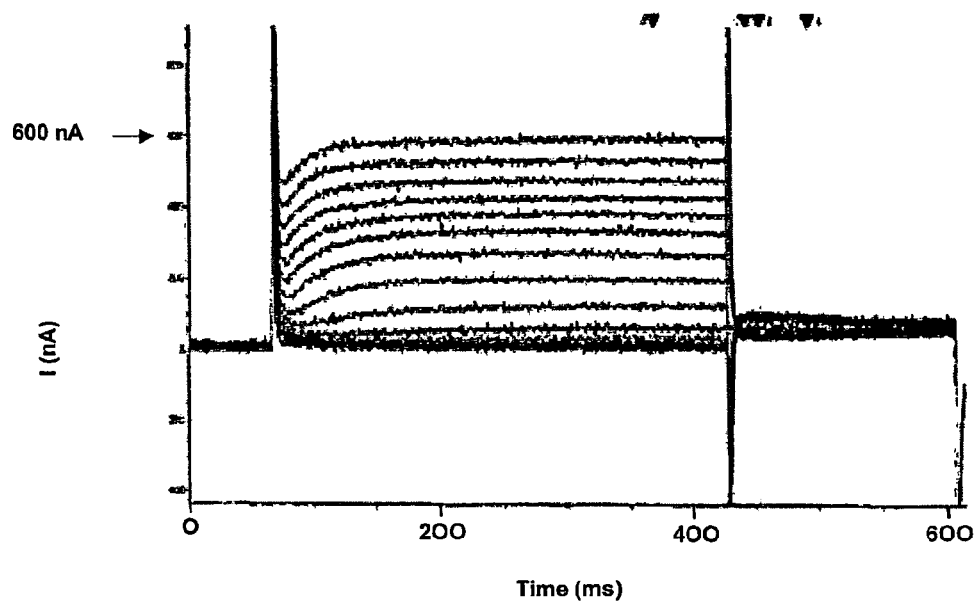
FIG. 6A shows the voltage clamp traces of the current generated by a homotetrameric potassium channels comprised of KCNQ2-15bx subunits.
Figure 6B:
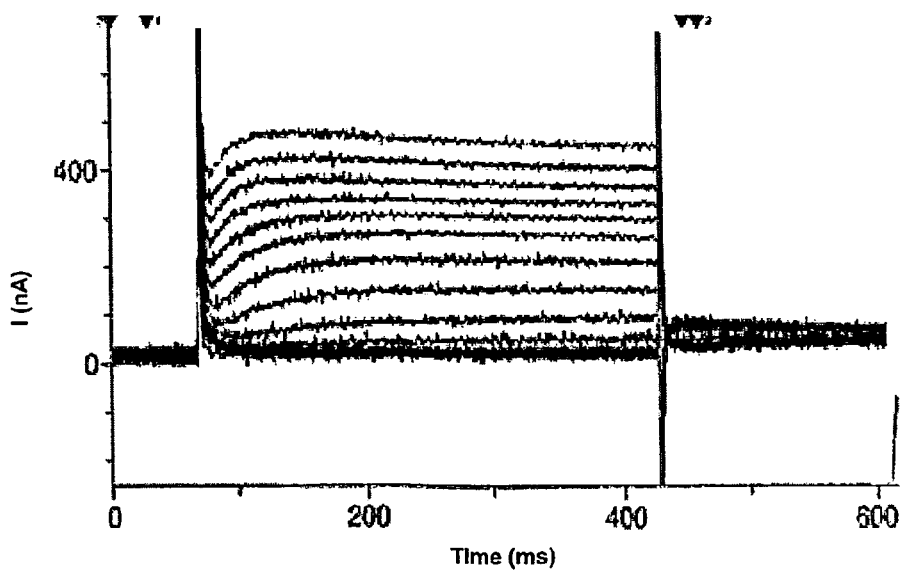
FIG. 6B shows the voltage clamp traces of the current generated by a homotetrameric potassium channels comprised of KCNQ2-15by subunits.

FIG. 6A and FIG. 6B show the voltage clamp traces corresponding to the currents generated at different voltages by KCNQ2-15bx (FIG. 6A) and by KCNQ2-15by (FIG. 6B) homotetrameric potassium channels. The slow activation that is observed on the traces is a characteristic feature of members of the KCNQ potassium channel family.

Example 10

Collection Of DNA Samples From Affected And Non-Affected Individuals

Donors were unrelated and healthy. The DNA from 100 individuals was extracted and tested for the detection of the biallelic markers.

30 ml of peripheral venous blood were taken from each donor in the presence of EDTA. Cells (pellet) were collected after centrifugation for 10 minutes at 2000 rpm. Red cells were lysed by a lysis solution (50 ml final volume: 10 mM Tris pH7.6; 5 mM MgCl 2; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:
3 ml TE 10-2 (Tris-HCl 10 mM, EDTA 2 mM)/NaCl 0.4 M
200 μl SDS 10%
500 μl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 μg/ml DNA). To determine the presence of proteins in the DNA solution, the OD 260/OD 280 ratio was determined. Only DNA preparations having a OD 260/OD 280 ratio between 1.8 and 2 were used in the subsequent examples described below.

The pool was constituted by mixing equivalent quantities of DNA from each individual.

Example 11

Amplification of Genomic DNA by PCR

The amplification of specific genomic sequences of the DNA samples of Example 10 was carried out on the pool of DNA obtained previously. In addition, 50 individual samples were similarly amplified.

PCR assays were performed using the following protocol:

| | |
|---|---|
| Final volume | 25 μl |
| DNA | 2 ng/μl |
| MgCl$_2$ | 2 mM |
| dNTP (each) | 200 μM |
| primer (each) | 2.9 ng/μl |
| Ampli Taq Gold DNA polymerase | 0.05 unit/μl |
| PCR buffer (10x = 0.1 M TrisHCl pH 8.3 0.5M KCl) | 1x |

Each pair of first primers was designed using the sequence information of genomic DNA sequences and the OSP software (Hillier & Green, 1991).

Primers Biallelic Markers Located in PPP2R2C

The genomic sequence of PPP2R2C that is shown as SEQ ID NO: 37 was constructed upon bioinformatic analysis based on (i) BAC clones constructed at Genset S. A.; (ii) BAC clones corresponding to EMBL Accesion Nos. AC114815.5, AC004599.6, AC122939.3 and AC004689.5; and (iii) RefseqN Accession No. NT_006051. The polymorphisms were identified as described in examples 12 and 13, and validated as described in example 14.

Biallelic Markers Located in the KCNQ2 Gene

The biallelic markers located in the KCNQ2 gene were found using data provided by Celera. Each of these markers were further validated as described in example 14.

Table 2A indicates the position on SEQ ID NO: 37 of pairs of primers that were used to amplify specific regions of PPP2R2C. Table 2B indicates the position of the primers on SEQ ID Nos 42 to 47, which were used to amplify specific regions of KCNQ2. The orientation of the primer is indicated in the third column. The sign (+1) indicates that the sequence of the primer is identical to the corresponding region of SEQ ID Nos. 37 and 42 to 47. The sign (−1) indicates that the sequence of the primer is complementary to the corresponding region of SEQ ID Nos. 37 and 42 to 47.

TABLE 2A

| Primer location in PPP2R2C | | |
|---|---|---|
| Name of the amplified region | Position on SEQ ID NO: 37 | Orientation |
| 24-257 | 109495 to 109512 | (+1) |
| | 109963 to 109982 | (−1) |
| 99-24169 | 83709 to 83729 | (+1) |
| | 84146 to 84164 | (−1) |

TABLE 2A-continued

Primer location in PPP2R2C

| Name of the amplified region | Position on SEQ ID NO: 37 | Orientation |
|---|---|---|
| 99-24175 | 117228 to 117248 | (+1) |
|  | 117659 to 117677 | (−1) |
| 24-247 | 99290 to 99309 | (+1) |
|  | 99719 to 99738 | (−1) |

TABLE 2B

Primer location in the KCNQ2 gene

| Name of the amplified region | SEQ ID No. | Position | Orientation |
|---|---|---|---|
| 30-4 | SEQ ID NO: 42 | 244 to 263 | (+1) |
|  |  | 324 to 343 | (−1) |
| 30-2 | SEQ ID NO: 43 | 240 to 258 | (+1) |
|  |  | 319 to 338 | (−1) |
| 30-17 | SEQ ID NO: 44 | 265 to 284 | (+1) |
|  |  | 345 to 364 | (−1) |
| 30-7 | SEQ ID NO: 45 | 272 to 291 | (+1) |
|  |  | 315 to 333 | (−1) |
| 30-84 | SEQ ID NO: 46 | 265 to 284 | (+1) |
|  |  | 334 to 353 | (−1) |
| 30-15 | SEQ ID NO: 47 | 248 to 267 | (+1) |
|  |  | 312 to 331 | (−1) |

Preferably, the primers contained a common oligonucleotide tail upstream of the specific bases targeted for amplification which was useful for sequencing.

The synthesis of these primers was performed following the phosphoramidite method, on a GENSET UFPS 24.1 synthesizer.

DNA amplification was performed on a Genius II thermocycler. After heating at 95° C. for 10 min, 40 cycles were performed. Each cycle comprised: 30 sec at 95° C., 54° C. for 1 min, and 30 sec at 72° C. For final elongation, 10 min at 72° C. ended the amplification. The quantities of the amplification products obtained were determined on 96-well microtiter plates, using a fluorometer and Picogreen as intercalant agent (Molecular Probes).

Example 12

Identification of Biallelic Markers from Amplified Genomic DNA

The sequencing of the amplified DNA obtained in Example 11 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis (ABI Prism DNA Sequencing Analysis software (2.1.2 version)).

The sequence data were further evaluated to detect the presence of biallelic markers within the amplified fragments. The polymorphism search was based on the presence of superimposed peaks in the electrophoresis pattern resulting from different bases occurring at the same position as described previously.

The locations of the biallelic markers detected in the fragments of amplification are as shown below in Tables 3A and 3B.

TABLE 3A

Biallelic Markers in the PPP2R2C gene

| amplified region | BM name | Strand | polymorphism All 1 | All 2 | BM position on SEQ ID NO: 37 |
|---|---|---|---|---|---|
| 24-257 | 24-257/320 | (−) | A | G | 109663 |
| 99-24169 | 99-24169/139 | (−) | A | G | 84026 |
| 99-24175 | 99-24175/218 | (−) | A | G | 117460 |
| 24-247 | 24-247/216 | (+) | A | G | 99505 |

TABLE 3B

Biallelic Markers in the KCNQ2 gene

| amplified region | BM name | Strand | polymorphism All 1 | All 2 | SEQ ID No. | BM position on indicated SEQ ID No. |
|---|---|---|---|---|---|---|
| 30-4 | 30-4/58 | (+) | A | G | SEQ ID NO: 42 | 301 |
| 30-2 | 30-2/62 | (+) | A | G | SEQ ID NO: 43 | 301 |
| 30-17 | 30-17/37 | (+) | A | G | SEQ ID NO: 44 | 301 |
| 30-7 | 30-7/30 | (+) | C | T | SEQ ID NO: 45 | 301 |
| 30-84 | 30-84/37 | (+) | A | G | SEQ ID NO: 46 | 301 |
| 30-15 | 30-15/54 | (+) | A | C | SEQ ID NO: 47 | 301 |

BM refers to "biallelic marker". All 1 and All 2 refer respectively to allele 1 and allele 2 of the biallelic marker. The (+) or (−) sign in the column "strand of BM" indicates the strand on which the indicated alternative alleles are found. SEQ ID Nos. 37 and 42 to 47 correspond to strands (+). As a matter of example, the biallelic marker 24-257/320 corresponds to a polymorphism "a or g" at position 109663 on strand (−). Thus the nucleotide at position 109663 of SEQ ID NO: 37 will be "y", which corresponds to "t or c" according to the standard PCT nomenclature. The biallelic marker 24-247/216 corresponds to a polymorphism "a or g" at position 99505 on strand (+). Thus the nucleotide at position 99505 of SEQ ID NO: 37 will be "r", which corresponds to "a or g" according to the standard PCT nomenclature.

Example 13

Identification of Polymorphisms by Comparison of Genomic DNA from Overlapping BACs Genomic DNA from multiple BAC clones derived from the same DNA donor sample and overlapping in regions of genomic DNA of SEQ ID NO: 37 was sequenced. Sequencing was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis (ABI Prism DNA Sequencing Analysis software (2.1.2 version)).

Example 14

Validation of the Polymorphisms Through Microsequencing

The biallelic markers identified in Examples 12 and 13 were further confirmed and their respective frequencies were determined through microsequencing. Microsequencing was carried out for each individual DNA sample described in Example 11.

Amplification from genomic DNA of individuals was performed by PCR as described above for the detection of the biallelic markers with the same set of PCR primers described in tables 1A and 1 B.

The preferred primers used in microsequencing were about 19 nucleotides in length and hybridized just upstream of the considered polymorphic base. According to the invention, the primers used for microsequencing are detailed in tables 4A and 4B.

TABLE 4A

Primers in the PPP2R2C gene

| amplified region | Marker name | Orientation of the primer | Position of the primer on SEQ ID NO: 37 | SEQ ID No. of the primer |
|---|---|---|---|---|
| 24-257 | 24-257/320 | (+1) | 109644 to 109662 | SEQ ID NO: 40 |
| 99-24169 | 99-24169/139 | (+1) | 84007 to 84025 | SEQ ID NO: 39 |
| 99-24175 | 99-24175/218 | (+1) | 117441 to 117459 | SEQ ID NO: 41 |
| 24-247 | 24-247/216 | (+1) | 99486 to 99504 | |

TABLE 4B

Primers in the KCNQ2 gene

| amplified region | Marker name | Orientation of the primer | SEQ ID No. | Position of the primer on indicated SEQ ID No. |
|---|---|---|---|---|
| 30-4 | 30-4/58 | (−1) | SEQ ID NO: 42 | 302 to 319 (primer B18) |
| 30-4 | 30-4/58 | (+1) | SEQ ID NO: 42 | 282 to 300 (primer A19) |
| 30-2 | 30-2/62 | (−1) | SEQ ID NO: 43 | 302 to 320 |
| 30-17 | 30-17/37 | (−1) | SEQ ID NO: 44 | 302 to 324 |
| 30-7 | 30-7/30 | (+1) | SEQ ID NO: 45 | 280 to 300 |
| 30-84 | 30-84/37 | (−1) | SEQ ID NO: 46 | 302 to 318 |
| 30-15 | 30-15/54 | (−1) | SEQ ID NO: 47 | 302 to 323 |

As for the primers in tables 2A and 2B, the sign (+1) in the column "orientation" indicates that the sequence of the primer is identical to the corresponding region of SEQ ID Nos. 37 and 42 to 47, and the sign (−1) indicates that the sequence of the primer is complementary to the corresponding region of SEQ ID Nos. 37 and 42 to 47.

The microsequencing reaction performed as follows. After purification of the amplification products, the microsequencing reaction mixture was prepared by adding, in a 20 µl final volume: 10 µmol microsequencing oligonucleotide, 1 U Thermosequenase (Amersham E79000G), 1.25 µl Thermosequenase buffer (260 mM Tris HCl pH 9.5, 65 mM MgCl$_2$), and the two appropriate fluorescent ddNTPs (Perkin Elmer, Dye Terminator Set 401095) complementary to the nucleotides at the polymorphic site of each biallelic marker tested, following the manufacturer's recommendations. After 4 minutes at 94° C., 20 PCR cycles of 15 sec at 55° C., 5 sec at 72° C., and 10 sec at 94° C. were carried out in a Tetrad PTC-225 thermocycler (MJ Research). The unincorporated dye terminators were then removed by ethanol precipitation. Samples were finally resuspended in formamide-EDTA loading buffer and heated for 2 min at 95° C. before being loaded on a polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal, or saturated, or whether the signals are ambiguous. In addition, the software identifies significant peaks (according to shape and height criteria). Among the significant peaks, peaks corresponding to the targeted site are identified based on their position. When two significant peaks are detected for the same position, each sample is categorized dassification as homozygous or heterozygous type based on the height ratio.

Example 15

Association Study Between Bipolar Disorder and the Biallelic Markers of the Invention 5.1. Collection of DNA Samples from Affected and Non-Affected Individuals The association studies were performed on two different populations. One collection of samples was provided by Hospital Pinero, Buenos-Aires, Argentina (the "Labimo" collection). The other collection of samples was provided by the University College of London (the "UCL" collection). Both collections are constituted by individuals that are affected or not by bipolar disorder.

A) The Labimo Collection a) Affected Population

206 DNA samples from patients suffering from bipolar disorder (cases) were collected for genotyping analysis.

All patients fulfilled DSM-IV and ICD-10 criteria for bipolar type I (ICD-10: F30.x, F31.x) or bipolar type II (ICD-10: F31.8). All patients were of Caucasian ethnic origin up to the $2^{nd}$ generation.

All potential patients suffering from a medical disorder or from a drug abuse were excluded.

According to DSM-IV criteria, 115 cases were classified as bipolar type I, 69 were bipolar type II, 22 were unclassified, and information concerning the type of bipolar disorder was lacking in 20 cases (8.5%)

The main phenotypic data of the cases were as follows:
  Mean age at first symptoms: 25.6 years (SD, 11; range, 8-58)
  Mean age at inclusion: 43.3 years (SD, 13.8; range, 17-76)
  Gender: 142 females and 84 males (ratio, 1.7)
  Ethnic origin: 213 were European Caucasian, 7 were non-European Caucasians, and information was lacking in 6 cases (2.5%)
  Family history of bipolar disorder was found in 18.5%, whereas schizophrenia was found in 0.9%.

b) Unaffected Population

201 DNA samples from individuals not suffering from bipolar disorder (controls) were collected for genotyping analysis.

All controls were individuals lacking personal or familial history of psychiatric disease.

The main phenotypic data of the controls were as follows:

Mean age: 43.8 years (SD, 12; range, 21-72)

Gender: 118 females and 83 males (ratio, 1.4)

180 controls were European Caucasian, and 21 had mixed ethnic origin c) Cases and Control Populations Selected for the Association Study The case control populations were matched for ethnicity and sex which resulted in 159 cases and 159 control individuals. Among the cases, 96 cases suffered from type I bipolar disorder, 56 cases suffered from type II bipolar disorder, and 7 cases suffered from an undetermined type of bipolar disorder. 33.8% of the cases were males. The mean age of the cases was of 43 and the median age was of 44. 41.4% of the controls were males. The mean age of the controls was of 44 and the median age was of 46.

The presence of population structure can result in spurious association, which is an association between phenotypes and markers that is not linked to any causative loci but due to a different ethnic origin. The Fst test is a general statistical tool for analyzing variances and that can be used to verify that a collection is homogeneous, i.e., that found associations are not linked to the structure of the population. The Fst value is calculated using random markers that are (i) unlinked and (ii) not associated with the trait to be studied. An Fst value close to 0 indicates that the collection is homogeneous and that any significant associations that are found are due to the trait under investigation (see, e.g., Bruce S. Weir, Genetic Data Analysis II, Edition Sinauer, San Francisco and Hartl and Clark, Populations genetics, Edition Sinauer, San Francisco). 66 random markers that were (i) unlinked and (ii) not associated with bipolar disorder were used to calculate the Fst value. An Fst value of 1.68e-01 was found for the found in the Labimo collection, indicating that this collection is homogeneous.

B) The UCL Collection a) Affected Population

All patients fulfilled DSM-IV criteria for bipolar type I (ICD-10: F30.x, F31.x) or bipolar type II (ICD-10: F31.8). All patients were unrelated individuals of Caucasian origins from the British Isles (including English, Welsh, Scottish and Irish) up to the $2^{nd}$ generation.

b) Unaffected Population 300 samples from unaffected control individuals (not suffering from bipolar disorder) were collected for genotyping analysis.

All control individuals showed (i) absence of personal history of psychiatric disease; and (ii) absence of familial history of psychiatric disease in first-degree relatives. All controls individuals of Caucasian origins from the British Isles (including English, Welsh, Scottish and Irish) up to the $2^{nd}$ generation.

c) Cases and Control Populations Selected for the Association Study

The population retained for the study was composed of 315 cases and 295 controls. Among the cases, 256 cases suffered from type I bipolar disorder, 26 cases suffered from type II bipolar disorder, and 33 cases suffered from an undetermined type of bipolar disorder. About 36% of the cases were males. The mean age of the cases was of 46 and the median age was of 46. 48% of the controls were males. The mean age of the controls was of 37 and the median age was of 32.

59 random markers that were (i) unlinked; and (ii) not associated with bipolar disorder were used to calculate the Fst value. A Fst value of 3.41e-01 was found for the UCL collection, indicating that this collection is homogeneous.

5.2. Association Studies

A) Genotyping of Affected and Control Individuals

The general strategy to perform the association studies was to individually scan the DNA samples from all individuals in each of the populations described above in order to establish the allele frequencies of biallelic markers, and among them the biallelic markers of the invention, in the diploid genome of the tested individuals belonging to each of these populations.

Frequencies of every biallelic marker in each population (cases and controls) were determined by performing microsequencing reactions on amplified fragments obtained by genomic PCR performed on the DNA samples from each individual. Genomic PCR and microsequencing were performed as detailed above in Examples 11 to 13 using the described PCR primers and microsequencing primers.

B) Single Biallelic Marker Frequency Analysis

The difference between the allelic frequencies in the unaffected population and in the population affected by bipolar disorder was calculated for all five markers located in the KCNQ2 gene, and for all four markers located in the PPP2R2C gene. The allelic frequency of markers between cases and controls were investigated using the Pearson Chi squared test for allelic frequency and genotypic frequency distributions. A significant difference between observed and expected alleles/genotypes of a specific marker between case and control populations implies an association between the gene harboring this particular biallelic marker and bipolar disease. Both allelic and genotypic p-values were calculated for all markers. The p-values in tables 5A and 5B indicate the probability of no association between a biallelic marker and bipolar disorder considering the frequency. A p-value under 5e-02 indicates a significant association between the biallelic marker and bipolar disorder.

Odds ratio determination is a way of comparing the probability of having the disease when carrying a given allele versus when not carrying the said allele. An odds ratio higher than 1 indicates that the probability of having bipolar disorder is higher when carrying one of the alternative alleles, haplotypes or genotypes than when carrying the other ones. The genotypic odds ratio allows the identification of the "risk" allele, haplotype or genotype for an associated biallelic marker. The genotypic odds ratio was calculated for one biallelic marker located in PPP2R2C and for two markers located in the KCNQ2 gene (tables 6A and 6B).

TABLE 5A p-values for biallelic markers located in PPP2R2C

| Marker Name | Location in PPP2R2C | Collection | Chosen allele | All. Freq Diff. | All. Odds Ratio | Allelic p-value | Genotypic p-value |
|---|---|---|---|---|---|---|---|
| 99-24169/139 | Intron 1d | UCL | A | 0.095 | 1.733 | 2.19e−04 | 3.61e−04 |
|  |  | Labimo | A | 0.002 | 1.012 | 9.46e−01 | 5.98e−01 |
| 24-247/216 | intron 4 | UCL | G | 0.047 | 1.275 | 7.75e−02 | 2.29e−02 |
|  |  | Labimo | G | 0.024 | 1.125 | 4.86e−01 | 7.65e−01 |
| 24-257/320 | Intron 5 | UCL | A | 0.018 | 1.079 | 5.52e−01 | 8.22e−01 |
|  |  | Labimo | A | 0.102 | 1.557 | 4.04e−03 | 1.19e−02 |
| 99-24175/218 | Intron 5 | UCL | G | 0.035 | 1.162 | 2.62e−01 | 3.99e−03 |
|  |  | Labimo | A | 0.096 | 1.546 | 6.69e−03 | 2.34e−02 |

TABLE 5B p-values for biallelic markers in the KCNQ2 gene

| Marker Name | Location in the KCNQ2 gene | Collection | Chosen allele | All. Freq Diff. | All. Odds Ratio | Allelic p-value | Genotypic p-value |
|---|---|---|---|---|---|---|---|
| 30-4/58 | 5' of the gene | UCL | — | — | — | — | — |
|  |  | Labimo | G | 0.03 | 1.24 | 3.03e−01 | 5.85e−01 |
| 30-2/62 | intron 1 | UCL | A | 0.05 | 1.23 | 7.76e−02 | 5.20e−03 |
|  |  | Labimo | A | 0.03 | 1.13 | 4.42e−01 | 1.15e−01 |
| 30-17/37 | intron 4 | UCL | A | 0.01 | 1.03 | 7.77e−01 | 9.12e−01 |
|  |  | Labimo | G | 0.03 | 1.13 | 4.70e−01 | 7.10e−01 |
| 30-7/30 | intron 12 | UCL | C | 0.05 | 1.21 | 1.05e−01 | 3.02e−02 |
|  |  | Labimo | C | 0.02 | 1.06 | 7.03e−01 | 5.32e−01 |
| 30-84/37 | 3' of gene | UCL | A | 0.02 | 1.20 | 3.06e−01 | 3.69e−01 |
|  |  | Labimo | — | — | — | — | — |
| 30-15/54 | 3' of gene | UCL | A | 0.01 | 1.06 | 6.92e−01 | 7.68e−01 |
|  |  | Labimo | — | — | — | — | — |

TABLE 6A genotypic odds ratios for a biallelic marker located in PPP2R2C

| Biallelic marker | collection | genotype | odds ratio | p-value |
|---|---|---|---|---|
| 99-24169/139 | UCL | AA vs GG | 1.9 | 8.50e−02 |
|  |  | AA vs AG | 2.06 | 7.20e−05 |
|  |  | AA vs (AG + GG) | 2.04 | 4.60e−05 |

TABLE 6B genotypic odds ratios for biallelic markers located in the KCNQ2 gene

| Biallelic marker | collection | genotype | odds ratio | p-value |
|---|---|---|---|---|
| 30-2/62 | UCL | (AG + GG) vs AA | 1.05 | 4.60E−01 |
|  |  | AG vs AA | 1.28 | 1.70E−01 |
|  |  | AA vs GG | 1.51 | 8.00E−02 |
|  |  | AG vs (GG + AA) | 1.62 | 3.00e−03 |
|  |  | (AG + AA) vs GG | 1.82 | 1.50e−03 |
| 30-7/30 | UCL | (CC + CT) vs TT | 1.04 | 4.40E−01 |
|  |  | TT vs CT | 1.14 | 2.90E−01 |
|  |  | (CC + TT) vs CT | 1.37 | 3.80e−02 |
|  |  | CC vs TT | 1.58 | 3.80e−02 |
|  |  | CC vs (TT + CT) | 1.71 | 7.00e−03 |

Biallelic Markers in PPP2R2C

Thus the four biallelic markers located in the PPP2R2C gene are found to be associated with bipolar disorder. More specifically, 99-24169/139 is found to be highly associated with bipolar disorder in the UCL collection (significant allelic and genotypic p-values). 24-257/320 and 99-24175/218 are highly associated with bipolar disorder in the Labimo collection (significant allelic p-values). In addition, 99-24175/218 is also associated with bipolar disorder in the UCL collection (significant genotypic p-value). 24-247/216 is associated with bipolar disorder in the UCL collection (significant genotypic p-value).

The risk allele for the 99-24169/139 biallelic marker is "A". The risk alleles for the 24-257/320 biallelic marker and for the 99-24175/218 biallelic marker are also "A". The risk genotype for the 99-24169/139 biallelic marker is "AA". Thus an individual carrying the genotype "AA" at biallelic marker 99-24169/13 is at risk of developing bipolar disorder.

Biallelic Markers in the KCNQ2 Gene

Two biallelic markers located in the KCNQ2 gene, 30-2/62 and 30-7/30, are associated with bipolar disorder. More specifically, 30-2/62 is found to be highly associated with bipolar disorder in the UCL collection (significant allelic and genotypic p-values). 30-7/30 is associated with bipolar disorder in the UCL collection (significant genotypic p-value).

The risk genotype for 30-2/62 is "AG". The risk genotype for 30-7130 is "CC". Thus individuals carrying the genotype "AG" at biallelic marker 30-2/62 and individuals carrying the genotype "CC" at biallelic marker 30-7/30 are at risk of developing bipolar disorder.

The association results of the single biallelic marker frequency analysis show that both the PPP2R2C gene and the KCNQ2 gene are associated with bipolar disorder. Accordingly, deregulation and/or dysfunction of KCNQ2 polypeptides and PP2A phosphatases comprising the PP2A/Bγ regulatory subunit contribute to the onset and to the development of bipolar disorder.

C) Haplotype Frequency Analysis

The analysis of haplotype frequencies cannot readily be derived from observed genotypic data. The EM (Expectation-Maximization) algorithm (Excoffier L & Slatkin M, 1995) allows the estimation of haplotypes for the population under investigation. Haplotype frequency estimations were performed by applying the OMNIBUS likelihood ratio test (PCT publication WO 01/091026)

The haplotype analysis was performed for two sets of markers located in PPP2R2C. The haplotype analysis for 24-257/320 and 99-24175/218 was performed in the Labimo collection. The haplotype analysis for 99-24169/139 and 24-247/216 was performed in the UCL collection. The results are shown in tables 7 (p-values) and 7B (odds ratios).

TABLE 7A

| markers | Samples | Haplotype | Chi-S | Ave Chi-S | SD Chi-S | Max Chi-S | p-value |
|---|---|---|---|---|---|---|---|
| 24-257/320 | Labimo | AA | 7.78 | 0.96 | 1.34 | 14.02 | 3.9e−03 |
| and | | AG | 0.02 | 1.02 | 1.40 | 11.19 | 8.79e−01 |
| 99-24175/218 | | GA | 0.14 | 0.96 | 1.35 | 11.62 | 6.77e−01 |
| | | GG | 7.35 | 0.98 | 1.35 | 14.31 | 5.5e−03 |
| 99-24169/139 | UCL | AA | 1.49641 | 1.03501 | 1.46687 | 14.67815 | 2.28e−01 |
| and | | AG | 5.19606 | 1.0854 | 1.52336 | 14.42852 | 2.73e−02 |
| 24-247/216 | | GA | 13.91081 | 1.29859 | 1.81182 | 16.01507 | 5e−04 |
| | | GG | 0.42929 | 1.57482 | 2.19562 | 23.4845 | 6.03e−01 |

TABLE 7B

| markers | haplotype | overall | cases | controls | odds ratio |
|---|---|---|---|---|---|
| 24-257/320 | AA | 60.9% | 65.9% | 55.5% | 1.55 |
| and | AG | 2.8% | 2.7% | 2.9% | 0.93 |
| 99-24175/218 | GA | 5.9% | 5.5% | 6.2% | 0.88 |
| | GG | 30.4% | 25.8% | 35.4% | 0.64 |
| 99-24169/139 and | AA | 60.0% | 62.0% | 58.2% | 1.17 |
| 24-247/216 | AG | 17.4% | 20.0% | 14.5% | 1.47 |
| | GA | 13.6% | 9.5% | 17.6% | 0.49 |
| | GG | 8.9% | 8.5% | 9.7% | 0.86 |

The risk haplotype for 24-257/320 and 99-24175/218 is "AA". The risk haplotype for 99-24169/139 and 24-247/216 is "AG". Thus an individual carrying the haplotype "AA" at biallelic markers 24-257/320 and 99-24175/218 is at risk of developing bipolar disorder, and an individual carrying the haplotype "AG" at biallelic markers 99-24169/139 and 24-247/216 is also at risk of developing bipolar disorder.

REFERENCES

1. Altschul et al. (1990) J Mol Biol, 215:403-410
2. Altschul et al., (1997) Nucleic Acids Res., 25:389-402
3. Andrieux et al. (2002) Genes Dev., 16:2350-2364
4. Biervert et al. (1998) Science, 279:403-406
5. Biervert et al. (1999) Genet., 104:234-240
6. Borresen et al. (1988) Mutat Res. 202:77-83
7. Dempster et al. (1977) JRSSB, 39:1-38
8. Detera-Wadleigh et al. (1999) Proc Natl Acad Sci USA, A96(10):5604-5609
9. Devereux et al. (1984) Nucleic Acids Res., 12:387-395
10. Elbashir et al. (2001) Genes Dev. 15:188-200
11. Ellington and Szostak (1990) Nature 346:818-822.
12. Excoffier and Slatkin, (1995) Mol Biol Evol. 12:921-7
13. Gamper et al. J. Neurosci. (2003) 23:84-95
14. Grantham (1974) Science, 185:862-864
15. Grompe et al. (1989) Proc Natl Acad Sci USA. 86:5888-5892
16. Hu et al. (2000) Genomics., 67:83-86
17. Kaelin et al. (1991) Cell, 64:521-532
18. Kaelin et al. (1992) Cell, 70:351-364
19. Kim et al. (2003) Anal Biochem. 316:251-258
20. Lessa et al. (1993) Mol Ecol. 2:119-129
21. Main et al. (2000) Mol Pharmacol, 58:253-262
22. Newton et al. (1989) Nucleic Acids Res. 17:2503-2516
23. Orita et al. (1989) Proc Natl Acad Sci USA 86:2766-2770
24. Pan et al. (2001) J. Physiol., 531:347-358
25. Pearson (1990) Methods in Enzymology, 183:63-99
26. Pearson and Lipman (1988) Proc Nat Acad Sci USA, 85:2444-2448
27. Ruano et al. (1990) Proc. Natl. Acad. Sci. USA. 87:6296-6300
28. Sarkar and Sommer, (1991) Biotechniques. 10-436-440
29. Schroeder et al., Epilepsia (2000) 41:1068-1069
30. Schwake et al. (2000) J. Biol. Chem., 275:13343-13348
31. Singh et al. (1998) Nat Genet, 18:25-29
32. Smith and Waterman (1981) Advances in Applied Mathematics, 2:482-489
33. Towbin et al. (1979) Proc Nat Acad Sci USA, 76:4350-4354
34. Wang et al. (1998) Science, 282:1890-1893
35. Wen et al. (2003) World J Gastroenterol. 9:1342-1346
36. Wu et al. (1989) Proc. Natl. Acad. Sci. USA. 86:2757-2760

The invention claimed is:

1. An isolated polypeptide comprising the amino acid sequence of SEQ ID NO: 2.

2. A purified polynucleotide encoding the polypeptide of SEQ ID NO: 2, or a polynucleotide fully complementary thereto.

3. The polynucleotide according to claim 2, wherein said polynucleotide comprises the polynucleotide sequence of SEQ ID NO: 1 or a polynucleotide fully complementary thereto.

4. A vector comprising a polynucleotide encoding the polypeptide of SEQ ID NO: 2.

5. A host cell comprising a vector that comprises a polynucleotide encoding the polypeptide of SEQ ID NO: 2.

6. A method of making a polypeptide, said method comprising the steps of culturing a host cell comprising a vector that comprises a polynucleotide encoding the polypeptide of SEQ ID NO: 2 under conditions suitable for the production of a polypeptide comprising SEQ ID NO: 2.

7. The method according to claim 6, further comprising the step of purifying said polypeptide comprising SEQ ID NO: 2 from the culture.

8. A composition comprising at least one polypeptide comprising the amino acid sequence of SEQ ID NO: 2 and a physiologically acceptable carrier.

* * * * *

UNITED STATES PATENT AND TRADEMARK OFFICE
CERTIFICATE OF CORRECTION

PATENT NO. : 7,442,519 B2
APPLICATION NO. : 10/519335
DATED : October 28, 2008
INVENTOR(S) : Laurent Cavarec et al.

It is certified that error appears in the above-identified patent and that said Letters Patent is hereby corrected as shown below:

Column 12,
Line 62, ""Phenotype"" should read --"phenotype"--.

Column 14,
Line 2, "such assay s" should read --such assays--.
Line 12, "alter native" should read --alternative--.

Column 16,
Line 2, "ncbi.nim.nih.gov)" should read --ncbi.nlm.nih.gov)--.

Column 17,
Line 47, "substancially the same" should read --substantially the same--.

Column 18,
Line 37, "complementery thereto" should read --complementary thereto--.
Line 43, "complementery thereto" should read --complementary thereto--.
Lines 49-50, "to a polynucleotides" should read --to a polynucleotide--.
Line 63, "NO; 3" should read --NO: 3--.

Column 23,
Line 23, "Accession No. 043526" should read --Accession No. O43526--.

Column 25,
Lines 11-12, "ho momeric" should read --homomeric--.
Line 53, "that (I)" should read --that (i)--.

Column 28,
Line 56, "consisting of 30-2162" should read --consisting of 30-2/62--.

Column 30,
Line 1, "marker 30-7130" should read --marker 30-7/30--.
Line 67, "Human fcetal" should read --Human foetal--.

UNITED STATES PATENT AND TRADEMARK OFFICE
CERTIFICATE OF CORRECTION

PATENT NO. : 7,442,519 B2
APPLICATION NO. : 10/519335
DATED : October 28, 2008
INVENTOR(S) : Laurent Cavarec et al.

It is certified that error appears in the above-identified patent and that said Letters Patent is hereby corrected as shown below:

Column 31,
Line 33, "SDI-Leu/-Trp and SDI-Leu/-Trp/-His/-Ade" should read --SD/-Leu/-Trp and SD/-Leu/-Trp/-His/-Ade--.
Line 35, "the He Yeast" should read --the Yeast--.

Column 33,
Line 32, "digestion With EcoRi" should read --digestion with EcoRi--.
Line 61, "pGAD7" should read --pGADT7--.

Column 34,
Line 42, "10 µl" should read --100 µl--.
Line 44, "SDI-Leu/-Trp/-His/-Ade" should read --SD/-Leu/-Trp/-His/-Ade--.

Column 36,
Line 50, "w performed" should read --was performed--.

Column 37,
Lines 19-20, "membrane were then blocked" should read --membrane was then blocked--.
Line 66, "phsophorylation" should read --phosphorylation--.

Column 39,
Line 9, "phophorylation" should read --phosphorylation--.

Column 40,
Line 17, "1 µd" should read --1 µl--.

Column 45,
Line 57, "10 µmol" should read --10 pmol--.

Column 46,
Line 20, "dassification" should read --classification--.

UNITED STATES PATENT AND TRADEMARK OFFICE
CERTIFICATE OF CORRECTION

PATENT NO. : 7,442,519 B2
APPLICATION NO. : 10/519335
DATED : October 28, 2008
INVENTOR(S) : Laurent Cavarec et al.

It is certified that error appears in the above-identified patent and that said Letters Patent is hereby corrected as shown below:

Column 50,
Line 64, "for 30-7130" should read --for 30-7/30--.

Signed and Sealed this

Twenty-eighth Day of April, 2009

JOHN DOLL
*Acting Director of the United States Patent and Trademark Office*